US007976840B2

(12) United States Patent
Ling et al.

(10) Patent No.: US 7,976,840 B2
(45) Date of Patent: Jul. 12, 2011

(54) USE OF ANTI-GL50 ANTIBODIES FOR THE DOWNMODULATION OF AN IMMUNE RESPONSE

(75) Inventors: Vincent Ling, Walpole, MA (US); Kyriaki Dunussi-Joannopoulos, Belmont, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 12/542,901

(22) Filed: Aug. 18, 2009

(65) Prior Publication Data

US 2010/0055091 A1 Mar. 4, 2010

Related U.S. Application Data

(62) Division of application No. 11/311,754, filed on Dec. 19, 2005, now Pat. No. 7,601,813, which is a division of application No. 10/318,855, filed on Dec. 12, 2002, now Pat. No. 7,521,532, which is a division of application No. 09/667,135, filed on Sep. 21, 2000, now Pat. No. 6,521,749.

(60) Provisional application No. 60/155,043, filed on Sep. 21, 1999.

(51) Int. Cl.
*A61K 39/395* (2006.01)
(52) U.S. Cl. .................................... 424/130.1
(58) Field of Classification Search ........................ None
See application file for complete search history.

(56) References Cited

U.S. PATENT DOCUMENTS

| 4,837,306 A | 6/1989 | Ling et al. |
| 5,580,756 A | 12/1996 | Linsley et al. |
| 6,130,316 A | 10/2000 | Freeman et al. |

FOREIGN PATENT DOCUMENTS

| EP | 984023 | 3/2000 |
| WO | 98/38216 | 9/1998 |
| WO | 99/15553 | 4/1999 |
| WO | 00/46240 | 8/2000 |

OTHER PUBLICATIONS

Huang Z., Pharmacology and Therapeutics, 2000, 86: 201-215.*
Blazar et al., J. Immunol., 1996, 157: 3250-3259.*
Iwai et al. (2003) Journal of Immunology, 171: 2848-2854 (provided by Applicant on Nov. 19, 2010).*
Iwai et al. (2002) Journal of Immunology, 169: 4332-4339 (provided by Applicant on Nov. 19, 2010).*
GenBank Accession No. NM.sub.—005191, version of Aug. 31, 2006.
GenBank Accession No. NM.sub.—015259, version of Jan. 29, 2005.
Aicher et al., "Characterization of human inducible costimulator ligand expression and function," J. Immunol., 164 (9):4689-96 (2000).
Attwood, T., "The Babel of Bioinformatics," Science, 290:471-473 (2000).
Benjafield et al., "G-protein beta3 subunit gene (GNB3) variant in causation of essential hypertension," Hypertension, 32(6):1094-7 (1998).
Brodie et al., "LICOS, a primordial costimulatory ligand," Curr. Biol., 10(6):333-336 (2000).
Butz et al., "A tripartite protein complex with the potential to couple synaptic vesicle exocytosis to cell adhesion in brain," Cell 94(6):773-782 (1998).
Database EMBL Acc. No. AB014553 for Homo sapiens mRNA for KIAA0653 protein, partial cds Jul. 15, 1998.
Database EMBL Acc. No. R23544 for yg34c12.rl Soares infant brain 1NIB *Homo sapiens* cDNA clone Image:34465 5', mRNA sequence Apr. 23, 1995.
Database Embl Acc. No. AI614037 for vg32f09.y1 Soares.sub.—mammary.sub.—gland.sub.—NbMMG Mus musculus cDNA clone Image:863081 5' similar to TR:O75144 O75144 KIAA0653 Protein; mRNA sequence Apr. 26, 1999.
GenBank Acc. No. Y08823 for *G. gallus* mRNA for CD80-like protein precursor, Sep. 30, 1997.
GenBank Acc. No. U67065 for *Mus musculus* butyrophilin (BTN) gene, promoter region and complete cds, Mar. 29, 1997.
GenBank Acc. No. AC006508 for *Mus musculus* Yp BAC GSMB-187H15 (Genome Systems Mouse BAC Library) complete sequence, Feb. 15, 2000.
GenBank Acc. No. AC005818 for *Mus musculus* chromosome 10 clone rp21-411d9 strain 129S6/SvEvTac, complete sequence, Aug. 29, 2000.
GenBank Acc. No. AF115517 for *Mus musculus* survivin40, survivin121 and survivin140 genes, alternative splice products, complete cds, Apr. 20, 1999.
GenBank Acc. No. Z18892 for *Mus musculus* desmin gene, Jun. 21, 1999.
GenBank Acc. No. AF087694 for *Mus musculus* veli 2 mRNA, complete cds, Nov. 20, 1998.
GenBank Acc. No. AF173082 for *Mus musculus* LIN-7 homolog 2 (MALS-2) mRNA, complete cds, Aug. 11, 1999.
GenBank Acc. No. BAA31628 for KIAA0653 protein [*Homo sapiens*], Feb. 6, 1999.
Hattori et al., "The DNA sequence of human chromosome 21," Nature 18;405(6784):311-9 (2000).
Henry et al., "Cloning, structural analysis, and mapping of the B30 and B7 multigenic families to the major histocompatibility complex (MHC) and other chromosomal regions," Immunogenetics, 46(5):383-95 (1997).
Hutlof et al., "ICOS is an inducible T-cell co-stimulator structurally and functionally related to CD28," Nature, 21:397 (6716):263-6 (1999).

(Continued)

Primary Examiner — Ilia Ouspenski

(57) ABSTRACT

The invention provides isolated nucleic acids molecules, designated GL50 nucleic acid molecules, which encode novel GL50 polypeptides. The invention also provides antisense nucleic acid molecules, recombinant expression vectors containing GL50 nucleic acid molecules, host cells into which the expression vectors have been introduced, and nonhuman transgenic animals in which a GL50 gene has been introduced or disrupted. The invention still further provides isolated GL50 polypeptides, fusion proteins, antigenic peptides and anti-GL50 antibodies. Diagnostic, screening, and therapeutic methods utilizing compositions of the invention are also provided.

16 Claims, 54 Drawing Sheets

OTHER PUBLICATIONS

Ishikawa et al., "Prediction of the coding sequences of unidentified human genes. X. The complete sequences of 100 new cDNA clones from brain which can code for large proteins in vitro," DNA Res. 5(3):169-176 (1998).

Jo et al., "Characterization of MALS/Velis-1, -2, and -3: a family of mammalian LIN-7 homologs enriched at brain synapses in association with the postsynaptic density-95/NMDA receptor postsynaptic complex," J. Neurosci. 19 (11):4189-4199 (1999).

Li et al., "Regulation of the mouse desmin gene: transactivated by MyoD, myogenin, MRF4 and Myf5," Nucleic Acids Res. 21(2):335-343 (1993).

Ling et al., "Embryonic stem cells and embryoid bodies express lymphocyte costimulatory molecules," Exp. Cell Res., 241(1):55-65 (1998).

Ling et al., "Cutting edge: Identification of GL50, a novel B7-like protein that functionally binds to ICOS receptor," J. Immunol., 164(4):1653-7 (2000).

Ling et al., Differential expression of inducible costimulator-ligand splice variants: lymphoid regulation of mouse GL50-B and human GL50 molecules, J. Immunol., 166(12):7300-8 (2001).

Metzler et al., "Solution structure of human CTLA-4 and delineation of a CD80/CD86 binding site conserved in CD28," Nature Structural Biol., 4:527-531 (1997).

Ogg et al., "Structural organization and mammary-specific expression of the butyrophilin gene," Mamm. Genome 7 (12):900-905 (1996).

Siffert et al., "Association of a human G-protein beta3 subunit variant with hypertension," Nat. Genet., 18(1):45-8 (1998).

Skolnick et al., "From genes to protein structure and function: novel applications of computational approaches in the genomic era," Trends in Biotech, 18(1):34-39 (2000).

Wang et al., "Costimulation of T cells by B7-H2, a B7-like molecule that binds ICOS," Blood, 96(8):2808-2813 (2000).

Yoshinaga et al., "T-cell co-stimulation through B7RP-1 and ICOS," Nature, 402(6763):827-32 (1999).

NCBI Accession No. 075144, Nonstructural protein NS1—Influenza A Virus, Jul. 16, 1999.

Greenwald et al., "The B7 Family Revisited," Annu. Rev. Immunol., 23:515-48 (2005).

GenBank Accession No. 005191, version of Aug. 31, 2006.

GenBank Accession No. NM 015259, version of Jan. 29, 2005.

* cited by examiner

FIG. 1A

```
          10         20         30         40         50         60         70         80         90        100
 1234567890 1234567890 1234567890 1234567890 1234567890 1234567890 1234567890 1234567890 1234567890 1234567890
CCGGAACCCC AACCGCTGCA ACTCTCCGCG TCCGAAATCC AGCATCCCGC AGTCTGCGCT CCGACCAATGC AGTAAAGTG TCCCTGTTTT GTGTCCTTGG    100
                                                                            M  Q  L  K  C   P  C  F  V  S  L  G
GAACCAGGCA GCCTGTTCG AAGAAGCTCC ATGTTCTAG CGGGTCTTT TCTGGTCTTG GTCTGTCTTT CTGCTGTTTG AGCAGCCTCT GTGCTGCCTC     200
  T  R  Q   P  V  W   K  K  L  H   V  S  S   G  F  F   S  G  L  G   L  F  L   L  L  L   S  S  L  C   A  A  S
TGCAGAGACT GAAGTCGGTG CAATGGTGGG CAGCTCAGCT GTGCTCAGCT GCATTGAACT CCACAGAGCC CATTCAACT GAGTGGTCT GTATGTCTAT    300
  A  E  T   E  V  G  A   M  V  G   S  N  V   V  L  S  C   I  D  P   H  R  R   H  F  N  L   S  G  L   Y  V  Y
TGGCAAATCG AAACCCAGA AGTTCGGTG ACTTACTACC TGCCTTACAA GTCCTCCAGG ATCAATGTGG ACAGTTCCTA CAAGAACAGG GCCCATCTGT    400
  W  Q  I   E  N  P   E  V  S  V   T  Y  Y  L   P  Y  K   N  V  S  P  G   I  N  V  D   S  S  Y   K  N  R  G  H  L  S
CCCTGGACTC CATGAAGCAG GGTAACTTCT CTCTGTACT CTGTGTACCT GAAGAAATGT ACCCCTCAGG ACACCTGAGA GTTCACATGC CGGGTATTA TGAATACAGC   500
  L  D  S   M  K  Q   G  N  F  S   L  Y  L   K  N  V   T  P  Q  D   T  Q  E   F  T  C   R  V  F  M   N  T  A
CACAGAGTTA GTCAAGATCT TGGAAGAGGT CCGTCTGCGC CCTGTGGCA CAGAGCCCAA AATTTCAGT CCTGTATTCG GGTACAATAG CTGATAGCTC CAACCCGGGC    600
  T  E  L   V  K  I  L   E  E  V   V  R  L   R  V  A  A   N  F  S   T  P  V   I  S  T  S   D  S  S   N  P  G
CAGGAACGTA CCTACACCTG CATGTCCAAG AATGGCTACC CAGAGAACAA CTGGTATTGG GGCTGTAATAGC CGGACAATAG CTAAATAAGC ACGGCTCTGC         700
  Q  E  R  T   Y  T  C   M  S  K   N  G  Y  P   E  P  N   L  Y  W   I  N  T  T   D  N  S   L  I  D   T  A  L  Q
AGATAACAC TGTCTACTG AACAAGTTGG GCCTGTATGA TGTAATCAGC GCAGAAAGTT TCACTGAAA TAACACAAAG AACCCACAA GATGTTCTGT GCTGCCTAGA    800
  N  N  T   V  Y  Y  L   N  K  L  G   L  Y  D   V  I  S   A  E  S  F   T  G  N   N  T  K   N  P  Q  E   T  H  N  E  L
GAATGTGGCT CTCCACCAGA ACATCACTAG CATGTCCCG GGCGCAGCGG CATTGGTTC GTGCTTCATA TAACAGAGGA CCGAAGCTAT ACAGACCCA TAATGAGTTA    900
  N  V  A   L  H  Q  N   I  T  S   I  S  Q   A  E  S  F   T  G  N   N  T  K   N  P  Q  E   T  H  N  E  L
AAGTCCTTG TCCCGTCCT TGCTGTACTG GCGGCAGGG CATTCGTTTC GCCAGCAGGG CATTCGTTTC CTTCATCATA TAACAGAGGA CCGAAGCTAT ACAGACCCA TAATGAGTTA  1000
  K  V  L   V  P  V  L   A  A  A  A   F  V  S   F  I  I   Y  R  R  T   R  P  H   R  S  Y   T  G  P  K
AGACTGTACA GCTTGAACTT ACAGACCACG CCTGACAGGA GGGTTTCTGT CAGGTGCCAC                                          1100
  T  V  Q  L   E  L  T   D  H  A
CTTCAGAGTG GACCCCACA GGCCTGGTGA CAGAGGACAA CGAGAGACAA CGAGCTGTCT GCTTATGGGC TGTGATGGAG GCCAGGAATC CTGGCTTTA CGAGGCACAG   1200
```

FIG. 1B

```
AGACTTCATC CCAGAAACCC CGAGGGAGAT CTCTCCAGTG GGCAGCAGCA ACATCATCGG AATATGGAGC CTCCGGTGAG CTGTCGGCAC AGAGCAGC    1300

AGCTGTGAG AAGATCCTTC CTTGGCACGT TACTACTCAG GCCTAGGAGC TTTATAAAAG AGCGTTTGAG CCACTCTGAA AGCCCTACAG AGTCACTGG    1400

AGACTTTCCC TGCAGGACCT TCAGTTGGGG AGGAAGCCTG ACTTTATTTA GGTCTCAGGC TACTTGGGCC TCTTCGAGGA TATGTGGGAT TTTGTCTACT    1500

GCAAACCTGT TTCTGGCTGA CAATGGTTGG GCTCAGAGGC ACTCAGCTTC ACAAACATCAA TGGGACACGC CTCATCCTTG ACTTCCTGTG GCTACAGAAG    1600

CTTTCCGAAA GCCTTGAGCT CTTTCAGACT GAACAGCTCT GCCCAGTCTC AGCAGCCCAT GAAGATCTCA CCTGGGTCTC CGTGTTGCTG    1700

GCCAGAATAG AGCTAGCTCT TTTGTTTCAA GATGGTTCTG CAAAGTTGGC TGCTTGGAAA CCTAGGGATG TATGTACAAG CTCCAGCCTG ATGCAGTAGG    1800

GGGCACGGAC TCCCCGATGG AACACAGTAT CTGACCCTAG GTGAGGGCAA GCTCCTCCC ACCGAGAGGA CTGGAAATTC TGGACCGTCA AGGCCTGTCT    1900

GCTATGTGGC TGGGGCTCAG TGTGTCAGAT TGCTGATGGA AGGAGTGAGA ACCCTGGGCT CAGGACTAGG AAGACCTGTC CATTTTTTT    2000

TTTTTTTAAT GCCCACATGG ACTTTTTATT CTTCACACCG ATGTATTCAA TGAGTGTAGA GAGAACTACT TAAGTCCTTC CCGAGTACCA AGCATTACCT    2100

ACCTGCAGAA TAGCAACTGT TGTTATGGGT CTTGAGTTGG CAGCTACAGC AAACAAGCAC AAGGAGCAGT TGGGGTCAA GAAGATGGGG TGCAGCGCCC    2200

CCAAGGACAG ACATTGGGA ATTAGTCGTC TCCCTGATGC CCAGAGTTCC CCAGGAACTC AGTGGGTCT GCGGCAGCAC AGTAGGAGTA TTCCTCCTAC    2300

TTTAACTTTT CTTGTCAGAC GTAGTTAGG TTCAGAAAGA GGTCAACTCA GCAAGCCAGC TAGCCGCCTT GGGGCACCAG ACACACTGCC CCCCACCCCC    2400

TGCTTATGTA GGCATTGGGA ACCCTTCACA GACCACTGGA TGTACAGTCA CCATCACCTG CTGATTCCAG CAGGCCCCCA CCTTCTGTGT GAATCCTGGG    2500
```

FIG. 1C

```
AGCACTCCCC TCTTACCCCT CACTGCCCCC CACCCCCTGC ACATCAGCAT TCATTAGATT TGCCCTGTAA CGTCTGATTC CTCCTTTATC TGGGTTGTAG    2600
ATGGGGCATA GTGACTCTA GAAACCTAAC AAGGGAATAA ATGTAAGATG TGCTTTCAAA AAAAAAAAA AAAAAAAAA AAAAAAAA                   2700
AAAAAAAAAA AAAAAAA                                                                                              2718
```

FIG. 2A

```
         10         20         30         40         50         60         70         80         90        100
1234567890 1234567890 1234567890 1234567890 1234567890 1234567890 1234567890 1234567890 1234567890 1234567890
ATGCAGCTAA AGTGTCCCTG TTTTGTGTCC TTTGGAACCA GGCAGCCTGT TTGGAAGAAG CTCCATGTTT CTAGCGGGTT CTTTTCTGGT CTTGGTCTGT    100
 M  Q  L  K   C  P  C   F  V  S    L  G  T  R   Q  P  V   W  K  K   L  H  V  S   G  F     F  S  G   L  G  L  F

TCTTGCTGCT GTTGAGCAGC CTCTGCTG GACTGAAGTC GGTGCAATGG CAGAGTTC ATCGAAAACC CAGAGTTTC GGTGACTTAC ACCTGCCTC      200
 L  L  L  S  S    L  C  A  A    S  A  E    T  E  V    G  A  M  V    G  S  N    V  V  L    P  E  V  S    V  T  Y

AGCCATTTC AACTTGAGTG GTCTGTATGT CTATTGGCAA ATCGAAAACC CAGAGTTTC GGTGACTTAC ACCTGCCTT ACAAGTCTCC AGGGATCAAT    300
 R  H  F     N  L  S  G   L  Y  V   V  Y  W  Q   I  E  N  P   E  V  S     V  T  Y    Y  L  P  Y   K  S  P   G  I  N

GTGGACAGTT CCTACAAGAA TTTATGAATA CAGCCGGGTA GCAGGTCAAG GTTAGTCAAG CGTACCTACA CCTGCATGTC CAAGAATGGC TACCCAGAGC    400
 V  D  S  S   Y  K  N   R  G  H    L  S  L  D    S  M  K    Q  G  N    F  S  L  Y    I  L  E  E    V  V  R    L  R  V

AGGAGTTCAC ATGCCGGGTA TTTATGAATA CAGCCGGGTA GTTAGTCAAG CGTACCTACA CCTGCATGTC CAAGAATGGC TACCCAGAGC    500
 E  F  T    C  R  V   F  M  N  T    A  T  E    L  V  K    I  L  E  E    V  V  R    L  R  V    A  A  N  F   S  T  P

TGTCATCAGC ACCTCTGATA GCTCCAACCC AGGCCAGGAA CTGCAGAATA AGACACGGCT CTGAACAAG CTTGGGCCTGT CAAGAATGGC TACCCAGAGC    600
 V  I  S    T  S  D  S    S  N  P    G  Q  E    R  T  Y  T    C  M  S    K  N  G   Y  P  E  P    N  L  Y    W  I  N

ACAACGGACA ATAGCCTAAT AGACACGGCT CTGAACAAG ACACTGTCTA CTTGAACAAG CAGAACATCA ACACAGAA CAGCACATTA AGGCTCCTT    700
 T  T  D  N    S  L  I    D  T  A    L  Q  N  N    T  V  Y    L  N  K    L  G  L  Y    D  V  I    S  T  L    R  L  P  W

GGACATCTCA TGGGGATGTT CTGTGCTCCG TAGAGAATGT GGCTCTCCAC CAGAACATCA TCTGGCGCA AGTTGTCACTG GAAATAACAC    800
 T  S  H    G  D  V   L  C  C  V    E  N  V    A  L  H    Q  N  I  T    S  I  S    Q  A  E    S  F  T  G    N  N  T

AAAGAACCCA CAGGAAACCC ACAATAATGA GTTAAAAGTC CTTGTCCCCG TCCTTGCTGT ACTGGCGGCA GCGGCATTCG TTTCCTTCAT CATATACAGA    900
 K  N  P    Q  E  T  H    N  N  E    L  K  V    L  V  P  V    L  A  V    L  A  A    A  A  F  V    S  F  I    I  Y  R

CGGACGGGTC CCCACCGAAG CTATACAGGA CCCAAGACTG TACAGCTTGA ACTTACAGAC ACTTGGCGCT CGGTCCCCTA CCAGGACTAT TTGATTCCAA    1000
 R  T  R  P    H  R  S    Y  T  G    P  K  T  V    Q  L     L  T  D    T  W  A  P    V  P  Y    Q  D  Y    L  I  P  R

GATATTTGAT GTCTCCATGC CTCAAAAACAC GTGGTTTACC ATAAAAGCCA CTGCTCATC TGTTCAGACC TCAGCCAGGTG CCAGAAGTCC    1100
 Y  L  M    S  P  C    L  K  T  R    G  L  P  .   K  P    L  S  H  L    F  R  P    L  R  L    Q  P  G  A  R  S  P

CACTTACCGA CACAAGCTAT GTAATGGGTC TGCTCTGCTC CAGCAGCATA GAACCCCCAA GCCCCAGGTT AAGACATTTT CAATGAGCAG    1200
 T  Y  R  V  Y  .
```

FIG. 2B

```
GAACCCAACC ATACTCACAG AGCTGGAGAC CGAGCCAGAT GCAGAAAAGA AGGCATGTTC CAGCCCATTA CATAGACATC TGAGGTGCCA CTGGGAGAT    1300

CCCAGAGCCC AAATTCACCG TGAATAGTGT TTGGTTTCAG ACCCAGGACA AGGGACTGAG GTGCATATTT TACACATCAA AACGGACCTG GCTTCCAGGT    1400

TCTCCCAGCA TCCCTCAGTC CCTACCTGGC ATACCCTGCC CCCAACCCTG AACTCTCCAG CCCAGGACCT GGGCTGCCCT TCCCCCAGAG GCTCCTCCCT    1500

ATATAATCCA GACATTTGT CTCCTCCTTT CCTCCCTCCC ACTCTCTTCT TTTCTCTCGA TGCGGATGCTC ATGCGGATGCT CGATGCTCAT GATCAAATGC    1600

TCCCTTCTCT CTTTTTCTCT CCCTCCCCCC CTTCCACCTC TTTCCTCACG GCAACTTTCC TGGCTTTGGT CCTAGTGAAC TCACTCACCT GAGAGTGATT    1700

CCCAATAAAC CCACCTTTAT ATAAAAAAAA AAAAAAAAAA AAAAAAAA    1759
```

FIG. 3A

```
mGL50-1  CCGGAACCCCC AACCGCTGCA ACTCTCCGCG TCCGAAATCC AGCATCCCGC AGTCTGCGCT CGCACCATGC   70
mGL50-2  ----------- ---------- ---------- ---------- ---------- ---------- -------ATGC    4 mGL50-1  AGCTAAAGTG TCCCTGTTTT GTGTCCTTGG GAACCAGGCA GCCTGTTTGG AAGAAGCTCC ATGTTTCTAG   140
mGL50-2  AGCTAAAGTG TCCCTGTTTT GTGTCCTTGG GAACCAGGCA GCCTGTTTGG AAGAAGCTCC ATGTTTCTAG    74 mGL50-1  CGGGTTCTTT TCTGGTCTTG GTCTGTTCTT GCTGCTGTTT AGCAGCCTCT GTGCTGCCTC TGCAGAGACT   210
mGL50-2  CGGGTTCTTT TCTGGTCTTG GTCTGTTCTT GCTGCTGTTT AGCAGCCTCT GTGCTGCCTC TGCAGAGACT   144 mGL50-1  GAAGTCGGTG CAATGGTGGG CAGCAATGTG GTGCTCAGCT GCATTGACCC CCACAGACGC CATTTCAACT   280
mGL50-2  GAAGTCGGTG CAATGGTGGG CAGCAATGTG GTGCTCAGCT GCATTGACCC CCACAGACGC CATTTCAACT   214 mGL50-1  TGAGTGGTCT GTATGTCTAT TGGCAAATCG AAAACCCAGA AGTTTCGGTG ACTTACTACC TGCCTTACAA   350
mGL50-2  TGAGTGGTCT GTATGTCTAT TGGCAAATCG AAAACCCAGA AGTTTCGGTG ACTTACTACC TGCCTTACAA   284 mGL50-1  GTCTCCAGGG ATCAATGTGG ACAGTTCCTA CAAGAACAGG GGCCATCTGT CCCTGGACTC CATGAAGCAG   420
mGL50-2  GTCTCCAGGG ATCAATGTGG ACAGTTCCTA CAAGAACAGG GGCCATCTGT CCCTGGACTC CATGAAGCAG   354 mGL50-1  GGTAACTTCT CTCTGTACCT GAAGAATGTC ACCCCTCAGG ATACCCAGGA GTTCACATGC CGGGTATTTA   490
mGL50-2  GGTAACTTCT CTCTGTACCT GAAGAATGTC ACCCCTCAGG ATACCCAGGA GTTCACATGC CGGGTATTTA   424 mGL50-1  TGAATACAGC CACAGAGTTA GTCAAGATCT TGGAAGAGGT GGTCAGGCTG CGTGTGGCAG CAAACTTCAG   560
mGL50-2  TGAATACAGC CACAGAGTTA GTCAAGATCT TGGAAGAGGT GGTCAGGCTG CGTGTGGCAG CAAACTTCAG   494 mGL50-1  TACACCTGTC ATCAGCACCT CTGATAGCTC CAACCCGGGC CAGGAACGTA CCTACACCTG CATGTCCAAG   630
mGL50-2  TACACCTGTC ATCAGCACCT CTGATAGCTC CAACCCGGGC CAGGAACGTA CCTACACCTG CATGTCCAAG   564 mGL50-1  AATGGCTACC CAGAGCCCAA CCTGTATTGG ATCAACACAA CGGACAATAG CCTAATAGAC ACGGCTCTGC   700
mGL50-2  AATGGCTACC CAGAGCCCAA CCTGTATTGG ATCAACACAA CGGACAATAG CCTAATAGAC ACGGCTCTGC   634
```

FIG. 3B

```
mGL50-1            AGAATAACAC TGTCTACTTG AACAAGTTGG GCCTGTATGA TGTAATCAGC ACATTAAGGC TCCCCTTGGAC    770
mGL50-2            AGAATAACAC TGTCTACTTG AACAAGTTGG GCCTGTATGA TGTAATCAGC ACATTAAGGC TCCCCTTGGAC    704 mGL50-1   ATCTCGTGGG GATGTTCTGT GCTGCGTAGA GAATGTGGCT CTCCACCAGA ACATCACTAG CATTAGCCAG          840
mGL50-2   ATCTCATGGG GATGTTCTGT GCTGCGTAGA GAATGTGGCT CTCCACCAGA ACATCACTAG CATTAGCCAG          754 mGL50-1            GCAGAAAGTT TCACTGGAAA TAACACAAAG AACCCACAGG AAACCCACAA TAATGAGTTA AAAGTCCTTG    910
mGL50-2            GCAGAAAGTT TCACTGGAAA TAACACAAAG AACCCACAGG AAACCCACAA TAATGAGTTA AAAGTCCTTG    824 mGL50-1            TCCCCGTCCT TGCTGTACTG GCGGCAGCGG CATTCGTTTC CTTCATCATA TACAGACGCA CGCGTCCCCA    980
mGL50-2            TCCCCGTCCT TGCTGTACTG GCGGCAGCGG CATTCGTTTC CTTCATCATA TACAGACGCA CGCGTCCCCA    894 mGL50-1            CCGAAGCTAT ACAGAGACCCA AGACTGTACA GCTTGAACTT ACAGACCACG CTTGACAGGA CTCCGGTCAG    1050
mGL50-2            CCGAAGCTAT ACAGAGACCCA AGACTGTACA GCTTGAACTT ACAGAC-A-- CTTG----GG- CTCCGGTC-C    964 mGL50-1   GATATGGACA GGGTTTCTGT GAGTTGCCAC CAGGTGGATG TCAGACACAA CTTCAGAGTG GACCCCACA           1120
mGL50-2   CCTAC----- CA GGACTATT-T GA--TT-CCA --A---GATA TTTGATGT-- CTCCA----- --CCTCAAAA          1026 mGL50-1   GGCGTGGTGA CAGAGACACA CGAGCTGTCT GCTTATGGGC TGTGATGGAG GCCAGGAATC CCTTGCTTTA        1190
mGL50-2   CACGTGGT-- --TTACCATAA -AAGCCACTG TCTCAT---- C TGT-T---CAG ACCA------ TCAGGCTCCA       1081 mGL50-1   -CGAGGC-AC AGAGACTTCA -TCCCAGAAA GC--CCGAGGG AGATCTCCC AGTGGG-CAG CAGCAACATC        1260
mGL50-2   GCCAGGTGCC AGAAGTCCCA CTTACGAGT CTACTGAGCA CAAGCTATGT AATGGGCTG C-TCTGCTCC           1150 mGL50-1   ATGGAATAT GGAGCCTGTC GTGAGCTGTC GCACAGAGA GCAGCAGCTT GTGAAAGAT CCTTCC-TTG            1325
mGL50-2   AGCAGCATA- TACAGACTG- --AAGCCCCA --AAGCCCCA GTTAAGACA TTTTCAATGA GC-AGGA-AC CCAACCATAC  1213 mGL50-1   GCACGTTACT ACTCAGGCCT AG--GAGCTT ATAAAAGA-- GC--GTTTGA AAGCCCTTGA TAGACCTACA          1394
mGL50-2   TCACAGAGCT --GGAGACCG AGCCAGATGC AGAAAAGAAG GCATGTTCCA GCCCATTACA TAGACATC-T          1280
```

FIG. 3C

```
mGL50-1  GA-GT-CTAC TGGAGACTTT CCCTGCAGGA CCTTCAGTTG GGGAGGAAGC CTGACTTTAT TTAGGTCTCA  1459
mGL50-2  GAGGTGCCAC TGGGGA-GAT CCCAG-AG-- CCCAAATTCA CCG-TGAATA GTG-TTTGGT TTCAGACCA   1344 mGL50-1  GGCTACTTGG GCCTCTTCGA GGATATGTGG GATTTTGTCT ACTGCAAACC TGTTTCTGGC TGACAATGGT  1527
mGL50-2  GG--ACAAGG GACT--GA-- GG--CT-TGC -ATATTTTAC ACATCAAAAC -GGACCTGGC TTCCA---GGT  1400 mGL50-1  TGGGCTCAGA GGCACTCAGC TTCACAGACAT CAAATGGGACA CGCCTCATCC TTGACTTCCT GTGGCTACAG  1597
mGL50-2  T-CTCCCAGC ATCCCTAG-- CCCCTACCTG GCATACCCTG C-CCCGAACCT CTGAACC-CT CCAGCC--CAG  1465 mGL50-1  AAGCT-----T TCGAAAAGCC TTGA-GCTCT A--CAG----C TCTGCCCAGT CTCAGCAGCC  1667
mGL50-2  GACCTGGGCT GCCCTTCCCC CAGAGAGCTG AATCCAGACAT TTTGTCCT CCTTTCTCC  1535 mGL50-1  CATGAAGAATC TCAACTCCAG CTTTC-CTG-G GTTGCTGGCC AGAATA-GAG GCTG--GCTCT  1727
mGL50-2  CTCCCA--CTC TCTTCTTTTC TCTCGATGCG ATGCTCATGC GATGCTCTT  CAAATGCTCC  1603 mGL50-1  TTTGTTTCAA GATGGTTCTG CAAAGTTGGC CCTAGGGATG TATGTACAAG CTCCAGGCTG  1790
mGL50-2  CTTCTCTC-- --TTTTCT-- CTCCCTCCC --CCTTT--CCA CACGGCAACT TTCCTGGCTT  1666 mGL50-1  ATGCAGTAGG GGGCACGGAC TC-CCCGA-- -TGGAACACA CCTAGGGAT---- ---GAGGGCAA  1860
mGL50-2  TGGTCCTA-- GTGAACTCAC TCACCTGAGA ATAAACCAC CTTTATATAA AAAAAAAAAA  1734 mGL50-1  GCTCCTTCCC ACGCAGAGGA CTGGAAATTC TGGACCGTCA AGGCCTGTCT GCTATGTGGC TGGGGCTCAG  1920
mGL50-2  AAAAAAAAAA AAAAAA----  ----------  ----------  ----------  ----------  1759 mGL50-1  TGCTGATGGA TGTGTGAGAT CTCAGGAATG AGGAGTGAGA ACCCTGGGCT CAGGACTAGG AAGACCTGTC  1990
mGL50-2  ----------  ----------  ----------  ----------  ----------  ----------  ----------  1759 mGL50-1  CATTTTTTTT TTTTTTTAAT GCCCACATGG ACTTTTTATT CTTCACACCG ATGTATTCAA TGAGTGTAGA  2060
mGL50-2  ----------  ----------  ----------  ----------  ----------  ----------  ----------  1759
```

FIG. 3D

```
mGL50-1    GAGAACTACT TAAGTCCTTC CCGAGTACAA AGCATTACCT ACCTGCAGAA TAGCAACTGT TGTTATGGGT    2130
mGL50-2    ---------- ---------- ---------- ---------- ---------- ---------- ----------    1759 mGL50-1    CTTGAGTTGG CAGCTACAGC AAACAAGCAC AAGGAGCAGT TGGGGTGCAA GAAGATGGGG TGCAGCGCCC    2200
mGL50-2    ---------- ---------- ---------- ---------- ---------- ---------- ----------    1759 mGL50-1    CCAAGGACAG ACATTTGGGA ATTAGTGGTC TCCCTGATGC CCATAGTTCC CCAGGAACTC AGGTGGGTCT    2270
mGL50-2    ---------- ---------- ---------- ---------- ---------- ---------- ----------    1759 mGL50-1    GCGGCAGCAC AGTAGGAGTA TTCCTCCTAC TTTAACTTTT CTTGTCAGAC GTAGTTTAGG TTCAGAAAGA    2340
mGL50-2    ---------- ---------- ---------- ---------- ---------- ---------- ----------    1759 mGL50-1    GGTCAACTCA GCAAGCCAGC TAGCCGCCTT GGGGCACCAG ACACACTGCC CCCCACCCCC TGCTTATGTA    2410
mGL50-2    ---------- ---------- ---------- ---------- ---------- ---------- ----------    1759 mGL50-1    GGCATTGGGA ACCCTTCACA GACCACTGGC TGTACAGTCA CCATCACCTG CTGATTCCAG CAGGCCCCCA    2480
mGL50-2    ---------- ---------- ---------- ---------- ---------- ---------- ----------    1759 mGL50-1    CCTTCTTGTG GAATCCTGGG AGCACTCCCT TCTTACCCCT CACTGCCCCC CACCCCCTGC ACATCAGCAT    2550
mGL50-2    ---------- ---------- ---------- ---------- ---------- ---------- ----------    1759 mGL50-1    TCATTAGATT TGCCCTGTAA CGTCTGATTC CTGCTTTATC TGGGTTGTAG ATGGGGCATA GTGACTTCTA    2620
mGL50-2    ---------- ---------- ---------- ---------- ---------- ---------- ----------    1759 mGL50-1    GAAACCTAAC AAGGGAATAA ATGTAAGATG TGCTTTCAAA AAAAAAAAAA AAAAAAAAAA AAAAAAAAAA    2690
mGL50-2    ---------- ---------- ---------- ---------- ---------- ---------- ----------    1759 mGL50-1    AAAAAAAAAA AAAAAAAA                                                              2718
mGL50-2    ---------- --------                                                              1759
``` mGL50-1 RT-PCR
Probe: mGL50-1 cDNA oligo (RLEE004)

mGL50-2 RT-PCR
Probe: mGL50-2 RACE oligo (RLEE002)

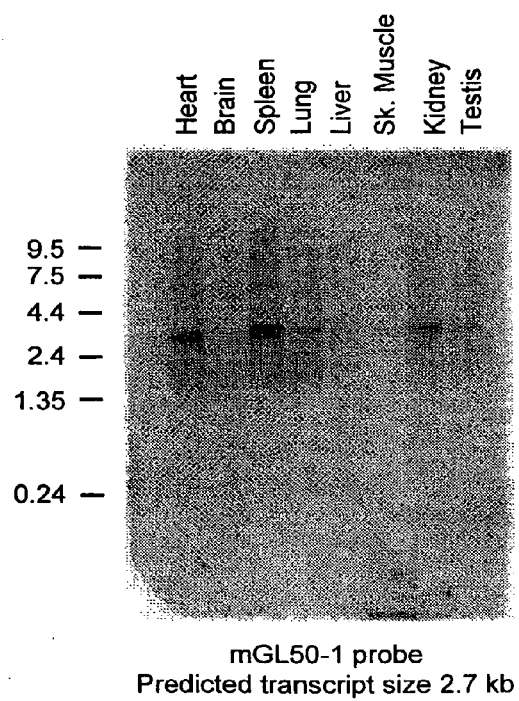 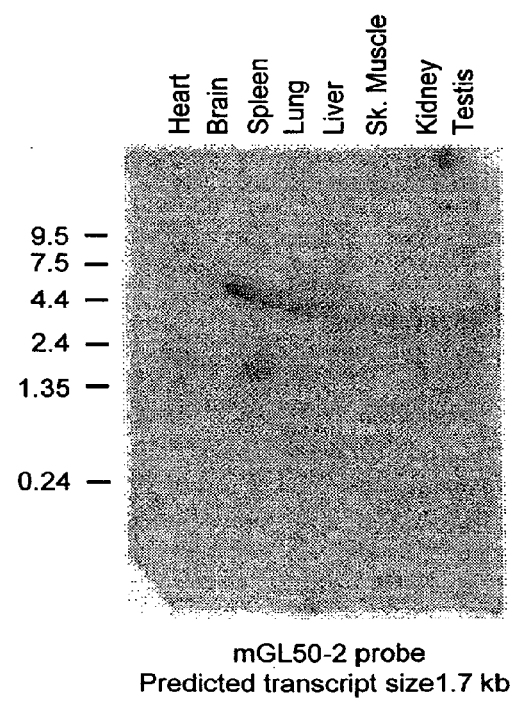
FIG. 5A — mGL50-1 probe, Predicted transcript size 2.7 kb
FIG. 5B — mGL50-2 probe, Predicted transcript size 1.7 kb

FIG. 6

```
          10         20         30         40         50
    1234567890 1234567890 1234567890 1234567890 1234567890
    ACAACAGCCT GCTGGACCAG GCTCTGCAGA ATGACACCGT CTTCTTGAAC   50
      N  S  L    L  D  Q    A  L  Q    N  D  T  V  F  L  N

ATGCGGGGCT TGTATGACGT GGTCAGCGTG CTGAGGATCG CACGGACCCC  100
      M  R  G  L    Y  D  V    V  S  V    L  R  I  A    R  T  P

CAGCGTGAAC ATTGGCTGCT GCATAGAGAA CGTGCTTCTG CAGCAGAACC  150
      S  V  N    I  G  C  C    I  E  N    V  L  L    Q  Q  N  L

TGACTGTCGG CAGCCAGACA GGAAATGACA TCGGAGAGAG AGACAAGATC  200
       T  V  G    S  Q  T    G  N  D    I    G  E  R    D  K  I

ACAGAGAATC CAGTCAGTAC CGGCGAGAAA AACGCGGCCA CGTGGAGCAT  250
       T  E  N  P    V  S  T    G  E  K    N  A  A  T    W  S  I

CCTGGCTGTC CTGTGCCTGC TTGTGGTCGT GGCGGTGGCC ATAGGCTGGG  300
       L  A  V    L  C  L  L    V  V  V    A  V  A    I  G  W  V

TGTGCAGGGA CCGATGCCTC CAACACAGCT ATGCAGGTGC CTGGGCTGTG  350
       C  R  D    R  C  L    Q  H  S  Y    A  G  A    W  A  V

AGTCCGGAGA CAGAGCTCAC TGAATCCTGG AACCTGCTCC TTCTGCTCTC  400
       S  P  E  T    E  L  T    E  S  W  N  L  L  L    L  L  S

GTGACTGACT GTGTTCTCTA TGCAACTTCC AATAAACCT CTTCATTTGA  450

AAAAAAAAAA                                             460
```

FIG. 7

```
AB014553 CDS1  MRLGSPGLLF LLFSSLRADT QEKEVRAMVG SDVELSCACP EGSRFDLNDV YVYWQTSESK TVVTYHIPQN SSLENVDSRY RNRALMSPAG MLRGDFSLRL  100
VL-10 CDS1     ---------- ---------- ---------- ---------- ---------- ---------- ---------- ---------- ---------- ----------

AB014553 CDS1  FNVTPQDEQK FHCLVLSQSL GFQEVLSVEV TLHVAANFSV FVVSAPHSPS QDELFTCTS  INGYPRPNVY WINKTDNSLL DQALQNDTVF LNMRGLYDVV   200
VL-10 CDS1     ---------- ---------- ---------- ---------- ---------- ---------- ---------- ----NSLL    DQALQNDTVF LNMRGLYDVV    24

AB014553 CDS1  SVLRIARTPS VNIGCCIENV LLQQNLTVGS QTGNDIGERD KITENPVSTG EKNAATWSIL AVLCLLVVVA VAIGWVCRDR CLQHSYAGAW AVSPETELTG   300
VL-10 CDS1     SVLRIARTPS VNIGCCIENV LLQQNLTVGS QTGNDIGERD KITENPVSTG EKNAATWSIL AVLCLLVVVA VAIGWVCRDR CLQHSYAGAW AVSPETELTE   124

AB014553 CDS1  EFAVGGSSRFM GAQGRLGCQL SFRVSRNFQK AKVPCLEQLL FLETQRSPRW CARHFLQPPL GMGWHPGVHF VTLRWDFPNM HRSRETSARP PRSPVPSPDQ   400
VL-10 CDS1     S--------W  ---------- ---------- ------NLL   L--------- ---------- ---------- ---------- ---------- ----------   130

AB014553 CDS1  GVQGGSRHRR PAPMGCPEWV QAPAPSPRGV SRAGPGTGAQ PPHGVQGGSR HRRPAPMGCP EWVQAPAPSP RGVSRAGPGT GAQPLWGVWS GSGHRQLLSV    500
VL-10 CDS1     ---------- ---------- ---------- ---------- ---------- ---------- ---------- ---------- ---------- --------LLS    133

AB014553 CDS1  AATPAALVCP SVPGAT                                                                                               516
VL-10 CDS1     ---------- ------                                                                                               133
```

FIG. 8

```
         10         20         30         40         50         60         70         80         90        100
1234567890 1234567890 1234567890 1234567890 1234567890 1234567890 1234567890 1234567890 1234567890 1234567890
GGCCCCGAGGT CTCCCGCCGC ACCATGCGGC TGGGCAGTCC TGGACGCTGC TTCCCTGCTCT TTCAGCAGCCT TCGAGCAGGA AGGAAGTCAG    100
            M  R  L  G  S  P  G  L  L  F  L  L  F  S  S  L  R  A  D  T  Q  E  K  E  V  R

AGCGATGGTA GGCAGCGACG TGGAGCTGAG CATCCCACAG AACAGCTCT CCTGAAGGAA GCCGTTTGA TTTAAATGAT GTTTACGTAT ATTGGCAAAC CAGTGAGTCG    200
 A  M  V  G  S  D  V  E  L  S  I  P  Q  N  S  S  L  E  N  V  D  S  R  Y  R  N  R  A  L  M  S  E  S

AAAACCGTGG TGACTACCA CATCCCACAG AACAGCTCT TGGAAAACGT GGACAGCCGC TACCGGAACC GAGCCCTGAT GTCACCGGCC GGCATGCTGC    300
 K  T  V  V  T  Y  H  I  P  Q  N  S  S  L  E  N  V  D  S  R  Y  R  N  R  A  L  M  S  P  A  G  M  L  R

GGGGCCGACTT CTCCCTGCGC TTGTTCAACG TCACCCCCCA GGACGAGCAG AAGTTCACT GCCTGGTGTT GAGCCAATCC CTGGGATTCC AGGAGGTTTT    400
 G  D  F  S  L  R  L  F  N  V  T  P  Q  D  E  Q  K  F  H  C  L  V  L  S  Q  S  L  G  F  Q  E  V  L

GAGCGTTGAG GTTACACTGC ATGTGGCAGC GTTACAAGC AAACTTCAGC GTGCCCGTCG CCCAGGATG AGCTCACCTT CACGTGTACA    500
 S  V  E  V  T  L  H  V  A  A  N  F  S  V  P  V  V  S  A  P  H  S  P  S  Q  D  E  L  T  F  T  C  T

TCCATAAACG GCTACCCCAG GCCCAACGTG TACTGGATCA ATAAGACGGA CCTGGACCAGG CTGCAGAA TGACACCGTC TTCTTGAACA    600
 S  I  N  G  Y  P  R  P  N  V  Y  W  I  N  K  T  D  N  S  L  D  Q  A  L  Q  N  D  T  V  F  L  N  M

TCCGGGCCCT GTATGACGTG GTCAGCGTGC TCAGGATCGC AGCGGTGAACA TTGGCTGCTG CATAGAGAAC GTGCTTCTGC AGCAGAACCT    700
 R  G  L  Y  D  V  V  S  V  L  R  I  A  R  T  P  S  V  N  I  G  C  C  I  E  N  V  L  L  Q  Q  N  L

GACTGTCGGC AGCCAGACGG GAAATGACAT CGGAGAGAGA GACAAGATCA CGGAGAATCC CAGTAGTACC GGGAGAAAA ACGGCCAC GTGGAGCATC    800
 T  V  G  S  Q  T  G  N  D  I  G  E  R  D  K  I  T  E  N  P  V  S  T  G  E  K  N  A  A  T  W  S  I

CTGGCCGTGC TGTGCCTGCT TGTGGTCGTG GCGGTGGCCA TAGGCTGGGT GTGCAGGGAC CGATGCCTCC AACACAGCTA TGCAGGTGCC TGGGCTGTGA    900
 L  A  V  L  C  L  L  V  V  V  A  V  A  I  G  W  V  C  R  D  R  C  L  Q  H  S  Y  A  G  A  W  A  V  S

GTCCCGGAGAC AGAGCTCACT GAATCCGGA ACCTGCTCCT TCTGCTCTCG TGA .                                            953
 P  E  T  E  L  T  E  S  W  N  L  L  L  L  S  *
``` hB7-2 mB7-1 hB7-1

AB014553 cDNA RT-PCR hGL50 cDNA RT-PCR

Probe: VL131 (GL50/AB014553 CDS) oligo hGL50 CDS Northern Blot

FIG. 12

```
                                                                                                                         *  *
hGL50    ------------ ------------ ------MRLGS PGLLFLLFSS LRADTQEKEV RAMVGSDVEL SCACPEGSRF DLNDYVYTWQ TSESKTVVTY HIPQNSSLEN  75
mGL50-1  MQLKCPCFVS LGTRQPVMRK LHVSSGFFSG LGLFLILLSS LCAASAETEV GAMVGSNVVL SCIDPHRRHF NLSGLIVTWQ IENPEVSVTY YLPYKSPGIN 100
hB7-2    ------------ ------------ --MDPQCTMG LSNILFVMAF LLSGAAPLKI QAYFNETADL PCQFANSQNQ SLSELVVFWQ .DQENLVLNE VYLGKEKFDS  77
mB7-2    ------------ ------------ --MDPRCTMG LAILIFVTVL LLSDAVSVET QAYFNGTAYL PCPFTKAQNI SLSELVVFWQ .DQQKIVLYE HYLGTEKLDS  77
hB7-1    ------MG HTRRQGTSPS K..CPYINF. FQLLVLAGLS HFCSGV.IHV TKEVKEVATL SCGH.NVSVE ELAQTRIYWQ .KEKKMVL.T MMSGDMN...  82
mB7-1    ------MACN CQLMQDTPLL KFPCPRL.I. LLFVLLIRLS QVSSDVDEQL SKSVKDKVLL PCRY.NSPHE DESEDRIYWQ .KHDKVVL.S VIAGKLK...  86
ID score ---14------ -1-127-2114 7144342-27 -7-5115--44 17283216-L 6c--141222 2974458BWQ -21-729812 -227424112

Signal Peptide                                                  IgV-like
                         *              * * * *                     *    *           *        * *     * * *
hGL50    VDSRYRNRAL MSPAGMLRGD FSLRLFNVTP QDEQKEHCLV .LSQSLGFQE VLSVEVTLHV AANFSVPVVS APHS..PSQD ELNFTCTSIN GYPRPN.VYW 171
mGL50-1  VDSSYKNRGH LSLDSMKQGN FSLYLRNVTP QDYQEKFHCLV QDYQEKFHCLV ILEEVVRLRV AANFSTPVIS TSDSSNPGQ. ERYTTCMSRN GYPEPN.LYW 198
hB7-2    VESKIMGRTS ED.....SDS WTLRLHNLQI KDKGLYQCII HHKKPTGMIR IHQMNSELSV LQQTLTELSV LANFSQPEIV PISNIT.ENV YINLTCSSIH GYPEPKKMSV 171
mB7-2    VNAKYLGRTS ED.....RNN WTLRLHNVQI KDMGSIDCFI QKKPPTGSII LANFSEPEIK LAQNVT.GNS GINLTCSKQ GHPKPKKMYF 171
hB7-1    IWPEYKNRRI ED....ITNN LSIVILALRP SDEGTTECVV LKYEKDAFKR KADFPTPSIS DFEIPT.SNI R.RIICTSKG GFPEPH.... 172
mB7-1    VWPEYKNRTL YD....NT.T YSLIILGIVL SDRGTTSCVV QKKERGTTEV KHLALVKLSI KADFSTPNIT ESGNPS.ADT K.RITCFASG GFPKPR.... 175
ID score 9251Y48R72 48----1-114 2894827625 3D1818-C18 1441144111 1621272L79 2A8F94P294 -1-614122- 1133C2712 G6P5P21141

IgV-like ctd.                                                                                IgC-like
         *  *         *                            * *              *                        *            *  *   *   *
hGL50    INKTDNSLLD QALQNDTVFL NMRGLIXDVVS VLRLAR...T PSVNIGCCIE NVLLQQNLIV GSQTGNDIGE ROKITENFVS TGERNAATWS ILAVLCLLVV 268
mGL50-1  INTDNSLLD TALQNNTVYL NKLGLIDVIS NVTELIDVSI SLSVSFPDVT SRGDVLCCVE NVALHQNITS ISQAESFTGN N...TKNFPQE T..HNNELKV LVFVLAVLAA 290
hB7-2    LLRTKNSTIE YDGIMQKSQD NVTELEVSI SLSLSFPDGV WHMTVVCVLE TDKTRLL..... .. SS.PFS IELEDPQPPP DHIPWITAVL PTVIICVMVF 263
mB7-2    LI..TNSTNE YGDNMQISQD NVTELFSIN PETELYAVSS KLDF...NMT TESMKIS.... .. SK.PLN FTQEFPSPQ. TYWKEITASV TVALLVML. 259
hB7-1    LSWLENGEEL NAINTTVSQD PESELYTISS QLDF....NTT RNHTIKCLIK YGHLRVN..... ..QTFNWN ITKQEHFPD. NLLPSWAIT LISVNGIFVI 260
mB7-1    FSWLENGREL PGINTTISQD PESELYTISS QLDF....NTT RNHTIKCLIK YGDAHV9..... .. EDETWE KPPEDP.PDS KNTLVLFGAG FGAVITVVVI 264
ID score 521S2N8223 1425322878 8248L94877 1L321112-9 14242-C258 32-4-25-1 ---11-1-4124 --14241P21 41-1-1-4-1 1147417241

IgC-like ctd.                                                                              Transmembrane hGL50    VAVAIGWVCR DRCLQH.SYA GAWAVSPETE LTESNLLALL LS-------- -------- -------- -------- 309
mGL50-1  AAF.VSFIIY RRTRPHRSYT GPKTV..QLE LTDHA----- -------- -------- -------- 322
hB7-2    CLILWK...W KKKKRPRNSY KCGTNTMERE ESEQTKRREK IHIPERSDEA QRVFKSSKTS SCDKSDTCF 329
mB7-2    LI.....H KKPNQPSRP. ...SNTASKL ERDSNADRET INLKELEPQI ASAKPNAE-- -------- 309
hB7-1    CCLTYCFAPR CRERRRNERL RRESVRPV-- -------- -------- -------- 288
mB7-1    VVIIKCFCKH RSCFRRNE.A SRETNNSLIF GPEEALAEQT VFL------- -------- 306
ID score 2241144---1 2211522211 1112511114 214----11- -1-1-1-- -------- --------

Cytoplasmic
         t.m. ctd.
```

FIG. 16

FIG. 18A mICOS-mIgG2am

Blockade:
Hamster Ig, 10 ug/ml
Rat IgG2a, 10 ug/ml

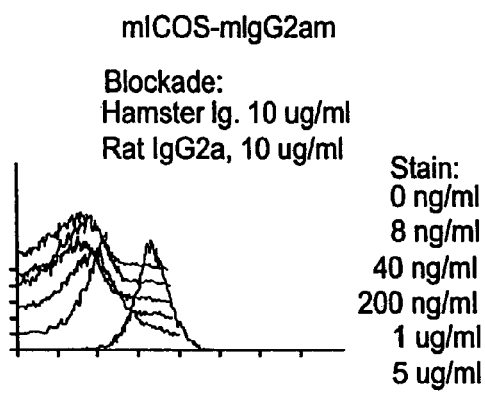

Stain:
0 ng/ml
8 ng/ml
40 ng/ml
200 ng/ml
1 ug/ml
5 ug/ml

FIG. 18C mCTLA4-mIgG2am

Blockade:
Hamster Ig, 10 ug/ml
Rat IgG2a, 10 ug/ml

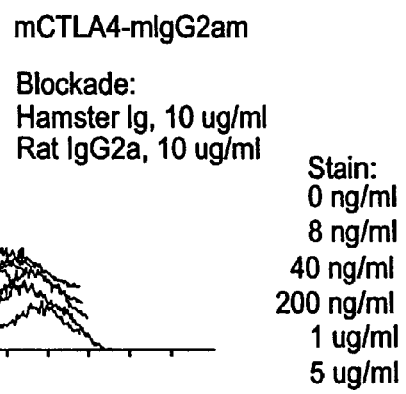

Stain:
0 ng/ml
8 ng/ml
40 ng/ml
200 ng/ml
1 ug/ml
5 ug/ml

FIG. 18B mICOS-mIgG2am

Blockade:
Anti-B7-1, 10 ug/ml
Anti-B7-2, 10 ug/ml

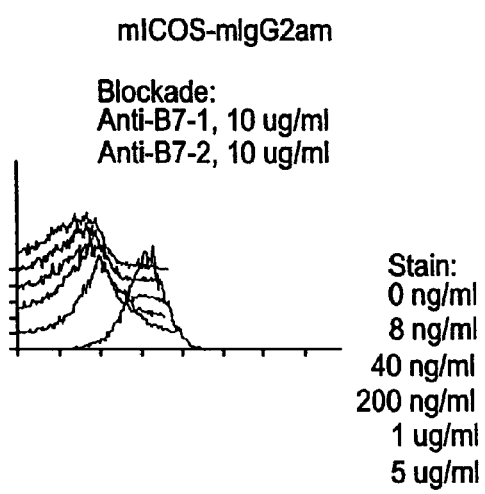

Stain:
0 ng/ml
8 ng/ml
40 ng/ml
200 ng/ml
1 ug/ml
5 ug/ml

FIG. 18D mCTLA4-mIgG2am

Blockade:
Anti-B7-1, 10 ug/ml
Anti-B7-2, 10 ug/ml

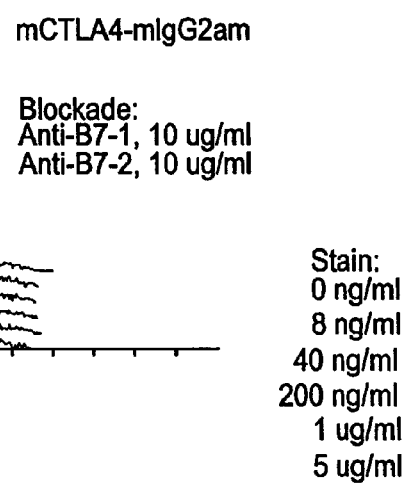

Stain:
0 ng/ml
8 ng/ml
40 ng/ml
200 ng/ml
1 ug/ml
5 ug/ml anti B7-1 FITC
mICOS-mIgG2am (PE)

anti B7-1 FITC mICOS-mIgG2am

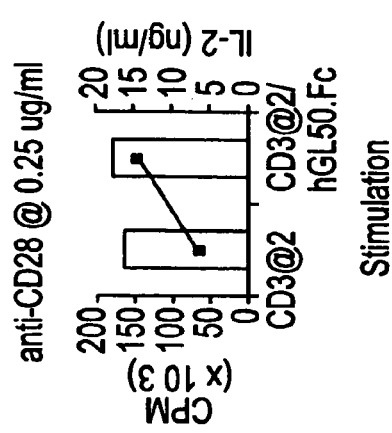
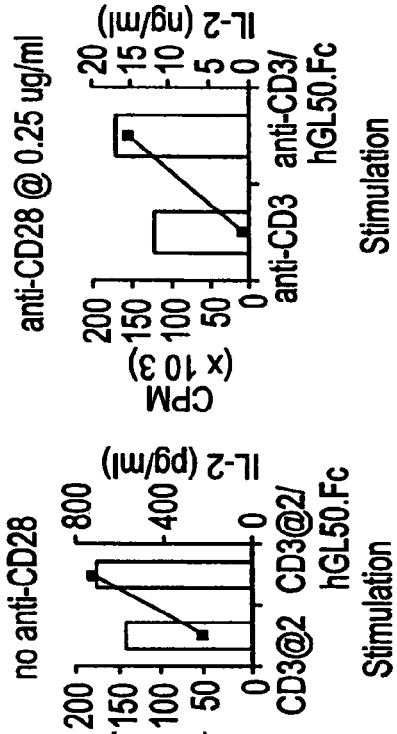
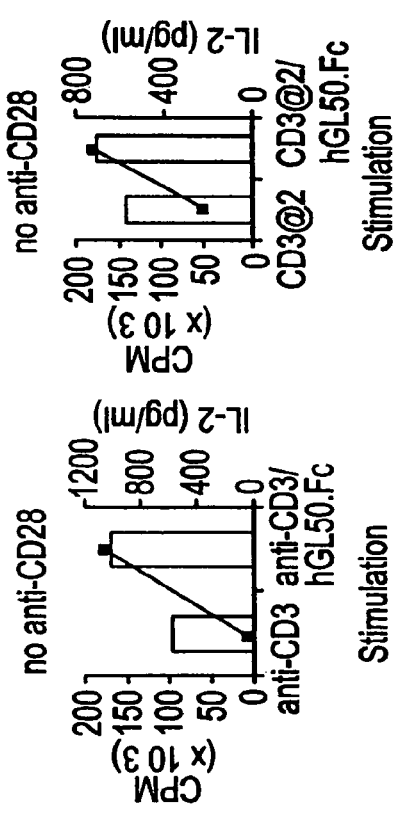
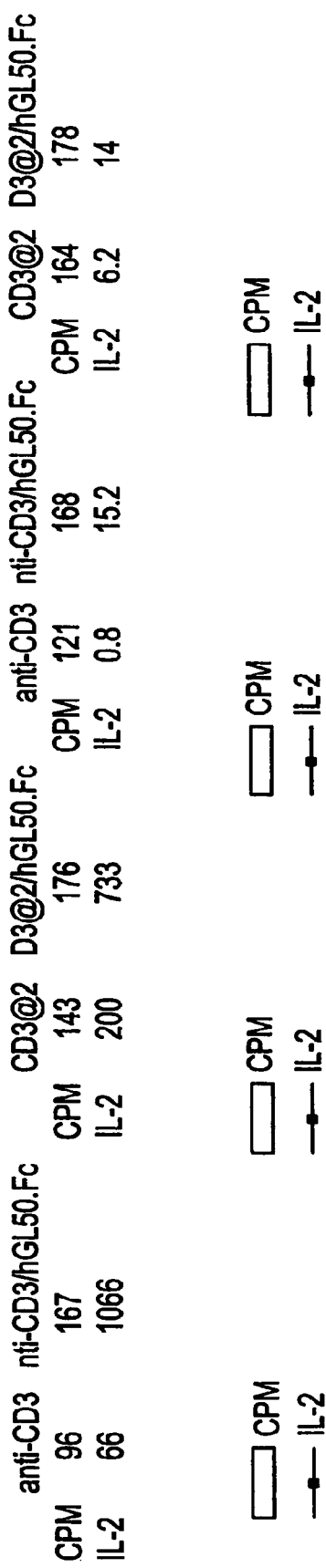

Non-treated

Treated with B7-2-IgG2a

FIG. 26A-1

```
              10         20         30         40         50         60         70         80         90        100
     1234567890 1234567890 1234567890 1234567890 1234567890 1234567890 1234567890 1234567890 1234567890 1234567890
     GAATTCGCCC TTGTCGACCC ACCATGGGGG TACTGCTCAC ACAGAGGACG CTGCTCAGTC TGGTCCTTGC ACTCCTGTTT CCAAGCATGG CCAGCATGGA    100
     ---------- ---------- ---------- ---X

AATCAATGGT TCTGCCAATT ATGAGATGTT TATATTTCAC AACGGAGGTG TACAAATTTT ATGCAAATAT CCTGACATTG TCCAGCAATT TAAAATGCAG    200

TTGCTGAAAG GGGGGCAAAT ACTCTGCGAT CTCACTAAGA CAAAAGAAG  TGGAAACACA GTGTCCATTA AGAGTCTGAA ATTCTGCCAT TCTCAGTTAT    300

CCAACAACAG CGTCTCTTTT TTTCTATACA ACTTGGACCA TTCTCATGCC AACTATTACT TCTGCAACCT ATCAATTTTT CATCCTCCTC CTTTTAAAGT    400

AACTCTTACA GGAGGATATT TGCATATTTA TGAATCACA  CTTTGTTGCC AGCTGAAGTT CGAGCCCCGC GGACCGACAA TCAAGCCCTG TCCTCCATGC    500

AAATGCCCAG GTAAGTCACT AGACCAGAGC TCCACTCCCG GGAGAATGGT AAGTGCTATA AACATGGGTG CACTAGAGGA TAAGCCATGT ACAGATCCAT    600

TTCCATCTCT CCCTCATCAGC ACCTAACCTC GAGGGTGGAC CATCCGTCTT CATCTCCCCT CCAAAGATCA AGATGTACT  CATGATCTCC CTGAGCCCCA    700

TAGTCACATG TGTGTGGTG  GATGTGAGCG AGGATGACCC AGATGTCCAG ATCAGCTGGT TTGTGAACAA CGTGGAAGTA CACACAGCTC AGACACAAAC    800

CCATGAGAGA GATTACAACA GTACTCTCCG GGTGGTCACT GCCCTCCCCA TCCAGCACCA GGACTGGATG AGTGGCAAGG CTTTCGCATG CGCCGTCAAC    900

AACAAAGACC TCCCAGCGCC CATCGAGAGA ACCATCTCAA AACCCAAAGG TGAGAGCTGC AGCCTGACTG CATGGGGGCT GGGATGGCCA TAAGGATAAA   1000

GGTCTGTGTG GACAGCCTTC TGCTTCAGCC ATGACCTTTG TGTATGTTTC TACCCTCACA GAGCTCCACA GGTATATGTC TTGCCTCCAC ACGGAAAAAC   1100

CAGAAGAAGA GATGACTAAG AAACAGGTCA CTCTGACCTG CATGGTCACA GACTTCATGC CTGAAGACAT TTACGTGGAG TGGACCAACA ACGGGAAAAC   1200
```

FIG. 26A-2

```
AGAGCTAAAC TACAAGAACA CTGAACCAGT CCTGGACTCT GATGGTTCTT ACTTCATGTA CAGCAAGCTG AGAGTGGAAA AGAAGAACTG GGTGGAAAGA   1300

AATAGCTACT CCTGTTCAGT GGTCCACGAG GTCTGCACA ATCACCACAC GACTAAGAGC TTCTCCCGGA CTCCGGGTAA ATGACTCAG CACCCACAAA   1400

ACTCTCAGGT CCAAAGAGAC ACCCACACTC ATCTCCATGC TTCCCTTGTA TAAATAAAGC ACCCAGCAAT GCCTGGGACC ATGTAAAAGG GCGAATTC   1498
```

FIG. 26B

```
         10         20         30         40         50
1234567890 1234567890 1234567890 1234567890 1234567890
MGVLLTQRTL LSLVLALLFP SMASMSMEINGS ANYEMFIFHN GGVQILCKYP    50

DIVQQFKMQL LKGGQILCDL TKTKGSGNTV SIKSLKFCHS QLSNNSVSFF    100

LYNLDHSHAN YYFCNLSIFD PPPFKVTLTG GYLHIYESQL CCQLKFEPRG    150

PTTKPCPPCK CPAPNLEGGP SVFIFPPKIK DVLMISLSPI VTCVVVDVSE    200

DDPDVQISWF VNNVEVHTAQ TQTHREDYNS TLRVVSALPI QHQDWMSGKA    250

FACAVNNKDL PAPIERTISK PKGSVRAPQV YVLPPPEEEM TKKQVTLTCM    300

VTDEMPEDIY VEWINNGKTE LNYKNIEPVL DSDGSYFMYS KLRVEKKNWV    350

ERNSYSCSVV HEGLHNHHTT KSFSRTPGK                          379
```

FIG. 27A-1

```
          10         20         30         40         50         60         70         80         90        100
 1234567890 1234567890 1234567890 1234567890 1234567890 1234567890 1234567890 1234567890 1234567890 1234567890
GAATTCGACCC TTGTCGACCC ACCATGGGGG TACAGCTCAC ACAGAGGACG CTGCTCAGTC TGGTCCTTGC ACTCCTGTTT CCAAGCATGG CCAGCATGGA    100
----------- ----------X

AATCAATGGC TCGGCCGATC ATAGAGATGTT TTCATTTCAC AATGGAGGTG TACAGATTTC TTGTAAATAC CCTGAGACTG TCCAGCAGTT AAAAATGCGA    200

TTGTTCAGAG AGAGAGAAGT CCTCTGCGAA CTCACCAAGA CCAAGGGAAG CGGAAATGCG GTGTCCATCA AGAATCCAAT GCTCTGTCTA TATCATCTGT    300

CAAACAACAG CGTCTCTTTT TTCCTAAACA ACCCAGACAG CTCCCAGGGA AGCTATTACT TCTGCAGCCT GTCCATTTTT GACCCACCTC CTTTTCAAGA    400

AAGGAACCTT AGTGGAGGAT ATTTGCATAT TTATGAATCC CAGCTCTGCT GCCAGCTGAA GCTCAGCCC GCCGGACCGA CAATCAAGCC CTGTCCTCCA    500

TGCAAAATGCC CAGGTAAGTC ACTAGACCAG AGTCCACTC CCGGGAGAAT GGTAAGTGCT ATAAACATCC CTGCACTAGA GGATAAGCCA TGTACAGATC    600

CATTTCCATC TCTCCTCATC AGCACCTAAC CTCGAGGGTG GACCCATCCGT CTTCATCTTC CCTCCAAAGA TCAAGGATGT ACTCATGATC TCCCTGAGCC    700

CCATAGTCAC ATGTGTGGTG GTGGATGTGA GCCAGGATGA CCCAGATGTC CAGATCAGCT GGTTTGTGAA CAACGTGGAA GTACACACAG CTCAGACACA    800

AACCCATAGA GAGGATTACA ACAGTACTCT CGGGGTGGTC AGTGCCCCTCC CCATTCCAGA CCAGGACTGG ATGAGTGCCA AGGCTTCGC ATGGCCCGTC    900

AACAACAAAG ACCTCCCAGC GCCCATCGAG AGAACCATCT CAAAACCCAA AGGTGAGAGC TGCAGCCCTGA CTGGGATGGG GCATAAGGAT             1000

AAAGGTCTCTGT GTGGACAGCC TTCTGCTTCA GCCATGACCT TTGTGTATGT TTCTACCCTC ACAGGTCAG TAAGAGCTCC ACAGTATAT GTCTTGCCTC    1100

CACCAGAAGA AGAGATGACT AAGAAACAGG TCACTCTGAC CTGCATGGTC ACAGACTTCA TGCCTGAAGA CATTACGTG GAGTGGACCA ACAACGGGAA    1200
```

FIG. 27A-2

```
AACAGAGCTA AACTACAAGA ACACTGAACC AGTCCTGGAC TCTGATGGTT CTTACTTCAT GTACAGCAAG CTGAGAGTGG AAAAGAAGAA CTGGGTGGAA    1300

AGAAATAGCT ACTCCTGTTC AGTGGTCCAC GAGGGTCTGC ACAATCACCA CACCACTAAG AGCTTCTCCC GGACTCCGGG TAAATGAGCT CAGCACCCAC    1400

AAAACTCTCA GGTCCAAAGA GACACCCACA CTCATCTCCA TGCTTCCCTT GTATAAATAA AGCACCCAGC AATGCCTGGG ACCATGTAAA AGGGCGAATT    1500
                                                                                                              1501
C
```

FIG. 27B

```
          10         20         30         40         50
 1234567890 1234567890 1234567890 1234567890 1234567890
 MGVLLTQRTL LSLVLALLFP SMASMEINGS ADHRMFSFHN GGVQISCKYP   50

ETVQQLKMRL FREREVLCEL TKTKGSGNAV SIKNPMLCLY HLSNNSVSFF  100

LNNPDSSQGS YYFCSLSIFD PPPFQERNLS GGYLHIYESQ LCCQLKLEPR  150

GPTIKPCPPC KCPAPNLEGG PSVFIFPPKI KDVLMISLSP IVTCVVVDVS  200

EDDPDVQISW FVNNVEVHTA QTQTHREDYN STLRVVSALP IQHQDWMSGK  250

AFACAVNNKD LPAPIERTIS KPKGSVRAPQ VYVLPPPEEE MKKQVTLIC   300

MVIDFMPEDI YVEWINNGKT ELNYKNTEPV LDSDGSYFMY SKLRVEKKNW  350

VERNSYSCSV VHEGLHNHHT TKSFSRTPGK                       380
```

FIG. 28A-1

```
                10         20         30         40         50         60         70         80         90        100
         1234567890 1234567890 1234567890 1234567890 1234567890 1234567890 1234567890 1234567890 1234567890 1234567890
GAATTCGCCC TTGTCGACCC ACCATGGGGG TACTGCTCAC ACAGAGGACG CTGCTCAGTC TGTCCTTGC ACTCCTGTTT CCAAGCATGG CCAGCATGA    100
---------- ---X

GAAGGAAGTC AGAGCGATGG TAGGCAGCGA CGTGGAGCTC AGCTCCGCTT GCCCTGAAGG AAGCCGTTTT GATTAAATG ATGTTTACGT ATATTGGCAA    200

ACCAGTGAGT CGAAAACCGT GGTGACCTAC CACATCCCAC AGAACAGCTC CTTGGAAAAC GTGGACAGCC AGAAGTTTCA CTGCCTGGTG CCGAGCCCTG    300

CCCGGCATGC GCGGGGCGAC TTCTCCCTGC GCTTGTTCAA CGTCACCCCC CAGGACGAGC GGTGCCCGT GCAAACTTCA CCCTGGGATT     400

CCAGGAGGTT TTGAGCGTTG ACGTTACACT GCATGTGGCA AGGCCCAAAC TGTACTGGAT CAATAAGACG GACAACAGCC CCTCCAGGA TGAGCTCACC    500

TTCACGTGTA CATCCATAAA CGGCTACCCC AGGCCCAAC TGCTCAGCGC CCAGCGTGAA GGACGACCCC AATGACACCG    600

TCTTCTTGAA CATGCGGGGC TTGTATGACG GCTGAGGATC GCACGGACCC CCAGCGTGAA CATTGGCTGC TGCATAGAGA ACGTGCTTCT    700

GCAGCAGAAC CTGACTGTCG GCAGCCAGAC AGAAAATGAC ATCGGAGAGA GAGACAAGAT CACAGAGAAT CCAGTCAGTA CCGGCGAGAA AAACGAGCCC    800

CCGGACCCGA CAATCAAGCC CTGTCCCTCCA TGCAAAATGCC CAGCTAAGTC ACTAGACCAG AGCTCCACTC CCGGGAGAAT GGTAAGTGCT ATAAACATCC    900

CTGCACTAGA GGATAAGCCA TGTACAGATC CATTCCATC TCTCCTCATC AGCACCTAAC CTCGAGGGTG GACCATCCGT CTTCATCTTC CCTCCAAAGA    1000

TCAAGGATGT ACTCATGGATC TCCCTGAGCC CCATAGTCAC AATGTGTGGTG GTGGATGTGA GCGAGGATGA GCGAGGATGA ACAGTACTCT CAGATCAGCT GGTTTGTGAA    1100

CAACGTGGAA GTACACACAG AACCCATAGA GAGGATTACA ACAGTACTCT CGGGGTGGTC AGTGCCCTCC CCATCCAGCA CCAAGACTGG    1200
```

FIG. 28A-2

```
ATGAGTGGCA AGGCTTTCGC ATGCGCCGTC AACAACAAAG ACCTCCCAGC GCCCATCGAG AGAACCATCT CAAAACCCAA AGTGAGAGC TGCAGCCTGA
                                                                                                          1300

CTGCATGGGG GCTGGGATGG GCATAAGGAT AAAGGTCTGT GTGGACAGCC TTCTGCCTTC GCCATGACCT TTGTGTATGT TTCTACCCTC ACAGGTCAG
                                                                                                          1400

TAAGAGCTCC ACAGTATAT GTCTTGCCTC CACCAGAAGA AGAGATGACT AAGAAACAGG TCACTCTGAC CTGCATGGTC CTGGACTTCA TGCCTGAAGA
                                                                                                          1500

CATTACGTG GAGTGGACCA ACAACGGGAA AACAGAGCTA AACTACAAGA ACACTGAACC AGTCCTGGAC TCTGATGGTT CTTACTTCAT GTACAGCAAG
                                                                                                          1600

CTGAGAGTGG AAAAGAAGAA CTGGGTGGAA AGAAATAGTT ACTCCCTGTC AGTGGTCCAC GAGGGTCTGC ACAATCACCA CACGACTAAG AGCTTCTCCC
                                                                                                          1700

GGACTCCCGGG TAAAATGAGCT CAGCACCCAC AAAACTCTCA GGTCCAAAGA GACACCCACA CTCGTCTCCA TGCTTCCCTT GTATAAATAA AGCACCCAGC
                                                                                                          1800

AATGCCTGGG ACCATGTAAA AGGGCGAATT C
                                                                                                          1831
```

FIG. 28B

```
         10         20         30         40         50
1234567890 1234567890 1234567890 1234567890 1234567890
MGVLLTQRTL LSLVLALLFP SMASMEKEVR AMVGSDVELS CACPEGSRFD    50

LNDVYVYWQT SESKTVVTYH IPQNSSLENV DSRYRNRALM SPAGMLRGDF   100

SLRLFNVTPQ DEQKFHCLVL SQSLGFQEVL SVEVTLHVAA NFSVPVVSAP   150

HSPSQDELTF TCTSINGYPR PNVYWINKTD NSLIDQALQN DTVFLNMRGL   200

YDVVSVLRIA RTPSVNIGCC IENVLLQQNL TVGSQTGNDI GERDKITENP   250

VSTGEKNEPR GPTIKPCPPC KCPAPNLEGG PSVFIFPPKI KDVLMISLSP   300

IVTCVVVDVS EDDPDVQISW FVNNVEVHTA QTQTHREDYN STLRVVSALP   350

IQHQDWMSGK AFACAVNNKD LPAPIERTIS KPKGSVRAPQ VYVLPPPEEE   400

MTKKQVTLTC MVTDFMPEDI YVEWTNNGKT ELNYKNTEPV LDSDGSYFMY   450

SKLRVEKKNW VERNSYSCSV VHEGLHNHHT                         490
```

FIG. 29A-1

```
          10         20         30         40         50         60         70         80         90        100
 1234567890 1234567890 1234567890 1234567890 1234567890 1234567890 1234567890 1234567890 1234567890 1234567890
CAGAATTCGC CCTTGTCGAC CCACCATGGG GGTACTGCTC ACACAGAGGA CGCTGCTCAG TCTGGTCCTT GCACTCCTGT TTCCAAGCAT GGCCAGCATG   100
---------- ---------- ----X

GAGACTGAAG TCGGTGCAAT GGTGGGCAGC AATGTGGTGC TCAGCTGCAT TGACCCCCAC AGACGCCATT TCAACTTGAG TGGTCTGTAT GTCTATTGGC   200

AAATCGAAAA CCCGGAAGTT TCGGTGACTT ACTACCTGCC TTACAAGTCT CCAGGGATCA ATGTGGACAG TTCCTACAAG AACAGGGGCC ATCTGTCCCT   300

GGACTCCATG AAGCAGGGTA ACTTCTCTCT GTACTTGAAG AATGTCACCC CTCAGGATAC CTTCAGTACA ACATGCCGGG TATTATGAA TACAGCCACA   400

GAGTTAGTCA AGATCTTGGA AGAGGTGGTC AGGCTCCGTG TGGCAGCAAA CCTGTCATCA GCACCTCTGA TAGCTCCAAC CCGGGGCAGG   500

AACGTACCTA CACCTGAATG TCCAAGAATG GCTACCAGGA GCCCAACCTG TATTGGATCA ACACAACGGA CAATAGCCTA ATAGACACGG CTCTGCAGAA   600

TAACACTGTC TACTTGAACA AGTTGGGCCT GTATGATGTA ATCAGCACAT TAAGGCTCCC TTGGACATCT CGTGGGGATG TTCTGTGCTG CGTAGAGAAT   700

GTGGCTCTCC ACCAGAACAT CACTAGCCAT AGCCAGGCAG AAAGTTTCAC TGGAAATAAC ACAAGAACC CACAGGAAAC CCACAATAAT GAGGCCCC    800

GCGGACCGAC AATCAAGCCC TGTCCTCCAT GCAAATGCCC AGTAAGTCA CTAGACCAGA GCTCCACTCC CGGGAGAATG GTAAGTGCTA TAAACATCCC   900

TGCACTAGAG GATAAGCCAT GTACAGATCC ATTTCCATCT CTCCTCATCA GCACCTAACC TCGAGGGTGG ACCATCCGTC TTCATCTCC CTCCAAAGAT   1000

CAAGGATGTA CTCATGATCT CCCTGAGCCC CATAGTCACA TGTGTGGTGG TGGATGTGAG CAGTACTCTC CGGGTGGTCA GTGCCCTCCC CAGGACTGGA   1100

AACGTGGAAG TACACACAGC TCAGACACAA ACCCATAGAG AGGATTACAA CAGTACTCTC CGGGTGGTCA GTGCCCTCCC CATCCAGCAC CAGGACTGGA   1200
```

FIG. 29A-2

```
TGAGTGGCAA GGCTTTCCGCA ACAACAAAGA CCTCCCAGCG CCCATGAGAA GAACCATCTC AAAACCCAAA GGTGAGAGCT GCAGCCTGAC    1300
TGCATGGGGG CTGGGATGGG CATAAGGATA AAGGTCTGTG TGGACAGCCT TCTGCTTCCT CCATGACCTT TGTGTATGTT TCTACCCTCA CAGGGTCAGT    1400
AAGAGCTCCA CAGGTATATG TCTTGCCTCC ACCAGAAGAA AGAAACAGGT CACTCTGACC TGCATGGTCA CAGACTTCAT GCCTGAAGAC    1500
ATTTACGTGG AGTGACCAA CAACGGGAAA ACAGGACTAA ACAGAACAGAA CACTGAACCA GTCCTGGACT CTGATGGTTC TTACTTCATG TACAGCAAGC    1600
TGAGAGTGGA AAAGAAGAAC TGGGTGGAAA GAAATAGCCA CTCCCTGTTCA GTGGTCCACG AGGGTCTCCA CAATCACCAC ACGACTAAGA GCTTCTCCCG    1700
GACTCCGGGT AAATGAGCTC ACCACCCGCA AAACTCTCAG GTCCAAAGAG ACACCCCACAC TCATCTCCAT GCTTCCCTTG TATAAATAAA GCAACCAGCA    1800
ATGCCTGGGA CCATATAAAA GGGCGAATTC    1830
```

FIG. 29B

```
         10         20         30         40         50
1234567890 1234567890 1234567890 1234567890 1234567890
MGVLLTQRTL LSLVLALLFP SMASMETEVG AMVGSNVVLS CIDPHRRHFN       50

LSGLYVYWQI ENPEVSVTYY LPYKSPGINV DSSYKNRGHL SLDSMKQGNF      100

SLYLKNVTPQ DTQEFTCRVF MNTATELVKI LEEVVRLRVA ANFSTPVIST      150

SDSSNPGQER TYTCMSKNGY PEPNLYWINT TDNSLIDTAL QNNTVYLNKL      200

GLYDVIDTLR LPWTSRGDVL CCVENVALHQ NITSISQAES. FTGNNTKNPQ     250

ETHNNEEPRG PTIKPCPPCK CPAPNLEGGP SVFIFPPKIK DVLMISLSPI      300

VTCVVVDVSE DDPDVQISWF VNNVEVHTAQ TQTHREDYNS TLRVVSALPI      350

QHQDWMSGKA FACAVNNKDL PAPIERTISK PKGSVRAPQV YVLPPPEEEM      400

TKKQVTLTCM VTDFMPEDIY VEWTNNGKTE LNYKNTEPVL DSDGSYFMYS      450

KLRVEKKNWV ERNSYSCSW HEGLHNHHTT KSFSRTPGK                   489
```

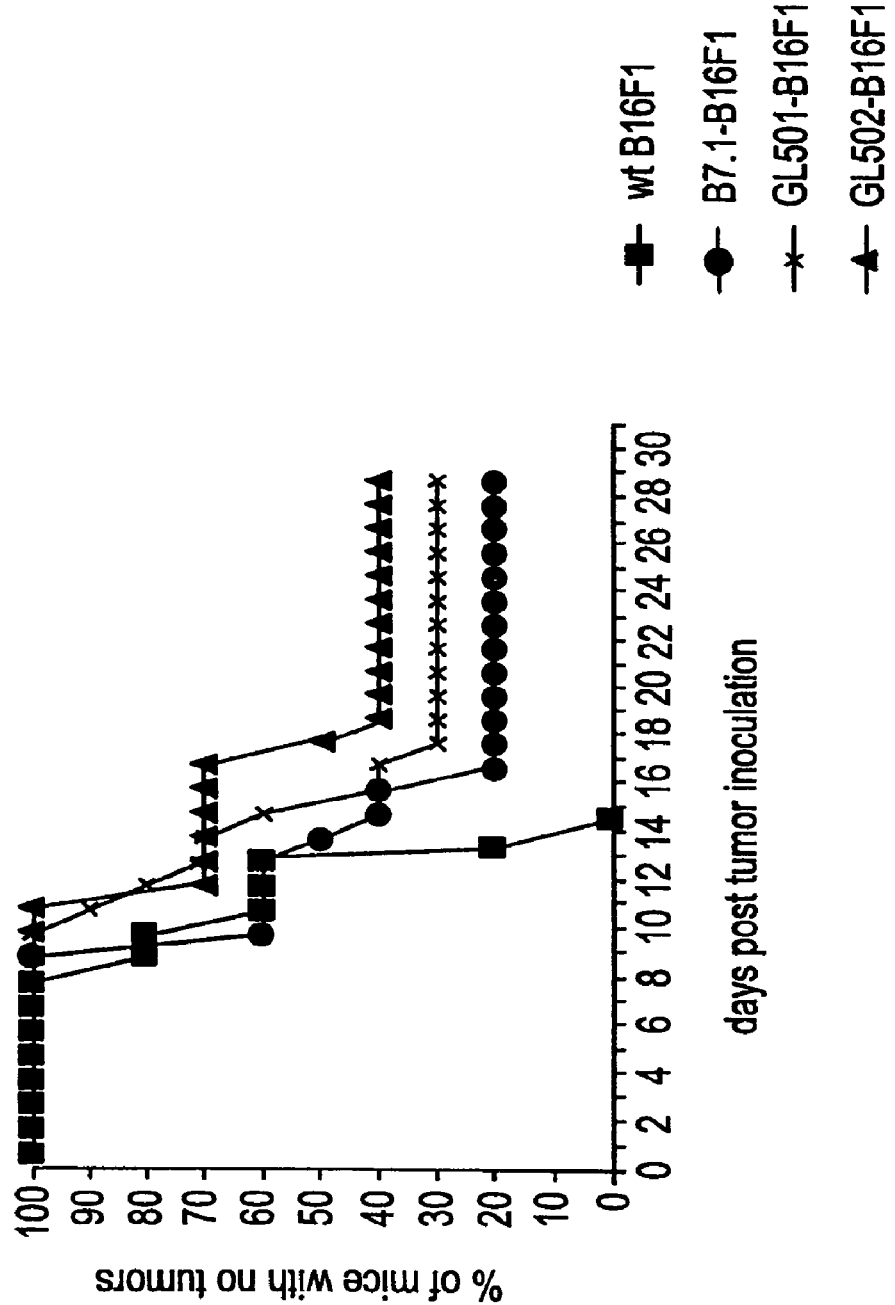

USE OF ANTI-GL50 ANTIBODIES FOR THE DOWNMODULATION OF AN IMMUNE RESPONSE

CROSS REFERENCE TO RELATED APPLICATIONS

This application is a divisional of U.S. Ser. No. 11/311,754, filed Dec. 19, 2005, which is a divisional of U.S. Ser. No. 10/318,855, now U.S. Pat. No. 7,521,532, filed Dec. 12, 2002, which is a divisional of U.S. Ser. No. 09/667,135, now U.S. Pat. No. 6,521,749, filed Sep. 21, 2000, which claims priority to U.S. Ser. No. 60/155,043, filed on Sep. 21, 1999. The entire contents of each of these applications are herein incorporated in their entirety by this reference.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165:302-319; Mueller, D. L. et al. (1990) *J. Immunol.* 144:3701-3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC restricted and is thought to be provided by one or more distinct cell surface molecules expressed by APCs (Jenkins, M. K. et al. (1988) *J. Immunol.* 140:3324-3330; Linsley, P. S. et al. (1991) *J. Exp. Med.* 173:721-730; Gimmi, C. D. et al. (1991) *Proc. Natl. Acad. Sci. USA* 88:6575-6579; Young, J. W. et al. (1992) *J. Clin. Invest* 90:229-237; Koulova, L. et al. (1991) *J. Exp. Med.* 173:759-762; Reiser, H. et al. (1992) *Proc. Natl. Acad. Sci. USA* 89:271-275; van-Seventer, G. A. et al. (1990) *J. Immunol.* 144:4579-4586; LaSalle, J. M. et al. (1991) *J. Immunol.* 147:774-80; Dustin, M. I. et al. (1989) *J. Exp. Med.* 169:503; Armitage, R. J. et al. (1992) *Nature* 357:80-82; Liu, Y. et al. (1992) *J. Exp. Med.* 175:437-445).

The CD80 (B7-1) and CD86 (B7-2) proteins, expressed on APCs, are critical costimulatory molecules (Freeman et al. (1991) *J. Exp. Med.* 174:625; Freeman et al. (1989) *J. Immunol.* 143:2714; Azuma et al. (1993) *Nature* 366:76; Freeman et al. (1993) *Science* 262:909). B7-2 appears to play a predominant role during primary immune responses, while B7-1, which is upregulated later in the course of an immune response, may be important in prolonging primary T cell responses or costimulating secondary T cell responses (Bluestone (1995) *Immunity* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S. et al. (1991) *J. Exp. Med.* 173:721-730; Gimmi, C. D. et al. (1991) *Proc. Natl. Acad. Sci. USA* 88:6575-6579; June, C. H. et al. (1990) *Immunol. Today* 11:211-6; Harding, F. A. et al. (1992) *Nature* 356:607-609). A second ligand, termed CTLA4 (CD152) is homologous to CD28 but is not expressed on resting T cells and appears following T cell activation (Brunet, J. F. et al. (1987) *Nature* 328:267-270). CTLA4 appears to be critical in negative regulation of T cell responses (Waterhouse et al. (1995) *Science* 270:985). Blockade of CTLA4 has been found to remove inhibitory signals, while aggregation of CTLA4 has been found to provide inhibitory signals that downregulate T cell responses (Allison and Krummel (1995) *Science* 270:932). The B7 molecules have a higher affinity for CTLA4 than for CD28 (Linsley, P. S. et al. (1991) *J. Exp. Med.* 174:561-569) and B7-1 and B7-2 have been found to bind to distinct regions of the CTLA4 molecule and have different kinetics of binding to CTLA4 (Linsley et al. (1994) *Immunity* 1:793).

In the past, reports of the existence of additional members of the B7 costimulatory family have been controversial. The antibody BB-1, appeared to recognize a subset of cells greater than either B7-1 or B7-2 positive cells, arguing for the existence of another B7-family member, B7-3. The identity of B7-3 had been in part thought to be answered by expression cloning of T-cell receptor invariant chain using the BB-1 antibody. Although invariant chain is not related to the B7 family, this molecule facilitated a low degree of costimulation when assessed by T cell proliferation assays.

Very recently, a novel surface receptor termed ICOS was described which had sequence identity with CD28 (24%) and CTLA4 (17%) (Hutloff et al. (1999) *Nature* 397:263; WO 98/38216). Unlike CD28, ICOS was shown to be upregulated on stimulated T cells and caused the secretion of a panel of cytokines distinct from those mediated by CD28 costimulation (Hutloff et al. (1999) *Nature* 397:263).

The importance of the B7:CD28/CTLA4 costimulatory pathway has been demonstrated in vitro and in several in vivo model systems. Blockade of this costimulatory pathway results in the development of antigen specific tolerance in murine and human systems (Harding, F. A. et al. (1992) *Nature* 356:607-609; Lenschow, D. J. et al. (1992) *Science* 257:789-792; Turka, L. A. et al. (1992) *Proc. Natl. Acad. Sci. USA* 89:11102-11105; Gimmi, C. D. et al. (1993) *Proc. Natl. Acad. Sci. USA* 90:6586-6590; Boussiotis, V. et al. (1993) *J. Exp. Med.* 178:1753-1763). Conversely, expression of B7 by B7 negative murine tumor cells induces T-cell mediated specific immunity accompanied by tumor rejection and long lasting protection to tumor challenge (Chen, L. et al. (1992) *Cell* 71:1093-1102; Townsend, S. E. and Allison, J. P. (1993) *Science* 259:368-370; Baskar, S. et al. (1993) *Proc. Natl. Acad. Sci. USA* 90:5687-5690.). Therefore, manipulation of the costimulatory pathways offers great potential to stimulate or suppress immune responses in humans.

SUMMARY OF THE INVENTION

The present invention is based, at least in part, on the discovery of novel nucleic acid molecules and polypeptides encoded by such nucleic acid molecules, referred to herein as GL50 molecules. Preferred GL50 molecules include antigens on the surface of professional antigen presenting cells (e.g., B lymphocytes, monocytes, dendritic cells, Langerhan cells) and other antigen presenting cells (e.g., keratinocytes, endothelial cells, astrocytes, fibroblasts, oligodendrocytes), which costimulate T cell proliferation, bind to costimulatory receptors ligands on T cells (e.g., CD28, CTLA4, and/or ICOS) and/or are bound by antibodies which recognize B7 family members, e.g., anti-GL50 antibodies.

The GL50 nucleic acid and polypeptide molecules of the present invention are useful, e.g., in modulating the immune response. Accordingly, in one aspect, this invention provides isolated nucleic acid molecules encoding GL50 polypeptides, as well as nucleic acid fragments suitable as primers or hybridization probes for the detection of GL50-encoding nucleic acids.

In one embodiment, a GL50 nucleic acid molecule of the invention is at least 50%, 55%, 60%, 65%, 70%, 75%, 80%, 85%, 90%, 95%, 98% or more identical to a nucleotide sequence (e.g., to the entire length of the nucleotide sequence) including SEQ ID NO: 1, 3, or 5, or a complement thereof.

In a preferred embodiment, the isolated nucleic acid molecule includes the nucleotide sequence shown SEQ ID NO: 1, 3, or 5, or a complement thereof. In another preferred embodiment, an isolated nucleic acid molecule of the invention encodes the amino acid sequence of a GL50 polypeptide.

Another embodiment of the invention features nucleic acid molecules, preferably the GL50 nucleic acid molecules, which specifically detect the GL50 nucleic acid molecules relative to nucleic acid molecules encoding non-GL50 polypeptides. For example, in one embodiment, such a nucleic acid molecule is at least 20, 30, 40, 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO: 1, 3, or 5, or a complement thereof.

In other preferred embodiments, nucleic acid molecules of the invention encode naturally occurring allelic variants of a human GL50 polypeptide, wherein the nucleic acid molecules hybridize to a nucleic acid molecule which includes SEQ ID NO: 1, 3, or 5 under stringent conditions.

Another embodiment of the invention provides an isolated nucleic acid molecule which is antisense to a GL50 nucleic acid molecule, e.g., the coding strand of a GL50 nucleic acid molecule.

Another aspect of the invention provides a vector comprising a GL50 nucleic acid molecule. In certain embodiments, the vector is a recombinant expression vector. In another embodiment, the invention provides a host cell containing a vector of the invention. The invention also provides a method for producing a polypeptide, preferably a GL50 polypeptide, by culturing in a suitable medium, a host cell, e.g., a mammalian host cell such as a non-human mammalian cell, of the invention containing a recombinant expression vector, such that the polypeptide is produced.

Another aspect of this invention features isolated or recombinant GL50 polypeptides and proteins.

In one embodiment, the isolated polypeptide is a human GL50 polypeptide.

In yet another embodiment, the isolated GL50 polypeptide is a soluble GL50 polypeptide.

In a further embodiment, the isolated GL50 polypeptide is expressed on the surface of a cell, e.g., has a transmembrane domain.

In a further embodiment, the isolated GL50 polypeptide plays a role in costimulating the cytokine secretion and/or proliferation of activated T cells. In another embodiment, the isolated GL50 polypeptide is encoded by a nucleic acid molecule having a nucleotide sequence which hybridizes under stringent hybridization conditions to a nucleic acid molecule comprising the nucleotide sequence of SEQ ID NO:1, 3, or 5.

Another embodiment of the invention features an isolated polypeptide, preferably a GL50 polypeptide, which is encoded by a nucleic acid molecule having a nucleotide sequence at least about 50%, 55%, 60%, 65%, 70%, 75%, 80%, 85%, 90%, 95%, 98% or more identity to a nucleotide sequence (e.g., to the entire length of the nucleotide sequence) including SEQ ID NO:1, 3, or 5 or a complement thereof.

Another embodiment of the invention features an isolated polypeptide, preferably a GL50 polypeptide, which is encoded by a nucleic acid molecule having a nucleotide sequence at least about 50%, 55%, 60%, 65%, 70%, 75%, 80%, 85%, 90%, 95%, 98% or more identity to an amino acid sequence (e.g., to the entire length of the amino acid sequence) including SEQ ID NO:2, 4, or 6.

This invention further features an isolated GL50 polypeptide which is encoded by a nucleic acid molecule having a nucleotide sequence which hybridizes under stringent hybridization conditions to a nucleic acid molecule comprising the nucleotide sequence of SEQ ID NO: 1, 3, or 5, or a complement thereof.

The polypeptides of the present invention can be operatively linked to a non-GL50 polypeptide (e.g., heterologous amino acid sequences) to form fusion proteins. The invention further features antibodies, such as monoclonal or polyclonal antibodies, that specifically bind polypeptides of the invention, preferably GL50 polypeptides. In addition, the GL50 polypeptides, e.g., biologically active polypeptides, can be incorporated into pharmaceutical compositions, which optionally include pharmaceutically acceptable carriers.

In another aspect, the present invention provides a method for detecting the presence of a GL50 nucleic acid molecule or polypeptide in a biological sample by contacting the biological sample with an agent capable of detecting a GL50 nucleic acid molecule or polypeptide such that the presence of a GL50 nucleic acid molecule or polypeptide is detected in the biological sample.

In another aspect, the present invention provides a method for detecting the presence of GL50 activity in a biological sample by contacting the biological sample with an agent capable of detecting an indicator of GL50 polypeptide activity such that the presence of the GL50 polypeptide activity is detected in the biological sample.

In another aspect, the invention provides a method for modulating GL50 polypeptide activity comprising contacting a cell capable of expressing GL50 polypeptide with an agent that modulates GL50 activity such that the GL50 activity in the cell is modulated. In one embodiment, the agent inhibits GL50 activity. In another embodiment, the agent stimulates GL50 activity. In one embodiment, the agent is an antibody that binds, preferably specifically, to a GL50 polypeptide. In another embodiment, the agent modulates expression of GL50 by modulating transcription of a GL50 gene or translation of a GL50 mRNA. In yet another embodiment, the agent is a nucleic acid molecule having a nucleotide sequence that is antisense to the coding strand of a GL50 mRNA or a GL50 gene.

In one embodiment, the methods of the present invention are used to treat a subject having a disorder (characterized by aberrant GL50 polypeptide or nucleic acid expression or activity) or a condition that would benefit from modulation, either up or downmodulation, of a GL50 molecule by administering an agent which is a GL50 modulator to the subject. In one embodiment, the GL50 modulator is a GL50 polypeptide. In another embodiment the GL50 modulator is a GL50 nucleic acid molecule. In another embodiment a GL50 modulator molecule that modulates the interaction between GL50 and a ligand of GL50 or a molecule that interacts with the intracellular domain of GL50. In yet another embodiment, the GL50 modulator is a peptide, peptidomimetic, or other small molecule. In a preferred embodiment, the disorder characterized by aberrant GL50 polypeptide or nucleic acid expression is an immune system disorder or condition that would benefit from modulation of a GL50 activity.

The present invention also provides a diagnostic assay for identifying the presence or absence of a genetic alteration characterized by at least one of (i) aberrant modification or mutation of a gene encoding a GL50 polypeptide; (ii) misregulation of the gene; and (iii) aberrant post-translational modification of a GL50 polypeptide, wherein a wild-type form of the gene encodes a polypeptide with a GL50 activity.

In another aspect the invention provides a method for identifying a compound that binds to or modulates the activity of a GL50 polypeptide. The method includes providing an indicator composition comprising a GL50 polypeptide having GL50 activity, contacting the indicator composition with a test compound, and determining the effect of the test compound on GL50 activity in the indicator composition to identify a compound that modulates the activity of a GL50 polypeptide.

In another aspect, the invention pertains to nonhuman transgenic animal that contains cells carrying a transgene encoding a GL50 member polypeptide.

In one embodiment, the present invention provides methods for treating cancer involving administering to a subject suffering from a tumor comprising administering a stimulatory form of a GL50 molecule. In a preferred embodiment, the stimulatory form of a GL50 molecule is a soluble form of GL50 and includes the extracellular domain of a costimulatory molecule. In one embodiment, the costimulatory molecule is monospecific. In one embodiment, the costimulatory molecule is dimeric. In one embodiment, the costimulatory molecule is bivalent.

In another preferred embodiment, the costimulatory molecule is fused to a second protein or polypeptide which includes a portion of an immunoglobulin molecule (e.g., a portion of an immunoglobulin molecule that includes cysteine residues; a portion of an immunoglobulin molecule that includes the hinge, CH2, and CH3 regions of a human immunoglobulin molecule; or a portion of an immunoglobulin molecule that includes the hinge, CH1, CH2, and CH3 regions of a human immunoglobulin molecule). In yet another embodiment, the portion of the immunoglobulin molecule has been modified to reduce complement fixation and/or Fc receptor binding.

In yet another aspect, the invention pertains to a method for reducing the proliferation of a tumor cell comprising contacting an immune cell with an activating form of a GL50 molecule such that an immune response to the tumor cell is enhanced and proliferation of the tumor cell is reduced.

In one embodiment, the activating form of a GL50 molecule is a soluble polypeptide comprising the extracellular domain of GL50.

In another embodiment, the activating form of a GL50 molecule is a cell associated polypeptide comprising the extracellular domain of GL50.

In yet another embodiment, the invention pertains to a method for screening for a compound which modulates GL50 mediated activation of an immune cell comprising: i) contacting a polypeptide comprising at least one GL50 polypeptide domain with a test compound and a GL50 binding partner and ii) identifying compounds that modulate the interaction of the polypeptide with the GL50 binding partner to thereby identify compounds that modulate GL50 mediated activation of an immune cell.

In one embodiment, the polypeptide comprises a GL50 domain selected from the group consisting of: a transmembrane domain, a cytoplasmic domain, and an extracellular domain.

In one embodiment, the domain is a splice variant of a GL50 cytoplasmic domain.

In one embodiment, the GL50 polypeptide domain comprises at least one amino acid substitution.

In one aspect, the invention pertains to a method for screening for a compound which modulates signal transduction in an immune cell comprising contacting an immune cell that expresses a GL50 molecule with a test compound and determining the ability of the test compound to modulate signal transduction via GL50 to thereby identify a compound with modulates a signal in an immune cell.

BRIEF DESCRIPTION OF THE DRAWINGS

FIG. 3 shows a sequence alignment of mGL50-1 and mGL50-2 product. Sequence divergence occurs at nucleotide 1027 for mGL50-1 and at 960 for mGL50-2.

FIG. 5 shows isoform specific Northern Blot analysis of mGL50-1 and mGL50-2.

FIG. 6 shows the nucleotide sequence of AB014553 RACE product. The boxed region is an area of divergence between the published AB014553 cDNA sequence and the RACE product. Final nested RACE primer extends from position 1 to 22, corresponding to nucleotides 655 to 676.

FIG. 7 shows an alignment of the translated RACE product and the published AB014553 cDNA. Divergence occurs at residues 299 of the published AB014553 cDNA and residues 123 of the RACE product.

FIG. 8 shows the sequence of human GL50 (hGL50).

FIG. 12 shows a pileup analysis of hGL50, mGL50-1, hB7-1, mB7-2, hB7-2, mB7-2 in which the signal peptide, Ig-like domains, transmembrane, and cytoplasmic domains are indicated. The Predicted hydrophobic transmembrane residues are underlined and asterisks denote residues which contribute to Ig structure. The extracellular cysteines and tryptophans, indicators of Ig structure, are shown in bold.

Dashes and arrowheads represent oligonucleotides used in RT-PCR analysis. Horizontal lines represent probes used in Northern blot analysis.

Figure 16:
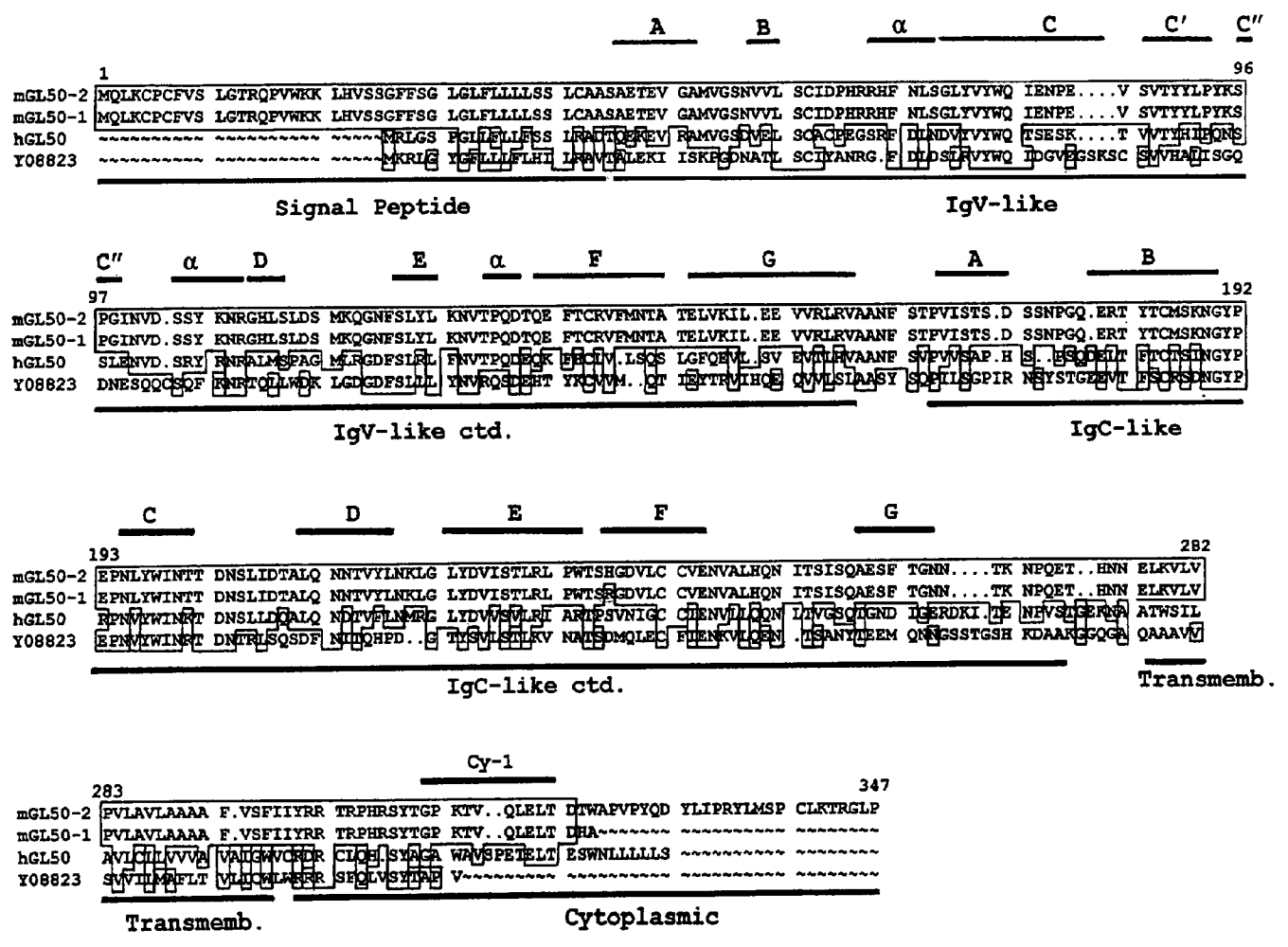

FIG. 16 depicts a protein sequence alignment between mGL50-1, mGL50-2, hGL50, and Y08823. Sequences were aligned with PileUp, and shared residues between these molecules are boxed. Letters above sequences denote secondary peptide structures as predicted for Y08823 based on the crystal structure of B7-1. The exon encoding hGL50 cytoplasmic domain 1 sequences is indicated by bar labeled Cy-1.

Figure 17:
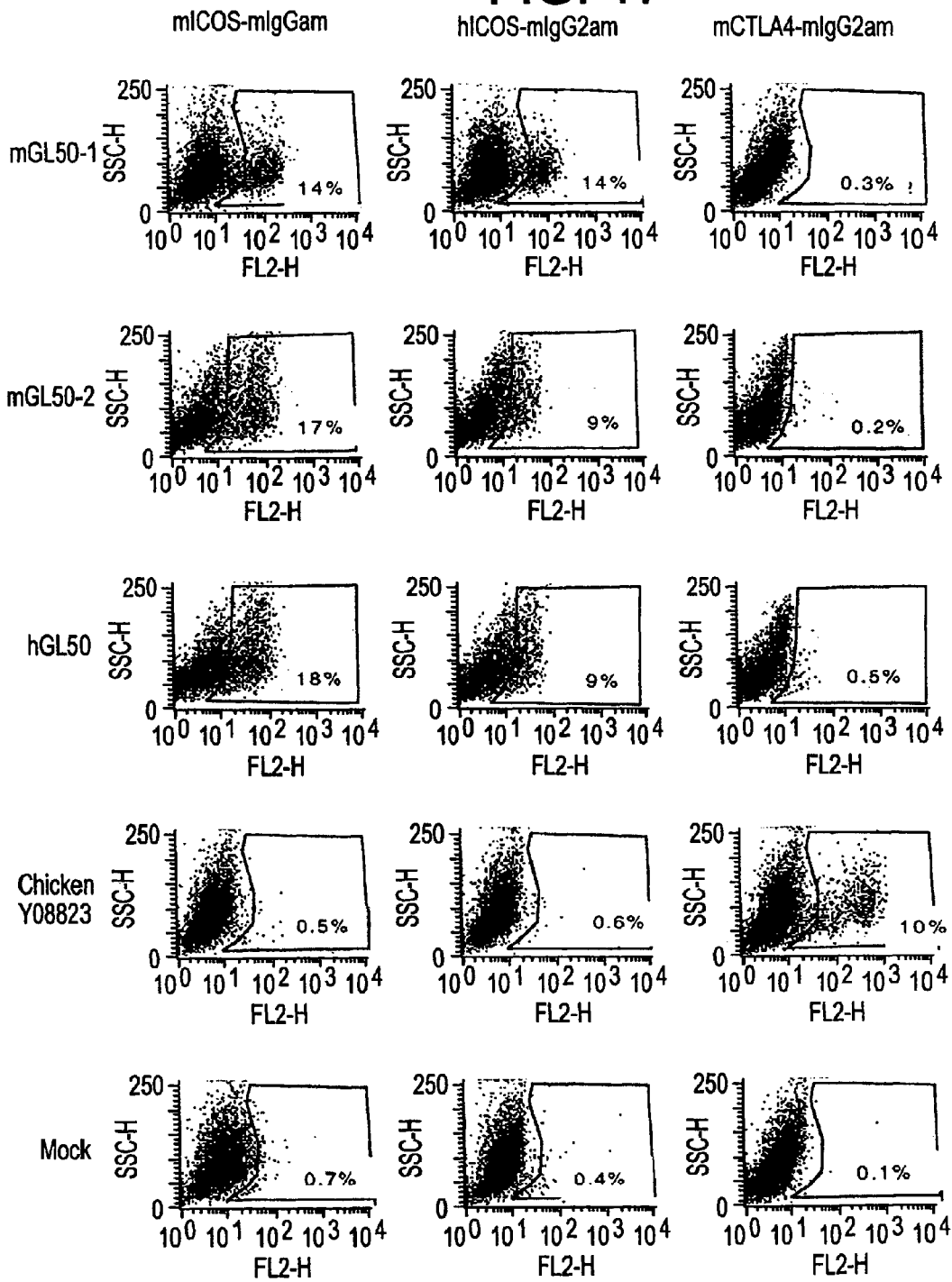

FIG. 17 depicts flow cytometric analysis of ICOS binding to mouse, human, and chicken GL50-related proteins. COS cells transfected with expression plasmids encoding mGL50-1, mGL50-2, hGL50, and the chicken B7-like protein Y08823 were incubated with mICOS-mIgG2am, hICOS-mIgG2am or mCTLA4-mIgG2am, followed by secondary staining with anti-mouse IgG2a biotin and detection with streptavidin-PE.

FIG. 18 depicts ICOS binding to WEHI 231. Titered amounts of mICOS-mIgG2am or mCTLA4-mIgG2am were used to stain WEHI 231 cells in the presence of blocking anti B7-1 and B7-2 antibodies or isotype controls.

Figure 19A:
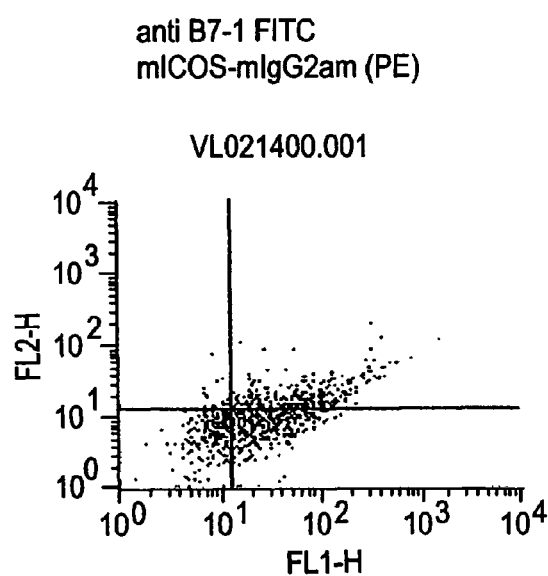
Figure 19B:
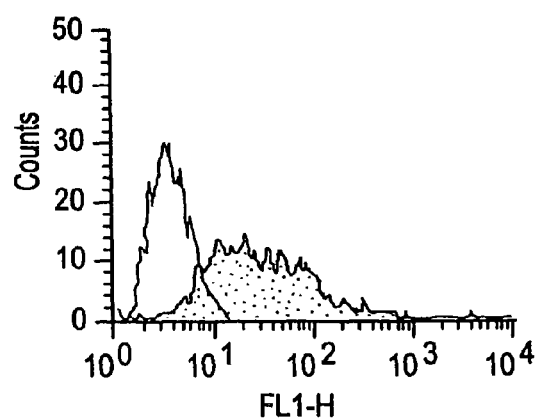
Figure 19C:
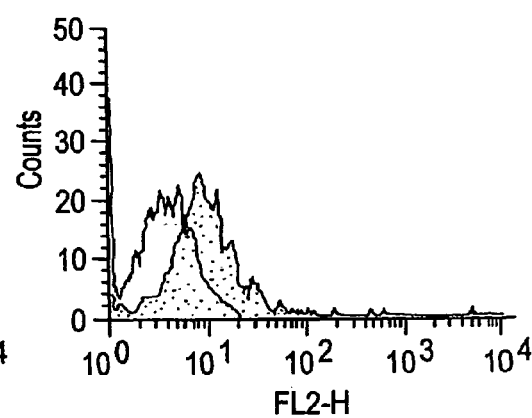

FIG. 19 depicts ICOS binding to undifferentiated ES cells. Analysis of undifferentiated ES cells counter stained with anti-B7-1 and mICOS-mIgG2am reagents resulted in the positive staining for both B7-1 and ICOS-ligand.

FIG. 20 depicts immunophenotyping of Balb/c and RAG1 −/− splenocyte subsets. Two dimensional plots of 10,000 stained cells are presented; samples with 50,000 data points are indicated by asterisks. (A) Enriched splenocytes from Balb/C or RAG1 −/− mice were stained with mICOS-mIgG2am and FITC-conjugated antibodies against CD3, CD24, CD45R/B220, pan NK, MHC class II, or CD40. To further phenotype the CD4+, ICOS-ligand+ cells, RAG1 −/− cells were stained with PE-labeled anti-CD4 and FITC-labeled anti-CD11c. (B) Enriched splenocytes from RAG1 −/− and Balb/C mice (untreated, ConA activated, or LPS activated) were stained with mICOS-mIgG2am and antibodies to CD4, CD8, CD19, CD11b, CD11c and CD69.

Figure 21A:
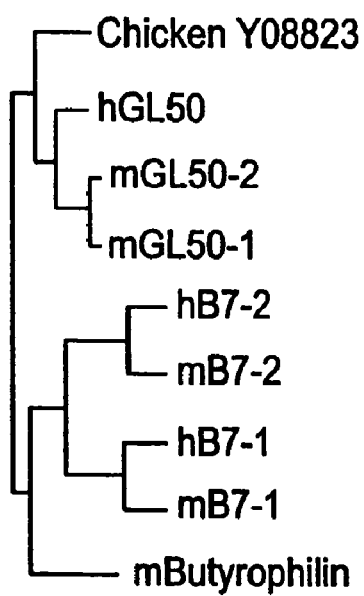
Figure 21B:
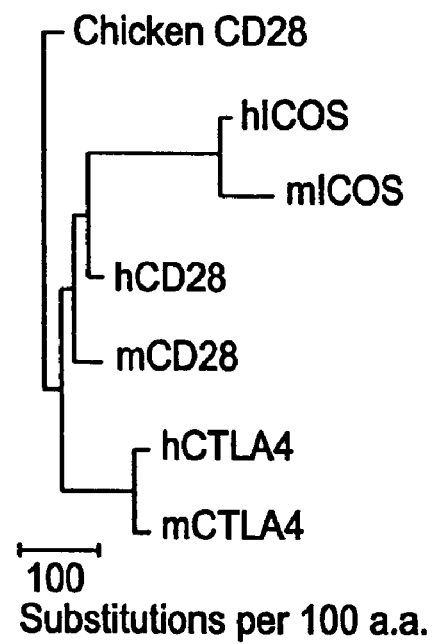
Figure 22E:
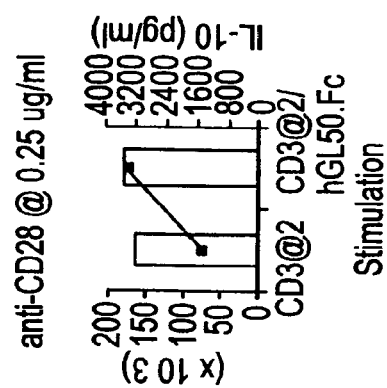
Figure 22F:
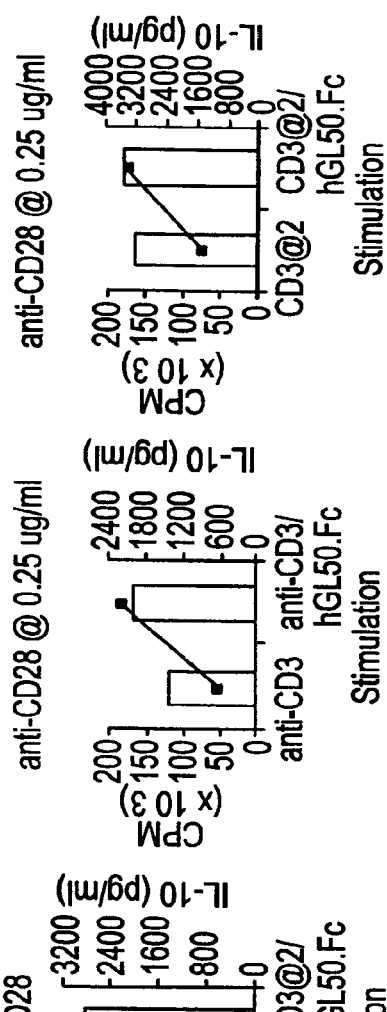
Figure 22G:
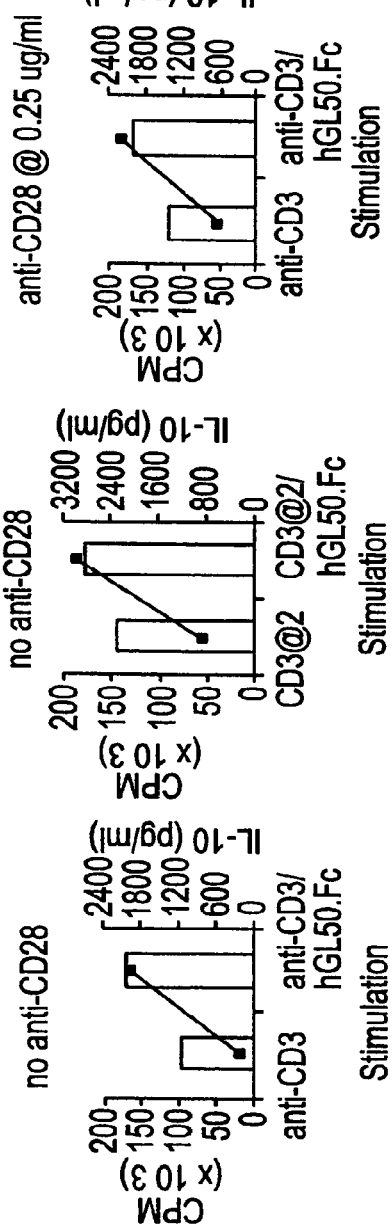
Figure 22H:

FIG. 21 depicts a phylogenetic representation of GL50/B7 ligands and CD28/CTLA4/ICOS receptors. Distance proportional phylograms were generated using values from Tables 5 (GL50/B7 ligands) and 6 (CD28/CTLA4/ICOS). Bars represent genetic distance expressed as substitutions per 100 amino acids. (A) Phylogram of GL50/B7 related proteins. Accession No. MMU67065_1 represents mouse butyrophilin. (B) Phylogram of ICOS/CD28/CTLA4 proteins.

FIG. 22 depicts proliferation and cytokine induction by GL50 costimulation of T cells, in the absence or presence of anti-CD28 blocking antibodies. Note: hGL50.Fc is the same as hGL50-IgG2am.

Figure 23A:
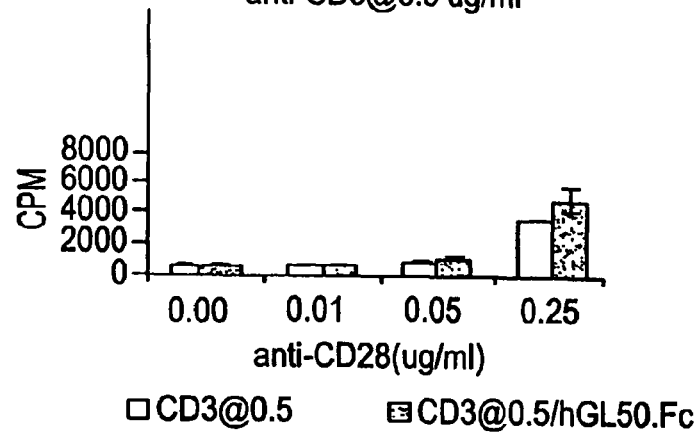
Figure 23B:
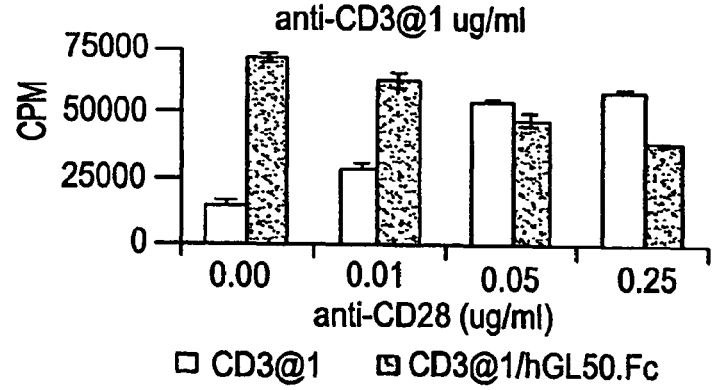
Figure 23C:
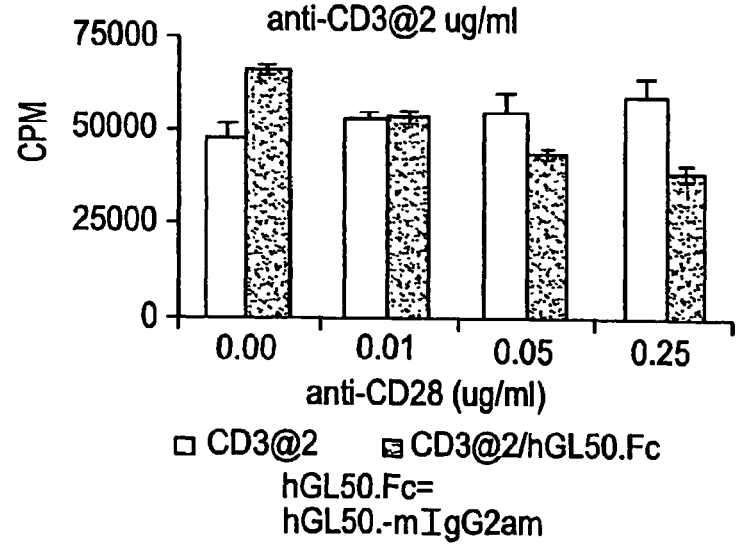

FIG. 23 depicts T cell proliferation induced by GL50 costimulation in the presence of varied concentrations of anti-CD28 blocking antibodies and anti-CD3 stimulation.

Figure 24B:
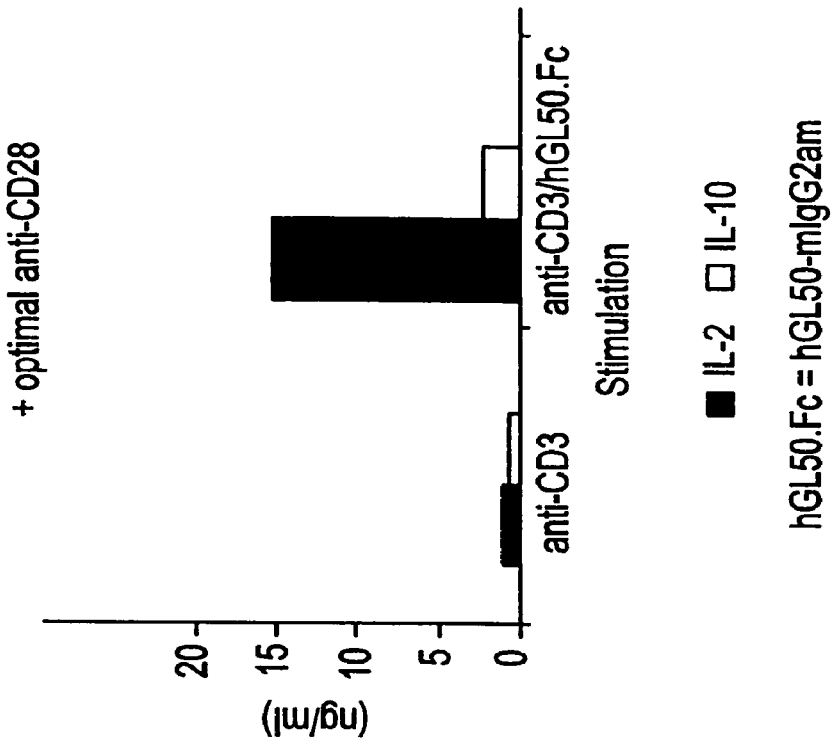
Figure 24A:
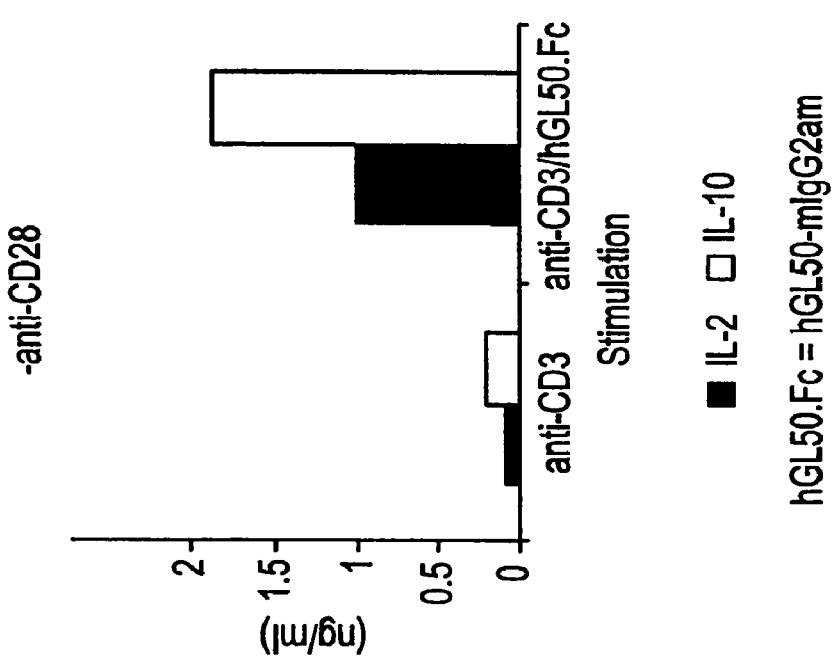

FIG. 24 depicts cytokine induction by GL50 costimulation in T cells in the absence or presence of CD28 stimulation.

FIG. 25 depicts the ability of GL50-IgG2a to inhibit tumor growth in mice.

FIG. 26 depicts the sequence of the hICOS-mIgG2am fusion protein. (A) The nucleotide sequence encoding hICOS-mIgG2am (set forth as SEQ ID NO:23). The oncostatin-M leader sequence is encoded by the underlined nucleotides. Boxed nucleotides encode the mouse IgG2am domain of the fusion protein. The translation initiation site is indicated by an X. Introns and untranslated regions are indicated by a dashed line. The stop codon is indicated by a double underline. (B) The predicted amino acid sequence (set forth as SEQ ID NO:24) of the hICOS-mIgG2am fusion protein.

FIG. 27 depicts the sequence of the mICOS-mIgG2am fusion protein. (A) The nucleotide sequence encoding mICOS-mIgG2am (set forth as SEQ ID NO:25). The oncostatin-M leader sequence is encoded by the underlined nucleotides. Boxed nucleotides encode the mouse IgG2am domain of the fusion protein. The translation initiation site is indicated by an X. Introns and untranslated regions are indicated by a dashed line. The stop codon is indicated by a double underline. (B) The predicted amino acid sequence (set forth as SEQ ID NO:26) of the mICOS-mIgG2am fusion protein.

FIG. 28 depicts the sequence of the hGL50-mIgG2am fusion protein. (A) The nucleotide sequence encoding hGL50-mIgG2am (set forth as SEQ ID NO:27). The oncostatin-M leader sequence is encoded by the underlined nucleotides. Boxed nucleotides encode the mouse IgG2am domain of the fusion protein. The translation initiation site is indicated by an X. Introns and untranslated regions are indicated by a dashed line. The stop codon is indicated by a double underline. (B) The predicted amino acid sequence (set forth as SEQ ID NO:28) of the hGL50-mIgG2am fusion protein.

FIG. 29 depicts the sequence of the mGL50-mIgG2am fusion protein. (A) The nucleotide sequence encoding mGL50-mIgG2am (set forth as SEQ ID NO:29). The oncostatin-M leader sequence is encoded by the underlined nucleotides. Boxed nucleotides encode the mouse IgG2am domain of the fusion protein. The translation initiation site is indicated by an X. Introns and untranslated regions are indicated by a dashed line. The stop codon is indicated by a double underline. (B) The predicted amino acid sequence (set forth as SEQ ID NO:30) of the mGL50-mIgG2am fusion protein.

Figure 30:
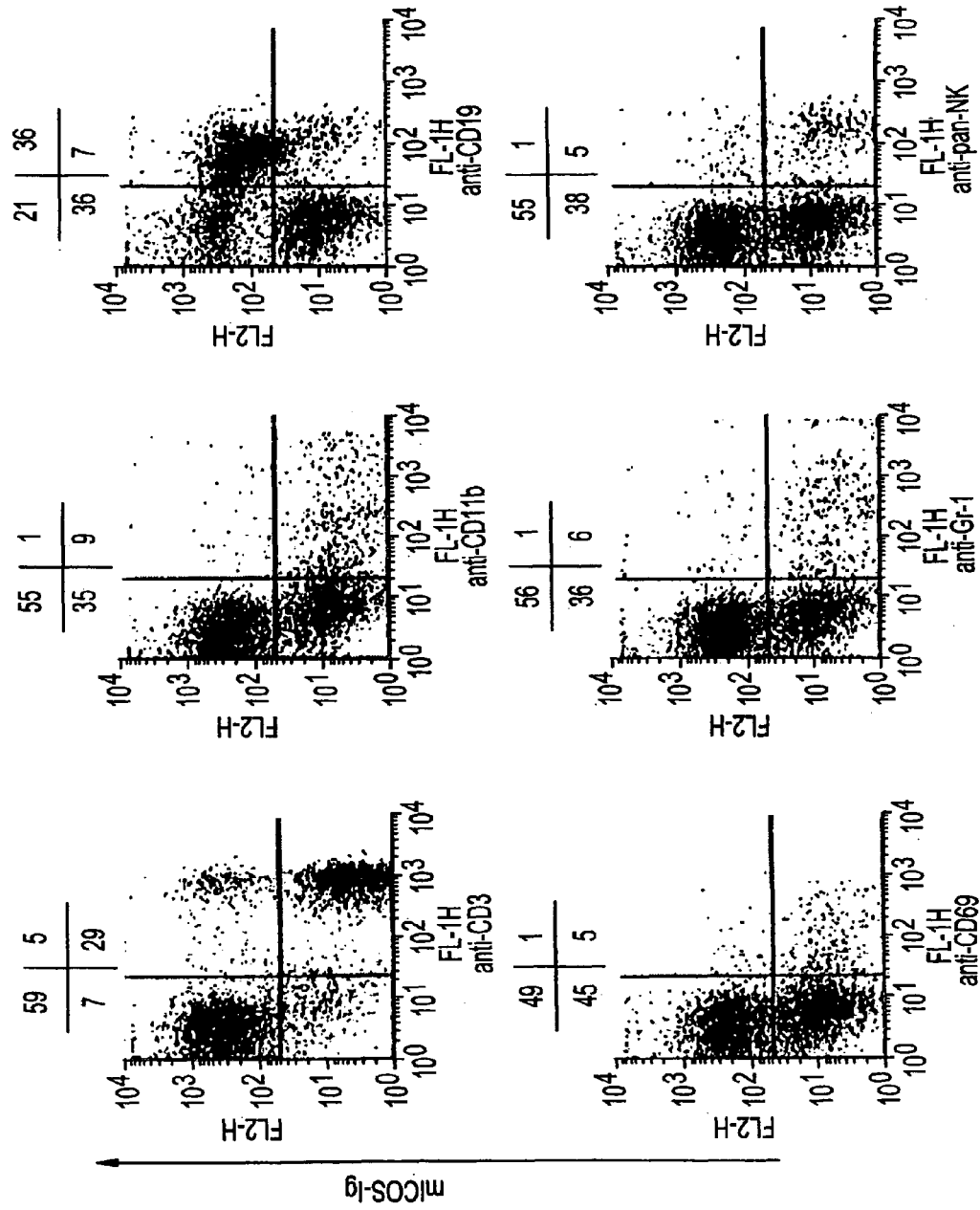

FIG. 30 depicts ICOS-Ig staining of various splenic cell types.

FIG. 31 depicts the reduction of tumorigenicity of tumor cells transfected with GL50.

DETAILED DESCRIPTION OF THE INVENTION

In addition to the previously characterized B lymphocyte activation antigens, e.g., B7-1 and B7-2, there are other antigens on the surface of antigen presenting cells (e.g., B cells, monocytes, dendritic cells, Langerhan cells, keratinocytes, endothelial cells, astrocytes, fibroblasts, oligodendrocytes) which costimulate T cells.

The present invention is based, at least in part, on the discovery of novel molecules, referred to herein as GL50 polypeptides. Murine GL50-1 (mGL50-1) was isolated from an IL-12 activated mouse lymph node library. The nucleotide sequence of mGL50-1 is shown in SEQ ID NO: 1. The derived polypeptide sequence of full length mouse mGL50-1 is shown in SEQ ID NO:2. The sequence shares approximately 20% sequence identity with mouse B7-1 and mouse B7-2. mGL50-1 encodes a 322 amino acid polypeptide containing a leader sequence, extracellular Ig-like domains, a hydrophobic transmembrane domain, and an intracellular domain comprising one tyrosine residue.

3' RACE PCR with mouse peripheral blood lymphocyte (PBL) RNA revealed an alternatively spliced form of mouse GL50 (mGL50-2). The nucleotide sequence of murine GL50-2 (mGL50-2) is shown in SEQ ID NO:3. The nucleotide sequence encoded a polypeptide having a divergent 27 amino acid intracellular domain, which included an additional three tyrosines, a 3' untranslated region with consensus polyadenylation signal, and a poly A tail which are shown in SEQ ID NO:4. Transcripts of both mGL50-1 and mGL50-2 were found by RT-PCR and Northern blot analysis and were predominantly localized in lymphoid organs of multiple tissue panels. The murine GL50 sequences identified were found to be related to a previously reported human brain cDNA clone, GenBank Accession Number AB014553.

3' RACE of human PBL cDNA was performed to identify human clones related to murine GL50. Clones encoding alternative 3' sequences were identified. The nucleotide sequence of the resulting human GL50 (hGL50 [AB014553-RACE]) clone is shown in SEQ ID NO:5. The nucleotide sequence encodes a 309 amino acid protein sharing about 26% amino acid sequence identity with the mGL50-1, 28% identity with mGL50-2, and amino acid sequence, approximately 13% amino acid sequence identity with human B7-1, and about 13% amino acid sequence identity with human and mouse B7-2.

Flow cytometric assays using murine GL50-1Ig fusion protein as a reagent demonstrated binding to COS transfectants expressing mouse ICOS, but not to cells expressing CD28 or CTLA4. These results confirm that GL50 molecules are novel members of the B7 family of molecules.

GL50 Nucleic Acid and Polypeptide Molecules

In one embodiment, the isolated nucleic acid molecules of the present invention encode eukaryotic GL50 polypeptides.

The GL50 family of molecules share a number of conserved regions, including signal domains, IgV domains and the IgC domains. For example, in the case of mGL50-1 (SEQ ID NO: 1), the consensus 2718 nucleotide mGL50-1 sequence encodes a 322 amino acid protein with a predicted mass of 36 kDa. Hydropathy plot of the open reading frame predicted a structure corresponding to a leader sequence (encoded by about nucleotides 67 to 195), an extracellular domain (encoded by about nucleotides 196 to 904), a hydrophobic transmembrane region (encoded by about nucleotides 905 to 961) and a potential intracellular cytoplasmic domain (encoded by about nucleotides 962 to 1032). Signal peptide cleavage was predicted at position 46 in the amino acid sequence. In one embodiment, the extracellular domain of a GL50 polypeptide comprises the IgV and IgC domains after cleavage of the signal sequence, but not the transmembrane and cytoplasmic domains of a GL50 polypeptide (e.g., corresponding to the amino acid sequence from about amino acid 47-277 of GL50-1 or the amino acid sequence from about amino acid 22 to about amino acid 278 of hGL50 as set forth in FIG. 16).

Analysis of the mGL50-1 amino acid sequence suggested structural similarity to an Ig-domain in the cytoplasmic domain of the protein. In keeping with an Ig-like structure, 4 cysteines were found in the extracellular domain, allowing for the possibility of intramolecular bonding and distinct structural conformation corresponding to an IgV-like domain and an IgC-like domain. These regions are both Ig superfamily member domains and are art recognized. These domains correspond to structural units that have distinct folding patterns known as Ig folds. Ig folds are comprised of a sandwich of two β sheets, each consisting of antiparallel β strands of 5-10 amino acids with a conserved disulfide bond between the two sheets in most, but not all, domains. IgC domains of Ig, TCR, and MHC molecules share the same types of sequence patterns and are referred to as C1-set within the Ig superfamily. Other IgC domains fall within other sets. IgV domains also share sequence patterns and are called V set domains. IgV domains are longer than C-domains and form an additional pair of β strands.

An alignment of the mGL50-2, mGL50-1, hGL50, and chicken Y08823 molecule are presented in FIG. 16. Each of the molecules comprises a signal peptide, an IgV-like domaine, an IgC-like domain, a transmembrane domaine and a cytoplasmic domain. Domains of mGL50-2, hGL50, and Y08823 corresponding to those in mGL50-1 are presented in FIG. 16.

A protein alignment was made of the GL50 polypeptides, the published AB014553 sequence, and the human and mouse B7-1 and B7-2 sequences using the Geneworks protein alignment program with the parameters set at: cost to open gap=5, cost to lengthen gap=5, minimum diagonal length=4, maximum diagonal offset=130, consensus cutoff=50%, and using the Pam 250 matrix. The results of the alignment are presented below in Table 1.

TABLE 1

Protein Alignment for G150-related proteins

| | AB014553 | hGL50 | mGL50-1 | mGL50-2 | hB7-2 | mB7-2 | hB7-1 | mB7-1 |
|---|---|---|---|---|---|---|---|---|
| ABO14553 | 100 | 59 | 26 | 28 | 13 | 13 | 13 | 7 |
| hGL50 | | 100 | 42 | 41 | 17 | 17 | 17 | 12 |
| GL50-1 | | | 100 | 92 | 19 | 19 | 20 | 14 |
| GL50-2 | | | | 100 | 20 | 21 | 20 | 13 |
| hB7-2 | | | | | 100 | 48 | 19 | 21 |
| mB7-2 | | | | | | 100 | 20 | 24 |
| hB7-1 | | | | | | | 100 | 41 |
| mB7-1 | | | | | | | | 100 |

Alignments were done using the Geneworks protein alignment program with the cost to open gap = 5, cost to lengthen gap = 5, min. diagonal length = 4, max. diagonal offset = 130, consensus cutoff = 50%, Pam 250 matrix.

Table 1 shows that the hGL50 polypeptide has approximately 59% amino acid sequence identity with the polypeptide encoded by AB014553 and approximately 40% amino acid sequence identity with mGL50-1 and mGL50-2. mGL50-1 and mGL50-2 share a higher degree of amino acid sequence identity, approximately 92%. The GL50 polypeptides share approximately 20% amino acid sequence identity with other B7 family molecules.

Another alignment was made to determine the extent of relatedness between murine GL50, hGL50, human B7-1, mouse B7-1, mouse B7-2, and human B7-2 protein sequences. Using a Pileup analysis (FIG. 12), 18 amino acid locations aligned identically between all six molecules within the extracellular domain. Of the 32 positions that define the predicted IgV-like and IgC-like folds of the B7 molecule, 13 are identically conserved between all six molecules, most notably the 4 cysteines that allow intramolecular folding of domains. Other areas of significant sequence conservation were also seen in the extracellular domain, but interestingly the identities of GL50 sequences in certain locations aligned more closely with either B7-1 or B7-2 (identity score of 8). For example, a valine residue corresponding to position 86 of mGL50-1 is shared by hGL50, and B7-2 sequences, but not B7-1. Likewise, the tyrosine at position 87 of mouse mGL50-1 is conserved at corresponding locations in hGL50 and B7-1, but not B7-2. Of the 16 positions with identity scores of 8, 5 positions are shared by mouse mGL50-1/hGL50 and B7-1, 4 positions are shared between mouse mGL50-1/hGL50 and B7-2, and 6 positions are shared between B7-1 and B7-2. Based on the peptide structure, these results suggest that the GL50 sequences occupy a phylogenetic space parallel to the B7 family of proteins.

Figure 13:
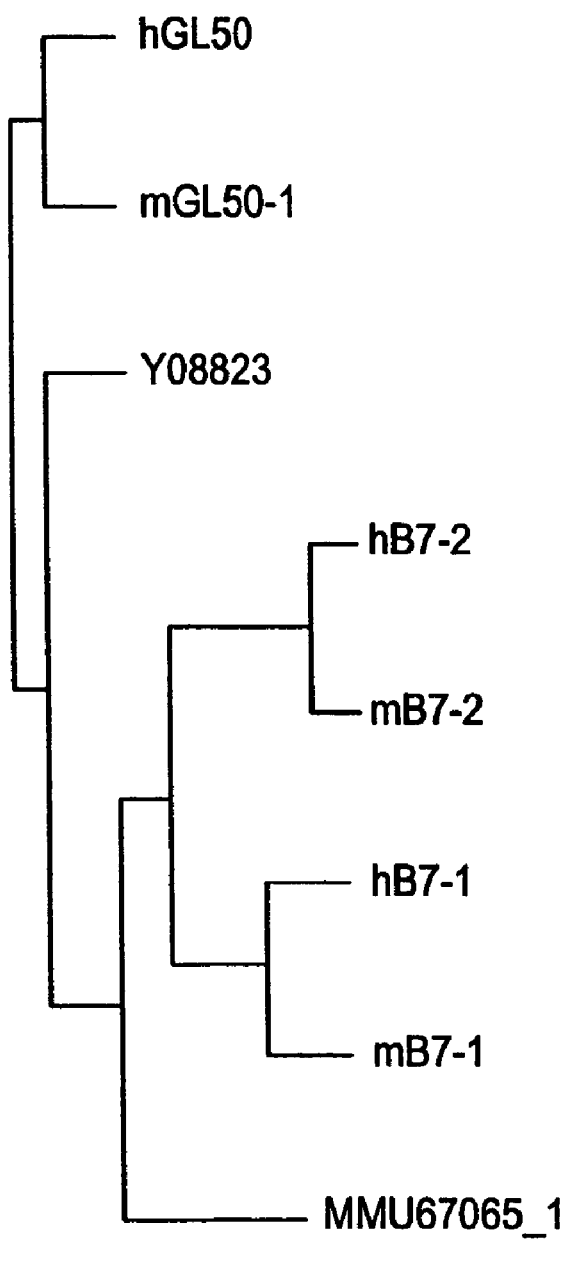
FIG. 13 shows dendrogram analysis representing genetic distances between B7-1, B7-2 and GL50 proteins. Y08823 is the chicken CD80-like protein and MM867065_1 is the mouse butyrophilin.

Molecular phylogeny analysis (GrowTree) measuring genetic distance in terms of substitutions per 100 amino acids resulted in a dendrogram (FIG. 13) with independent clustering of mouse/hGL50 (85), m/hB7-2(68) and m/hB7-1 (88). As an outgroup, mmu67065_1 (mouse butyrophilin) was used. The chicken clone Y08823 also was found to be more closely aligned with the GL50 sequences (~140) than the B7 sequences (215-320), indicating that these sequences comprised a distinct subfamily of proteins. Distances between the GL50, B7-2 and B7-1 branches were high (216-284), suggesting that large numbers of substitutions have occurred between these molecules since the inception of the human and rodent lineage. The genetic distances among the GL50 nucleic acid molecules are presented below in Table 2.

TABLE 2

Genetic Distances among B7 family members

| | hGL50 | mGL50-1 | YO8823 | hB7-2 | mB7-2 | hB7-1 | mB7-1 | mmu67065_1 |
|---|---|---|---|---|---|---|---|---|
| hGL50 | 0 | 85 | 142 | 284 | 263 | 226 | 260 | 188 |
| mGL50-1 | | 0 | 139 | 225 | 216 | 229 | 257 | 223 |
| YO8823 | | | 0 | 235 | 322 | 215 | 223 | 223 |
| hB7-2 | | | | 0 | 68 | 222 | 190 | 215 |
| mB7-2 | | | | | 0 | 88 | 211 | 21 |
| hB7-1 | | | | | | 0 | 88 | 211 |
| mB7-1 | | | | | | | 0 | 271 |
| mmu67065_1 | | | | | | | | 0 |

Various aspects of the invention are described in further detail in the following subsections:

I. DEFINITIONS

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4). An inhibitory signal as transduced by an inhibitory receptor can occur even if a costimulatory receptor (such as CD28) in not present on the immune cell and, thus, is not simply a function of competition between inhibitory receptors and costimulatory receptors for binding of costimulatory molecules (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

In addition to differences in types of receptors, different forms of costimulaotry molecules can be either activating or inhibitory. For example, in the case of an activating receptor a signal can be transmitted e.g., by a multivalent form of a costimulatory molecule that results in crosslinking of an activating receptor, or a signal can be inhibited, e.g., by a form of a costimulatory molecule that binds to an activating receptor, but fails to transmit an activating signal, e.g., by competing with activating forms of costimulatory molecules for binding to the receptor. (Certain soluble forms of costimulatory molecules can be inhibitory, however, there are instances in which a soluble molecule can be stimulatory). Similarly, depending upon the form of costimulatory molecule that binds to an inhibitory receptor, either a signal can be transmitted (e.g., by a multivalent form of a costimulatory molecule that results in crosslinking of an activating receptor) or a signal can be inhibited (e.g., by a form of a costimulatory molecule that binds to an inhibitory receptor, but fails to transmit an inhibitory signal). The effects of the various modulatory agents can be easily demonstrated using routine screening assays as described herein.

As used herein, the term "costimulate" with reference to activated immune cells includes the ability of a "costimulatory molecule" to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "activating receptor" includes immune cell receptors that bind antigen, complexed antigen (e.g., in the context of MHC molecules), or bind to antibodies. Such activating receptors include T cell receptors (TCR), B cell receptors (BCR), cytokine receptors, LPS receptors, complement receptors, and Fc receptors.

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

As used herein, the term "inhibitory signal" refers to a signal transmitted via an inhibitory receptor (e.g., CTLA4) on a immune cell. Such a signal antagonizes a signal via an activating receptor (e.g., via a TCR, CD3, BCR, or Fc molecule) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "adjuvant" includes agents which potentiate the immune response to an antigen (e.g., a tumor-associated antigen). Adjuvants can be administered in conjunction with costimulatory molecules to additionally augment the immune response.

As used herein, the term "monospecific" includes molecules which have only one specificity, i.e., they specifically bind to their cognate ligand, e.g., CD28, CThA4, or ICOS on T cells. Such monospecific agents have not been engineered to include additional specificities and, thus, do not bind in a targeted manner to other cell surface molecules. As used herein the term "oligospecific" includes molecules having more than one specificity, e.g., having an additional specificity for a molecule other than afor their cognate ligand, e.g., a specificity for a cell surface molecule, such as a tumor associated antigen or a T cell receptor. As used herein, the term "bivalent" includes soluble costimulatory molecules that have two binding sites for interaction with their ligand per molecule. As used herein, the term "dimeric" includes forms that are present as homodimers, i.e., as a unit comprised of two identical subunits which are joined together, e.g., by disulfide bonds. As used herein, the term "multimeric" includes soluble forms having more than two subunits.

In another embodiment, an activating form of a GL50 molecule is a soluble GL50 molecule. As used herein, the term "soluble" includes molecules, e.g., costimulatory molecules, which are not cell associated. Soluble costimulatory molecules retain the function of the cell associated molecules from which they are derived, e.g., they are capable of binding to their cognate ligands on T cells and mediating signal transduction via a CD28 and/or CTLA4 molecule on a T cell, however, they are in soluble form, i.e., are not membrane bound. Preferably, the soluble compositions comprise an extracellular domain of a costimulatory molecule.

Preferably, such a soluble form of a GL50 comprises at least a portion of the extracellular domain of a GL50 molecule. As used herein, the term "extracellular domain of a GL50 molecule" includes a portion of a GL50 molecule which, in the cell-associated form of the GL50 molecule, is extracellular. Preferably, the extracellular domain is the extracellular domain of a human GL50 molecule. In one embodiment, a soluble costimulatory molecule comprises an extracellular domain of a GL50 molecule and further comprises a signal sequence.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

The GL50 polypeptide and nucleic acid molecules comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

The GL50 molecules described herein are members of a larger family of molecules, the B7 family of costimulatory molecules. The term "B7 family" or "B7 molecules" as used herein includes costimulatory molecules that share sequence homology with B7 polypeptides, e.g., with B7-1, B7-2, B7-3 (recognized by the antibody BB-1), and/or GL50. For example, as shown in Table 1 above, human B7-1 and human B7-2 share approximately 20% amino acid sequence identity. In addition, the B7 family of molecules share a common function, e.g., the ability to bind to a B7 family ligand (e.g., one or more of CD28, CTLA4, or ICOS) and/or the ligands on immune cells and have the ability to inhibit or induce costimulation of immune cells.

As used herein, the term "activity" with respect to a GL50 polypeptide includes activities which are inherent in the structure of a GL50 polypeptide. The term "activity" includes the ability to modulate a costimulatory signal in activated T cells and induce proliferation and/or cytokine secretion. In addition, the term "activity" includes the ability of a GL50 polypeptide to bind its natural ligand or binding partner. Preferably, the ligand to which a GL50 polypeptide binds is an ICOS molecule. As used herein "activating forms" of costimulatory molecules transmit a signal via a costimulatory receptor (e.g., a signal which activates an immune cell if the receptor is an inhibitory receptor which transmits a costimulatory signal (e.g., CD28 or ICOS) or an inhibitory signal if the receptor is one which transmits a negative signal to an immune cell (e.g., CTLA4). Inhibitory forms of a costimulatory molecule prevent transmission of a signal to an immune cell (e.g., either a costimulatory signal or a negative signal).

As used herein, the term "tumor" includes both benign and malignant (cancerous) neoplasias, (e.g., carcinomas, sarcomas, leukemias, and lymphomas). The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, a "naturally-occurring" nucleic acid molecule refers to an RNA or DNA molecule having a nucleotide sequence that occurs in nature (e.g., encodes a natural protein).

As used herein, an "antisense" nucleic acid molecule comprises a nucleotide sequence which is complementary to a "sense" nucleic acid molecule encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., GL50). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g. humanized, chimeric, etc. Preferably, antibodies of the invention bind specifically or substantially specifically to GL50 molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds GL50 is substantially free of antibodies that specifically bind antigens other than GL50). Moreover, an isolated antibody may be substantially free of other cellular material and/or chemicals.

As used herein, "binding partner" is a target molecule or a molecule with which a GL50 polypeptide binds or interacts in nature (e.g., a ligand or an intracellular interactor molecule (such as a molecule that acts either upstream or downstream of GL50 in a signal transduction pathway)), such that a GL50 activity is achieved.

The term "signal transduction" is intended to encompass the processing of physical or chemical signals from the extracellular environment through the cell membrane and into the cell, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation. A "signaling pathway" refers to the components involved in "signal transduction" of a particular signal into a cell.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |

-continued

| | |
|---|---|
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a GL50 polypeptide of the invention (or any portion thereof) can be used to derive the GL50 amino acid sequence, using the genetic code to translate the DNA or RNA molecule into an amino acid sequence. Likewise, for any GL50-amino acid sequence, corresponding nucleotide sequences that can encode GL50 polypeptide can be deduced from the genetic code (which, because of its redundancy, will produce multiple nucleic acid sequences for any given amino acid sequence). Thus, description and/or disclosure herein of a GL50 nucleotide sequence should be considered to also include description and/or disclosure of the amino acid sequence encoded by the nucleotide sequence. Similarly, description and/or disclosure of a GL50 amino acid sequence herein should be considered to also include description and/or disclosure of all possible nucleotide sequences that can encode the amino acid sequence.

II. ISOLATED NUCLEIC ACID MOLECULES

One aspect of the invention pertains to isolated nucleic acid molecules that encode GL50 polypeptides or biologically active portions thereof, as well as nucleic acid fragments sufficient for use as hybridization probes to identify GL50-encoding nucleic acid molecules (e.g., GL50 mRNA) and fragments for use as PCR primers for the amplification or mutation of GL50 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid (i.e., sequences located at the 5' and 3' ends of the nucleic acid) in the genomic DNA of the organism from which the nucleic acid molecule is derived. For example, in various embodiments, the isolated GL50 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" GL50 nucleic acid molecule may, however, be linked to other nucleotide sequences that do not normally flank the GL50 sequences in genomic DNA (e.g., the GL50 nucleotide sequences may be linked to vector sequences). In certain preferred embodiments, an "isolated" nucleic acid molecule, such as a cDNA molecule, also may be free of other cellular material. However, it is not necessary for the GL50 nucleic acid molecule to be free of other cellular material to be considered "isolated" (e.g., a GL50 DNA molecule separated from other mammalian DNA and inserted into a bacterial cell would still be considered to be "isolated").

A nucleic acid molecule of the present invention, e.g., a nucleic acid molecule having the nucleotide sequence of SEQ ID NO: 1, 3, or 5, or a portion thereof, can be isolated using standard molecular biology techniques and the sequence information provided herein. For example, using all or portion of the nucleic acid sequence of SEQ ID NO: 1, 3, or 5, as a hybridization probe, GL50 nucleic acid molecules can be isolated using standard hybridization and cloning techniques (e.g., as described in Sambrook, J. et al. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO: 1, 3, or 5 can be isolated by the polymerase chain reaction (PCR) using synthetic oligonucleotide primers designed based upon the sequence of SEQ ID NO: 1, 3, or 5, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to GL50 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1, 3, or 5.

In one embodiment, an isolated nucleic acid molecule of the invention comprises a nucleic acid molecule which is a complement of the nucleotide sequence shown in SEQ ID NO: 1, 3, or 5, or a portion of any of these nucleotide sequences. A nucleic acid molecule which is complementary to the nucleotide sequence shown in SEQ ID NO:1, 3, or 5, is one which is sufficiently complementary to the nucleotide sequence shown in SEQ ID NO:1, 3, or 5, respectively, such that it can hybridize to the nucleotide sequence shown in SEQ ID NO: 1, 3, or 5, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO: 1, 3, or 5, or a portion of any of these nucleotide sequences.

Moreover, the nucleic acid molecule of the invention can comprise only a portion of the nucleic acid sequence of SEQ ID NO: 1, 3, or 5, for example a fragment which can be used as a probe or primer or a fragment encoding a biologically active portion of a GL50 polypeptide. The nucleotide sequence determined from the cloning of the GL50 genes allows for the generation of probes and primers designed for use in identifying and/or cloning other GL50 family members, as well as GL50 family homologues from other species. The probe/primer typically comprises a substantially purified oligonucleotide. In one embodiment, the oligonucleotide comprises a region of nucleotide sequence that hybridizes under stringent conditions to at least about 12 or 15, preferably about 20 or 25, more preferably about 30, 35, 40, 45, 50, 55, 60, 65, 75, or 100 consecutive nucleotides of a sense sequence of SEQ ID NO:1, 3, or 5, or of a naturally occurring allelic variant or mutant of SEQ ID NO: 1, 3, or 5. In another embodiment, a nucleic acid molecule of the present invention comprises a nucleotide sequence which is at least about 400, 450, 500, 550, 600, 650, 700, 750, 800, 900, 1000, or 1100 nucleotides in length and hybridizes under stringent hybridization conditions to a nucleic acid molecule of SEQ ID NO: 1, 3, or 5.

In another embodiment, a nucleic acid molecule of the invention comprises at least about 100, 200, 300, 400, 500, 600, 700, 800, 900, 1000, or 1100 contiguous nucleotides of SEQ ID NO:1, 3, or 5.

In one embodiment, a nucleic acid molecule of the invention, e.g., for use as a probe, does not include the portion of SEQ ID NO:1 from about nucleotides 1-370 of SEQ ID NO:5.

Preferably, an isolated nucleic acid molecule of the invention comprises at least a portion of the coding region of SEQ ID NO:1 (shown in nucleotides 67-1032) or SEQ ID NO:3 (shown in nucleotides 1-1041) or SEQ ID NO:5 (shown in nucleotides 24-950). In another embodiment, a nucleic acid molecule of the invention comprises the entire coding region of SEQ ID NO:1, 3, or 5.

In other embodiments, a nucleic acid molecule of the invention has at least 70% identity, more preferably 80% identity, and even more preferably 90% identity with a nucleic acid molecule comprising: at least about 300, 400, 500, 600, 700, 800, or at about 900 nucleotides of SEQ ID NO:1, 3, or 5, or at least about 1000 or 1100 contiguous nucleotides of SEQ ID NO:1 or 3.

Probes based on the GL50 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a GL50 polypeptide, such as by measuring a level of a GL50-encoding nucleic acid in a sample of cells from a subject e.g., detecting GL50 mRNA levels or determining whether a genomic GL50 gene has been mutated or deleted.

A nucleic acid fragment encoding a "biologically active portion of a GL50 polypeptide" can be prepared by isolating a portion of the nucleotide sequence of SEQ ID NO:1, 3, or 5, which encodes a polypeptide having a GL50 biological activity (the biological activities of the GL50 polypeptides are described herein), expressing the encoded portion of the GL50 polypeptide (e.g., by recombinant expression in vitro) and assessing the activity of the encoded portion of the GL50 polypeptide.

Nucleic acid molecules that differ from SEQ ID NO: 1, 3, or 5 due to degeneracy of the genetic code, and thus encode the same a GL50 member protein as that encoded by SEQ ID NO:1, 3, or 5 are encompassed by the invention. Accordingly, in another embodiment, an isolated nucleic acid molecule of the invention has a nucleotide sequence encoding a protein having an amino acid sequence shown in SEQ ID NO:2, 4 or 6. In another embodiment, an isolated nucleic acid molecule of the invention has a nucleotide sequence encoding a GL50 polypeptide.

In addition to the GL50 nucleotide sequences shown in SEQ ID NO:1, 3, or 5, it will be appreciated by those skilled in the art that DNA sequence polymorphisms that lead to changes in the amino acid sequences of the GL50 polypeptides may exist within a population (e.g., the human population). Such genetic polymorphism in the GL50 genes may exist among individuals within a population due to natural allelic variation. As used herein, the terms "gene" and "recombinant gene" refer to nucleic acid molecules which include an open reading frame encoding a GL50 polypeptide, preferably a mammalian GL50 polypeptide, and can further include non-coding regulatory sequences, and introns. Such natural allelic variations include both functional and non-functional GL50 polypeptides and can typically result in 1-5% variance in the nucleotide sequence of a GL50 gene. Any and all such nucleotide variations and resulting amino acid polymorphisms in GL50 genes that are the result of natural allelic variation and that do not alter the functional activity of a GL50 polypeptide are intended to be within the scope of the invention.

Moreover, nucleic acid molecules encoding other GL50 family members and, thus, which have a nucleotide sequence which differs from the GL50 family sequences of SEQ ID NO: 1, 3, or 5 are intended to be within the scope of the invention. For example, another mGL50-1 can be identified based on the nucleotide sequence of hGL50. Moreover, nucleic acid molecules encoding GL50 polypeptides from different species, and thus which have a nucleotide sequence which differs from the GL50 sequences of SEQ ID NO: 1, 3, or 5 are intended to be within the scope of the invention. For example, an ortholog of the mGL50-1 can be identified based on the murine nucleotide sequence.

Nucleic acid molecules corresponding to natural allelic variants and homologues of the GL50 molecules of the invention can be isolated, e.g., based on their homology to the GL50 nucleic acids disclosed herein using the cDNAs disclosed herein, or portions thereof, as hybridization probes according to standard hybridization techniques. For example, a GL50 DNA can be isolated from a human genomic DNA library using all or portion of SEQ ID NO: 1, 3, or 5 as a hybridization probe and standard hybridization techniques (e.g., as described in Sambrook, J., et al. *Molecular Cloning: A Laboratory Manual*. 2nd, ed., Cold Spring Harbor Laboratory, Cold Spring Harbor, N.Y., 1989). Moreover, a nucleic acid molecule encompassing all or a portion of a GL50 gene can be isolated by the polymerase chain reaction using oligonucleotide primers designed based upon the sequence of SEQ ID NO:1, 3, or 5. For example, mRNA can be isolated from cells (e.g., by the guanidinium-thiocyanate extraction procedure of Chirgwin et al. (1979) *Biochemistry* 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1, 3, or 5. A nucleic acid molecule of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a GL50 nucleotide sequence can be prepared by standard synthetic techniques, e.g., using an automated DNA synthesizer.

In another embodiment, an isolated nucleic acid molecule of the invention can be identified based on shared nucleotide sequence identity using a mathematical algorithm. Such algorithms are outlined in more detail below (see, e.g., section III).

In another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO: 1, 3, or 5. In other embodiment, the nucleic acid molecule is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of SEQ ID NO: 1, 3, or 5 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). In addition to the GL50 nucleotide sequences shown in SEQ ID NO:1, 3, or 5 it will be appreciated by those skilled in the art that DNA sequence polymorphisms that lead to minor changes in the nucleotide or amino acid sequences of a GL50 may exist within a population. Such genetic polymorphism in a GL50 gene may exist among individuals within a population due to natural allelic variation. Such natural allelic variations can typically result in 1-2% variance in the nucleotide sequence of the gene. Such nucleotide variations and resulting amino acid polymorphisms in a GL50 that are the result of natural allelic variation and that do not alter the functional activity of a GL50 polypeptide are within the scope of the invention.

In addition to naturally-occurring allelic variants of GL50 sequences that may exist in the population, the skilled artisan will further appreciate that minor changes may be introduced by mutation into nucleotide sequences, e.g., of SEQ ID NO: 1, 3, or 5, thereby leading to changes in the amino acid sequence of the encoded protein, without altering the functional activity of a GL50 polypeptide. For example, nucleotide substitutions leading to amino acid substitutions at "non-essential" amino acid residues may be made in the sequence of SEQ ID NO: 1, 3, or 5. A "non-essential" amino acid residue is a residue that can be altered from the wild-type sequence of a GL50 nucleic acid molecule (e.g., the sequence of SEQ ID NO: 1, 3, or 5) without altering the functional activity of a GL50 molecule. Exemplary residues which are non-essential and, therefore, amenable to substitution, can be identified by one of ordinary skill in the art by performing an amino acid alignment of B7 family members (or of GL50 family members) and determining residues that are not conserved. Such residues, because they have not been conserved, are more likely amenable to substitution.

Accordingly, another aspect of the invention pertains to nucleic acid molecules encoding GL50 polypeptides that contain changes in amino acid residues that are not essential for a GL50 activity. Such GL50 polypeptides differ in amino acid sequence from SEQ ID NO:2, 4, or 6-yet retain an inherent GL50 activity. An isolated nucleic acid molecule encoding a non-natural variant of a GL50 polypeptide can be created by introducing one or more nucleotide substitutions, additions or deletions into the nucleotide sequence of SEQ ID NO: 1, 3, or 5 such that one or more amino acid substitutions, additions or deletions are introduced into the encoded protein. Mutations can be introduced into SEQ ID NO:1, 3, or 5 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a GL50 is preferably replaced with another amino acid residue from the same side chain family.

Alternatively, in another embodiment, mutations can be introduced randomly along all or part of a GL50 coding sequence, such as by saturation mutagenesis or rational cassette mutagenesis, and the resultant mutants can be screened for their ability to bind to a ligand, or to bind to intracellular interactor molecules to identify mutants that retain functional activity. Following mutagenesis, the encoded GL50 mutant protein can be expressed recombinantly in a host cell and the functional activity of the mutant protein can be determined using assays available in the art for assessing a GL50 activity.

Accordingly, another aspect of the invention pertains to nucleic acid molecules encoding GL50 polypeptides that contain changes in amino acid residues that are not essential for activity. Homology alignments, such as the pile-up analysis shown herein, can be used to select amino acids which may be amenable to alteration. For example, the 18 amino acid locations which aligned identically between all six molecules within the extracellular domain are well conserved and are, therefore, less likely to be amenable to alteration. Similarly, of the 32 positions that define the predicted IgV-like and IgC-like folds of the B7 family molecules, 13 are identically conserved between all six molecules, most notably the 4 cysteines that allow intramolecular folding of domains.

Therefore, these amino acids are unlikely to be amenable to alteration. Other areas of significant sequence conservation were also seen in the extracellular domain. For example, valine residue corresponding to position 86 of mGL50-1 is shared by hGL50, and B7-2 sequences may not be amenable to alteration. Likewise, the tyrosine at position 87 of mouse mGL50-1 which is conserved at corresponding locations in hGL50 and B7-1. The 16 positions with identity scores of 8 (5 positions are shared by mouse mGL50-1/hGL50 and B7-1, 4 positions shared between mouse mGL50-1/hGL50 and B7-2, and 6 positions are shared between B7-1 and B7-2) may not be amenable to alteration. In addition, positions in the transmembrane and/or cytoplasmic domains conserved among the GL50 family members (in particular tyrosind residues in the transmembrane or cytoplasmic domain of a GL50 molecule). Again, these positions are unlikely to be amenable to alteration if GL50 activity is to be maintained.

Yet another aspect of the invention pertains to non-naturally occurring GL50 molecules nucleic acid molecules which are chimeric in that they comprise a nucleic acid sequence encoding GL50 transmembrane or cytoplasmic domain which they do not naturally comprise. For example, in one embodiment, transmembrane and/or cytoplasmic domains of a GL50 domain can be "swapped" or "shuffled" using standard molecular biology techniques to create GL50 molecules that have altered signal transduction properties as compared to a naturally occurring GL50 molecule. Such nucleic acid and polypeptide molecules are also embraced by the invention.

In yet another aspect, GL50 nucleic acid molecules can be engineered to comprise nucleic acid sequences encoding at least a portion of another B7 family member, e.g., B7-1 or B7-2. For example, using standard techniques, nucleic acid molecules can be made that encode hybrid GL50/B7 molecules with ligand binding and/or signaling properties that differ from those seen in naturally occurring molecules. For example, in one embodiment, the sequence of chicken GL50 (Y08823) can be used to design molecules with altered signaling and/or binding properties. The sequence similarity between avian GL50 and mammalian forms of the molecule and their difference in ligand preference can be exploited to this end. For instance, progressive substitution of residues conserved between avian GL50-like protein (Y08823) and GL50 with those found in GL50 (to make the molecule more GL50-like) may result in a functional molecule that binds to ICOS and CD28 and CTLA4. Ig-fusion or other constructs comprising hybrid GL50/B7 proteins can be used to achieve differential activation or inhibition of target cell populations and skewing of T cell phenotypes. Such nucleic acid and polypeptide molecules are also embraced by the invention.

Yet another aspect of the invention pertains to isolated nucleic acid molecules encoding a GL50 fusion proteins. Such nucleic acid molecules, comprising at least a first nucleotide sequence encoding a GL50 polypeptide, polypeptide or peptide operatively linked to a second nucleotide sequence encoding a non-GL50 polypeptide, polypeptide or peptide, can be prepared by standard recombinant DNA techniques.

In a preferred embodiment, a mutant GL50 polypeptide can be assayed for the ability to: 1) costimulate (or inhibit the costimulation of, e.g., in soluble form) the proliferation and/or effector function (e.g., cytokine secretion (such as, for example IL-2 or IL-10) of activated T cells; 2) bind to an anti-B7 antibody; and/or 3) bind to a GL50 ligand (e.g., to CD28, CTLA4, and/or ICOS).

In addition to the nucleic acid molecules encoding GL50 polypeptides described above, another aspect of the invention pertains to isolated nucleic acid molecules which are antisense thereto. An "antisense" nucleic acid molecule comprises a nucleotide sequence which is complementary to a "sense" nucleic acid molecule encoding a protein, e.g., complementary to the coding strand of a double-stranded cDNA molecule or complementary to an mRNA sequence. Accordingly, an antisense nucleic acid molecule can hydrogen bond to a sense nucleic acid molecule. The antisense nucleic acid molecule can be complementary to an entire GL50 coding strand, or only to a portion thereof. In one embodiment, an antisense nucleic acid molecule is antisense to a "coding region" of the coding strand of a nucleotide sequence encoding GL50. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding GL50. The term "noncoding region" refers to 5' and 3' sequences which flank the coding region that are not translated into amino acids (i.e., also referred to as 5' and 3' untranslated regions).

Given the coding strand sequences encoding GL50 disclosed herein, antisense nucleic acid molecules of the invention can be designed according to the rules of Watson and Crick base pairing. The antisense nucleic acid molecule can be complementary to the entire coding region of GL50 mRNA, but more preferably is an oligonucleotide which is antisense to only a portion of the coding or noncoding region of GL50 mRNA. For example, the antisense oligonucleotide can be complementary to the region surrounding the translation start site of GL50 mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a GL50 polypeptide to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid molecule of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) *Nature* 334:585-591)) can be used to catalytically cleave GL50 mRNA transcripts to thereby inhibit translation of GL50 mRNA. A ribozyme having specificity for a GL50-encoding nucleic acid can be designed based upon the nucleotide sequence of a GL50 disclosed herein (e.g., SEQ ID NO: 1, 3, or 5). For example, a derivative of a Tetrahymena L-19 IVS RNA can be constructed in which the nucleotide sequence of the active site is complementary to the nucleotide sequence to be cleaved in a GL50-encoding mRNA. See, e.g., Cech et al. U.S. Pat. No. 4,987,071; and Cech et al. U.S. Pat. No. 5,116,742. Alternatively, GL50 mRNA can be used to select a catalytic RNA having a specific ribonuclease activity from a pool of RNA molecules. See, e.g., Bartel, D. and Szostak, J. W. (1993) *Science* 261:1411-1418.

Alternatively, GL50 gene expression can be inhibited by targeting nucleotide sequences complementary to the regulatory region of the GL50 (e.g., the GL50 promoter and/or enhancers) to form triple helical structures that prevent transcription of the GL50 gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioessays* 14(12):807-15.

In yet another embodiment, the GL50 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. and Nielsen, P. E. (1996) *Bioorg Med. Chem.* 4(1):5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra; Perry-O'Keefe et al. (1996) *Proc. Natl. Acad. Sci. USA* 93:14670-675.

PNAs of GL50 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of GL50 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup and Nielsen (1996) supra)); or as probes or primers for DNA sequencing or hybridization (Hyrup and Nielsen (1996) supra; Perry-O'Keefe (1996) supra).

In another embodiment, PNAs of GL50 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of GL50 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) *Nucleic Acids Res.* 24(17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acids Res.* 17:5973-88). PNA monomers are then coupled in a stepwise manner to produce a chimeric molecule with a 5' PNA segment and a 3' DNA segment (Finn et al. (1996) supra). Alternatively, chimeric molecules can be synthesized with a 5' DNA segment and a 3' PNA segment (Peterser, K. H. et al. (1975) *Bioorganic Med. Chem. Lett.* 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Biotechniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

III. ISOLATED GL50 POLYPEPTIDES AND ANTI-GL50 ANTIBODIES

One aspect of the invention pertains to isolated GL50 polypeptides, and biologically active portions thereof, as well as polypeptide fragments suitable for use as immunogens to raise anti-GL50 antibodies. In one embodiment, native GL50 polypeptides can be isolated from cells or tissue sources by an appropriate purification scheme using standard protein purification techniques. In another embodiment, GL50 polypeptides are produced by recombinant DNA techniques. Alternative to recombinant expression, a GL50 polypeptide or polypeptide can be synthesized chemically using standard peptide synthesis techniques.

An "isolated" or "purified" protein or biologically active portion thereof is substantially free of cellular material or other contaminating proteins from the cell or tissue source from which the GL50 polypeptide is derived, or substantially free from chemical precursors or other chemicals when chemically synthesized. The language "substantially free of cellular material" includes preparations of GL50 polypeptide in which the protein is separated from cellular components of the cells from which it is isolated or recombinantly produced. In one embodiment, the language "substantially free of cellular material" includes preparations of GL50 polypeptide having less than about 30% (by dry weight) of non-GL50 polypeptide (also referred to herein as a "contaminating protein"), more preferably less than about 20% of non-GL50 polypeptide, still more preferably less than about 10% of non-GL50 polypeptide, and most preferably less than about 5% non-GL50 polypeptide. When the GL50 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of GL50 polypeptide in which the protein is separated from chemical precursors or other chemicals which are involved in the synthesis of the protein. In one embodiment, the language "substantially free of chemical precursors or other chemicals" includes preparations of GL50 polypeptide having less than about 30% (by dry weight) of chemical precursors or non-GL50 chemicals, more preferably less than about 20% chemical precursors or non-GL50 chemicals, still more preferably less than about 10% chemical precursors or non-GL50 chemicals, and most preferably less than about 5% chemical precursors or non-GL50 chemicals.

Another aspect of the invention pertains to isolated GL50 polypeptides. Preferably, the GL50 polypeptides comprise the amino acid sequence encoded by SEQ ID NO: 1, 3, or 5. In another preferred embodiment, the protein comprises the amino acid sequence of SEQ ID NO:2, 4, or 6. In other embodiments, the protein has at least 50%, at least 60% amino acid identity, more preferably 70% amino acid identity, more preferably 80%, and even more preferably, 90% or 95% amino acid identity with the amino acid sequence shown in SEQ ID NO:2, 4, or 6.

In other embodiments, the invention provides isolated portions of a GL50 polypeptide. GL50 polypeptides comprising a GL50 polypeptide domain. Exemplary GL50 polypeptide domains are shown in FIG. 12 and include, IgV-like, IgC-like, transmembrane, and cytoplasmic domains.

The invention further pertains to soluble forms of GL50 polypeptides. Such forms can be naturally occurring or can be engineered and can comprise, e.g., an extracellular domain of a GL50 polypeptide. In one embodiment, the extracellular domain of a GL50 polypeptide comprises the IgV and IgC domains after cleavage of the signal sequence, but not the transmembrane and cytoplasmic domains of a GL50 polypeptide (e.g., corresponding to the amino acid sequence from about amino acid 47-279 of SEQ ID NO:2 or about amino acid 22-258 of SEQ ID NO:6).

Biologically active portions of a GL50 polypeptide include peptides comprising amino acid sequences sufficiently homologous to or derived from the amino acid sequence of the GL50 polypeptide, which include less amino acids than the full length GL50 polypeptides, and exhibit at least one activity of a GL50 polypeptide. Typically, biologically active portions comprise a domain or motif with at least one activity of the GL50 polypeptide. A biologically active portion of a GL50 polypeptide can be a polypeptide which is, for example, at least 10, 25, 50, 100, 150, 200 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100). The percent identity between the two sequences is a function of the number of identical positions shared by the sequences, taking into account the number of gaps, and the length of each gap, which are introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. A non-limiting example of a mathematical algorithm utilized for comparison of sequences is the algorithm of Karlin and Altschul (1990) *Proc. Natl. Acad. Sci. USA* 87:2264, modified as in Karlin and Altschul (1993) *Proc. Natl. Acad Sc. USA* 90:5873. Such an algorithm is incorporated into the NBLAST and XBLAST programs (version 2.0) of Altschul, et al. (1990) J. Mol. Biol. 215:403. BLAST nucleotide searches can be performed with the NBLAST program score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Research 25(17):3389. When utilizing BLAST and Gapped BLAST programs, the default parameters of the respective programs (e.g., XBLAST and NBLAST) can be used. See http://www.ncbi.nlm.nih.gov. Another preferred, non-limiting example of an algorithm utilized for the comparison of sequences is the algorithm of Myers and Miller, CABIOS (1989). Such an algorithm is incorporated into the ALIGN program (version 2.0 or 2.OU) which is part of the GCG sequence alignment software package. When utilizing the ALIGN program for comparing amino acid sequences, a PAM120 weight residue table, a gap length penalty of 12, and a gap penalty of 4 can be used.

As another example, the alignment program in Geneworks program (by Oxford Molecular; e.g., version 2.5.1) can be used with the parameters set as follows: gap creation=16, extension penalty=4, scoring matrix=fastadna.cmp, and a constant PAM factor.

Another non-limiting example of a mathematical algorithm utilized for the alignment of protein sequences is the Lipman-Pearson algorithm (Lipman and Pearson (1985) *Science* 227:1435). When using the Lipman-Pearson algorithm, a PAM250 weight residue table, a gap length penalty of 12, a gap penalty of 4, and a Kutple of 2 can be used. A preferred, non-limiting example of a mathematical algorithm utilized for the alignment of nucleic acid sequences is the Wilbur-Lipman algorithm (Wilbur and Lipman (1983) *Proc. Natl. Acad. Sci. USA* 80:726). When using the Wilbur-Lipman algorithm, a window of 20, gap penalty of 3, Ktuple of 3 can be used. Both the Lipman-Pearson algorithm and the Wilbur-Lipman algorithm are incorporated, for example, into the MegAlign program (e.g., version 3.1.7) which is part of the DNASTAR sequence analysis software package.

Additional algorithms for sequence analysis are known in the art, and include ADVANCE and ADAM., described in Torelli and Robotti (1994) *Comput. Appl. Biosci.* 10:3; and FASTA, described in Pearson and Lipman (1988) *Proc. Natl. Acad. Sci. USA* 85:2444.

In a preferred embodiment, the percent identity between two amino acid sequences is determined using the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2, 3, 4, 5, or 6.

Protein alignments can also be made using the Geneworks global protein alignment program (e.g., version 2.5.1) with the cost to open gap set at 5, the cost to lengthen gap set at 5, the minimum diagonal length set at 4, the maximum diagonal offset set at 130, the consensus cutoff set at 50% and utilizing the Pam 250 matrix.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to GL50 nucleic acid molecules of the invention. BLAST protein searches can be performed with the XBLAST program, score=50, wordlength=3 to obtain amino acid sequences homologous to GL50 polypeptide molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used. For example, the nucleotide sequences of the invention can be analyzed using the default Blastn matrix 1-3 with gap penalties set at: existence 11 and extension 1. The amino acid sequences of the invention can be analyzed using the default settings: the Blosum62 matrix with gap penalties set at existence 11 and extension 1. See http://www.ncbi.nlm.nih.gov.

The presence of divergent carboxyl regions on RACE clones illustrated by sequence alignments suggest that alternate signaling functions may be performed by these distinct molecules by the additional tyrosines in the intracellular domain of these molecules. To date, only sporadic studies have been performed to determine whether intracellular signaling for either B7-1 or B7-2. On the basis of the presence of cytoplasmic domain tyrosines on GL50 sequences, one can predict that such signaling events exist. Inspection of the cytoplasmic domains of mouse and human B7-1 and B7-2 show negligible similarity and it has also been suggested that the B7 cytoplasmic domain may be completely dispensable, based on the reported ability of B7 molecules to function in gpi-anchored constructs completely lacking cytoplasmic sequences. Accordingly, in one embodiment, tyrosine residues in the intracellular domain of a GL50 tyrosine molecule can be altered to modulate intracellular signally via a GL50 polypeptide.

The invention also provides GL50 chimeric or fusion proteins. As used herein, a GL50 "chimeric protein" or "fusion protein" comprises a GL50 polypeptide operatively linked to a non-GL50 polypeptide. An "GL50 polypeptide" refers to a polypeptide having an amino acid sequence corresponding to GL50 polypeptide, whereas a "non-GL50 polypeptide" refers to a polypeptide having an amino acid sequence corresponding to a protein which is not substantially homologous to the GL50 polypeptide, e.g., a protein which is different from the GL50 polypeptide and which is derived from the same or a different organism. Within a GL50 fusion protein the GL50 polypeptide can correspond to all or a portion of a GL50 polypeptide. In a preferred embodiment, a GL50 fusion protein comprises at least one biologically active portion of a GL50 polypeptide, e.g., an extracellular domain of a GL50 polypeptide. Within the fusion protein, the term "operatively linked" is intended to indicate that the GL50 polypeptide and the non-GL50 polypeptide are fused in-frame to each other. The non-GL50 polypeptide can be fused to the N-terminus or C-terminus of the GL50 polypeptide.

For example, in one embodiment, the fusion protein is a GST-GL50 member fusion protein in which the GL50 member sequences are fused to the C-terminus of the GST sequences. In another embodiment, the fusion protein is a GL50 member-HA fusion protein in which the GL50 member nucleotide sequence is inserted in a vector such as pCEP4-HA vector (Herrscher, R. F. et al. (1995) *Genes Dev.* 9:3067-3082) such that the GL50 member sequences are fused in frame to an influenza hemagglutinin epitope tag. Such fusion proteins can facilitate the purification of a recombinant GL50 member or can be used when a molecule that does not bind to an Fc receptor is desired.

A GL50 fusion protein can be produced by recombinant expression of a nucleotide sequence encoding a first peptide having GL50 activity and a nucleotide sequence encoding second peptide corresponding to a moiety that alters the solubility, affinity, stability or valency of the first peptide, for example, an immunoglobulin constant region. Preferably, the first peptide consists of a portion of the of a GL50 polypeptide (e.g., a portion of amino acid residues (after cleavage of a signal sequence, e.g., corresponding to about amino acids 1-44 of SEQ ID NO:2) of the sequence shown in SEQ ID NO:2, 4, or 6 that is sufficient to costimulate activated T cells. The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964, 5,580,756, 5,844,095 and the like, incorporated herein by reference).

Particularly preferred GL501 g fusion proteins include the extracellular domain portion or variable region-like domain of a hGL50 coupled to an immunoglobulin constant region. The immunoglobulin constant region may contain genetic modifications which reduce or eliminate effector activity inherent in the immunoglobulin structure. For example, DNA encoding the extracellular portion of a GL50 polypeptide can be joined to DNA encoding the hinge, CH2 and CH3 regions of human IgCγ1 and/or IgCγ4 modified by site directed mutagenesis, e.g., as taught in WO 97/28267.

The nucleotide and amino acid sequences of exemplary soluble GL50 and ICOS constructs are presented in FIGS. 26-29. FIG. 26 sets forth exemplary human ICOS fusion protein nucleic acid and amino acid sequence, FIG. 27 sets forth an exemplary murine ICOS fusion protein nucleic acid and amino acid sequence, FIG. 28 sets forth an exemplary human GL50 fusion protein nucleic acid and amino acid sequence, and FIG. 29 sets forth an exemplary murine GL50 fusion protein nucleic acid and amino acid sequence.

A resulting GL50-Ig fusion protein may have altered solubility, binding affinity, stability and/or valency (i.e., the number of binding sites available per molecule) and may increase the efficiency of protein purification. Fusion proteins and peptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a GL50 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termin, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, Ausubel et al. eds. John Wiley & Sons: 1992). Moreover, many expression vectors are commercially available that already encode a fusion moiety (e.g., a GST polypeptide or an HA epitope tag). A GL50 encoding nucleic acid can be cloned into such an expression vector such that the fusion moiety is linked in-frame to the GL50 polypeptide.

In another embodiment, the fusion protein is a GL50 polypeptide containing a heterologous signal sequence at its N-terminus. In certain host cells (e.g., mammalian host cells), expression and/or secretion of GL50 can be increased through use of a heterologous signal sequence.

The GL50 fusion proteins of the invention can be incorporated into pharmaceutical compositions and administered to a subject in vivo. Use of GL50 fusion proteins may be useful therapeutically for the treatment of immunological disorders, e.g., autoimmune diseases or in the case of transplantation. Moreover, the GL50-fusion proteins of the invention can be used as immunogens to produce anti-GL50 antibodies in a subject, to purify GL50 ligands and in screening assays to identify molecules which inhibit the interaction of GL50 with a GL50 ligand.

The present invention also pertains to variants of the GL50 polypeptides which function as either GL50 agonists (mimetics) or as GL50 antagonists. Variants of the GL50 polypeptides can be generated by mutagenesis, e.g., discrete point mutation or truncation of a GL50 polypeptide. An agonist of the GL50 polypeptides can retain substantially the same, or a subset, of the biological activities of the naturally occurring form of a GL50 polypeptide. An antagonist of a GL50 polypeptide can inhibit one or more of the activities of the naturally occurring form of the GL50 polypeptide by, for example, competitively modulating a cellular activity of a GL50 polypeptide. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the GL50 polypeptide.

In one embodiment, variants of a GL50 polypeptide which function as either GL50 agonists (mimetics) or as GL50 antagonists can be identified by screening combinatorial libraries of mutants, e.g., truncation mutants, of a GL50 polypeptide for GL50 polypeptide agonist or antagonist activity. In one embodiment, a variegated library of GL50 variants is generated by combinatorial mutagenesis at the nucleic acid level and is encoded by a variegated gene library. A variegated library of GL50 variants can be produced by, for example, enzymatically ligating a mixture of synthetic oligonucleotides into gene sequences such that a degenerate set of potential GL50 sequences is expressible as individual polypeptides, or alternatively, as a set of larger fusion proteins (e.g., for phage display) containing the set of GL50 sequences therein. There are a variety of methods which can be used to produce libraries of potential GL50 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential GL50 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477.

In addition, libraries of fragments of a GL50 polypeptide coding sequence can be used to generate a variegated population of GL50 fragments for screening and subsequent selection of variants of a GL50 polypeptide. In one embodiment, a library of coding sequence fragments can be generated by treating a double stranded PCR fragment of a GL50 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the GL50 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of GL50 polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify GL50 variants (Arkin and Youvan (1992) $Proc.\ Natl.\ Acad.\ Sci.\ USA$ 89:7811-7815; Delagrave et al. (1993) $Protein\ Eng.$ 6(3):327-331).

In one embodiment, cell based assays can be exploited to analyze a variegated GL50 library. For example, a library of expression vectors can be transfected into a cell line which ordinarily synthesizes and secretes GL50. The transfected cells are then cultured such that GL50 and a particular mutant GL50 are secreted and the effect of expression of the mutant on GL50 activity in cell supernatants can be detected, e.g., by any of a number of enzymatic assays. Plasmid DNA can then be recovered from the cells which score for inhibition, or alternatively, potentiation of GL50 activity, and the individual clones further characterized.

In addition to GL50 polypeptides consisting only of naturally-occurring amino acids, GL50 peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human GL50, but have one or more peptide linkages optionally replaced by a linkage selected from the group consisting of: —CH2NH—, —CH2S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci. pp.* 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH)CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of a GL50 amino acid sequence with a D-amino acid of the same type (e.g., D-lysine in place of L-lysine) can be used to generate more stable peptides. In addition, constrained peptides comprising a GL50 amino acid sequence or a substantially identical sequence variation can be generated by methods known in the art (Rizo and Gierasch (1992) *Annu Rev. Biochem.* 61:387, incorporated herein by reference); for example, by adding internal cysteine residues capable of forming intramolecular disulfide bridges which cyclize the peptide.

The amino acid sequences of GL50 polypeptides identified herein will enable those of skill in the art to produce polypeptides corresponding to GL50 peptide sequences and sequence variants thereof. Such polypeptides can be produced in prokaryotic or eukaryotic host cells by expression of polynucleotides encoding a GL50 peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis, and used e.g., as agonists or antagonists of a GL50/GL50 ligand interaction. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

An isolated GL50 polypeptide, or a portion or fragment thereof, can be used as an immunogen to generate antibodies that bind GL50 using standard techniques for polyclonal and monoclonal antibody preparation. A full-length GL50 polypeptide can be used or, alternatively, the invention provides antigenic peptide fragments of GL50 for use as immunogens. The antigenic peptide of GL50 comprises at least 8 amino acid residues and encompasses an epitope of GL50 such that an antibody raised against the peptide forms a specific immune complex with GL50. Preferably, the antigenic peptide comprises at least 10 amino acid residues, more preferably at least 15 amino acid residues, even more preferably at least 20 amino acid residues, and most preferably at least 30 amino acid residues.

Alternatively, an antigenic peptide fragment of a GL50 polypeptide can be used as the immunogen. An antigenic peptide fragment of a GL50 polypeptide typically comprises at least 8 amino acid residues of the amino acid sequence shown in SEQ ID NO:2, 4, or 6 and encompasses an epitope of a GL50 polypeptide such that an antibody raised against the peptide forms an immune complex with a GL50 molecule. Preferred epitopes encompassed by the antigenic peptide are regions of GL50 that are located on the surface of the protein, e.g., hydrophilic regions. In one embodiment, an antibody binds substantially specifically to a GL50 molecule. In another embodiment, an antibody binds specifically to a GL50 polypeptide.

Preferably, the antigenic peptide comprises at least about 10 amino acid residues, more preferably at least about 15 amino acid residues, even more preferably at least about 20 amino acid residues, and most preferably at least about 30 amino acid residues. Preferred epitopes encompassed by the antigenic peptide are regions of a GL50 polypeptide that are located on the surface of the protein, e.g., hydrophilic regions, and that are unique to a GL50 polypeptide. In one embodiment such epitopes can be specific for a GL50 polypeptides from one species, such as mouse or human (i.e., an antigenic peptide that spans a region of a GL50 polypeptide that is not conserved across species is used as immunogen; such non conserved residues can be determined using an alignment such as that provided herein). A standard hydrophobicity analysis of the GL50 polypeptide can be performed to identify hydrophilic regions.

A GL50 immunogen typically is used to prepare antibodies by immunizing a suitable subject, (e.g., rabbit, goat, mouse or other mammal) with the immunogen. An appropriate immunogenic preparation can contain, for example, a recombinantly expressed GL50 polypeptide or a chemically synthesized GL50 peptide. The preparation can further include an adjuvant, such as Freund's complete or incomplete adjuvant, or similar immunostimulatory agent. Immunization of a suitable subject with an immunogenic GL50 preparation induces a polyclonal anti-GL50 antibody response.

Accordingly, another aspect of the invention pertains to anti-GL50 antibodies. Polyclonal anti-GL50 antibodies can be prepared as described above by immunizing a suitable subject with a GL50 immunogen. The anti-GL50 antibody titer in the immunized subject can be monitored over time by standard techniques, such as with an enzyme linked immunosorbent assay (ELISA) using immobilized a GL50 polypeptide. If desired, the antibody molecules directed against a GL50 polypeptide can be isolated from the mammal (e.g., from the blood) and further purified by well known techniques, such as protein A chromatography to obtain the IgG fraction. At an appropriate time after immunization, e.g., when the anti-GL50 antibody titers are highest, antibody-producing cells can be obtained from the subject and used to prepare monoclonal antibodies by standard techniques, such as the hybridoma technique originally described by Kohler and Milstein (1975) *Nature* 256:495-497 (see also, Brown et al. (1981) *J. Immunol* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.*, 3:231-36). Briefly, an immortal cell line (typically a myeloma) is fused to lymphocytes (typically splenocytes) from a mammal immunized with a GL50 immunogen as described above, and the culture supernatants of the resulting hybridoma cells are screened to identify a hybridoma producing a monoclonal antibody that binds specifically to a GL50 polypeptide.

Any of the many well known protocols used for fusing lymphocytes and immortalized cell lines can be applied for the purpose of generating an anti-GL50 monoclonal antibody (see, e.g., Galfre, G. et al. (1977) *Nature* 266:55052; Gefter et al. (1977) supra; Lerner (1981) supra; Kenneth, Monoclonal Antibodies, supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a GL50 molecule, e.g., using a standard ELISA assay.

As an alternative to preparing monoclonal antibody-secreting hybridomas, a monoclonal anti-GL50 antibody can be identified and isolated by screening a recombinant combinatorial immunoglobulin library (e.g., an antibody phage display library) with a GL50 to thereby isolate immunoglobulin library members that bind a GL50 polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al International Publication No. WO 91/17271; Winter et al. International Publication WO 92/20791; Markland et al International Publication No. WO 92/15679; Breitling et al International Publication WO 93/01288; McCafferty et al International Publication No. WO 92/01047; Garrard et al. International Publication No. WO 92/09690; Ladner et al. International Publication No. WO 90/02809; Fuchs et al (1991) *Biotechnology* (NY) 9:1369-1372; Hay et al (1992) *Hum. Antibod. Hybridomas* 3:81-85; Huse et al (1989) *Science* 246:1275-1281; Griffiths et al (1993) *EMBO J.* 12:725-734; Hawkins et al (1992) *J. Mol. Biol.* 226:889-896; Clarkson et al (1991) *Nature* 352:624-628; Gram et al (1992) *Proc. Natl. Acad. Sci. USA* 89:3576-3580; Garrard et al (1991) *Biotechnology* (NY) 9:1373-1377; Hoogenboom et al. (1991) *Nucleic Acids Res.* 19:4133-4137; Barbas et al (1991) *Proc. Natl. Acad. Sci. USA* 88:7978-7982; and McCafferty et al (1990) *Nature* 348:552-554.

Additionally, recombinant anti-GL50 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al International Patent Publication PCT/US86/02269; Akira et al. European Patent Application 184,187; Taniguchi, M. European Patent Application 171,496; Morrison et al European Patent Application 173,494; Neuberger et al. PCT Application WO 86/01533; Cabilly et al. U.S. Pat. No. 4,816,567; Cabilly et al European Patent Application 125,023; Better et al. (1988) *Science* 240:1041-1043; Liu et al (1987) *Proc. Natl. Acad. Sci. USA* 84:3439-3443; Liu et al. (1987) *J. Immunol.* 139:3521-3526; Sun et al (1987) *Proc. Natl. Acad. Sci.* 84:214-218; Nishimura et al (1987) *Cancer Res.* 47:999-1005; Wood et al (1985) *Nature* 314:446-449; and Shaw et al (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al (1986) *Nature* 321:552-525; Verhoeyan et al (1988) *Science* 239:1534; and Beidler et al (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable geneic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al (1995) *Proc. Natl. Acad. Sci. USA* 92:3137-3141; PCT Publication No. WO 94/02610 by Marasco et al.; and PCT Publication No. WO 95/03832 by Duan et al.).

In one embodiment, an antibody for use in the instant invention is a bispecific antibody. A bispecific antibody has binding sites for two different antigens within a single antibody molecule. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridomna technology (Staerz and Bevan (1986) *Proc. Natl. Acad. Sci. USA*, 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. For example, bispecific agents that bind to the T cell receptor complex, the B cell receptor complex, CD40, CD40 ligand, CD2, or CD45 (in addition to GL50 or ICOS) can be developed.

An anti-GL50 antibody (e.g., monoclonal antibody) can be used to isolate a GL50 polypeptide by standard techniques, such as affinity chromatography or immunoprecipitation. Anti-GL50 antibodies can facilitate the purification of natural GL50 polypeptides from cells and of recombinantly produced GL50 polypeptides expressed in host cells. Moreover, an anti-GL50 antibody can be used to detect a GL50 polypeptide (e.g., in a cellular lysate or cell supernatant). In addition, antibodies to GL50 can be used to block the interaction between GL50 and a ligand or binding partner. Detection can be facilitated by coupling (i.e., physically linking) the antibody to a detectable substance. Accordingly, in one embodiment, an anti-GL50 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, and $^{3}$H.

Yet another aspect of the invention pertains to anti-GL50 antibodies that are obtainable by a process comprising:

(a) immunizing an animal with an immunogenic GL50 polypeptide, or an immunogenic portion thereof unique to a GL50 polypeptide; and (b) isolating from the animal antibodies that specifically bind to a GL50 polypeptide.

IV. RECOMBINANT EXPRESSION VECTORS AND HOST CELLS

Another aspect of the invention pertains to vectors, preferably expression vectors, containing a nucleic acid encoding a GL50 family protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., GL50 family proteins, mutant forms of GL50 polypeptides or portions thereof, fusion proteins, and the like).

In one embodiment of the invention, vectors comprising only a transmembrane or intracellular domain of a GL50 molecule can be engineered. Such constructs can be used to modulate intracellular signaling via GL50 molecules, e.g., and act as dominant negative mutants.

The recombinant expression vectors of the invention can be designed for expression of GL50 polypeptides in prokaryotic or eukaryotic cells. For example, GL50 polypeptides can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized therapeutically, in GL50 activity assays, (e.g., direct assays or competitive assays described in detail below), or to generate antibodies specific for GL50 polypeptides, for example.

Examples of suitable inducible non-fusion *E. coli* expression vectors include pTrc (Amann et al. (1988) *Gene,* 69:301-315) and pET 11d (Studier et al. (1990) *Methods Enzymol.* 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in *E. coli* is to express the polypeptide in a host bacteria with an impaired capacity to proteolytically cleave the recombinant polypeptide (Gottesman, S. (1990) *Methods Enzymol.* 185:119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the GL50 expression vector is a yeast expression vector. Examples of vectors for expression in yeast *S. cerivisae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and picZ (Invitrogen Corp, San Diego, Calif.).

Alternatively, a GL50 polypeptide can be expressed in insect cells using baculovirus expression vectors. Baculovirus vectors available for expression of polypeptides in cultured insect cells (e.g., Sf9 cells) include the pAc series (Smith et al. (1983) *Mol. Cell Biol.* 3:2156-2165) and the pVL series (Lucklow, V. A., and Summers, M. D. (1989) *Virology* 170:31-39).

In yet another embodiment, a nucleic acid molecule of the invention is expressed in mammalian cells using a mammalian expression vector. Examples of mammalian expression vectors include pMex-NeoI, pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al. *Molecular Cloning: A Laboratory Manual. 2nd ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Moreover, inducible regulatory systems for use in mammalian cells are known in the art, for example systems in which gene expression is regulated by heavy metal ions (see e.g., Mayo et al (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, Nouer, L., ed. CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al (1987) *Nature* 329:734-736; Israel and Kaufman (1989) *Nucleic Acids Res.* 17:2589-2604; and PCT Publication No. WO 93/23431), FK506-related molecules (see e.g., PCT Publication No. WO 94/18317) or tet-racyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Accordingly, in another embodiment, the invention provides a recombinant expression vector in which a GL50 DNA is operatively linked to an inducible eukaryotic promoter, thereby allowing for inducible expression of a GL50 polypeptide in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to GL50 mRNA. Regulatory sequences operatively linked to a nucleic acid molecule cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a GL50 polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a GL50 polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a GL50 polypeptide. Accordingly, the invention further provides methods for producing a GL50 polypeptide using the host cells of the invention. In one embodiment, the method comprises culturing the host cell of invention (into which a recombinant expression vector encoding a GL50 polypeptide has been introduced) in a suitable medium such that a GL50 polypeptide is produced. In another embodiment, the method further comprises isolating a GL50 polypeptide from the medium or the host cell.

Certain host cells of the invention can also be used to produce non-human transgenic animals. For example, in one embodiment, a host cell of the invention is a fertilized oocyte or an embryonic stem cell into which GL50-coding sequences have been introduced. Such host cells can then be used to create non-human transgenic animals in which exogenous GL50 sequences have been introduced into their genome or homologous recombinant animals in which endogenous GL50 sequences have been altered. Such animals are useful for studying the function and/or activity of a GL50 polypeptide and for identifying and/or evaluating modulators of GL50 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous GL50 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a GL50-encoding nucleic acid into the male pronucleus of a fertilized oocyte, e.g., by microinjection, retroviral infection, and allowing the oocyte to develop in a pseudopregnant female foster animal. The mGL50-1 sequence of SEQ ID NO:1, 3, or 5 can be introduced as a transgene into the genome of a non-human animal. Alternatively, a nonhuman homologue of a hGL50 gene, such as a mouse or rat GL50 gene, can be used as a transgene. Alternatively, a GL50 gene homologue, such as another GL50 family member, can be isolated based on hybridization to the GL50 family cDNA sequences of SEQ ID NO:1, 3, or 5 (described further in subsection I above) and used as a transgene. Intronic sequences and polyadenylation signals can also be included in the transgene to increase the efficiency of expression of the transgene. A tissue-specific regulatory sequence(s) can be operably linked to a GL50 transgene to direct expression of a GL50 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a GL50 transgene in its genome and/or expression of GL50 mRNA in tissues or cells of the animals. A transgenic founder animal can then be used to breed additional animals carrying the transgene. Moreover, transgenic animals carrying a transgene encoding a GL50 polypeptide can further be bred to other transgenic animals carrying other transgenes.

To create a homologous recombinant animal, a vector is prepared which contains at least a portion of a GL50 gene into which a deletion, addition or substitution has been introduced to thereby alter, e.g., functionally disrupt, the GL50 gene. The GL50 gene can be a human gene (e.g., the SEQ ID NO: 1, 3, or 5), but more preferably, is a non-human homologue of a hGL50 gene (e.g., a cDNA isolated by stringent hybridization with the nucleotide sequence of SEQ ID NO: 1, 3, or 5). For example, a mouse GL50 gene can be used to construct a homologous recombination vector suitable for altering an endogenous GL50 gene in the mouse genome. In a preferred embodiment, the vector is designed such that, upon homologous recombination, the endogenous GL50 gene is functionally disrupted (i.e., no longer encodes a functional protein; also referred to as a "knock out" vector). Alternatively, the vector can be designed such that, upon homologous recombination, the endogenous GL50 gene is mutated or otherwise altered but still encodes a functional protein (e.g., the upstream regulatory region can be altered to thereby alter the expression of the endogenous GL50 polypeptide). In the homologous recombination vector, the altered portion of the GL50 gene is flanked at its 5' and 3' ends by additional nucleic acid sequence of the GL50 gene to allow for homologous recombination to occur between the exogenous GL50 gene carried by the vector and an endogenous GL50 gene in an embryonic stem cell. The additional flanking GL50 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced GL50 gene has homologously recombined with the endogenous GL50 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule.

Examples of such enzyme-assisted integration systems include the Cre recombinase-lox target system (e.g., as described in Baubonis, W. and Sauer, B. (1993) *Nuc. Acids Res.* 21:2025-2029; and Fukushige, S, and Sauer, B. (1992) *Proc. Natl. Acad. Sci. USA* 89:7905-7909) and the FLP recombinase-FRT target system (e.g., as described in Dang, D. T. and Perrimon, N. (1992) *Dev. Genet.* 13:367-375; and Fiering, S. et al. (1993) *Proc. Natl. Acad. Sci. USA* 90:8469-8473). Tetracycline-regulated inducible homologous recombination systems, such as described in PCT Publication No. WO 94/29442 and PCT Publication No. WO 96/01313, also can be used.

For example, in another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. PHARMACEUTICAL COMPOSITIONS

GL50 modulators ("active compounds") of the invention (e.g., GL50 inhibitory or stimulatory agents, including GL50 nucleic acid molecules, polypeptides, antibodies, or compounds identified as modulators of a GL50 activity) can be incorporated into pharmaceutical compositions suitable for administration. Such compositions typically comprise the nucleic acid molecule, polypeptide, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a GL50 polypeptide, nucleic acid molecule, or anti-GL50 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a dosage range for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. USES AND METHODS OF THE INVENTION

The nucleic acid molecules, polypeptides, protein homologues, and antibodies described herein can be used in one or more of the following methods: a) methods of treatment, e.g., up- or down-modulating the immune response; b) screening assays; c) predictive medicine (e.g., diagnostic assays, prognostic assays, monitoring clinical trials, and pharmacogenetics). The isolated nucleic acid molecules of the invention can be used, for example, to express GL50 polypeptide (e.g., via a recombinant expression vector in a host cell in gene therapy applications), to detect GL50 mRNA (e.g., in a biological sample) or a genetic alteration in a GL50 gene, and to modulate GL50 activity, as described further below. The GL50 polypeptides can be used to treat disorders characterized by insufficient or excessive production of GL50 inhibitors. In addition, the GL50 polypeptides can be used to screen for naturally occurring GL50 ligands, to screen for drugs or compounds which modulate GL50 activity, as well as to treat disorders characterized by insufficient or excessive production of GL50 polypeptide or production of GL50 polypeptide forms which have decreased or aberrant activity compared to GL50 wild type polypeptide. Moreover, the anti-GL50 antibodies of the invention can be used to detect and isolate GL50 polypeptides, regulate the bioavailability of GL50 polypeptides, and modulate GL50 activity e.g., modulate immune responses.

A. Methods of Treatment:

The present invention provides for both prophylactic and therapeutic methods of treating a subject at risk of (or susceptible to) a disorder or having a disorder associated with aberrant GL50 expression or activity or a disorder that would benefit from modulation of GL50 activity.

1. Prophylactic Methods

In one aspect, the invention provides a method for preventing in a subject, a disease or condition associated with an aberrant GL50 expression or activity, by administering to the subject a GL50 polypeptide or an agent which modulates GL50 polypeptide expression or at least one GL50 activity. Subjects at risk for a disease which is caused or contributed to by aberrant GL50 expression or activity can be identified by, for example, any or a combination of diagnostic or prognostic assays as described herein. Administration of a prophylactic agent can occur prior to the manifestation of symptoms characteristic of GL50 aberrancy, such that a disease or disorder is prevented or, alternatively, delayed in its progression. Depending on the type of GL50 aberrancy or condition, for example, a GL50 polypeptide, GL50 agonist or GL50 antagonist agent can be used for treating the subject. The appropriate agent can be determined based on screening assays described herein.

2. Therapeutic Methods

Another aspect of the invention pertains to methods of modulating GL50 expression or activity for therapeutic purposes. Accordingly, in an exemplary embodiment, the modulatory method of the invention involves contacting a cell with a GL50 polypeptide or agent that modulates one or more of the activities of GL50 polypeptide associated with the cell. An agent that modulates GL50 polypeptide activity can be an agent as described herein, such as a nucleic acid or a polypeptide, a naturally-occurring target molecule of a GL50 polypeptide (e.g., a GL50 ligand), a GL50 antibody, a GL50 agonist or antagonist, a peptidomimetic of a GL50 agonist or antagonist, or other small molecule. In one embodiment, the agent stimulates one or more GL50 activities. Examples of such stimulatory agents include agents that stimulate the interaction of GL50 with a stimulatory receptor or inhibit the interaction of GL50 with an inhibitory receptor, e.g., active GL50 polypeptide, certain soluble forms of GL50 molecules, and a nucleic acid molecule encoding GL50 polypeptide that has been introduced into the cell. In another embodiment, the agent inhibits one or more GL50 activities. Examples of such inhibitory agents include agents that diminish the interaction of GL50 and a costimulatory receptor or promote the interaction between GL50 and an inhibitory receptor, e.g., antisense GL50 nucleic acid molecules, anti-GL50 antibodies, and GL50 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder that would benefit from modulation of a GL50 polypeptide, e.g., a disorder which would benefit from up- or down-modulation of the immune response, or which is characterized by aberrant expression or activity of a GL50 polypeptide or nucleic acid molecule. In one embodiment, the method involves administering an agent (e.g., an agent identified by a screening assay described herein), or combination of agents that modulates (e.g., upregulates or downregulates) GL50 expression or activity. In another embodiment, the method involves administering a GL50 polypeptide or nucleic acid molecule as therapy to compensate for reduced or aberrant GL50 expression or activity.

Stimulation of GL50 activity is desirable in situations in which GL50 is abnormally downregulated and/or in which increased GL50 activity is likely to have a beneficial effect. Likewise, inhibition of GL50 activity is desirable in situations in which GL50 is abnormally upregulated and/or in which decreased GL50 activity is likely to have a beneficial effect.

3. Downregulation of Immune Responses

It is possible to downregulate the function of a GL50 polypeptide, and thereby downregulate immune responses, in a number of ways. Downregulation may be in the form of inhibiting or blocking an immune response already in progress or may involve preventing the induction of an immune response. The functions of activated T cells may be inhibited, e.g., by suppressing T cell responses or by inducing specific tolerance in T cells, or by leading to the production of cytokines that dampen the immune response. Immunosuppression of T cell responses is generally an active, non-antigen-specific, process which leads to decreased T cell responsiveness and may require continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen where the reexposure occurs in the absence of the tolerizing agent.

For example, GL50 polypeptides, (including nonactivating forms of a GL50 polypeptide) or anti-GL50 antibodies that result in the failure to deliver a costimulatory signal to T cells that have received a primary activation signal, can be used to block GL50 the interaction between GL50 and its ligand(s) on T cells and thereby provide a specific means by which to cause immunosuppression and/or induce tolerance in a subject. Such blocking or inhibitory forms of GL50 polypeptides and fusion proteins and blocking antibodies can be identified by their ability to inhibit T cell proliferation and/or cytokine production when added to an in vitro costimulation assay as described herein and known in the art. In contrast to the inhibitory forms of a GL50 polypeptide, activating forms (such as an intact cell surface GL50 polypeptide and certain soluble forms of GL50) preferably transmit a costimulatory signal to the T cells, resulting in an increased secretion of cytokines (e.g., IL-10) when compared to activated T cells that have not received a costimulatory signal.

In one embodiment, fusion proteins comprising a GL50 first peptide fused to a second peptide having an activity of another B lymphocyte antigen (e.g., B7-1 or B7-2) can be used to modify T cell mediated immune responses. Alternatively, two separate peptides having an activity of B lymphocyte antigens, (for example, a GL50 polypeptide plus a B7-2 and/or B7-1 polypeptide), or a combination of blocking antibodies (e.g., antibodies against a GL50 polypeptide with anti-B7-2 and/or anti-B7-1 monoclonal antibodies) can be combined as a single composition or administered separately (simultaneously or sequentially), to upregulate or downregulate T cell mediated immune responses in a subject. Furthermore, a therapeutically active amount of one or more peptides having a GL50 polypeptide activity, with B7-1 and/or B7-2 activity can be used in conjunction with other immunomodulating reagents to influence immune responses. Examples of other immunomodulating reagents include blocking antibodies, (e.g., against CD28, CTLA4, and/or ICOS, or against other T cell markers, or against cytokines), fusion proteins (e.g., CTLA4Ig), or immunosuppressive drugs, (e.g., rapamycin, cyclosporine A or FK506).

The peptides produced from the nucleic acid molecules of the present invention may also be useful in the construction of therapeutic agents which block T cell function by destruction of the T cell. For example, as described, soluble, secreted forms of a GL50 polypeptide or antibodies that bind to a ligand on a T cell can be used. Such secreted forms can be constructed by standard genetic engineering techniques. By linking a soluble form of a GL50 polypeptide or antibody to a toxin such as ricin, an agent capable of preventing T cell activation can be made. Infusion of one or a combination of immunotoxins, (e.g., GL50-ricin with B7-2-ricin and/or B7-1-ricin), into a patient may result in the death of T cells, particularly of activated T cells that express higher amounts of CD28, CTLA4, and/or ICOS or GL50.

Another method of preventing the function of a GL50 polypeptide is through the use of an antisense or triplex oligonucleotide. For example, an oligonucleotide complementary to the area around a GL50 polypeptide translation initiation site, can be synthesized. One or more antisense oligonucleotides can be added to cell media, typically at 200 µg/ml, or administered to a patient to prevent the synthesis of a GL50 polypeptide. The antisense oligonucleotide is taken up by cells and hybridizes to a GL50 mRNA to prevent translation. Alternatively, an oligonucleotide which binds double-stranded DNA to form a triplex construct to prevent DNA unwinding and transcription can be used. As a result of either, synthesis of a GL50 polypeptide is blocked.

Downregulating or preventing one or more GL50 polypeptide functions, e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a GL50 polypeptide alone or in conjunction with a monomeric form of a different B7 peptide (e.g., B7-1, B7-2) or blocking antibody), prior to transplantation can lead to the binding of the molecule to the natural ligand(s) on the immune cells without transmitting the corresponding costimulatory signal. Blocking B lymphocyte antigen function in this manner prevents cytokine synthesis by immune cells, such as T cells and, thus, acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens. For example, it may be desirable to block the function of B7-1 and GL50, B7-2 and GL50, or B7-1 and B7-2 and a GL50 polypeptide, by administering a soluble form of a combination of peptides having an activity of each of these antigens or blocking antibodies against these antigens (separately or together in a single composition) prior to transplantation. Alternatively, inhibitory forms of GL50 polypeptides can be used with other suppressive agents such as blocking antibodies against other T cell markers or against cytokines, other fusion proteins, e.g., CTLA4Ig, or immunosuppressive drugs.

The efficacy of particular blocking reagents in preventing organ transplant rejection or GVHD can be assessed using animal models that are predictive of efficacy in humans. Because B7 polypeptides display amino acid conservation across species, it is likely that other GL50 antigens can function across species, thereby allowing use of reagents composed of human proteins in animal systems. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., *Science,* 257: 789-792 (1992) and Turka et al., *Proc. Natl. Acad. Sci. USA,* 89: 11102-11105 (1992). In addition, murine models of GVHD (see Paul ed., *Fundamental Immunology,* Raven Press, New York, 1989, pp. 846-847) can be used to determine the effect of blocking function of a GL50 polypeptide in vivo on the development of that disease.

Blocking a GL50 polypeptide function, e.g., by use of a peptide having a GL50 polypeptide activity alone or in combination with a peptide having B7-1 activity and/or a peptide having B7-2 activity, may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology,* Raven Press, New York, 1989, pp. 840-856).

The IgE antibody response in atopic allergy is highly T cell dependent and, thus, inhibition of B lymphocyte antigen induced T cell activation may be useful therapeutically in the treatment of allergy and allergic reactions. An inhibitory form of a GL50 polypeptide, such as a peptide having a GL50 polypeptide activity alone or in combination with another B lymphocyte antigen, such as B7-1 or B7-2, can be administered to an allergic subject to inhibit T cell mediated allergic responses in the subject. Inhibition of GL50 costimulation of T cells may be accompanied by exposure to allergen in conjunction with appropriate MHC molecules. Allergic reactions may be systemic or local in nature, depending on the route of entry of the allergen and the pattern of deposition of IgE on mast cells or basophils. Thus, it may be necessary to inhibit T cell mediated allergic responses locally or systemically by proper administration of an inhibitory form of a GL50 polypeptide.

Inhibition of T cell activation through blockage of a GL50 antigen function may also be important therapeutically in viral infections of T cells. For example, in the acquired immune deficiency syndrome (AIDS), viral replication is stimulated by T cell activation. Blocking a GL50 function could lead to a lower level of viral replication and thereby ameliorate the course of AIDS. In addition, it may also be desirable to block the function of a combination of B lymphocyte antigens i.e., GL50 with B7-2 and/or B7-1.

In one embodiment of the invention, a GL50 family member preferentially induces IL-10 secretion by a T cell (Hutloff et al. (1999) *Nature* 397:263). IL-10, while promoting the development of Th2 type responses, also leads to downmodulation of the production of certain cytokines, and a downmodulation of cell mediated immunity, e.g., by decreasing macrophage activation (Bai et al. (1997) *Clin. Immunol. Immunopathol.* 83:117; Koch et al. (1996) *J. Exp. Med.* 184: 741; deVries (1995) *Ann. Med.* 27:537). Accordingly, in one embodiment of the invention, increasing the activity of a GL50 family member can lead to downmodulation of a cell-mediated immune response. Thus, in one embodiment of the invention cell-mediated immune responses are decreased by increasing GL50 activity.

4. Upregulation of Immune Responses

Upregulation of an immune response, e.g., by promoting a stimulatory activity of GL50 may also be useful in therapy. Upregulation of immune responses may be in the form of enhancing an existing immune response or eliciting an initial immune response. For example, enhancing an immune response through stimulating GL50 activity may be useful in cases of viral infection. Viral infections are cleared primarily by cytolytic T cells. In accordance with the present invention, it is believed that GL50 polypeptide interacting with its natural ligand(s) on T cells may result in an increase in the cytolytic activity of at least some T cells. The addition of an activating form of GL50, alone, or in combination with an activating form of a different B7 family polypeptide to stimulate T cell activity through the costimulation pathway would thus be therapeutically useful in situations where more rapid or thorough clearance of virus would be beneficial. These would include viral skin diseases such as Herpes or shingles, in which cases the mono-valent or multi-valent soluble GL50 polypeptide or combination of such peptide with a peptide having B7-1 activity and/or a peptide having B7-2 activity is delivered topically to the skin. In addition, systemic viral diseases such as influenza, the common cold, and encephalitis might be alleviated by the administration of stimulatory forms of GL50 systemically.

Alternatively, anti-viral immune responses may be enhanced in an infected patient by removing T cells from the patient, costimulating the T cells in vitro with viral antigen-pulsed APCs either expressing a GL50 peptide (alone or in combination with a peptide having B7-1 activity and/or a peptide having B7-2 activity) or together with a stimulatory form of a soluble GL50 peptide (alone or in combination with a peptide having B7-1 activity and/or a peptide having B7-2 activity) and reintroducing the in vitro activated T cells into the patient. Another method of enhancing anti-viral immune responses would be to isolate infected cells from a patient, transfect them with a nucleic acid molecule encoding a peptide having the activity of a B lymphocyte antigen as described herein such that the cells express all or a portion of a GL50 antigen on their surface, and reintroduce the transfected cells into the patient. The infected cells would now be capable of delivering a costimulatory signal to, and thereby activate, T cells in vivo.

Stimulatory forms of GL50 molecules may also be used prophylactically in vaccines against various pathogens. Immunity against a pathogen, e.g., a virus, could be induced by vaccinating with a viral protein along with a stimulatory form of a GL50 polypeptide in an appropriate adjuvant. Alternately, an expression vector which encodes genes for both a pathogenic antigen and a peptide having the activity of a GL50 antigen, e.g., a vaccinia virus expression vector engineered to express a nucleic acid molecule encoding a viral protein and a nucleic acid molecule encoding a GL50 polypeptide as described herein, can be used for vaccination. DNA vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) *J. Biotechnol.* 44:37)). Alternatively, DNA vaccines can be administered by non-invasive means. For example, pure or lipid-formulated DNA can be delivered to the respiratory system or targeted elsewhere, e.g., Peyers patches by oral delivery of DNA (Schubbert (1997) *Proc. Natl. Acad. Sci. USA* 94:961). Attenuated microorganisms can be used for delivery to mucosal surfaces. (Sizemore et al. 1995. *Science.* 270:29). In one embodiment, antigen is administered concurrently with a stimulatory form of a GL50 molecule.

In another application, upregulation or enhancement of GL50 function may be useful in the induction of tumor immunity. In one embodiment, the GL50 molecule is cell associated. Tumor cells (e.g., sarcoma, melanoma, lymphoma, leukemia, neuroblastoma, carcinoma) transfected with a nucleic acid encoding at least one GL50 antigen can be administered to a subject to overcome tumor-specific tolerance in the subject. If desired, the tumor cell can be transfected to express a combination of B7 polypeptides (e.g., B7-1, B7-2, GL50). For example, tumor cells obtained from a patient can be transfected ex vivo with an expression vector directing the expression of a GL50 polypeptide alone, or in conjunction with a peptide having B7-1 activity and/or B7-2 activity. The transfected tumor cells are returned to the patient to result in expression of the peptides on the surface of the transfected cell. Alternatively, gene therapy techniques can be used to target a tumor cell for transfection in vivo.

The presence of the peptide having the activity of a GL50 molecule on the surface of the tumor cell provides the necessary costimulation signal to T cells to induce a T cell mediated immune response against the transfected tumor cells. In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, GL50) induces a T cell mediated immune response against the transfected tumor cell. Optionally, a gene encoding an antisense construct which blocks expression of an MHC class II associated protein, such as the invariant chain, can also be cotransfected with a DNA encoding a GL50 polypeptide to promote presentation of tumor associated antigens and induce tumor specific immunity. Expression of B7-1 by B7 negative murine tumor cells has been shown to induce T cell mediated specific immunity accompanied by tumor rejection and prolonged protection to tumor challenge in mice (Chen, L. et al. (1992) *Cell* 71:1093-1102; Townsend, S. E. and Allison, J. P. (1993) *Science* 259:368-370; Baskar, S. et al. (1993) *Proc. Natl. Acad. Sci. USA* 90:5687-5690). Thus, the induction of a T cell mediated immune response in a human subject may be sufficient to overcome tumor-specific tolerance in the subject.

In another embodiment, an activating form of one or more GL50 peptides (e.g., expressed on a cell surface) can be administered to a tumor-bearing patient to provide a costimulatory signal to T cells in order to induce anti-tumor immunity using techniques that are known in the art.

In a specific embodiment, T cells are obtained from a subject and cultured ex vivo to expand the population of T cells. In a further embodiment the T cells are then administered to a subject. T cells can be stimulated to proliferate in vitro by, for example, providing to the T cells a primary activation signal and a costimulatory signal, as is known in the art. Various forms of GL50 polypeptides can also be used to costimulate proliferation of T cells. In one embodiment T cells are cultured ex vivo according to the method described in PCT Application No. WO 94/29436. The costimulatory molecule can be soluble, attached to a cell membrane or attached to a solid surface, such as a bead.

B. Identification of Cytokines Induced by GL50 Mediated Costimulation

The GL50 molecules as described herein can be used to identify cytokines which are produced by T cells in response to stimulation by a GL50 polypeptide. T cells can be suboptimally stimulated in vitro with a primary activation signal, such as phorbol ester, anti-CD3 antibody or preferably antigen in association with an MHC class II molecule, and given a costimulatory signal by a stimulatory form of GL50 antigen, for instance by a cell transfected with nucleic acid encoding a GL50 polypeptide and expressing the peptide on its surface or by a soluble, stimulatory form of the peptide. Known cytokines released into the media can be identified by ELISA or by the ability of an antibody which blocks the cytokine to inhibit T cell proliferation or proliferation of other cell types that is induced by the cytokine. An IL-4 ELISA kit is available from Genzyme (Cambridge Mass.), as is an IL-7 blocking antibody. Blocking antibodies against IL-9 and IL-12 are available from Genetics Institute (Cambridge, Mass.).

An in vitro T cell costimulation assay as described above can also be used in a method for identifying novel cytokines which may be induced by costimulation. For example, where stimulation of the CD28/CTLA4 pathway seems to enhance IL-2 secretion, stimulation of the ICOS pathway seems to enhance IL-10 secretion (Hutloff et al. 199. Nature 397:263). If a particular activity induced upon costimulation, e.g., T cell proliferation, cannot be inhibited by addition of blocking antibodies to known cytokines, the activity may result from the action of an unknown cytokine. Following costimulation, this cytokine could be purified from the media by conventional methods and its activity measured by its ability to induce T cell proliferation.

To identify cytokines which may prevent the induction of tolerance, an in vitro T cell costimulation assay as described above can be used. In this case, T cells would be given the primary activation signal and contacted with a selected cytokine, but would not be given the costimulatory signal. After washing and resting the T cells, the cells would be rechallenged with both a primary activation signal and a costimulatory signal. If the T cells do not respond (e.g., proliferate or produce cytokines) they have become tolerized and the cytokine has not prevented the induction of tolerance. However, if the T cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a GL50 blocking reagent together with a cytokine blocking antibody to a subject.

C. Identification of Molecules which Influence Costimulation

Another application of the peptide having the activity of a novel B lymphocyte antigen of the invention is the use of one or more of these peptides in screening assays to discover as yet undefined molecules which are modulators of costimulatory ligand binding and/or of intracellular signaling through T cells following costimulation. For example, a solid-phase binding assay using a peptide having the activity of a GL50 molecule, could be used to identify molecules to which GL50 binds and/or which inhibit binding of the antigen with an appropriate T cell ligand (e.g., CD28, CTLA4, or ICOS). In addition, an in vitro T cell costimulation assay as described above could be used to identify molecules which interfere with intracellular signaling through the T cells following costimulation as determined by the ability of these molecules to inhibit T cell proliferation and/or cytokine production (yet which do not prevent binding of a GL50 molecule to its ligand). For example, the compound cyclosporine A and rapamycin inhibit T cell activation through stimulation via the T cell receptor pathway but not via the CD28/CTLA4 pathway. Therefore, a different intracellular signaling pathway is involved in costimulation. Molecules which interfere with intracellular signaling via the CD28/CTLA4 and/or ICOS pathway may be effective as immunosuppressive agents in vivo with or without the use of an additional immunosuppressant such as cyclosporine A or rapamycin.

D. Identification of Molecules which Modulate Expression of a GL50 Polypeptide

The antibodies produced using the proteins and peptides of the current invention can be used in a screening assay for molecules which modulate the expression of GL50 polypeptide on cells. For example, molecules which effect intracellular signaling which leads to induction of expression GL50 polypeptides e.g., in response to activation signals, can be identified by assaying expression of one or more GL50 polypeptides on the cell surface. Reduced immunofluorescent staining by an anti-GL50 antibody in the presence of the molecule would indicate that the molecule inhibits intracellular signals. Molecules which upregulate GL50 polypeptide expression result in an increased immunofluorescent staining. Alternatively, the effect of a molecule on expression of a GL50 polypeptide can be determined by detecting cellular GL50 mRNA levels using a probe of the invention. For example, a cell which expresses a GL50 polypeptide can be contacted with a molecule to be tested, and an increase or decrease in GL50 mRNA levels in the cell detected by standard technique, such as Northern hybridization analysis or conventional dot blot of mRNA or total poly($A^+$)RNAs using a mGL50-1 probe labeled with a detectable marker. Molecules which modulate expression of a GL50 polypeptide may be useful therapeutically for either upregulating or downregulating immune responses alone or in conjunction with soluble blocking or stimulating reagents. For instance, a molecule which inhibits expression of GL50 could be administered together with a GL50 blocking reagent for immunosuppressive purposes. Molecules which can be tested in the above-described assays include cytokines such as IL4, γINF, IL-10, IL-12, GM-CSF and prostaglandins.

E. Screening Assays:

The invention provides a method (also referred to herein as a "screening assay") for identifying modulators, i.e., candidate or test compounds or agents (e.g., peptides, peptidomimetics, small molecules or other drugs) which bind to GL50 polypeptides or portions thereof, have a stimulatory or inhibitory effect on, for example, GL50 expression or GL50 activity.

In one embodiment, the invention provides assays for screening candidate or test compounds which bind to or modulate the activity of a GL50 polypeptide or polypeptide or biologically active portion thereof, e.g., modulate the ability of GL50 polypeptide to interact with a binding partner (e.g., a cognate ligand or intracellular interactor). For example, in one embodiment, portions of the extracellular domain of GL50 can be used. In another embodiment, portions of the cytoplasmic domain of a GL50 molecule can be used. In another embodiment, portions of the transmembrane domain of a GL50 molecule can be used.

In one embodiment, variant forms of a polypeptide comprising a GL50 domain can be used in a screening assay. For example, GL50 domains comprising an amino acid alteration (e.g., that have been mutagenized using, for example random or cassette mutagenesis) can be used in the subject screening assays. Alternatively, splicing variants of GL50 intracellular domains (e.g., GL50-1 intracellular domain, GL50-2 cytoplasmic domain or additional exons identified upon sequencing of chromosome 21 or identified by RACE PCR) can be to screen for compounds. Such GL50 variants can be used to identify compounds with activity against a range of GL50 molecules and can identify amino acid residues essential for GL50 activity.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In another embodiment, an assay is a cell-based assay comprising contacting a cell expressing a GL50 target molecule (e.g., a GL50 ligand such as ICOS or intracellular interactor molecule) with a test compound and determining the ability of the test compound to modulate (e.g. stimulate or inhibit) the activity of the GL50 target molecule. In one embodiment, a GL50 target molecule is identified, e.g., in a two or three hybrid assay. In another embodiment, a GL50 interactor molecule is identified using standard methods for crosslinking GL50 to neighboring molecules followed by immunoprecipitation using anti-GL50 antibodies.

In one embodiment, portions of the transmembrane and/or intracellular regions as defined by hydropathy plots or domains as defined by exon structure can be as bait in 2-hybrid assays to determine binding partners to these domains. Interacting proteins can be used in assays to quantitate the degree of GL50 binding to interaction partners potentially for production or quality control assays. In another embodiment, cytoplasmic domain splice variants can be used in different 2-hybrid assays to collect the entire range of protein interactors that bind to any GL50 splice variant.

Determining the ability of the test compound to modulate the activity of a GL50 target molecule can be accomplished, for example, by determining the ability of the GL50 polypeptide to bind to or interact with the GL50 target molecule or its ligand. Determining the ability of the GL50 polypeptide to bind to or interact with a ligand of a GL50 molecule can be accomplished, e.g., by direct binding.

In a direct binding assay, the GL50 polypeptide could be coupled with a radioisotope or enzymatic label such that binding of the GL50 polypeptide to a GL50 target molecule can be determined by detecting the labeled GL50 polypeptide in a complex. For example, GL50 molecules, e.g., GL50 polypeptides, can be labeled with $^{125}I$, $^{35}S$, $^{14}C$, or $^{3}H$, either directly or indirectly, and the radioisotope detected by direct counting of radioemmission or by scintillation counting. Alternatively, GL50 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between GL50 and its target molecule, without the labeling of any of the interactants. For example, a microphysiometer can be used to detect the interaction of GL50 with its target molecule without the labeling of either GL50 or the target molecule. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the GL50 polypeptide to bind to or interact with a GL50 binding partner can be accomplished by determining the activity of the binding partner. For example, the activity of the target molecule can be determined by detecting induction of a cellular second messenger of the target (e.g., to phosphorylate GL50 or another substrate on tyrosine residues), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response. For example, determining the ability of the GL50 polypeptide to bind to or interact with a GL50 target molecule can be accomplished, for example, by measuring the ability of a compound to downmodulate T cell costimulation in a proliferation assay, or by interfering with the ability of a GL50 polypeptide to bind to antibodies that recognize a portion of the GL50 polypeptide.

In yet another embodiment, an assay of the present invention is a cell-free assay in which a GL50 polypeptide or biologically active portion thereof is contacted with a test compound and the ability of the test compound to bind to the GL50 polypeptide or biologically active portion thereof is determined. Binding of the test compound to the GL50 polypeptide can be determined either directly or indirectly as described above. In a preferred embodiment, the assay includes contacting the GL50 polypeptide or biologically active portion thereof with a known compound which binds GL50 to form an assay mixture, contacting the assay mixture with a test compound, and determining the ability of the test compound to interact with a GL50 polypeptide, wherein determining the ability of the test compound to interact with a GL50 polypeptide comprises determining the ability of the test compound to preferentially bind to GL50 polypeptide or biologically active portion thereof as compared to the known compound.

In another embodiment, the assay is a cell-free assay in which a GL50 polypeptide or biologically active portion thereof is contacted with a test compound and the ability of the test compound to modulate (e.g., stimulate or inhibit) the activity of the GL50 polypeptide or biologically active portion thereof is determined. Determining the ability of the test compound to modulate the activity of a GL50 polypeptide can be accomplished, for example, by determining the ability of the GL50 polypeptide to bind to a GL50 target molecule or ligand by one of the methods described above for determining direct binding. Determining the ability of the GL50 polypeptide to bind to a GL50 target molecule can also be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a GL50 polypeptide can be accomplished by determining the ability of the GL50 polypeptide to further modulate the activity of a GL50 target molecule (e.g., a GL50 mediated signal transduction pathway component). For example, the activity of the effector molecule on an appropriate target can be determined, or the binding of the effector to an appropriate target can be determined as previously described.

In yet another embodiment, the cell-free assay involves contacting a GL50 polypeptide or biologically active portion thereof with a known compound which binds the GL50 polypeptide to form an assay mixture, contacting the assay mixture with a test compound, and determining the ability of the test compound to interact with the GL50 polypeptide, wherein determining the ability of the test compound to interact with the GL50 polypeptide comprises determining the ability of the GL50 polypeptide to preferentially bind to or modulate the activity of a GL50 target molecule.

The cell-free assays of the present invention are amenable to use of both soluble and/or membrane-bound forms of proteins (e.g., GL50 polypeptides or biologically active portions thereof, or receptors to which GL50 binds). In the case of cell-free assays in which a membrane-bound form a protein is used (e.g., a cell surface GL50 receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylammnio]-2-hydroxy-1-propane sulfonate (CHAPSO), or N-dodecyl=N,N-dimethyl-3-ammonio-1-propane sulfonate.

In one embodiment of the above assay methods of the present invention, it may be desirable to immobilize either GL50 or its target molecule to facilitate separation of complexed from uncomplexed forms of one or both of the proteins, as well as to accommodate automation of the assay. Binding of a test compound to a GL50 polypeptide, or interaction of a GL50 polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/GL50 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or GL50 polypeptide, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of GL50 binding or activity determined using standard techniques.

Other techniques for immobilizing proteins on matrices can also be used in the screening assays of the invention. For example, either a GL50 polypeptide or a GL50 target molecule can be immobilized utilizing conjugation of biotin and streptavidin. Biotinylated GL50 polypeptide or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with GL50 polypeptide or target molecules but which do not interfere with binding of the GL50 polypeptide to its target molecule can be derivatized to the wells of the plate, and unbound target or GL50 polypeptide trapped in the wells by antibody conjugation. Methods for detecting such complexes, in addition to those described above for the GST-immobilized complexes, include immunodetection of complexes using antibodies reactive with the GL50 polypeptide or target molecule, as well as enzyme-linked assays which rely on detecting an enzymatic activity associated with the GL50 polypeptide or target molecule.

In another embodiment, modulators of GL50 expression are identified in a method wherein a cell is contacted with a candidate compound and the expression of GL50 mRNA or protein in the cell is determined. The level of expression of GL50 mRNA or protein in the presence of the candidate compound is compared to the level of expression of GL50 mRNA or protein in the absence of the candidate compound. The candidate compound can then be identified as a modulator of GL50 expression based on this comparison. For example, when expression of GL50 mRNA or protein is greater (e.g., statistically significantly greater) in the presence of the candidate compound than in its absence, the candidate compound is identified as a stimulator of GL50 mRNA or protein expression. Alternatively, when expression of GL50 mRNA or protein is less (e.g., statistically significantly less) in the presence of the candidate compound than in its absence, the candidate compound is identified as an inhibitor of GL50 mRNA or protein expression. The level of GL50 mRNA or protein expression in the cells can be determined by methods described herein for detecting GL50 mRNA or protein.

In yet another aspect of the invention, the GL50 polypeptides, e.g., soluble or membrane bound molecules or portions thereof (e.g., transmembrane or cytoplasmic portions), can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with GL50 ("GL50-binding proteins" or "GL50-bp") and are involved in GL50 activity. Such GL50-binding proteins are also likely to be involved in the propagation of signals by the GL50 polypeptides or GL50 targets as, for example, downstream elements of a GL50-mediated signaling pathway. Alternatively, such GL50-binding proteins may be GL50 inhibitors.

The two-hybrid system is based on the modular nature of most transcription factors, which consist of separable DNA-binding and activation domains. Briefly, the assay utilizes two different DNA constructs. In one construct, the gene that codes for a GL50 polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a GL50-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the GL50 polypeptide.

This invention further pertains to novel agents identified by the above-described screening assays. Accordingly, it is within the scope of this invention to further use an agent identified as described herein in an appropriate animal model. For example, an agent identified as described herein (e.g., a GL50 modulating agent, an antisense GL50 nucleic acid molecule, a GL50-specific antibody, or a GL50-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

F. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

GL50 has been mapped to human chromosome 21q22. Accordingly, portions or fragments of GL50 nucleotide sequences (both coding and non-coding), described herein, can be used to correlate these sequences with genes associated with disease.

The physical position of a sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the GL50 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The GL50 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the GL50 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The GL50 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1, 3, or 5, can comfortably provide positive individual identification with a panel of primers which each yield a noncoding amplified sequence of 100 bases. If predicted coding sequences are used, a more appropriate number of primers for positive individual identification would be 500-2,000.

If a panel of reagents from GL50 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial GL50 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the GL50 nucleotide sequences or portions thereof having a length of at least 20 bases, preferably at least 30 bases.

The GL50 nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such GL50 probes can be used to identify tissue by species and/or by organ type.

In a similar fashion, these reagents, e.g., GL50 primers or probes can be used to screen tissue culture for contamination (i.e. screen for the presence of a mixture of different types of cells in a culture).

G. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining GL50 polypeptide and/or nucleic acid expression as well as GL50 activity, in the context of a biological sample (e.g., blood, serum, cells, tissue) to thereby determine whether an individual is afflicted with a disease or disorder, or is at risk of developing a disorder, associated with aberrant GL50 expression or activity. The invention also provides for prognostic (or predictive) assays for determining whether an individual is at risk of developing a disorder associated with GL50 polypeptide, nucleic acid expression or activity. For example, mutations in a GL50 gene can be assayed in a biological sample. Such assays can be used for prognostic or predictive purpose to thereby prophylactically treat an individual prior to the onset of a disorder characterized by or associated with GL50 polypeptide, nucleic acid expression or activity.

Another aspect of the invention pertains to monitoring the influence of agents (e.g., drugs, compounds) on the expression or activity of GL50 in clinical trials.

These and other agents are described in further detail in the following sections.

1. Diagnostic Assays

An exemplary method for detecting the presence or absence of GL50 polypeptide or nucleic acid in a biological sample involves obtaining a biological sample from a test subject and contacting the biological sample with a compound or an agent capable of detecting GL50 polypeptide or nucleic acid (e.g., mRNA, genomic DNA) that encodes GL50 polypeptide such that the presence of GL50 polypeptide or nucleic acid is detected in the biological sample. A preferred agent for detecting GL50 mRNA or genomic DNA is a labeled nucleic acid probe capable of hybridizing to GL50 mRNA or genomic DNA. The nucleic acid probe can be, for example, a hGL50 nucleic acid, such as the nucleic acid of SEQ ID NO: 1, 3, or 5, or a portion thereof, such as an oligonucleotide of at least 15, 30, 50, 100, 250 or 500 nucleotides in length and sufficient to specifically hybridize under stringent conditions to GL50 mRNA or genomic DNA. Other suitable probes for use in the diagnostic assays of the invention are described herein.

A preferred agent for detecting GL50 polypeptide is an antibody capable of binding to GL50 polypeptide, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect GL50 mRNA, protein, or genomic DNA in a biological sample in vitro as well as in vivo. For example, in vitro techniques for detection of GL50 mRNA include Northern hybridizations and in situ hybridizations. In vitro techniques for detection of GL50 polypeptide include enzyme linked immunosorbent assays (ELISAs), Western blots, immunoprecipitations and immunofluorescence. In vitro techniques for detection of GL50 genomic DNA include Southern hybridizations. Furthermore, in vivo techniques for detection of GL50 polypeptide include introducing into a subject a labeled anti-GL50 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting GL50 polypeptide, mRNA, or genomic DNA, such that the presence of GL50 polypeptide, mRNA or genomic DNA is detected in the biological sample, and comparing the presence of GL50 polypeptide, mRNA or genomic DNA in the control sample with the presence of GL50 polypeptide, mRNA or genomic DNA in the test sample.

The invention also encompasses kits for detecting the presence of GL50 in a biological sample. For example, the kit can comprise a labeled compound or agent capable of detecting GL50 polypeptide or mRNA in a biological sample; means for determining the amount of GL50 in the sample; and means for comparing the amount of GL50 in the sample with a standard. The compound or agent can be packaged in a suitable container. The kit can further comprise instructions for using the kit to detect GL50 polypeptide or nucleic acid.

2. Prognostic Assays

The diagnostic methods described herein can furthermore be utilized to identify subjects having or at risk of developing a disease or disorder associated with aberrant GL50 expression or activity. For example, the assays described herein, such as the preceding diagnostic assays or the following assays, can be utilized to identify a subject having or at risk of developing a disorder associated with GL50 polypeptide, nucleic acid expression or activity. Thus, the present invention provides a method for identifying a disease or disorder associated with aberrant GL50 expression or activity in which a test sample is obtained from a subject and GL50 polypeptide or nucleic acid (e.g., mRNA, genomic DNA) is detected, wherein the presence of GL50 polypeptide or nucleic acid is diagnostic for a subject having or at risk of developing a disease or disorder associated with aberrant GL50 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether an agent (e.g., an agonist, antagonist, peptidomimetic, protein, peptide, nucleic acid, small molecule, or other drug candidate) can be administered to a subject to treat a disease or disorder associated with aberrant GL50 expression or activity. Thus, the present invention provides methods for determining whether a subject can be effectively treated with an agent for a disorder associated with aberrant GL50 expression or activity in which a test sample is obtained and GL50 polypeptide or nucleic acid expression or activity is detected (e.g., wherein the abundance of GL50 polypeptide or nucleic acid expression or activity is diagnostic for a subject that can be administered the agent to treat a disorder associated with aberrant GL50 expression or activity).

The methods of the invention can also be used to detect genetic alterations in a GL50 gene, thereby determining if a subject with the altered gene is at risk for a disorder associated with the GL50 gene. In preferred embodiments, the methods include detecting, in a sample of cells from the subject, the presence or absence of a genetic alteration characterized by at least one of an alteration affecting the integrity of a gene encoding a GL50-protein, or the mis-expression of the GL50 gene. For example, such genetic alterations can be detected by ascertaining the existence of at least one of 1) a deletion of one or more nucleotides from a GL50 gene; 2) an addition of one or more nucleotides to a GL50 gene; 3) a substitution of one or more nucleotides of a GL50 gene, 4) a chromosomal rearrangement of a GL50 gene; 5) an alteration in the level of a messenger RNA transcript of a GL50 gene, 6) aberrant modification of a GL50 gene, such as of the methylation pattern of the genomic DNA, 7) the presence of a non-wild type splicing pattern of a messenger RNA transcript of a GL50 gene, 8) a non-wild type level of a GL50 polypeptide, 9) allelic loss of a GL50 gene, and 10) inappropriate post-translational modification of a GL50 polypeptide. As described herein, there are a large number of assay techniques known in the art which can be used for detecting alterations in a GL50 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the GL50 gene (see Abravaya et al. (1995) *Nucleic Acids Res.* 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a GL50 gene under conditions such that hybridization and amplification of the GL50 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a GL50 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in GL50 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in GL50 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the GL50 gene and detect mutations by comparing the sequence of the sample GL50 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the GL50 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type GL50 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GL50s obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a GL50 sequence, e.g., a wild-type GL50 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in GL50 genes. For example, single strand conformation polymorphism (SSCP) may be used to detect differences in electrophoretic mobility between mutant and wild type nucleic acids (Orita et al. (1989) *Proc. Natl. Acad. Sci. USA:* 86:2766, see also Cotton (1993) *Mutat. Res.* 285:125-144; and Hayashi (1992) *Genet. Anal. Tech. Appl.* 9:73-79). Single-stranded DNA fragments of sample and control GL50 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting Gc-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell. Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a GL50 gene.

Furthermore, any cell type or tissue in which GL50 is expressed may be utilized in the prognostic assays described herein.

VII. ADMINISTRATION OF GL50 MODULATING AGENTS

GL50 modulating agents of the invention are administered to subjects in a biologically compatible form suitable for pharmaceutical administration in vivo to either enhance or suppress T cell mediated immune response. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a GL50 modulating agent may vary according to factors such as the disease state, age, sex, and weight of the individual, and the ability of peptide to elicit a desired response in the individual. Dosage regima may be adjusted to provide the optimum therapeutic response. For example, several divided doses may be administered daily or the dose may be proportionally reduced as indicated by the exigencies of the therapeutic situation.

The GL50 modulating agent (e.g., a peptide, a nucleic acid molecule, or an antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound. For example, to administer GL50 modulating agent by other than parenteral administration, it may be necessary to coat the peptide with, or co-administer the peptide with, a material to prevent its inactivation.

A GL50 modulating agent may be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al., (1984) *J Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a GL50 polypeptide or anti-GL50 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one embodiment of the present invention a therapeutically effective amount of an antibody to a GL50 polypeptide is administered to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Monitoring the influence of agents (e.g., drugs or compounds) on the expression or activity of a GL50 polypeptide can be applied not only in basic drug screening, but also in clinical trials. For example, the effectiveness of an agent determined by a screening assay as described herein to increase GL50 gene expression, protein levels, or upregulate GL50 activity, can be monitored in clinical trials of subjects exhibiting decreased GL50 gene expression, protein levels, or downregulated GL50 activity. Alternatively, the effectiveness of an agent determined by a screening assay to decrease GL50 gene expression, protein levels, or downregulate GL50 activity, can be monitored in clinical trials of subjects exhibiting increased GL50 gene expression, protein levels, or upregulated GL50 activity. In such clinical trials, the expression or activity of a GL50 gene, and preferably, other genes that have been implicated in a disorder can be used as a "read out" or markers of the phenotype of a particular cell.

For example, and not by way of limitation, genes, including GL50, that are modulated in cells by treatment with an agent (e.g., compound, drug or small molecule) which modulates GL50 activity (e.g., identified in a screening assay as described herein) can be identified. Thus, to study the effect of agents on a GL50 associated disorder, for example, in a clinical trial, cells can be isolated and RNA prepared and analyzed for the levels of expression of GL50 and other genes implicated in the GL50 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of GL50 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a GL50 polypeptide, mRNA, or genomic DNA in the pre-administration sample; (iii) obtaining one or more post-administration samples from the subject; (iv) detecting the level of expression or activity of the GL50 polypeptide, mRNA, or genomic DNA in the post-administration samples; (v) comparing the level of expression or activity of the GL50 polypeptide, mRNA, or genomic DNA in the pre-administration sample with the GL50 polypeptide, mRNA, or genomic DNA in the post administration sample or samples; and (vi) altering the administration of the agent to the subject accordingly. For example, increased administration of the agent may be desirable to increase the expression or activity of GL50 to higher levels than detected, i.e., to increase the effectiveness of the agent. Alternatively, decreased administration of the agent may be desirable to decrease expression or activity of GL50 to lower levels than detected, i.e. to decrease the effectiveness of the agent. According to such an embodiment, GL50 expression or activity may be used as an indicator of the effectiveness of an agent, even in the absence of an observable phenotypic response.

This invention is further illustrated by the following examples which should not be construed as limiting. The contents of all references, patents and published patent applications cited throughout this application, as well as the Figures and the Sequence Listing are incorporated herein by reference.

EXAMPLES

The following materials and methods were used in the examples.

Mouse strain and RNA isolation: Mice (C57Bl/6) injected with 10E5 MB49 bladder carcinoma cells were treated with 1 μg/mouse recombinant IL12 on days 7-11 and 14-18. RNA was isolated from lymph nodes on days 9 (75%), 12 (20%) and 19 (5%) were subsequently pooled. RNA was extracted using RNAStat 60 (teltest B) followed by poly A+ RNA enrichment using poly Attract magnetic isolation system (Promega). cDNAs were synthesized with superscript RT (Gibco BRL). Additional cDNA sources include a mouse fetal thymus library (C3H/Hej) and mouse peripheral blood lymphocytes derived from cardiac puncture of C57Bl/6).

Signal trap: Signal trap protocols were followed as described by Jacobs et al. (1997. Gene. 198: 289). Briefly, size fractionated cDNAs were unidirectionally cloned into the invertase expression plasmid pSUC2T7M13ORI. An expression library of plasmid clones was generated in *E. coli* and subsequently introduced into the invertase deficient suc2–strain of yeast. Signal trapped clones represented in the yeast library were selected by 2 day culture in YPR agar plates. Three hundred and thirty three clones were picked at random, miniprepped and sequenced.

Sequence analysis: TBlastX, FastX, pFam, Pileup, GrowTree and Sigcleave of GCG Wisconsin package, and Geneworks 2.5.1 was used for DNA sequence manipulation, database searching and sequence analysis. In FIG. 12, identity scores for pileup analysis was determined according to the following values: 1× pair=1; 2× pair=2; 3× pair=3; 3-of-a-kind=4; 3-of-a-kind plus 1× pair=5; 2×3-of-a-kind=6; 4-of-a-kind=7; 4-of-a-kind plus 1× pair=8; 5-of-a-kind=9. The Lasergene DNAstar Genequest module was used for delineating intron-exon boundaries of hGL50 against Genbank Accession #HS21C098. Further analysis was performed with the SeqWeb Wisconsin GCG package using TFASTA, TBLASTN, ProfileScan. Distance-proportional phylograms were generated by GrowTree based on genetic distance using Kimura correction algorithms. Graphical output was subsequently reformatted to reflect family clusters.

3' rapid amplification of cDNA ends: 3' RACE was performed using primers (GL50) VL118 (CCCGCAGTCT-GCGCTCGCACC; SEQ ID NO:7), VL116 (GTCGAC-CCACCATGCAGCTAAAGTGTCCCTG; SEQ ID NO: 8), (AB014553) VL 141 (CGTGTACTGGATCAATAA-GACGG; SEQ ID NO:9), VL142 (ACAACAGCCTGCTG-GACCAGGC; SEQ ID NO:10), (Poly A-oligo) VL054 (CCAGTGAGCAGAGTGACG; SEQ ID NO:11), VL055 (GAGGACTCGAGCTCAAGC; SEQ ID NO:12). Mouse peripheral blood lymphocytes (PBLs) were enriched for lymphocytes by density centrifugation using lymphocyte M according to the manufacturer's protocol. Human PBLs were isolated by Ficoll-paque density centrifugation of human leukopac samples. Total RNA was extracted from lymphocytes as described below. Reverse transcription was accomplished using primer VL053 (CCAGTGAGCAGAGTGACGAG-GACTCGAGCTCAAGCTTTTTTTTTTTT; SEQ ID NO:18), 5 µg of total RNA and SuperScript RT (Gibco-BRL) according to the manufacturer's protocols in 20 µl reactions. 0.5-1.0 µl of RT-synthesized cDNAs were used per RACE procedure. 3' RACE was performed according to the method of Frohman, M. A. (1993) *Methods Enzymol.* 218:340-356.

RNA isolation and analysis: Total RNA was derived from CCE ES cells, Swiss Webster embryos/yolk sacs and C57Bl/6 peripheral blood lymphocytes and was extracted using RNAstat 60 (Tel-Test B, Friendswood Tex.) accompanied with Phase-lock gel barrier (Eppendorf). RNA was fractionated using Northern Max system (Ambion) and blotted onto ZetaProbe GT (BioRad) according to the manufacturer's protocols. Multiple tissue RNA panels were purchased (Clontech) and used according to the manufacturer's instructions. Blots were hybridized to radiolabeled DNA fragments encompassing either nucleotides 984-1340 of the mGL50-2 clone (357 bp; SEQ ID NO:3), corresponding to the 3' untranslated region, while fragments corresponding to the coding sequence of mGL50 were used to detect both mGL50-1 and mGL50-2 transcripts. Hybridizations were performed at 65° C. with Express Hyb (Clontech) overnight and subsequently washed with 0.1×SSC and 1% SDS at hybridization temperatures until a suitable signal to noise ratio was reached. Blots were exposed to phosphoimage plates and autoradiographic film for imaging.

Gene expression analysis: For RT-PCR analysis, first strand cDNA synthesis was performed as described above for RACE procedures, followed by duplicate 25 µl amplification reactions (using Advantage Taq, Clontech) with the primers RLEE 001 and RLEE005 for mGL50-1 and primers RLEE 001 and RLEE003 for mGL50-2. Primers GAPDH-F and GAPDH-R were used as positive amplification controls. The oligonucleotides GAPDH-F (TGAAGGTCGGTGT-GAACGGATTTGGC; SEQ ID NO:19); GAPDH-R (CATG-TAGGCCATGAGGTCCACCAC (SEQ ID NO:20); RLEE001 (CATCACTAGCATTAGCCAGGC; SEQ ID NO: 13); RLEE003 (TGATGTTGTGAAGCTGAGTGC; SEQ ID NO: 14); RLEE005 (TCATGAGCATCGAGCATCG; SEQ ID NO: 15); VL 142 (ACAACAGCCTGCTGGACCAGGC; SEQ ID NO:10); VL162B (TCACGAGAGCAGAAGGAG-CAGGTTCC; SEQ ID NO:16); and VL163B (GGGC-CCCCCAGAACCTGCTGCTTCC; SEQ ID NO: 17) were designed for the PCR amplification of the extracellular domain regions of mGL50-1, GL50-RACE, AB014553 cDNA and AB014553-RACE clones. Mouse and human cDNA panels derived from poly A+ RNA encompassing lymphoid and nonlymphoid tissues (Clontech) was used as a source for PCR analysis. Cycling conditions were 5 min 95° C. denaturing step followed by 35 cycles of 1 min at 95° C., 1 min at 60° C., and 1 min at 72° C. The reaction was terminated following a 10 min 72° C. extension. Cycling conditions for mGL50 and mGL50-2 PCR were 95° C. for 1 min, 60° C. for 1 min, and 72° C. for 2 min. for 33 cycles, while GAPDH PCR was performed using 30 cycles.

For Northern blot analysis, commercially prepared RNA blots (Clontech) were hybridized to radiolabeled DNA fragments encompassing nucleotides 1065-1588 of mGL50-1 (494 bp; SEQ ID NO: 1), or nucleotides 984-1340 of the mGL50-2 clone (357 bp; SEQ ID NO:3).

Flow cytometry: COS cells were transfected with mGL50-1 or DAP-12 cDNA in pcDNA3.1-CTGFP expression vectors. Transfection was accomplished using lipofectamine transfection reagent (Life Technologies) according to manufacturer's protocols. Cells were harvested 3 days after transfection. 10% Rabbit serum was used to block non-specific binding to cells. Cells were stained at room temperature for 20 minutes with 200 ng of fusion proteins in 100 µl of PBS 2% FCS. Cells were washed and secondary staining performed with PE-linked goat anti-mouse IgG. Cells were stained with propidium iodide immediately prior to flow cytometry. Positive COS transfection control was performed with hCTLA4 cDNA followed by identification of positively staining cells with PE-linked anti CTLA4.

Cell suspensions for cytometric analysis were isolated from Balb/c splenocytes (~3 months old) and washed once with DMEM, 10% (vol/vol) heat-inactivated fetal calf serum (JR BioScience), 2 mM L-glutamine, 100 U/ml penicillin, 100 µg/ml streptomycin (Irvine Scientific, Santa Ana, Calif.), 20 µM 2-betamercaptoethanol (Sigma Co., St. Louis, Mo.), MEM sodium pyruvate, and MEM Non-essential amino acids (Life Technologies, Rockville, Md.). Red blood cells were lysed with ACT lysing buffer and washed once. Splenocytes (~1×10$^7$ cells/ml/well) from Balb/c mice were cultured with 25 µg/ml LPS (Sigma) or 10 ng/ml PMA, 1 µg/ml ionomycin. Cells were stained with FITC-labeled antibodies (BD-Pharmingen) and mICOS-mIgG2am reagent, followed by flow cytometric analysis using the FACalibur and CellQuest software package (BD). Cell separation was performed using anti-FITC microbead magnetic selection (Miltenyi Biotec) followed by flow cytometric determination of T-cell enrichment.

Ig fusion proteins: Fusion proteins of IgG2a with mICOS, hICOS, mGL50-1, and hGL50 were constructed for use in the following examples. The notation IgG2am indicates that the IgG2a domain was mutated to reduce effector function (as in Steurer, W. et al. (1995) *J. Immunol.* 155:1165-74). The nucleotide and amino acid sequences of hICOS-mIgG2am are presented in FIG. 26 and set forth as SEQ ID NOs:23 and 24, respectively. The nucleotide and amino acid sequences of mICOS-mIgG2am are presented in FIG. 27 and set forth as SEQ ID NOs:25 and 26, respectively. The nucleotide and amino acid sequences of hGL50-mIgG2am are presented in FIG. 28 and set forth as SEQ ID NOs:27 and 28, respectively. The nucleotide and amino acid sequences of mGLl50-mIgG2am are presented in FIG. 29 and set forth as SEQ ID NOs:29 and 30, respectively.

Example 1

Figure 20A:
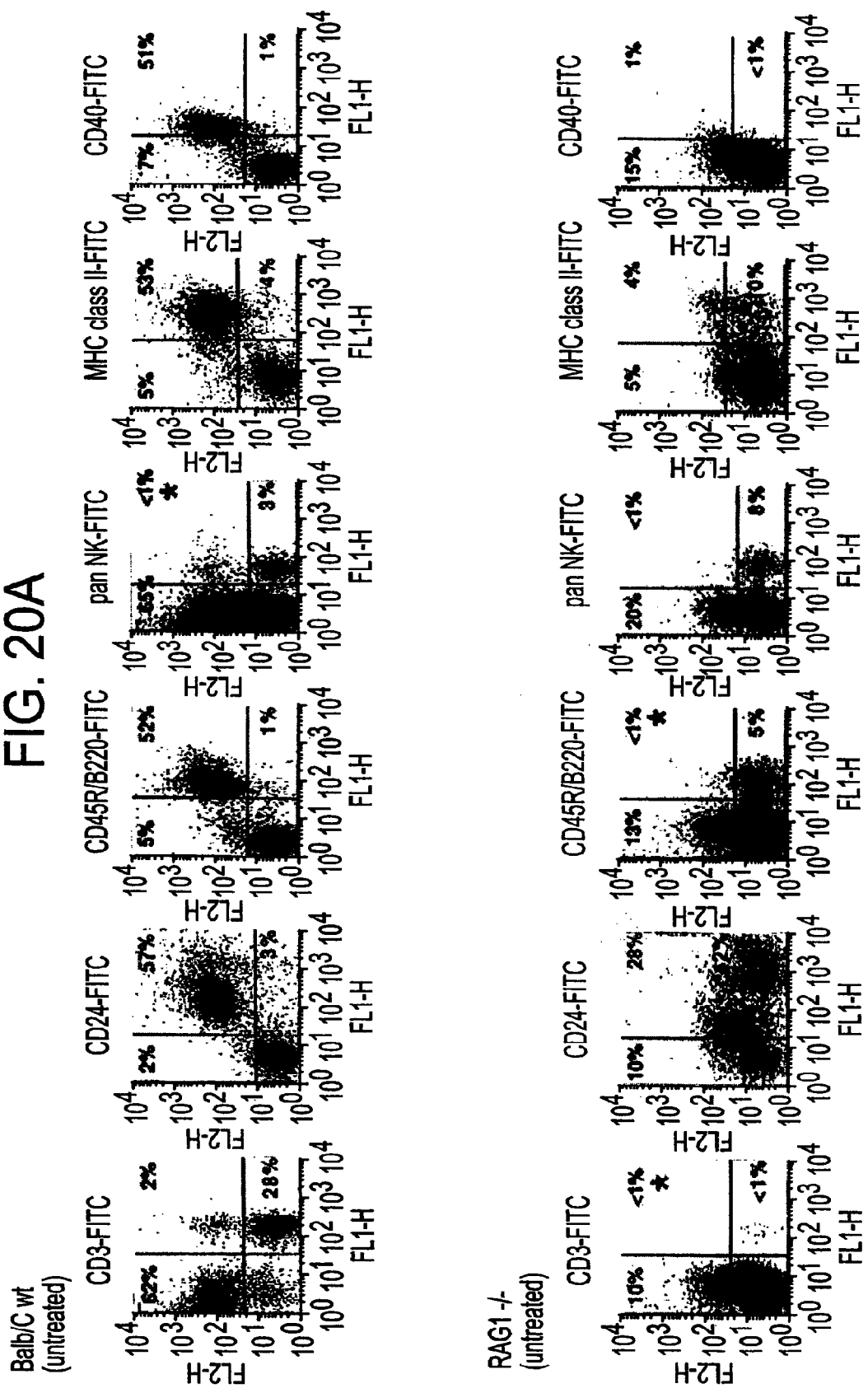
Figures 1, 20B:
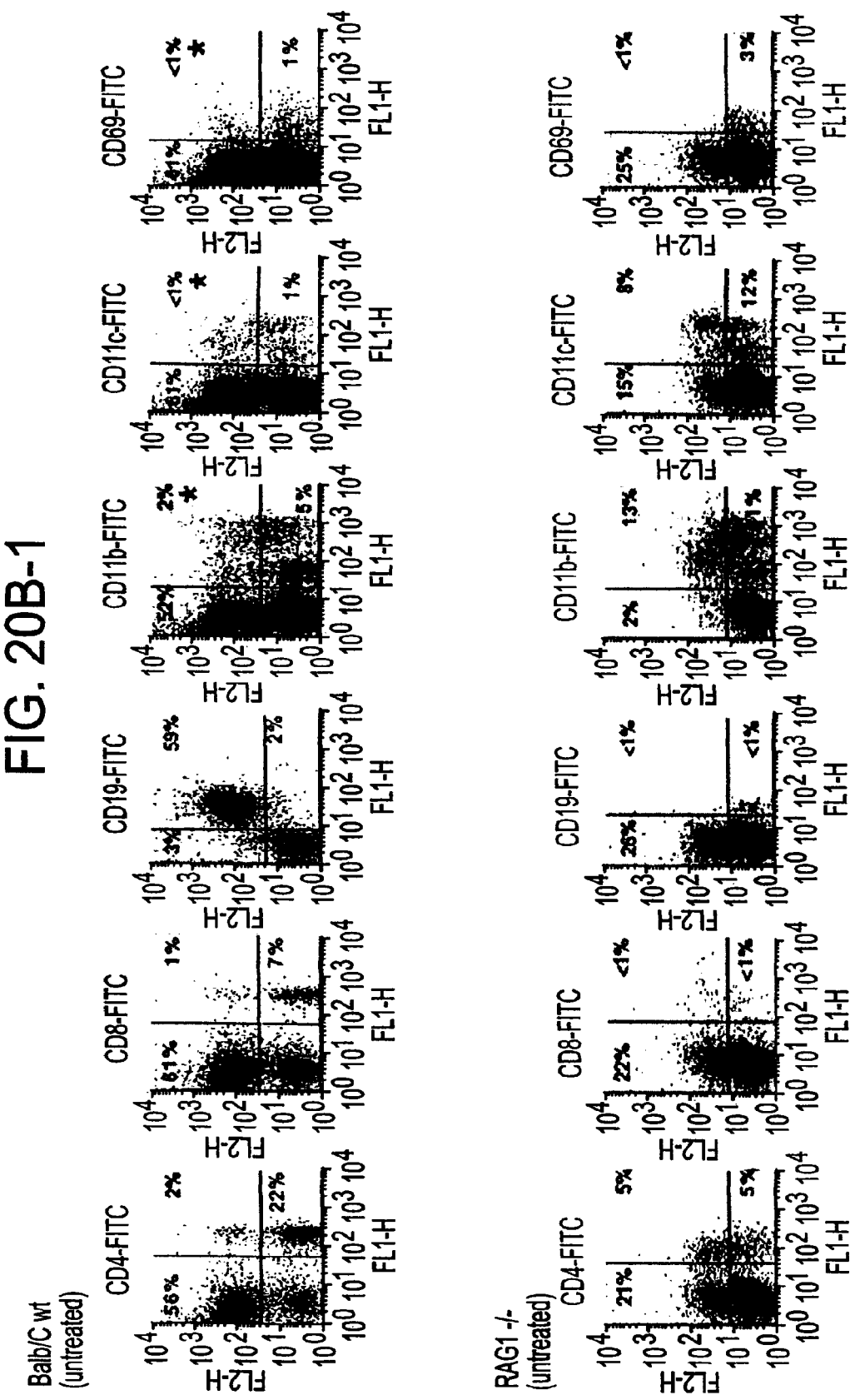
FIG. 1 shows the complete nucleotide sequence of murine GL50-1 (mGL50-1), based on signal sequence clone (position 1-519) and RecA isolated clone (position 374-2718). Predicted nucleotides encoding a signal sequence are boxed and the hydrophobic transmembrane domain is underlined.

Isolation of mGL50-1 Molecules cDNAs encoding secreted proteins derived from RNA of IL-12 treated mouse lymph nodes were placed under genetic selection for signal sequences by using the *Saccharomyces* cerevisiae signal sequence trap method (Jacobs et al). Of a total of 333 cDNA:invertase clones isolated and sequenced, 1 partial cDNA clone with limited sequence identity with B7-1 was identified and termed mGL50-1 (FIG. 1, SEQ ID NO:1). RecA mediated full length cDNA isolation from a mouse fetal thymus cDNA library resulted in the generation of 4 additional cDNA clones that contained 3' untranslated regions as well as overlapping the partial signal trapped sequence clone.

The consensus 2718 nucleotide mGL50-1 sequence encoded a 322 amino acid protein with a predicted mass of 36 kDa. Hydropathy plot of the open reading frame predicted a structure corresponding to a leader sequence (from about amino acids 1-46 of SEQ ID NO:2; encoded by about nucleotides 67 to 195 of SEQ ID NO: 1), an extracellular domain (from about amino acids 47-279 of SEQ ID NO:2; encoded by about nucleotides 196 to 904 of SEQ ID NO: 1), a hydrophobic transmembrane region (from about amino acids 280-298 of SEQ ID NO:2; encoded by about nucleotides 905 to 961 of SEQ ID NO: 1) and a potential intracellular cytoplasmic domain (from about amino acids 299-322 of SEQ ID NO:2; encoded by about nucleotides 962 to 1032 of SEQ ID NO: 1). Signal peptide cleavage was predicted at position 46 in the amino acid sequence. Analysis of mGL50-1 by Pfam protein motif prediction program suggested structural similarity to Ig-domain in the cytoplasmic domain of the protein. In keeping with an Ig-like structure, 4 cysteines were found in the extracellular domain, allowing for the possibility of intramolecular bonding and distinct structural conformation corresponding to an IgV-like domain and an IgC-like domain, based on domain delineation. FastX sequence comparison in which translated proteins are searched through GenBank database yielded a number of identified cDNA clones with sequence similarities including AB014553, B7-1, B7-2, and Y08823. Corresponding domains in polypeptides in the B7 family are shown in FIG. 12.

Example 2

Isolation of an Alternatively Spliced Form of GL50

Figure 15:
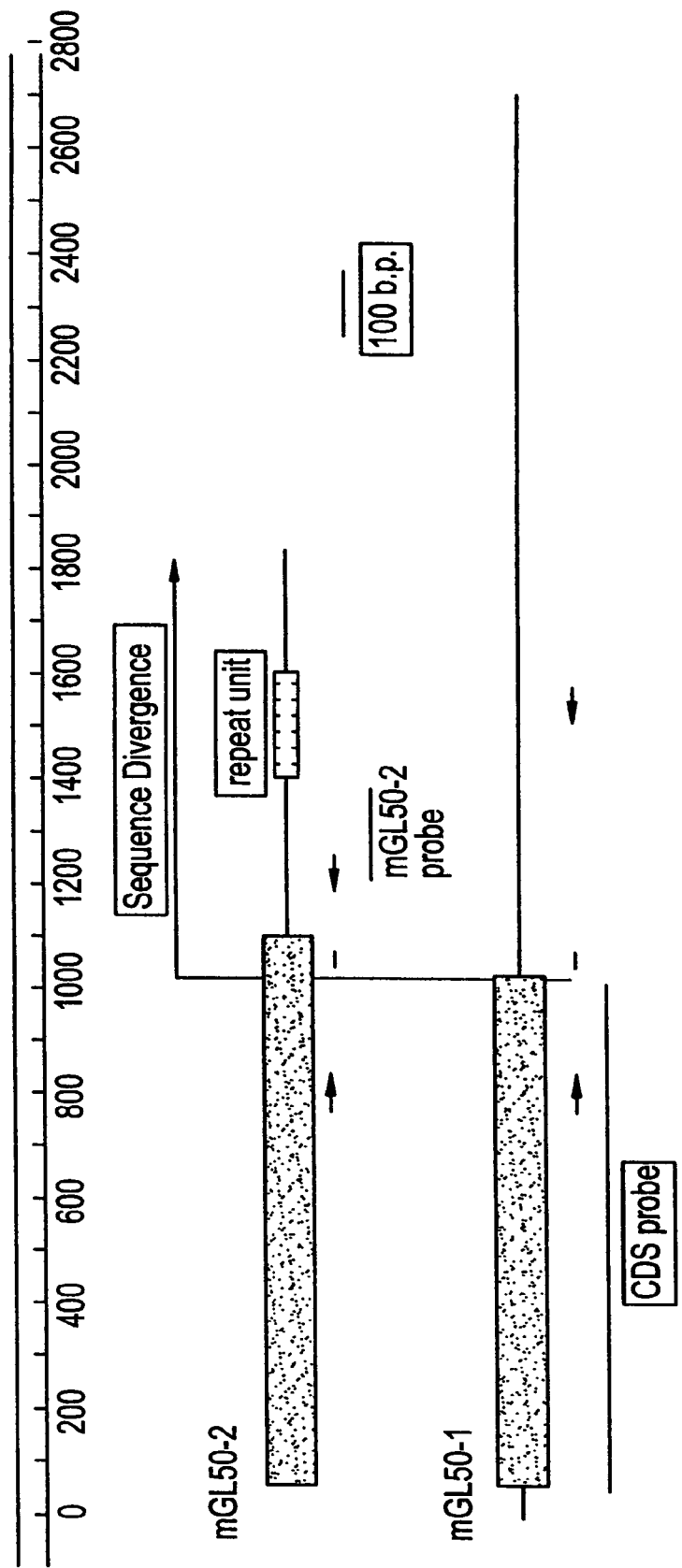
FIG. 15 depicts a schematic diagram of mGL50-1 and mGL50-2. Sequence divergence, indicated by vertical line, occurs at nucleotide 1027 for mGL50-1 and 960 for mGL50-2. The repetitive sequence (hatched box) is found in the 3' UTR of mGL50-2 encompassing nucleotides 1349-1554.
Figures 2, 20B:
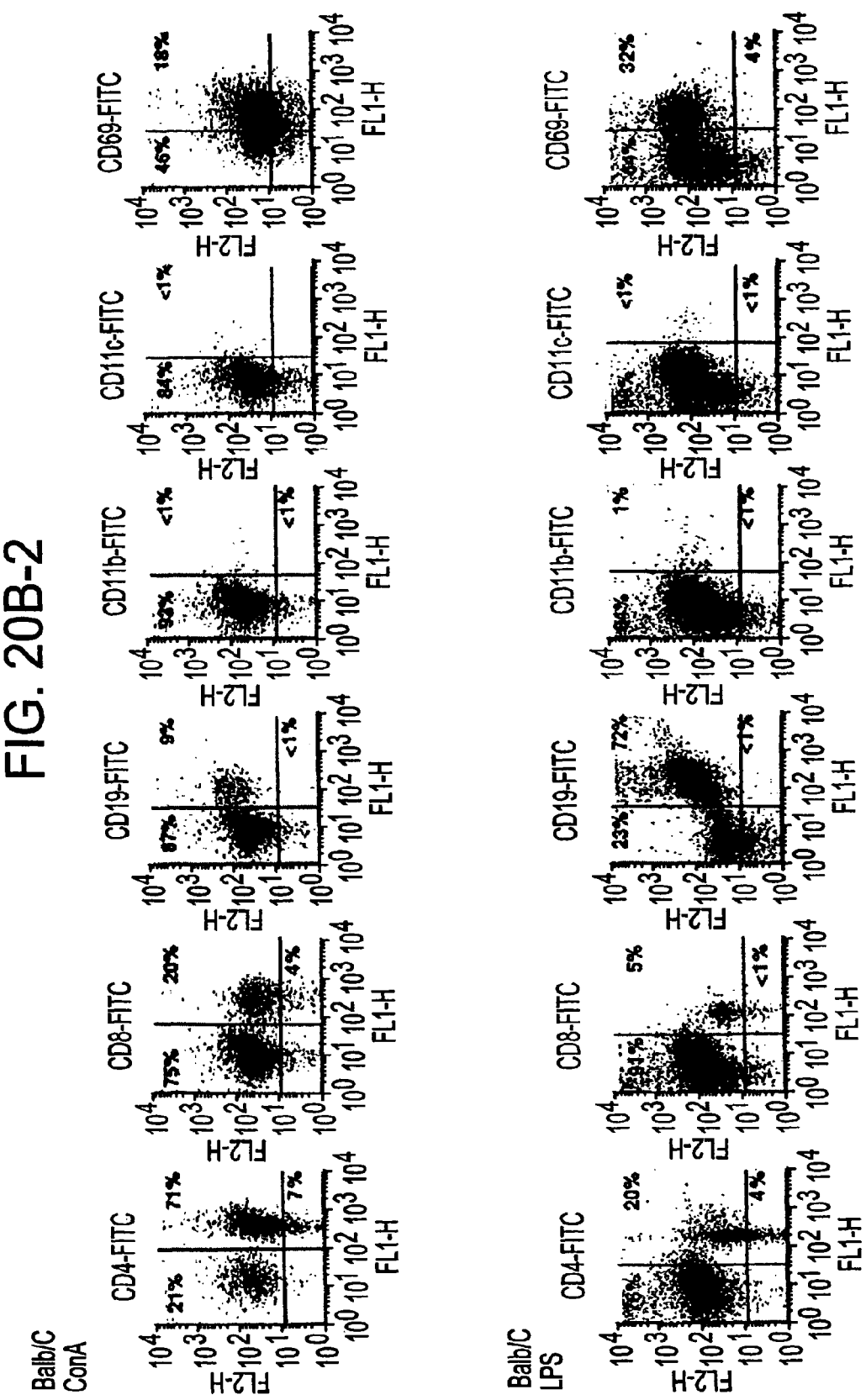
FIG. 2 shows the nucleotide sequence of murine GL50-2 (mGL50-2) product.

To determine the extent of transcript heterogeneity, 3' RACE was performed to isolate splice variants of murine GL50-1. Using specific, nested 5' oligonucleotide primers corresponding to sequences upstream and including the initiation start site of mGL50-1, amplified PCR products were generated from cDNAs derived from mouse PBLs. Upon hybridization to radiolabeled oligonucleotides internal to mGL50-1 coding region, clear hybridization signals were detected. Subsequent cloning of positively hybridizing PCR products followed by sequence analysis revealed RACE sequences of which none were identical to the consensus mGL50-1 sequence derived from the mouse fetal thymus library. Two sets of PCR products, represented by multiple clones with extensive polyadenylation of differing lengths, were found to encode an alternatively spliced form of GL50. One representative product, a 1759 bp product, termed mGL50-2, encoded a polypeptide 347 amino acid residues in length with a predicted molecular mass of 39 kDa (FIG. 2, FIG. 15).

An alignment of mGL50-1 and mGL50-2 is presented in FIG. 3. Alignment of the mGL50-1 and mGL50-2 sequences demonstrated complete identity from nucleotide 67 (initiation methionine/mGL50-2 RACE priming site) to nucleotide 1027 of the cDNA, with the exception of two nucleotides found in multiple mGL50-2 products (nucleotides 531 and 710, leading to an arginine to histidine residue at 237 of the predicted amino acid sequence (FIG. 3)). These two nucleotide discrepancies are most probably due to strain differences between the mice used for the RNA starting material, since multiple separate PCR products encoded identical mismatches. Sequences downstream of position 1027 of mGL50-1 and position 961 of mGL50-2 were divergent between the two molecules (FIG. 3). Both mGL50-1 and mGL50-2 sequences contained a consensus AATAAA polyadenylation signal upstream from the poly-A tail (13 bp for mGL50-2, 16 bp for mGL50-1). As a result of the alternative 3' sequences encoding the carboxy terminus, mGL50-2 lacked the final 2 amino acids of mGL50-1 but incorporated an additional 27 novel amino acids in the cytoplasmic domain. The predicted amino acid sequence of mGL50-2 indicated the presence of three unique tyrosine residues, Y325, Y328, and Y333, in the carboxy terminus, in addition to the tyrosine residues Y299 and Y307 shared by both the mGL50-1 and mGL50-2 molecules. GenBank database search revealed no cDNA sequences with similarity to the divergent coding 3' domain of the mGL50-2 product, with the exception of a complex repetitive sequence (bases 1349-1554) also found in numerous genomic sequences (e.g. Accession numbers AC005818, AC006508, and AF115517), as well as in known mRNAs (mouse desmin: Z18892; and mouse servivin: AF115517). No such untranslated repetitive sequences were found in mGL50-1.

Example 3

Identification of a Human Ortholog of GL50

After the murine GL50 clones were identified, database search and subsequent comparisons suggested that mouse mGL50-1 and mGL50-2 clones may have homology with a cDNA isolated from human brain, KIAA clone 0653 (accession # AB014553; Ishikawa et al. (1998) *DNA Res.* 5:169). AB014553 has been described as a 4.3 kb cDNA localized on chromosome 21, encoding a putative 558 amino acid protein with a molecular mass of 60 kDa. Because both the length of the AB014553 cDNA and the encoded protein were nearly 2 fold greater than mGL50-1, it was not likely that AB014553 was a human ortholog of the mouse GL50 sequences. However, analysis of the first 303 residues of the deduced AB014553 protein sequence indicated similarity with mGL50-1, excluding the signal peptide region of the cDNA.

Because AB014553 was derived by size fractionation of large cDNAs, AB014553 was believed to represent a variant transcript that also existed as a smaller gene product. To address whether such a smaller product existed, 3' RACE analysis of human PBLs with oligonucleotides primers (VL 142 (ACAACAGCCTGCTGGACCAGGC; SEQ ID NO: 10) and VL141 (CGTGTACTGGATCAATAAGACGG; SEQ ID NO:9)) corresponding to extracellular domains of AB014553 with sequence homology with GL50 were performed. Four RACE products were isolated which encoded an open reading frame identical to AB014553 from amino acid residue 24 (starting point of RACE primer) to residue 123 (FIG. 6). From residue 123 onward, the AB014553 RACE product diverged from the cDNA sequence resulting in an alternative 88 nucleotides with a 3' coding region encoding 9 amino acids, termination codon, and a short untranslated domain. This alternative 3' region resulted in a premature termination codon in the AB014553 RACE clone as compared to AB014553 cDNA (FIG. 7). The predicted total length of the deduced polypeptide encoded by this alternatively transcribed product, after merging with shared 5' sequences of AB014553 cDNA was 309 amino acids, consistent with a human protein orthologous to mouse GL50 protein sequences, referred to as hGL50 (FIG. 8).

Example 4

Alignment with Chicken B7-1

Upon alignment with a previously characterized chicken B7-1 (Accession No. Y08823), a pattern of conserved cytoplasmic domain sequences emerged between these molecules. Within the intracellular region, hGL50 protein sequences exhibited 34% identity (9/26 residues aligned) with mGL50-1, while chicken Y08823 exhibited 57% identity (8/14 residues aligned) with either human or mouse GL50 or GL50-2 resulting in a consensus motif of (R)(R)(R)[XX](O)(H)(X/–)SY(T)(G)(P) (SEQ ID NO:21), wherein amino acids in brackets are variable between the three genes, amino acids in parentheses are shared between two of the three genes, and amino acids without brackets or parentheses are shared by all three genes. A FastA database search for proteins with homology to this motif yielded two mouse entries, Veli-2 (Accession No. AF087694) and MALS-2, a C. elegans LIN-7 homolog (Accession No. AF173082), encoding identical sequences with the motif RRRQQHHSYT (SEQ ID NO:22). This unique domain is localized at the carboxy terminus of Veli-2 but is not present in the isoforms Veli-1 or Veli-3, and extends beyond the area of homology with C. elegans LIN-7.

Example 5

Figure 4A:
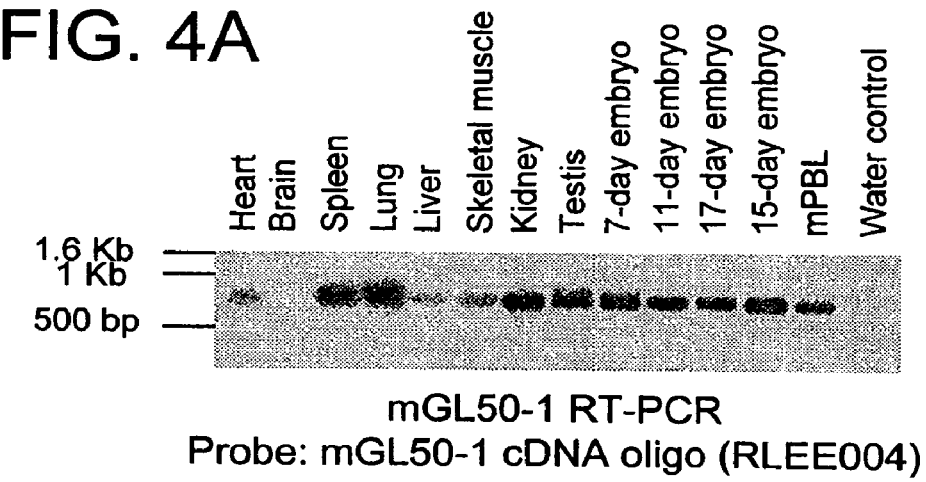
FIG. 4 shows isoform specific RT-PCR of mGL50-1 and mGL50-2.
Figure 4B:
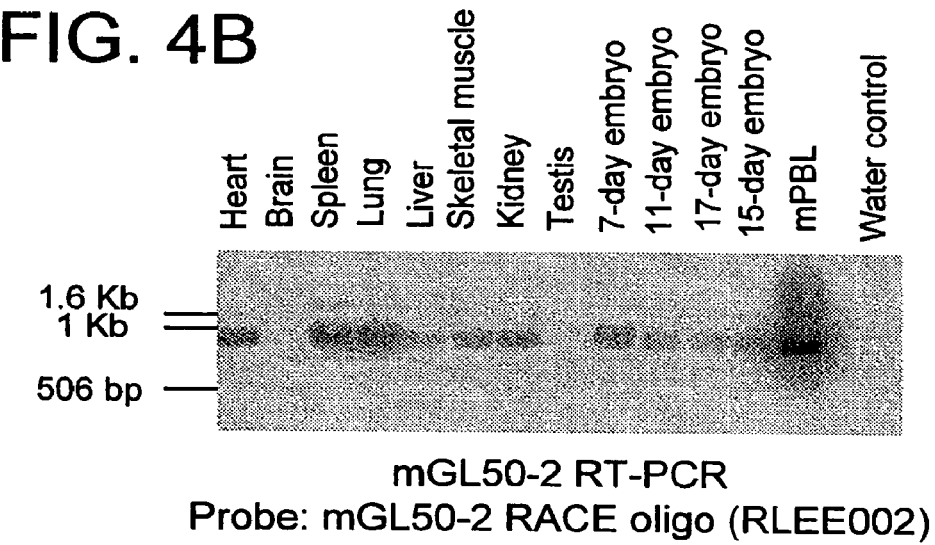
Figure 4C:
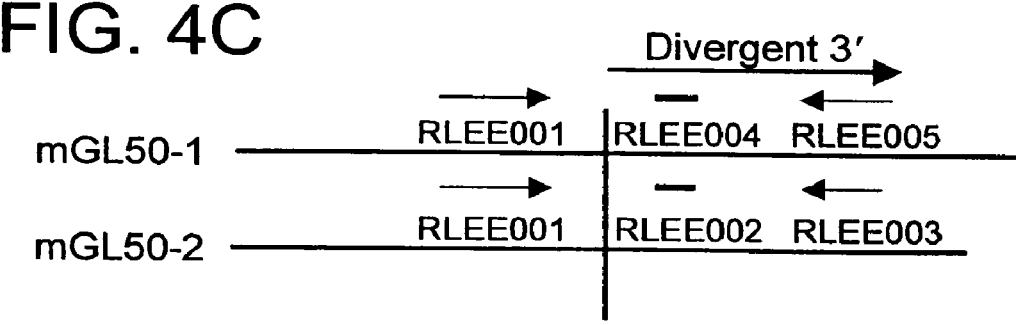
Figure 9A:
FIG. 9 shows hydropathy plot analysis of GL50, merged AB014553 RACE product (hGL50), and mouse and human B7-1 and B7-2. Significant hydropathy profiles are seen between GL50 and AB014553.
Figure 9B:
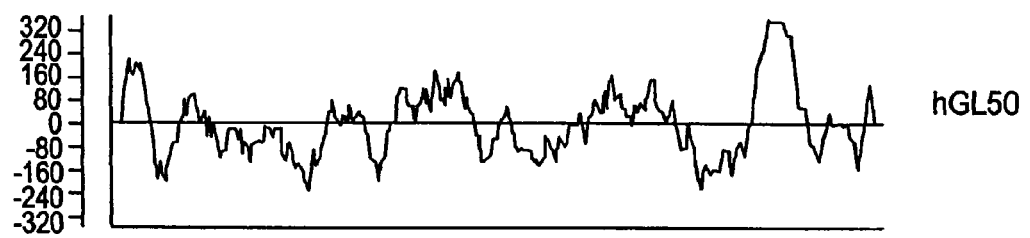
Figure 9C:
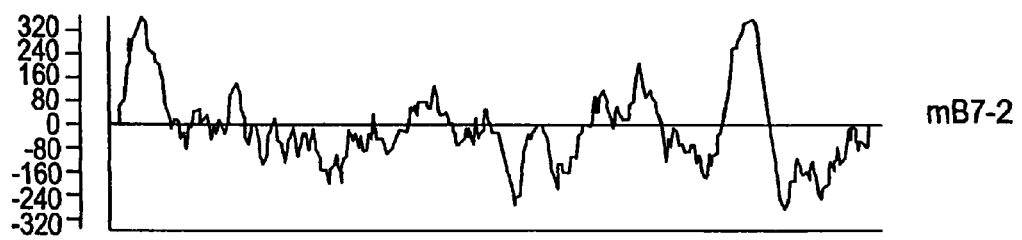
Figure 9D:
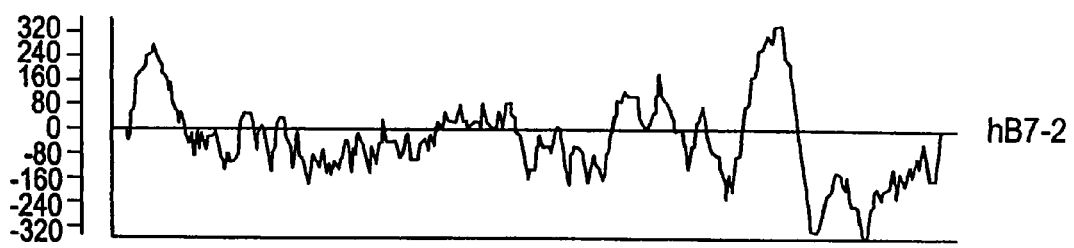
Figure 9E:
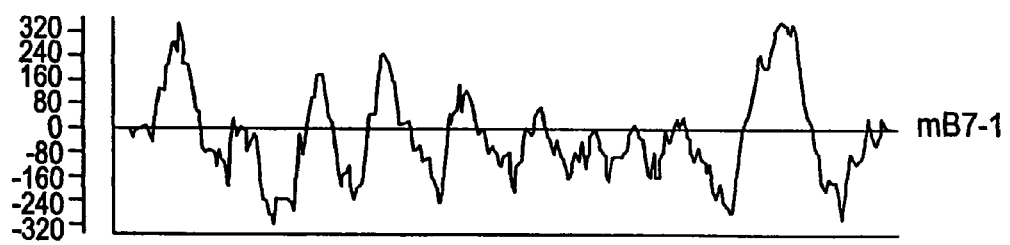
Figure 9F:
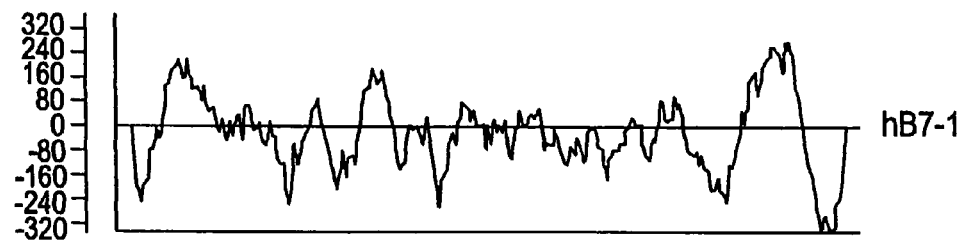
Figure 10A:
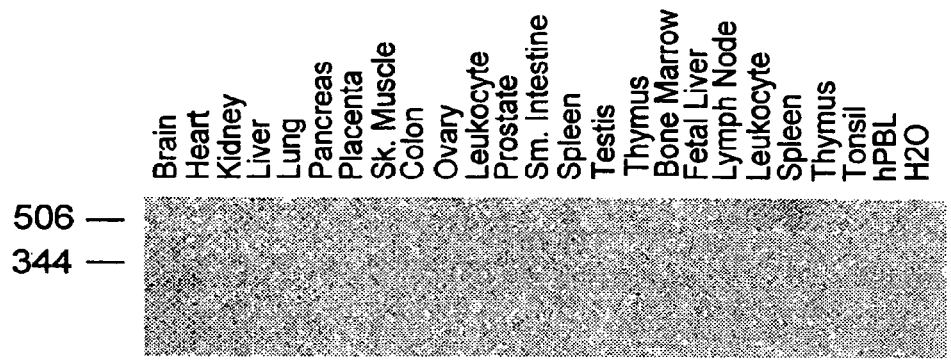
FIG. 10 shows RT-PCR Southern blot analysis of the published AB014553 cDNA and AB014553 RACE products.
Figure 10B:
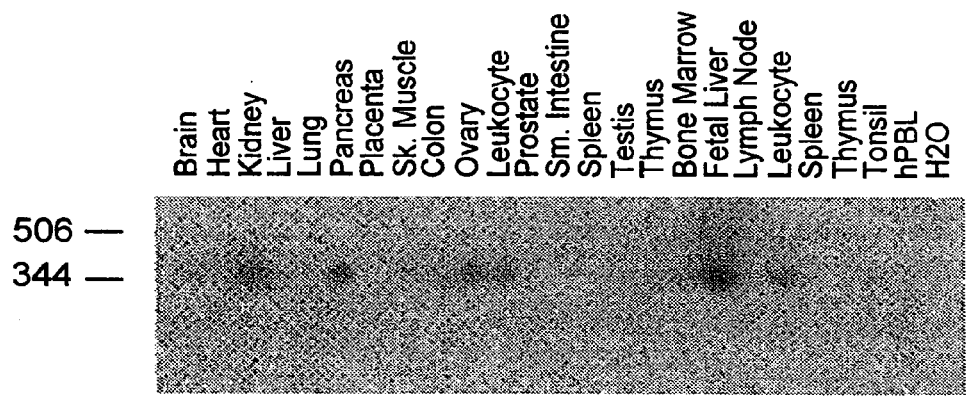
Figure 10C:
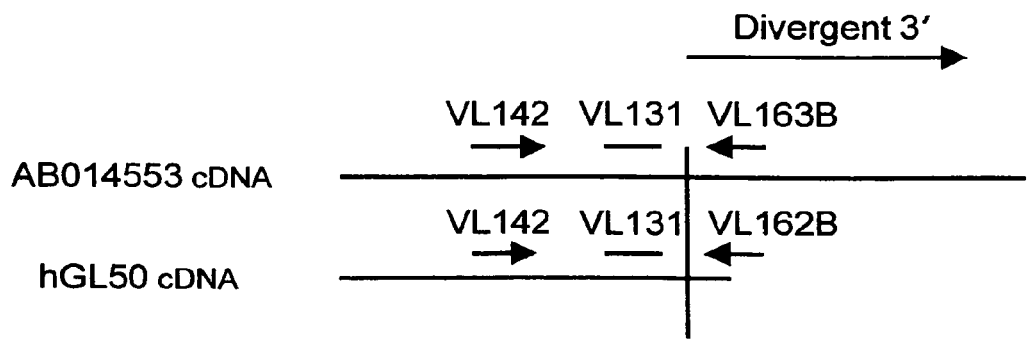

Expression of GL50 Molecules mGL50-1 and mGL50-2 specific RT-PCR reactions on commercial cDNA panels resulted in abundant PCR products generated in heart, spleen, lung, liver, skeletal muscle, kidney, testis, 7-15 day embryo and PBL. Negligible product was detected with brain samples for either transcripts while low levels of product was detected in testis samples for mGL50-2 (FIG. 4). By Northern blot analysis of commercial RNA blots using probes specific to either the shared extracellular domain of mGL50-1 and mGL50-2 or to the 3' untranslated regions of either mGL50-2 or mGL50-1, differential hybridization was found between the two molecules. Whereas both the extracellular domain probe and the mGL50-1 specific probe hybridized to an ~2.7 kb message clearly detectable in heart, brain, spleen, lung, liver, skeletal muscle, kidney and testis samples (identical to the pattern previously seen in blots specific for mGL50-1 (Ling et al. (2000) J. Immunol. 164: 1653-7), the mGL50-2 specific probe hybridized to a 1.7 kb transcript detected only in heart, spleen and kidney samples, suggesting that mGL50-2 transcripts were concurrently transcribed as a limited subset of tissues with the highest expression mGL50-1 (FIG. 5). In poly A+ RNA blots, hybridization using the mGL50-2 3' UTR specific probe was clearly detected in samples representing undifferentiated ES cells, day 10 embryoid bodies, day 12.5 embryonic yolk sac, and day 15 fetal liver. In contrast, hybridization using the mGL50-1 cDNA coding sequence probe clearly revealed transcript in all samples examined To assess the tissue distribution of AB014553 cDNA and AB014553 RACE clones, RT-PCR/southern blot analyses were performed under similar conditions as for the GL50 sequences described above. Using oligonucleotides primers specific for the amplification of published AB014553 cDNA (VL142 (ACAACAGCCTGCTGGACCAGGC; SEQ ID NO: 10) and VL 163B (GGGCCCCCCAGAACCTGCT-GCTTCC; SEQ ID NO: 17)), PCR resulted in the complete absence of any detectable AB014553 cDNA signal for all samples tested (FIG. 10). Possible explanations for the lack of RT-PCR products representing published AB014553 cDNA sequences may be the use of non-optimized oligonucleotides, extremely low-abundance of the target transcript, or actual absence of this form of the product. RT-PCR conditions specific for AB014553 RACE using oligonucleotide primers VL142 and VL162B resulted in the detection of a 350 bp amplification product in kidney, lung, ovary, fetal liver, and leukocyte, with the highest level of amplified product detected in fetal liver. Surprisingly, virtually no signal was detected in spleen, lung, thymus, or lymph nodes. These results are consistent with the published report of AB014553 transcript distribution (Ishikawa et al. (1998) *DNA Res.* 5:169) in a smaller survey of a tissue cDNA panel, but does not complement the tissue distribution patterns observed for the GL50 molecules.

Figure 11:
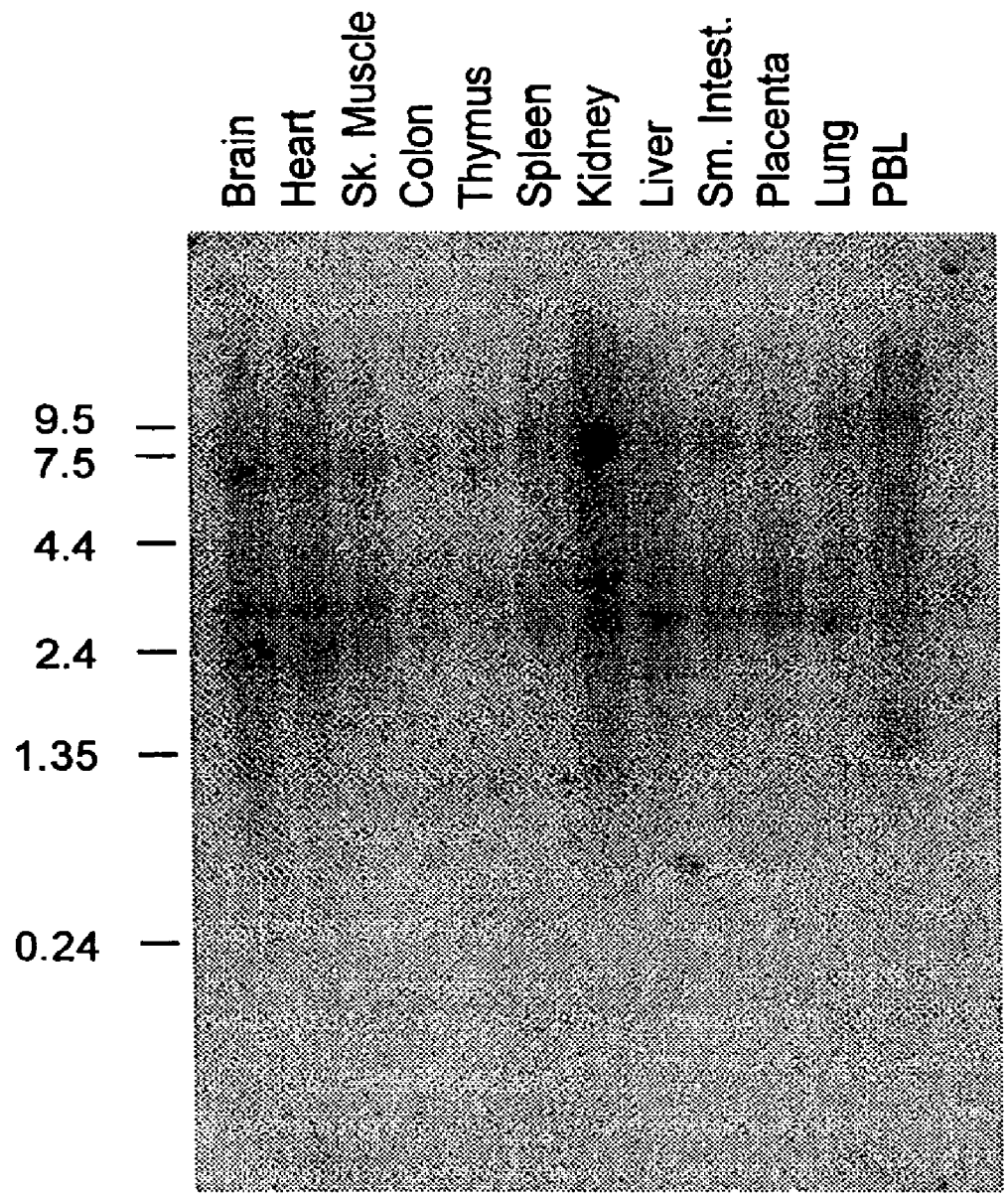
FIG. 11 shows northern analysis of multiple human tissue RNA blots. The coding sequences of the hGL50/AB014553 were used as probes.

Unlike the mGL50-1 and mGL50-2 clones in which lengthy and divergent 3' untranslated regions were present, AB014553 RACE products contained only 88 bp of sequence that diverged from that of AB014553 cDNA. Because of this, it was not possible to design nucleotide probes of sufficient specific activity for the detection of the RACE product. Using coding region probe for hGL50 northern hybridizations were performed on commercial human multiple tissue RNA blots to assess transcript distribution (FIG. 11). Results indicated the presence of a number of transcripts found in all tissues with approximate molecular size of 2.4 kg, 3.0 kb, 7.0 kb, with highest levels of signal present in brain, heart, kidney, and liver samples. Low hybridization signals were detected in colon and thymus. An additional transcript of 8.5 kb was detected in a subset of the panel, including thymus, spleen, kidney, liver, lung and PBL while a 3.8 kb transcript was detected in lung and PBL sample. A unique 1.1 kb transcript was detected only in PBL samples and corresponded to the predicted size of hGL50 if 5' and 3' untranslated sequences were included. Determination of other minor transcripts was difficult due to the limits of the sensitivity range of the blot. None of the obvious transcripts correlate with the 4.3 kb published AB014553 cDNA, suggesting that this sequence may not exist in nature or may be expressed at levels lower than detectable limits. Comparison between hGL50 blots and hGL50 RT-PCR surveys share the common feature of having the greatest signal in kidney tissues and less signal in lymphoid related tissues such as thymus, spleen and PBL.

Example 6

Relationship of the GL50 Polypeptides to Other Polypeptides

To determine the extent of relatedness between mGL50-1, hGL50, and human and mouse B7-1 and B7-2, protein sequence alignments were performed. From Pileup analysis (FIG. 12), 18 amino acid locations aligned identically between all six molecules within the extracellular domain. Of the 32 positions that define the predicted IgV-like and IgC-like folds of the B7 molecule, 13 are identically conserved between all six molecules, most notably the 4 cysteines that allow intramolecular folding of domains. Other areas of significant sequence conservation were also seen in the extracellular domain, but interestingly the identities of hGL50/ mGL50 sequences in certain locations aligned more closely with either B7-1 or B7-2 (identity score of 8). For example, valine residue corresponding to position 77 of mGL50-1 is shared by hGL50, and murine and human B7-2 sequences, but not B7-1. Likewise, the tyrosine at position 78 of mGL50-1 is conserved at corresponding locations in hGL50 and murine and human B7-1, but not B7-2. Of the 16 positions with identity scores of 8, 5 positions are shared by mGL50-1/hGL50 and B7-1, 4 positions are shared between mGL50-1, hGL50 and B7-2, and 6 positions are shared between B7-1 and B7-2.

Based on the peptide structure, these results suggest that the mGL50/hGL50 sequences occupies a phylogenetic space parallel to the B7 family of proteins. Molecular phylogeny analysis (GrowTree) measuring genetic distance in terms of substitutions per 100 amino acids resulted in a dendrogram (FIG. 13) with independent clustering of mGL50/hGL50 (85), m/hB7-2(68) and m/hB7-1 (88). As an outgroup, mmu67065_1 (mouse butyrophilin) was used. The chicken clone Y08823 also was found to be more aligned with the GL50/AB014553 sequences (~140) than the B7 sequences (215-320), indicating that these sequences comprised a distinct subfamily of proteins. Distances between the GL50/AB014553, B7-2 and B7-1 branches were high (216-284), suggesting that large numbers of substitutions have occurred between these molecules since the inception of the human and rodent lineage.

Mouse and human CTLA4 (see e.g., Dariavach, P. et al. (1988) *Eur. J. Immunol.* 18:1901; GenBank Accession Number L15006; U.S. Pat. No. 5,434,131) and ICOS (Hutloff et al. (1999) *Nature* 397:263; WO 98/38216) were also analyzed for phylogenetic relationships using the same parameters. Genetic distances revealed a pattern that was distinct to that seen for the B7-like proteins. As indicated in previous reports, the genetic distance between the mouse and human ICOS and CD28 (176-2570) was closer than that of CTLA4 (261-405). By comparison, the genetic distance between CD28 and CTLA4 was much smaller (143-1670), indicating that the structural relationships between the members of the receptor family were not parallel to that of the ligand family.

Example 7

Demonstration of Binding of GL50 to ICOS

Figure 14A:
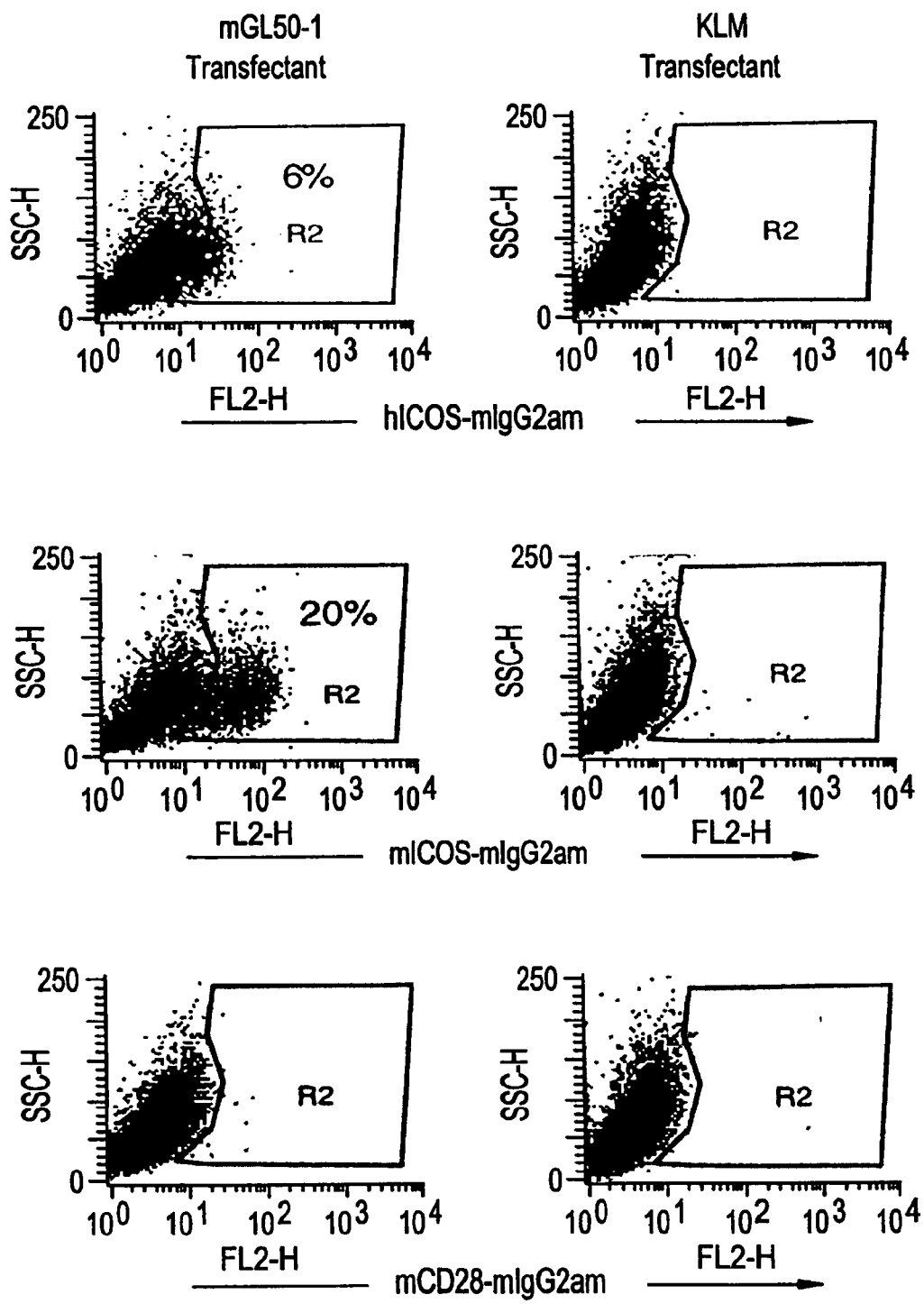
FIG. 14 shows results of a GL50 COS transfection study. mGL50-1 was expressed in COS cells followed by staining with either ICOS-Ig, CD28-Ig, CTLA4-Ig. Binding of ICOS Ig by cells expressing mGL50-1 was detected.
Figure 14B:
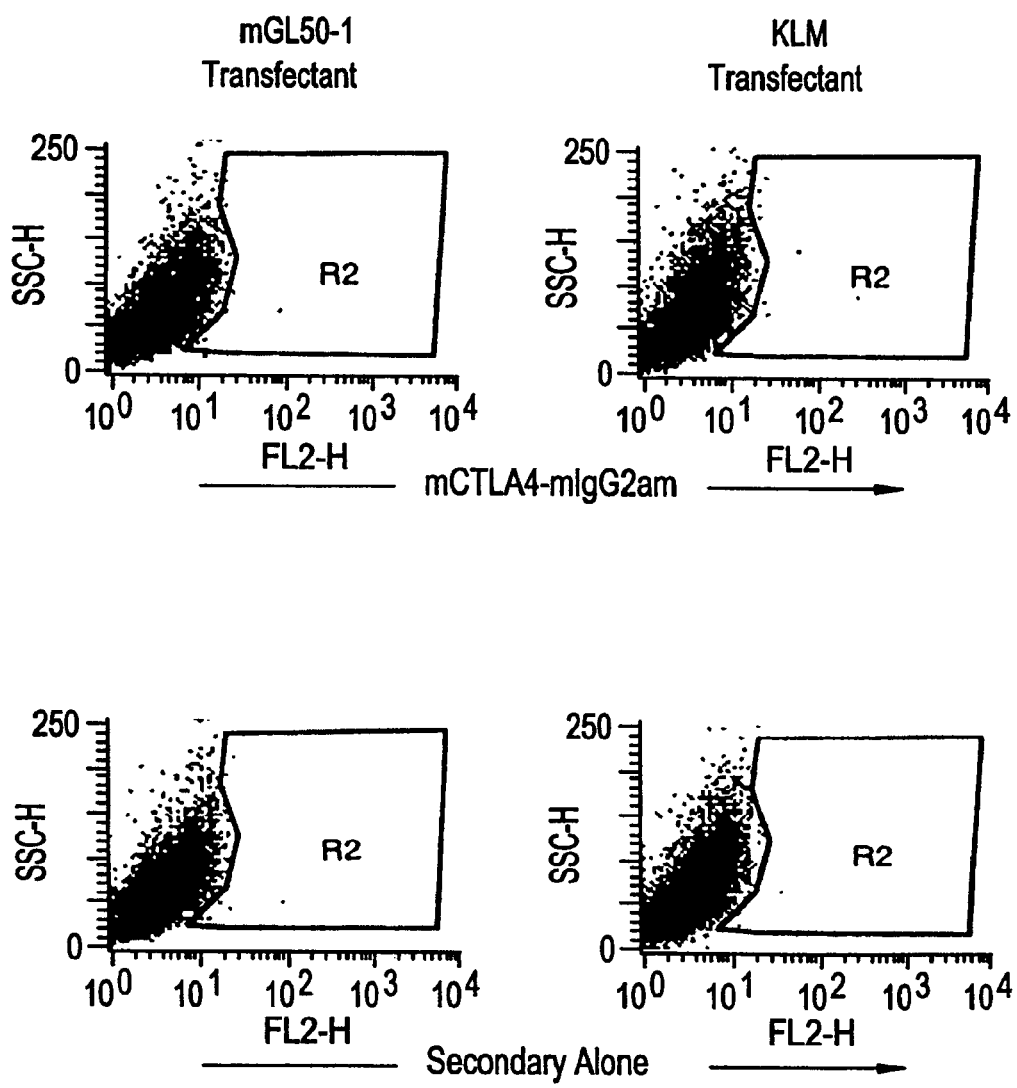

To determine whether GL50 was a ligand for murine CTLA4, CD28 or ICOS, transfection binding studies were performed with mGL50-1 expression vectors (FIG. 14). mGL50-1 or human DAP-12 negative control cDNA were transfected into COS cells followed by staining with either ICOS-Ig, CD28-Ig or CTLA-4-Ig fusion proteins or normal murine Ig. COS cells were stained two days after transfection with 5 µg/ml of fusion protein, followed by goat anti-mouse PE labeled antibody. By flow cytometry, binding of GL50 transfected COS cells was detected only by the ICOS-Ig reagent (15%), while negligible binding was detected for CD28-Ig, CTLA4-Ig or the normal mouse Ig used as a negative staining reagent. No binding of any fusion protein was detected for the DAP-12 cDNA transfectants. These results suggest that GL50 is a ligand for ICOS-Ig.

Although not found under the specific binding conditions herein, it may be that GL50 is also capable of signaling through either CD28 or CTLA-4 given the published data showing the weaker binding activity of the B7 molecules to CD28 than CTLA-4 (Greenfield, E. A. et al. (1998) *Crit. Rev. Immunol.* 18:389) in cell based assays.

Example 8 mGL50-2 Transcripts Encode Functional Cell Surface Proteins

To demonstrate that mGL50-2 transcripts encode functional cell surface proteins, vectors expressing the mGL50 coding regions under the transcriptional control of EF-1alpha promoter were used to transfect COS cells. By flow cytometry, both mICOS-mIgG2am and hICOS-mIgG2am were found to bind mGL50-1 and mGL50-2 transfected cells (9-14%) while negligible binding was observed with mCTLA4-mIgG2am (<1%), indicating that the domains encoded by the additional residues in the alternate carboxytail found in mGL50-2 do not affect surface mobilization of this protein (FIG. 17). It is also notable that hICOS-mIgG2am binds both molecules, suggesting that the ICOS receptors, like CTLA4 and CD28 receptors, retain ligand binding capacity when assayed against targets across primate/rodent species boundaries. Other mouse cells lines were examined for the presence of surface ICOS-ligand. WEHI231 cells have been previously shown to have surface expression of both B7-1 and B7-2, whereas ES cells have been shown to display only B7-1. mCTLA4-mIgG2am staining of WEHI 231 cells was clearly detectable using 8 ng/ml of reagent, while mICOS-mIgG2am staining was minimally detectable at levels starting at 1 µg/ml. These results suggest that the binding affinity of mCTLA4-mIgG2am reagent to the B7 molecules is at least 100 fold greater than mICOS-mIgG2am reagent binding to GL50 on WEHI cells, similar to the low binding affinity measured between CD28-Ig and B7 proteins. In the presence of blocking antibodies, mCTLA4-mIgG2am binding to WEHI 231 was totally abrogated, while no effect on mICOS-mIgG2am binding to cells was observed, confirming that neither WEHI 231 B7-1 nor B7-2 potentiates specific binding with mICOS-mIgG2am (FIG. 18). To corroborate evidence from RNA blot analysis demonstrating the presence of GL50 in cells representative of the very early embryonic environment (see above), undifferentiated CCE ES cells were analyzed by direct staining with antibodies to B7-1 and indirect staining with mICOS-mIgG2am fusion protein. Undifferentiated ES cells stained with anti-B7-1 (FIG. 19) revealed a one-log fluorescence shift over background, consistent with previous observations (Ling, V. et al. (1998) *Exp. Cell. Res.* 241:55-65), and a half-log fluorescence shift over background with mICOS-mIgG2am staining, demonstrating the simultaneous surface display of both B7 and OL50 type molecules in a system that reflects the undifferentiated inner cell mass of early preimplantation embryos.

Example 9

Expression of GL50 on Splenocyte Subpopulations

Phenotypic analysis of the major splenic cell types exhibitin GL50 surface proteins revealed mICOS-mIg binding to be most readily detectable on phenotypic CD19+B cells, although it was apparent that other splenic cell types exhibited ICOS-Ig staining (see FIG. 30). To further identify other freshly isolated cells that display GL50, wild type Balb/C splenocytes were compared to RAG1 –/– splenocytes lacking mature B and T cells. The results are presented in FIG. 20 and Table 3.

TABLE 3

| Antibody stain | Balb/C | | | RAG1-/- | | |
|---|---|---|---|---|---|---|
| | n = | % of Total Splenocytes | % ICOS-Ig positive | n = | % of Total Splenocytes | % ICOS-Ig positive |
| anti-CD3 | 10,000 | 30% | 10% | 50,000 | <1% | — |
| anti-CD4 | 10,000 | 25% | 8% | 10,000 | 11% | 45% |
| anti-CD8a | 10,000 | 9% | 10% | 50,000 | <1% | — |
| anti-CD19 | 10,000 | 65% | 97% | 50,000 | <1% | — |
| anti-CD24 | 10,000 | 64% | 94% | 10,000 | 67% | 28% |
| anti-CD45R/B220 | 10,000 | 61% | 97% | 50,000 | 6% | 5% |
| anti-CD11B | 50,000 | 8% | 26% | 10,000 | 37% | 31% |
| anti-CD11C | 50,000 | 2% | 43% | 10,000 | 20% | 55% |
| anti-pan NK | 50,000 | 3% | 20% | 10,000 | 9% | 3% |
| anti class II | 10,000 | 65% | 95% | 10,000 | 27% | 3% |
| anti CD40 | 10,000 | 61% | 97% | 10,000 | <1% | — |
| anti CD69 | 10,000 | 2% | 25% | 50,000 | 3% | 5% |

Figure 20C:
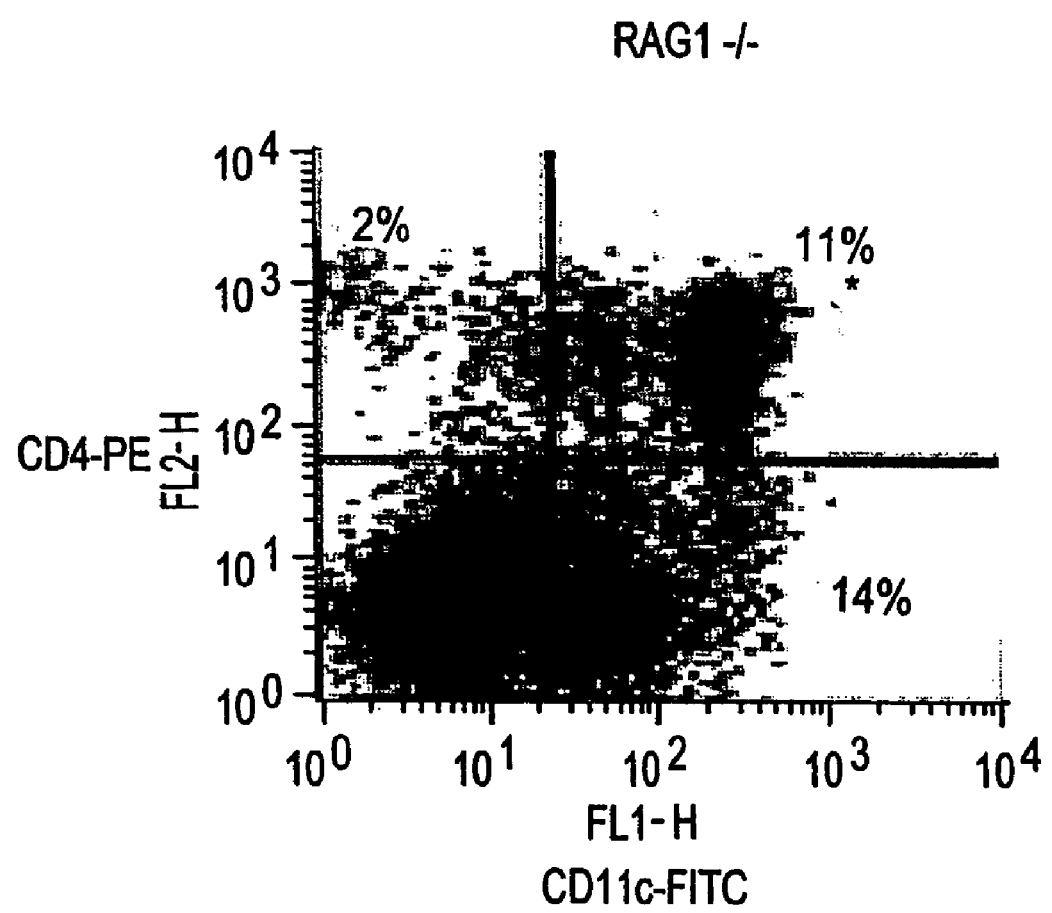

As expected, Balb/C splenocytes revealed high levels of mICOS-mIgG2am binding (FIGS. 20A and B) to phenotypic B cells (CD19, B220, CD40>94%), while lower levels were found on phenotypic T cells and T cell subsets (CD3+, CD4+, and CD8+; <10%), macrophages (CD11b, 26%), dendritic cells (CD11c, 43%) and NK-cells (pan-NK, 20%). mICOS-mIgG2am binding was also detected on the more general lymphoid markers CD24 and class II (94%) cells. Northern blot analysis (using an mGL50-1 specific probe) demonstrated that GL50 transcripts are expressed in the splenocytes of RAG1 -/- mice. This suggested that in the absence of mature T or B cells, GL50 was still expressed on other splenocyte subpopulations. Consistent with these observations, analysis of RAG1 -/- splenocytes (FIG. 20B) demonstrated that they are CD3-, CD8-, CD19-, and CD40-, and that the remaining CD11b+ (35%) and CD11c+ (55%) cells are readily counterstained with mICOS-mIgG2am. Low levels (<5%) of ICOS-Ig staining were also apparent in B220+, panNK+, and CD69+ cells. It is not currently understood why there is a disparity in mICOS-mIg staining levels between these three markers on RAG1 -/- splenocytes, when compared with the higher levels detected in Balb/c splenocytes. mICOS-mIgG staining of CD4+ (45%) and CD24+(28%) cells was also apparent in RAG1 -/- splenocytes despite the absence of staining for other T cell markers. CD4+ staining has previously been reported on dendritic cells (Aicher, A. et al. (2000) *J. Immunol.* 164:4689-96), and this was supported by the presence of a CD4+, CD11c+ double positive cell population in these mice (FIG. 20C). The presence of GL50 transcripts in conjunction with mICOS-mIgG binding of phenotypic macrophage and dendritic cell subsets in RAG1 -/- splenocytes verifies the presence of ICOS-ligand on professional antigen presenting cells that may potentiate signaling through ICOS in vivo.

Example 10

Expression of GL50 Splice Variant mRNAs in Splenocyte Subpopulations and Embryonic Cells Because ICOS-ligand appeared to exist as at least two splice variants, experiments were performed to semi-quantitatively assess the presence GL50-1 and GL50-2 transcripts in splenocyte cell populations. Balb/C splenocytes cultured in the presence of LPS or ConA were found to upregulate ICOS-ligand in all splenocytes examined (FIG. 20). To determine if preferential stimulation of these cells caused differential upregulation of GL50-1 or GL50-2 transcripts, GL50-1 and GL50-2 transcripts were detected by RT-PCR using transcript specific oligonucleotide primers and hybridization probe sets. The results are presented in Table 4.

TABLE 4

| | RT-PCR Analysis of mGL50 Isoforms | | | | | | | | |
|---|---|---|---|---|---|---|---|---|---|
| | Balb/C w.t. | | | LPS | | | ConA | | |
| | mGL50 | mGL50-B | GAPDH | mGL50 | mGL50-B | GAPDH | mGL50 | mGL50-B | GAPDH |
| Spleen | + | + | (+) | + | + | (+) | + | +/- | (+) |
| CD4 | + | + | (+) | + | +/- | (+) | + | +/- | (+) |
| CD8 | - | - | (+) | +/- | - | (+) | + | +/- | (+) |
| CD19 | ++ | ++ | (+) | ++ | ++ | (+) | + | - | (+) |
| RAG-1 -/- Spleen | + | +/- | (+) | | | | | | |
| RAG-1 -/- CD11c | + | + | (+) | | | | | | |
| RAG-1 -/- CD11b | + | +/- | (+) | | | | | | |
| F5M | + | - | (+) | | | | | | |
| F5M LPS | + | +/- | (+) | | | | | | |
| WEHI 231 | + | +/- | (+) | | | | | | |
| D0 ES cells | ++ | ++ | (+) | | | | | | |
| D11.5 Embryo | + | + | (+) | | | | | | |

TABLE 4-continued

RT-PCR Analysis of mGL50 Isoforms

| | Balb/C w.t. | | | LPS | | | ConA | | |
|---|---|---|---|---|---|---|---|---|---|
| | mGL50 | mGL50-B | GAPDH | mGL50 | mGL50-B | GAPDH | mGL50 | mGL50-B | GAPDH |
| D12.5 Embryo | ++ | + | (+) | | | | | | |
| D11.5 Yolk Sac | ++ | + | (+) | | | | | | |
| Water Control | — | — | — | | | | | | |

Amplifications were performed in duplicate followed by autoradiographic detection of blotted GL50 samples.
− represents the absence of signal in duplicate samples.
+/− represents the presence of signal in one of the duplicate samples.
+ represents the presence of signal within both members of duplicate samples.
++ represents autoradiographic saturation of signal within duplicate samples.
(+) represents visual detection of amplified GAPDH products by ethidium bromide staining Balb/C CD4+, CD8+ and CD19+ cell subsets and RAG1 −/− CD11b+ and CD11c+ cell subsets were enriched to >90% purity by bead separation. Duplicate RT-PCR analyses of quantity-normalized RNA samples revealed GL50-1 and GL50-2 transcripts to be present in non-treated CD4+ T-cells and CD19+B cells, consistent with results from flow cytometric analysis. However, neither GL50-1 nor GL50-2 transcripts were amplified in CD8+ T cells, despite surface protein detection by FACS and enrichment of ICOS-ligand positive cells. It is possible that CD8 GL50 expression is below the threshold of detectability by RT-PCR, or that CD8+ ICOS-ligand is yet another variant of GL50 not targeted for detection by this assay. Also, one cannot rule out the possibility that the form of ICOS ligand appearing on CD8+ cells may not be GL50-1 or GL50-2, as described herein, or that the CD8+ ICOS ligand may originate elsewhere as a soluble protein and become transferred to this cell type. LPS activation led to a profile similar to that seen for control cells, with the exception that low levels of GL50-1 were detected in CD8+ samples, suggesting that LPS stimulation of B cells may indirectly upregulate expression of this form of ICOS-ligand on T cells. ConA stimulation of splenocytes resulted in the amplification of GL50-1 transcripts across all samples with a decrease of product in CD19+ cells. GL50-2 transcripts were induced in CD8+ samples and were not detected in CD19+ samples. The decrease of amplified product of both GL50-1 and GL50-2 in CD19+ cells suggests a regulation of B cell transcription upon exposure to ConA. In RAG1 −/− splenocytes, GL50-1 and GL50-2 were detected in CD11b+ and CD11c+ positive cells, while cultured dendritic F5M and WEHI231 cells exhibited GL50-1 transcripts. Low levels of GL50-2 were detected in WEHI 231 and LPS activated F5M cells, while no amplified product was detected in uninduced F5M cells. In samples representing embryonic tissues, GL50-1 and GL50-2 were detected in all samples, with abundant levels of both splice variants present on D0 ES cells. High levels of GL50-1 were also detected in day 12.5 embryo and 11.5 yolk sac samples. These results correlate with the degree of transcript hybridization shown by RNA blot analysis (see above).

Example 11

The Chicken GL50-Like Molecule Y08823 Does Not Bind ICOS

Very recently, the crystal structure of B7-1 was resolved at the three angstrom level, revealing a structure comprised of parallel, 2-fold rotationally symmetric homodimers with charged residues in the amino-terminal domain of B7-1 responsible for direct interactions with CD28/CTLA4. Human and mouse GL50, B7-1, and B7-2 protein sequences exhibit 19-27% sequence identity (Table 5) suggesting that they may also share structural similarities.

TABLE 5

Alignment scores between GL50, B7-1, and B7-2 related proteins

| | | Percent Sequence Identity | | | | | | | |
|---|---|---|---|---|---|---|---|---|---|
| | | hGL50 | Y08823 | mGL50 | mGL50-B | hB7-2 | mB7-2 | hB7-1 | mB7-1 |
| Genetic Distance | hGL50 | — | 36 | 44 | 44 | 19 | 24 | 25 | 22 |
| | Y08823 | 138 | — | 37 | 37 | 28 | 23 | 26 | 30 |
| | mGL50 | 85 | 131 | — | 99 | 24 | 25 | 24 | 27 |
| | mGL50-B | 85 | 131 | 0.4 | — | 26 | 23 | 26 | 26 |
| | hB7-2 | 270 | 230 | 221 | 221 | — | 51 | 26 | 30 |
| | mB7-2 | 251 | 310 | 200 | 200 | 68 | — | 24 | 28 |
| | hB7-1 | 243 | 224 | 247 | 247 | 222 | 243 | — | 45 |
| | mB7-1 | 261 | 223 | 282 | 282 | 190 | 182 | 88 | — |
| | mmu67065 | 188 | 219 | 214 | 214 | 207 | 248 | 220 | 269 |

Previous analysis of Y08823 suggested that beta strands forming the DEB and non-twisted AGFCC'C" beta sheets within the amino terminal domain were predicted to be conserved between Y08823 and B7-1 (Ikemizu, S. et al. (2000) *Immunity* 12:51-60). Interestingly, the highest degree of predicted secondary structure conservation between the GL50 sequences and Y08823 was also within the regions encompassing the DEB beta sheets of the corresponding amino terminal domain. Predictions based on these structural homologies suggest that sequence identities in this region could provide key interdomain electrostatic contacts and conserve hydropathicity within the interdomain core, resulting in a similar molecular framework shared by the GL50 and B7 molecules (FIG. 16). Based on these observations, chicken Y08823 was assessed for the ability to bind ICOS receptors. Sequences representing the mature Y08823 peptide were obtained by RT-PCR and subcloned into an expression vector, which upon transfection of COS cells, yielded a functional surface protein. Y08823 transfected cells were found to bind CTLA4-Ig but not to hICOS-mIgG2am nor mICOS-mIgG2am (FIG. 17). Although it cannot be ruled out that the binding of Y08823 to ICOS occurs at levels below detection, based on the assay conditions used here, it is not likely that the GL50-like protein Y08823 can cross-function as a ligand for human or mouse ICOS receptors.

Structural and genetic similarity suggests that B7/GL50 type proteins are conserved across extreme phylogenetic boundaries, and implicit in this interpretation is that mechanistic pathways utilizing these proteins are also shared. The evidence that these proteins have similar functions in T cell signaling raise the question of the absolute number and the origins of costimulatory ligands, their cognate receptors, and derivative spliced variants that exist. Other proteins that fit into the B71 g-superfamily structure include MOG and butyrophilin, but these proteins have not been determined to participate as ligands in any costimulatory pathway (Henry, J. et al. (1999) Immunol. Today 20:285-8). With the sequence availability of chromosome 21 (Hattori, M. et al. (2000) Nature 405:311-9), the genomic organization of the human ICOS-ligand was determined, indicating the presence of at least 2 splice variants in the form of hGL50 (Ling, V. et al. (2000) J. Immunol 164:1653-7) and KIAA clone 0653 (Genbank Accession No. AB014453). Among the members of the B7-like genes, the genomic structure of B7-1, B7-2, butyrophilin, and hGL50 have been reported. Although the absolute number of exons that comprise these genes varies from 5 to 12, these genes share structure, in that distinct exons encode the two Ig-like extracellular domains, one exon encodes the transmembrane domain, and multiple exons encode the cytoplasmic domain (e.g., two exons for hGL50, two exons for B7-2 (Jellis, C. E. et al. (1995) Immunogenetics 42:85-9; Borriello, F. et al. (1995) J. Immunol. 155:5490-7), one to two exons for B7-1 (Borriello, F. et al. (1994) J. Immunol. 153: 5038-48), and three exons for butyrophilin (Ogg, S. L. et al. (1996) Mamm. Genome 7:900-5)). For KIAA0653, the splice junction between exons encoding cytoplasmic domains 1 and 2 is not used, resulting in a read-through of 2.9 kb into the putative intron 6. Upon alignment of KIAA0653 with chromosome 21 BAC clone HS21C098, the alternative 3' cytoplasmic domain of KIAA0653 was not found to be in agreement: eight sequence discrepancies were found, comprised of 7 mismatches and one 17 bp deletion. In contrast, exon sequence alignment of human GL50 to HS21C098 revealed no sequence dissimilarities up to and including the polyadenylation site. The examples set forth above show that human GL50, mGL50-1, and variant mGL50-2 show some amino acid sequence identity near the splice site for cytoplasmic domains 1 and 2 (mGL50-1 residues 316-318: E-L-T; FIG. 16). The shared point of splice variation between hGL50/AB014553 and between mGL50-1/mGL50-2 suggests the potential of a conserved mechanism that allows or promotes alternative splicing of cytoplasmic domain 2, perhaps to offer alternate signaling through the combinatorial addition of alternate functional domains. The observation that mGL50-2 and the original mGL50-1 are transcribed with differing tissue specificity supports the notion that regulation of these molecules in cell signaling is dependent on physiological locale and activation state.

The existence of a conserved intracellular motif between mammalian GL50 and avian Y08823, along with the presence of multiple forms of GL50 with divergent carboxyl regions, further suggests that differences in the intracellular domain of these molecules may lead to distinct signaling functions. This is further supported by the presence of 3 additional tyrosine residues found in the intracellular domain of mGL50-2, in addition to the 2 shared with mGL50-1. This contrasts with the structure of B7-1 and B7-2, where the intracellular regions lack any obvious conserved sequences and have been deleted without impairment of costimulatory activity, suggesting that intracellular signaling is not a key feature of these B7 proteins (Brunschwig, E. B. et al. (1995) J. Immunol. 155:5498-505). The conserved motif of hGL50, although predicted to be in the intracellular portion of the molecule by hydrophobicity analysis, was found to be encoded by the exon 5 transmembrane domain, and not the exon 6 cytoplasmic domain-1. In the chicken Y08823 cDNA clone, sequence homology terminates within three amino acid residues following the corresponding exon 6/cytoplasmic domain-1. If the genomic organization of hGL50 is maintained in Y08823, where the conserved motif is encoded by the intracellular portion of the exon-5 transmembrane domain, then it is possible that DNA segments orthologous to exon 6 and exon 7, encoding cytoplasmic domains 1 and 2 in hGL50, may be completely absent in chicken. In the structural studies of the B7 cytoplasmic domain, it is argued that those sequences may be completely dispensable (Brunschwig, E. B. et al. (1995) J. Immunol. 155:5498-505). However, the fact that alternate cytoplasmic exons are used in B7-1 and GL50 suggests that the addition of alternate exon domains may have occurred during the time when the novel B7-like proteins were generated. The B7-like butyrophilin proteins are encoded by a number of splice variants, the predominant form of which contains a cytoplasmic domain 3 encoding a intracellular Ring finger motif which is perhaps used in transducing signaling from this molecule (Ogg, S. L. et al. (1996) Mamm. Genome 7:900-5). These observations support the idea that other ligand type molecules, such as GL50 and Y08823, with the conserved intracellular motif from exon-5 and other cytoplasmic domains, may have alternate roles as signal delivery and a signal receptor molecules, depending on the environmental millieu in which the is cell is found.

To clearly define the cell subsets that show surface expression of GL50, comparative phenotyping of RAG1 −/− and Balb/C splenocyte subsets was performed. The examples set forth above show that freshly isolated CD4+ and CD8+ cells, as well as RAG1 −/− CD11c+ cells contained subpopulations of ICOS-ligand expressing cells. These results are distinct from previous studies where ICOS-ligand was reported to be absent in T-cell lines (Aicher, A. et al. (2000) J. Immunol. 164(9):4689-96) and some dendritic cell lines (Yoshinaga, S. K. et al. (1999) Nature 402:827-32). RT-PCR analysis of purified cell subsets confirmed that both GL50-1 and GL50-2 were expressed in the same cells suggesting that both transcripts may contribute to the surface display of ICOS binding. In addition to antigen presenting cells, it was demonstrated that the initial expression of costimulatory ligands occurs early in the ES cell model of embryonic development with the presence of B7-1 and GL50-1 transcripts in undifferentiated cells and in embryoid bodies cultured 10 days in vitro Ling, V. et al. (1998) Exp. Cell Res. 241:55-65). In this study, it is further demonstrated that by RNA analysis, GL50-2 transcripts are found within these tissues. By day 9 of embryoid body differentiation, emergent hematopoietic cells phenotypically resemble yolk sac hematopoietic progenitors in vivo, as evidenced by the potential of c-kit+/PECAM-1+ cells to produce mixed hematopoietic progenitors and CD45+ cells to produce macrophage progenitors in colony-forming assays (Ling, V. and Neben, S. (1997) *J. Cell Physiol.* 171:104-15; Ling, V. et al. (1997) *Eur. J. Immunol.* 27:509-14). These CD45+ cells were also found to be B7-1+ and B7-2$^+$, strongly suggesting costimulatory ligand expression occurs very early in lymphopoiesis. Correspondingly, high levels of GL50-1 and GL50-2 expression were found in sites of embryonic hematopoiesis such as embryonic day yolk sac and fetal liver. It is noteworthy that ICOS-ligand is inducible in embryonic fibroblast cultures, a cell type derived from a time point prior to definitive lymphopoiesis, suggesting that the mechanism for costimulatory signaling cascade may be poised independently of the initial formation of adaptive immune response. It has been postulated that metazoans share common evolvable pathways that occur at the phylotypic stage of embryogenesis, and that certain core physiological processes which have special properties relevant to complex development are reflected during this time period of embryonic development and later in adult physiology (Kirschner, M. and Gerhart, J. (1998) *Proc. Natl. Acad. Sci. USA* 95:8420-7). It remains to be determined whether costimulatory ligands are part of some core processes utilized by both embryos and adult systems.

Despite the large genetic distance between the B7 family members, the fact that primate and rodent B7-1 and B7-2 retain cross-binding to CTLA4 and CD28 across phylogenetic lines suggests tolerance of nucleotide replacement within these signaling molecules through the time course of natural history. To compare the phylogenetic divergence pattern between costimulatory ligands and their receptors, protein sequences of CTLA4 (Genbank Accession Nos. NM_009843 and NM_005214), CD28 (Accession Nos. NM_007642, NM_006139, and X67915), and ICOS (Genbank Accession No. AJ250559 and Genseq Accession No. V53199) receptors from mouse, human and chicken were analyzed. When represented in graphical format, the genetic distance values of these receptors (Table 6) revealed a pattern (FIG. 21) in which distances between ICOS and CD28 proteins were closer than distances between ICOS and CTLA4.

When comparing receptor sequence relationships between species, distance values for human CD28/ICOS (176) were smaller than those for mouse CD28/ICOS (257). Likewise, human CTLA4/ICOS distance values (261) were also found to be smaller than mouse CTLA4/ICOS distances (405). These data suggest that structure of ICOS molecule is more likely derived from the form of CD28 rather than CTLA4. In contrast, phylogenetic analysis of the costimulatory ligands demonstrated that the distance values between GL50 and B7-1 (243-282) were nearly equivalent to the distance values between GL50 and B7-2 (200-270). Y08823 was found to exhibit higher sequence identity and lower genetic distance (36-37%; 131-138) to mouse and human GL50 proteins than to B7 proteins (23-30%, 230-310). The near-equivalent genetic distances between the GL50 and the B7-1/B7-2 family members and the non-equivalent genetic distance between the ICOS and the CD28/CTLA4 family members implies that the evolutionary/functional constraints guiding the receptor family is different from those guiding the ligand family.

Phylogenetic sequence relationships may reflect genomic placement of these molecules: B7-1 and B7-2 co-localize to mouse chromosome 16 and human chromosome 3, while CTLA4, CD28, and ICOS co-localize to mouse chromosome 1 and to human chromosome 2q33. In contrast, the GL50 genetic loci are not linked to the B7 loci; human GL50 is located at chromosome 21q22 (Hattori, M. et al. (2000) *Nature* 405:311-9) while mouse GL50 is located on chromosome 10. By TFastX analysis, no additional GL50-like homologs were identified in chromosome 21, suggesting that GL50 may not exist as a family of genes clustered together like B7-1 and B7-2. With respect to Y08823, it is not clear whether this molecule is a true ortholog of B7-1 or whether Y08823 represents a novel B7-like molecule whose ortholog has not been defined in mammalian systems. However, from the 23-30% sequence identity shared between B7s and Y08823, including multiple amino acid replacements at charged residue sites, it was surprising that these proteins retain functional crossbinding to CTLA4 (O'Regan, M. N. et al. (1999) *Immunogenetics* 49:68-71). The unexpected result of Y08823 bearing stronger structural resemblance to GL50, yet retaining binding properties characteristic of B7-1 and B7-2, suggests that structural and functional constraints to the divergence of these costimulatory ligands are low.

Numerous scenarios may account for the differing genetic distances measured between receptor families and ligand families. It is possible that the genes encoding the GL50/B7 family of proteins emerged earlier than genes encoding the CD28/CTLA4 receptors. The formation of genes encoding the ICOS receptor may have arisen later during phylogeny and may be based on the structure of CD28, thus resulting in a greater similarity to CD28 than CTLA4 molecules. This hypothesis may account for the numerous B7-like proteins that exist, while relatively few CD28-like receptors have been described. It is notable that certain exons of CTLA4 retain remarkable sequence constraint, even at the level of synonymous DNA mutations, suggesting the presence of a yet-to-be-defined mechanism that protects that locus from random mutations (Ling, V. et al. (1999) *Genomics* 60:341-355). It may be that a mutation constraining mechanism regulates the

TABLE 6

Alignment Scores between ICOS, CTLA4 and CD28

|  |  | Percent Sequence Identity | | | | | | |
|---|---|---|---|---|---|---|---|---|
|  |  | hICOS | mICOS | hCTLA4 | mCTL4 | hCD28 | mCD28 | chCD28 |
| Genetic | hICOS | — | 69 | 21 | 20 | 28 | 24 | 21 |
| Distance | mICOS | 41 | — | 17 | 16 | 25 | 21 | 20 |
|  | hCThA4 | 250 | 368 | — | 74 | 30 | 29 | 32 |
|  | mCTLA4 | 272 | 466 | 33 | — | 31 | 32 | 31 |
|  | hCD28 | 175 | 205 | 165 | 154 | — | 67 | 50 |
|  | mCD28 | 217 | 257 | 167 | 149 | 44 | — | 48 |
|  | chCD28 | 246 | 278 | 152 | 156 | 79 | 85 | — | costimulatory receptor region over the length of the CTLA4/CD28/ICOS loci, or that the added selection pressure upon the intracellular signaling domain of these receptors is sufficient to maintain a lower rate of divergence.

Costimulatory ligands and receptors belong to the Ig-superfamily of proteins, which have been defined as those proteins that share homology to immunoglobulins at the 10-20% range, with characteristic intrachain disulfide bonds. Ig-superfamily proteins are widely distributed among proteins of different functions and between vertebrate phylogenies. The appearance of arthropods and chordates dates back 600 million years, and it has been suggested that molecules representing the putative progenitors of the Ig-superfamily are even more ancient, probably being present in the acoelomates such as flatworms and nematodes. The notion that the Ig-superfamily of proteins is at least as ancient is supported by the finding that some Ig-like proteins such as N-CAM are found in mammals as well as insects. The immunological "big bang" event (Marchalonis, J. J. et al. (1998) *Immunol. Rev.* 166:103-22, and references therein) which gave rise to the Ig-based, combinatorial adaptive immune system theoretically appeared during the emergence of jawed fish 450 million years ago over a geologically brief time span of 10-20 million years. Currently, no mechanism by which the immunoglobulin system may have emerged from the Ig-superfamily of molecules has been clearly defined. However, theories have been proposed that suggest that genes encoding Ig-domains and recombinase enzymes necessary for the combinatorial immune system were horizontally transferred on a sufficiently large enough scale to offer a selective advantage (Bernstein, R. M. et al. (1996) *Proc. Natl. Acad. Sci. USA* 93:9454-9). Notably absent is a foundation for a comprehensive biochemical framework incorporating the salient signaling features of Ig-superfamily costimulatory molecules which serve to trigger cell activation, promote immunoglobulin molecule maturation, and influence class switching. Although it is not currently known whether extant members of the ancient chondriethyes lineage such as sharks have costimulatory molecules, the fact that costimulation related proteins such as CD28 and Y08823 are present in chickens suggests that some type of costimulatory pathway was present in members of the avian lineage, which emerged at least 300 million years ago (Burt, D. W. et al. (1999) *Nature* 402:411-3), opening the possibility that the Y08823 molecule represents a contemporary cousin to both the GL50 and B7 molecules with a stronger resemblance to a prototypic costimulatory ligand, rather than being a true ortholog of either GL50 or B7. In contrast to the avian lineage, it is postulated that the mouse and human lineages separated approximately 100 million years ago, with the mouse genome undergoing extensive chromosomal rearrangements (Burt, D. W. et al. (1999) *Nature* 402:411-3) compared to those seen in chickens and humans. It is not known whether these rearrangements may have led to the chromosomal separation between the B7 family members and the genes encoding GL50 molecules. It is also not known if avian ICOS or variants thereof exist.

Example 12

Soluble GL50 can Costimulate Human T Cells

The ability of soluble hGL50-mIgG2am to costimulate human T cells was determined using a T cell costimulation assay. Naïve CD4+ T cells were purified and plated at 10% cells per well. Cells were stimulated with anti-CD3 on beads, using one bead per cell and 1 or 2 µg anti-CD3 per $10^7$ beads. Cells were treated with hGL50-mIgG2am on beads, using one bead per cell and 3 µg hGL50-mIgG2am per 107 beads. CD28 signaling was provided (using anti-CD28 (Pharmingen)) or stimulated to determine whether modulation of CD28 mediated costimulation had any effect on hGL50-mIgG2am mediated costimulation.

IL-2 production, IL-10 production, and proliferation (3H incorporation) were assayed as indicators of costimulation. Cytokines and proliferation were measured 72 hours after stimulation.

As shown in FIG. 22, hGL50-mIgG2am (also called hGL50.Fc) can costimulate T cells, as shown by the increase in proliferation as well as the induction of IL-2 and IL-10 production. In the presence of antibodies to CD28, which induces CD28 mediated costimulation, IL-2 production is also induced. FIG. 23 shows the effects of varying concentrations of anti-CD3 and anti-CD28 on proliferation and cytokine production.

FIG. 24 shows that adding anti-CD28 to T cells stimulated with anti-CD3 or anti-CD3 and soluble hGL50-mIgG2am (to stimulate CD28 mediated costimulation) induces IL-2 production, but does not influence hGL50 mediated IL-10 production.

Example 13

Treatment of Murine Tumors Using ICOS/GL50 Pathway Stimulation

Figure 25A:
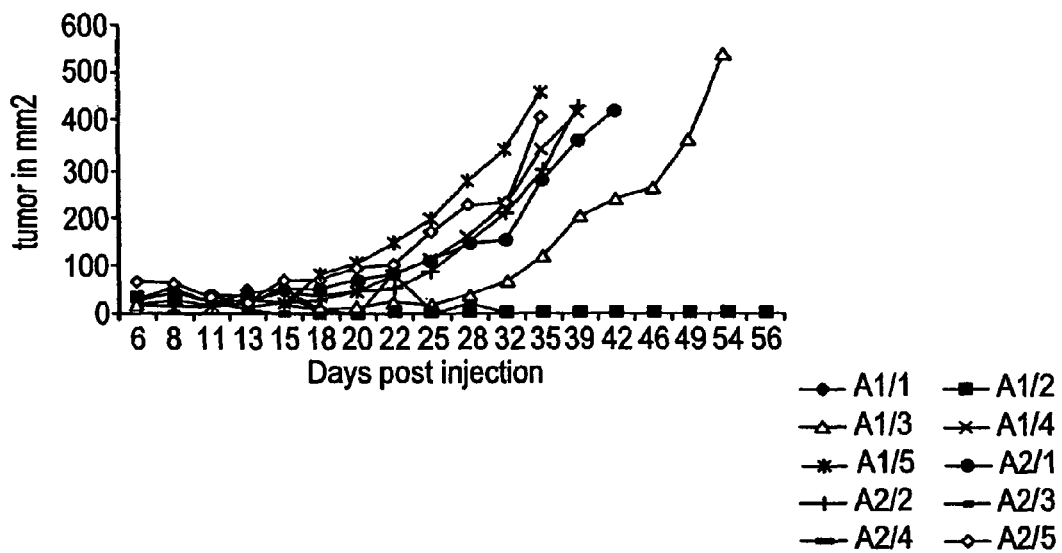
Figure 25B:
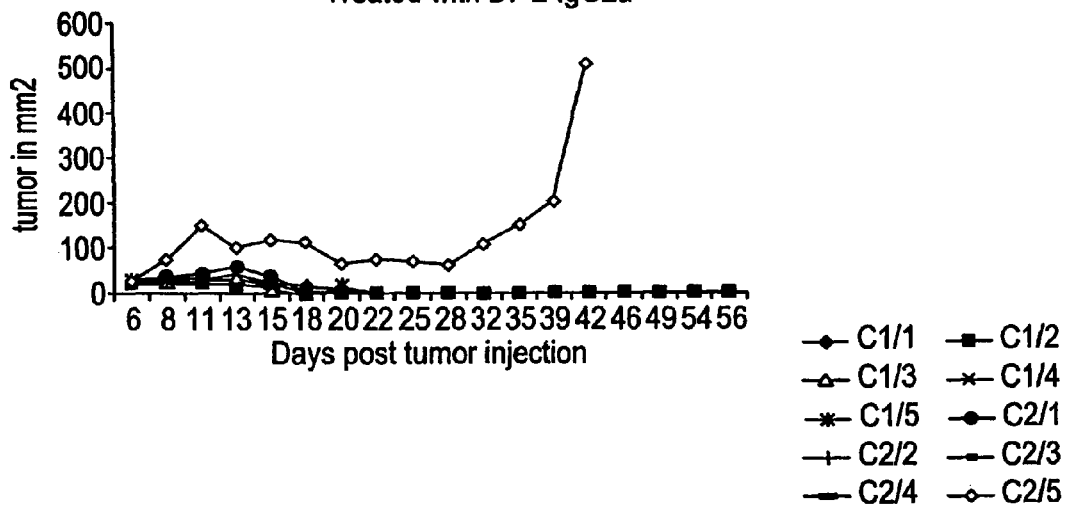
Figure 25C:
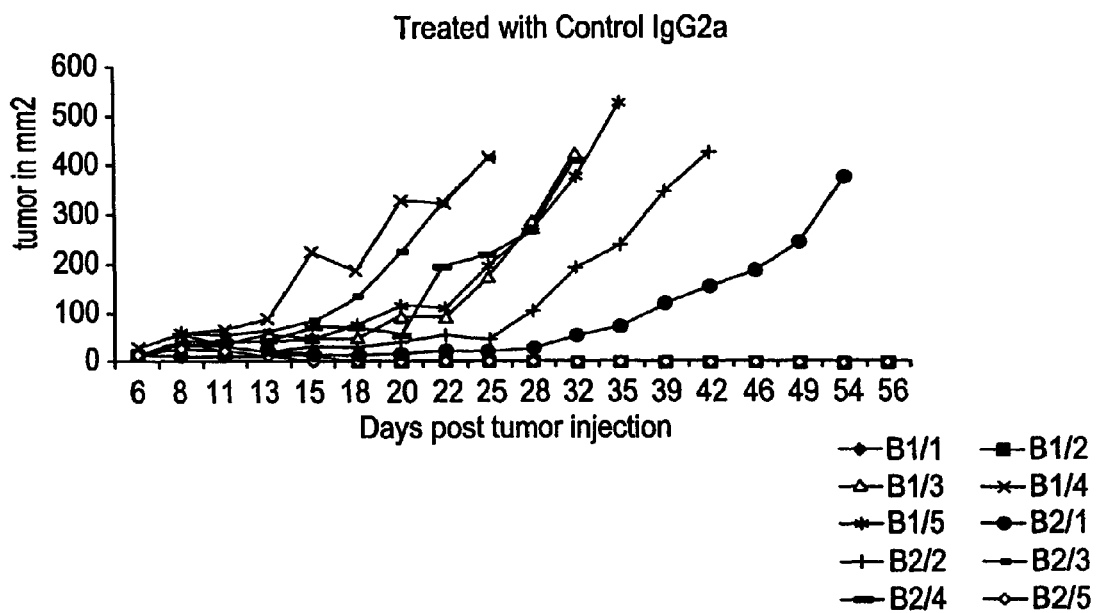
Figure 25D:
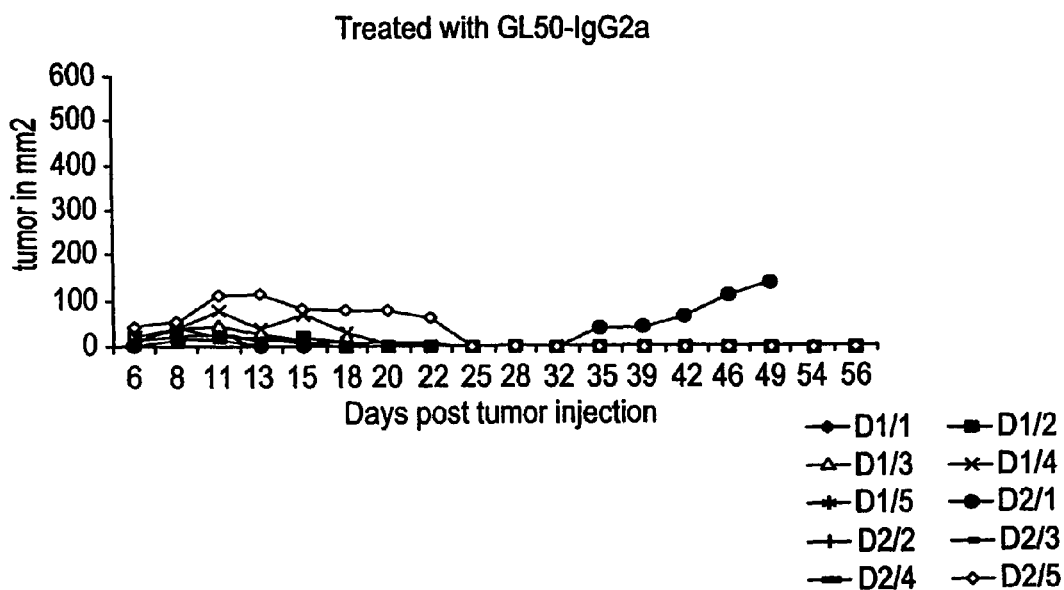
Figure 25E:
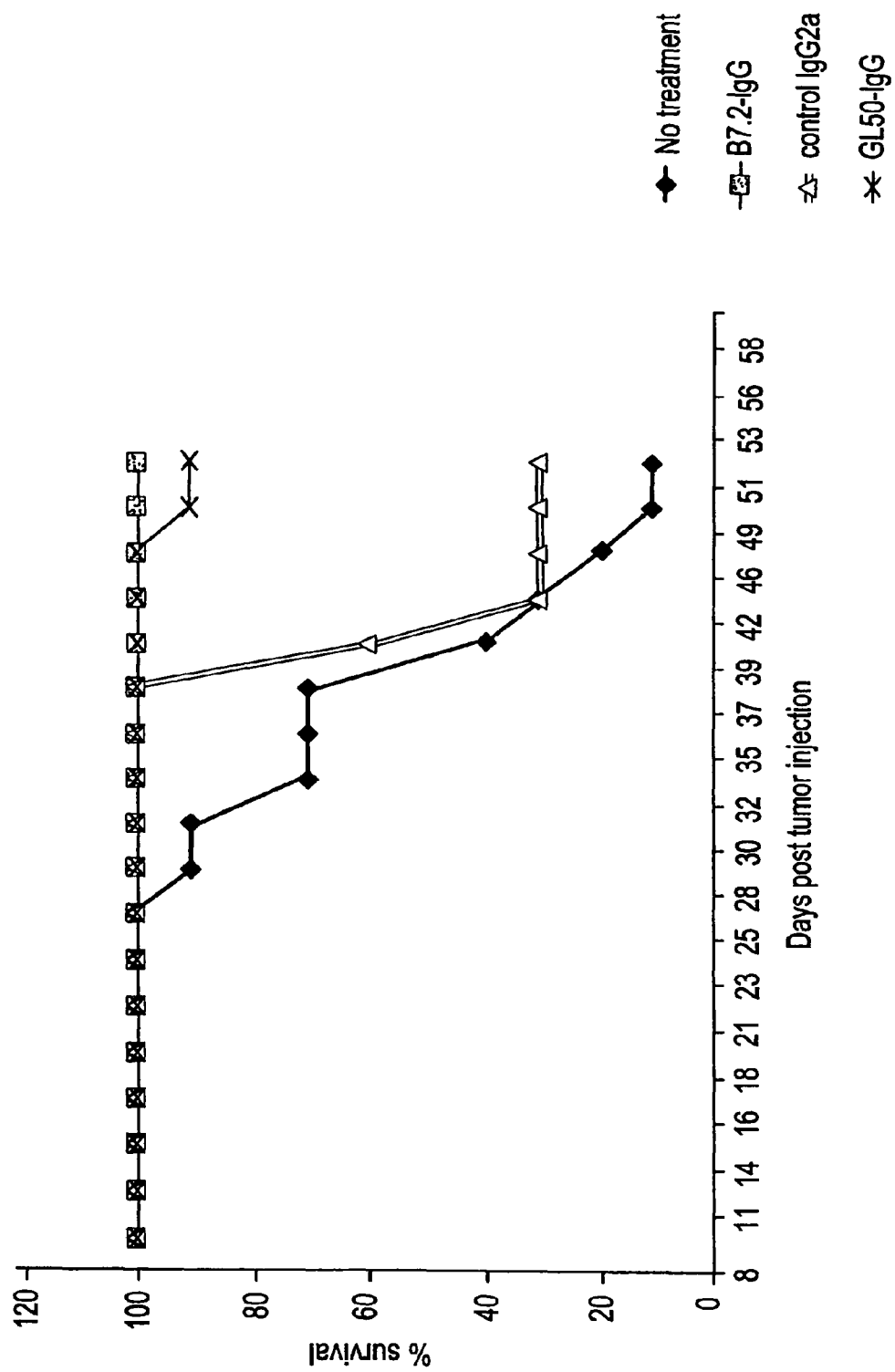
Figure 31B:
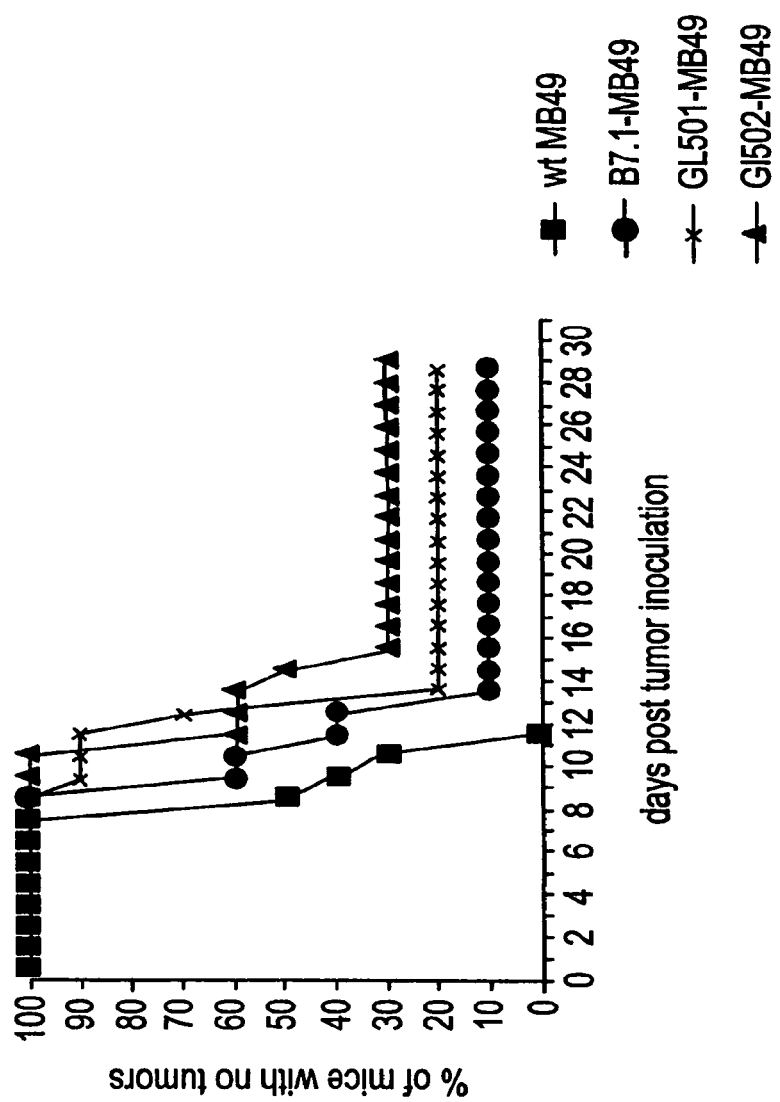

As of yet, the role of ICOS/GL50 costimulation in the generation of antitumor responses has not been reported. In this study, the relative efficacy of ICOS/GL50 costimulation was compared to CD28/B7 costimulation in various murine tumor models. For systemic treatment of tumor bearing animals, murine B7.2-IgG2a and GL50-IgG2a fusion proteins were generated, which consist of the extracellular domain of B7.2 or GL50, respectively, and the Fc portion of murine IgG2a. Murine isotype IgG2a was used as a control. Mice bearing MethA or B16F1 melanoma tumors were treated subcutaneously with 50 µg/injection of GL50-IgG2a or B7.2-IgG2a fusion protein twice weekly for three weeks. In the MethA model, treatment with B7.2-IgG2a resulted in up to 100% tumor regression (FIG. 25A) and cure of the mice (FIG. 25E), and treatment with GL50-IgG2a resulted in up to 60-90% cure of mice (FIG. 25E) and in 40% significant tumor growth delay (FIG. 25D). In the B16F1 melanoma, systemic treatment with either protein led to comparable significant tumor growth delay. In both tumor models, control IgG2a treatment had no effect (FIGS. 25A, C, and E). In tumor vaccines studies, the B16F1 melanoma and the MB49 bladder carcinoma models were used; Tumor cells were transduced with a vector containing the EF-1 alpha promoter expressing either murine B7.1 or GL50, and G418 (neomycin) selected tumor cells were injected subcutaneously for in vivo tumorigenicity experiments. Expression of GL50 and B7-1 on tumor cells was determined by FACS analysis using an anti-mB7-1 monoclonal antibody (Pharmingen, clone 16-10A1) or ICOS-IgG2a fusion protein. The results demonstrate: (i) in the B16F1 model, 40% of the mice injected with GL50 expressing tumor cells and 20% of the mice injected with B7.1 expressing tumor cells reject their tumors (FIG. 31A); (ii) in the MB49 model, 30% of the mice injected with GL50 expressing tumor cells and 10% of the mice injected with B7.1 expressing tumor cells reject their tumors (FIG. 31B). These results indicate that enhanced in vivo ICOS/GL50 interactions, provided either by soluble GL50-IgG or GL50 expression on tumor cells, has significant antitumor activity that is comparable to the well described antitumor efficacy of the CD28/B7 pathway in murine tumor models.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A method for downmodulating an immune response in a subject comprising administering to the subject an antibody or an antigen-binding portion of an antibody which selectively binds to a polypeptide of SEQ ID NO: 2, 4 or 6.

2. The method of claim 1, further comprising administering at least one antibody which binds to a B7-1 or B7-2 molecule.

3. The method of claim 1, wherein the antibody or the antigen-binding portion of an antibody selectively binds to a polypeptide of SEQ ID NO: 6.

4. The method of claim 1, wherein the antibody the antigen-binding portion of an antiboselectively binds to a polypeptide of SEQ ID NO: 2 or 4.

5. The method of claim 1, wherein the antibody or the antigen-binding portion of an antibody is a humanized antibody.

6. The method of claim 1, wherein the antibody or the antigen-binding portion of an antibody is a bispecific antibody.

7. The method of claim 1, wherein the antibody or the antigen-binding portion of an antibody is administered after the subject has undergone an organ transplantation procedure.

8. The method of claim 1, wherein the antibody or the antigen-binding portion of an antibody is administered before the subject has undergone an organ transplantation procedure 9. The method of claim 1, wherein the subject has an autoimmune disease.

10. A method for downmodulating an immune response in a subject comprising administering to the subject an antibody or an antigen-binding portion of an antibody which selectively binds to a polypeptide encoded by of SEQ ID NO: 1, 3 or 5.

11. The method of claim 10, wherein the antibody or the antigen-binding portion of an antibody selectively binds to a polypeptide of SEQ ID NO: 5.

12. The method of claim 10, wherein the antibody the antigen-binding portion of an antiboselectively binds to a polypeptide of SEQ ID NO: 1 or 3.

13. The method of claim 10, wherein the antibody or the antigen-binding portion of an antibody is a humanized antibody.

14. The method of claim 10, wherein the antibody or the antigen-binding portion of an antibody is a bispecific antibody.

15. The method of claim 10, wherein the subject has undergone an organ transplantation procedure.

16. The method of claim 10, wherein the subject has an autoimmune disease.

* * * * *

SEQUENCE LISTING

```
<160> NUMBER OF SEQ ID NOS: 38

<210> SEQ ID NO 1
<211> LENGTH: 2718
<212> TYPE: DNA
<213> ORGANISM: Mus musculus
<220> FEATURE:
<221> NAME/KEY: CDS
<222> LOCATION: (67)..(1032)

<400> SEQUENCE: 1
ccggaacccc aaccgctgca actctccgcg tccgaaatcc agcatccgc agtctgcgct      60 cgcacc atg cag cta aag tgt ccc tgt ttt gtg tcc ttg gga acc agg      108
       Met Gln Leu Lys Cys Pro Cys Phe Val Ser Leu Gly Thr Arg
         1               5                  10 cag cct gtt tgg aag aag ctc cat gtt tct agc ggg ttc ttt tct ggt    156
Gln Pro Val Trp Lys Lys Leu His Val Ser Ser Gly Phe Phe Ser Gly
 15                  20                  25                  30 ctt ggt ctg ttc ttg ctg ctg ttg agc agc ctc tgt gct gcc tct gca    204
Leu Gly Leu Phe Leu Leu Leu Leu Ser Ser Leu Cys Ala Ala Ser Ala
                 35                  40                  45 gag act gaa gtc ggt gca atg gtg ggc agc aat gtg gtg ctc agc tgc    252
Glu Thr Glu Val Gly Ala Met Val Gly Ser Asn Val Val Leu Ser Cys
             50                  55                  60 att gac ccc cac aga cgc cat ttc aac ttg agt ggt ctg tat gtc tat    300
Ile Asp Pro His Arg Arg His Phe Asn Leu Ser Gly Leu Tyr Val Tyr
         65                  70                  75 tgg caa atc gaa aac cca gaa gtt tcg gtg act tac tac ctg cct tac    348
Trp Gln Ile Glu Asn Pro Glu Val Ser Val Thr Tyr Tyr Leu Pro Tyr
     80                  85                  90 aag tct cca ggg atc aat gtg gac agt tcc tac aag aac agg ggc cat    396
Lys Ser Pro Gly Ile Asn Val Asp Ser Ser Tyr Lys Asn Arg Gly His
 95                 100                 105                 110 ctg tcc ctg gac tcc atg aag cag ggt aac ttc tct ctg tac ctg aag    444
Leu Ser Leu Asp Ser Met Lys Gln Gly Asn Phe Ser Leu Tyr Leu Lys
                115                 120                 125 aat gtc acc cct cag gat acc cag gag ttc aca tgc cgg gta ttt atg    492
Asn Val Thr Pro Gln Asp Thr Gln Glu Phe Thr Cys Arg Val Phe Met
            130                 135                 140 aat aca gcc aca gag tta gtc aag atc ttg gaa gag gtg gtc agg ctg    540
Asn Thr Ala Thr Glu Leu Val Lys Ile Leu Glu Glu Val Val Arg Leu
        145                 150                 155 cgt gtg gca gca aac ttc agt aca cct gtc atc agc acc tct gat agc    588
Arg Val Ala Ala Asn Phe Ser Thr Pro Val Ile Ser Thr Ser Asp Ser
    160                 165                 170 tcc aac ccg ggc cag gaa cgt acc tac acc tgc atg tcc aag aat ggc    636
Ser Asn Pro Gly Gln Glu Arg Thr Tyr Thr Cys Met Ser Lys Asn Gly
175                 180                 185                 190 tac cca gag ccc aac ctg tat tgg atc aac aca acg gac aat agc cta    684
Tyr Pro Glu Pro Asn Leu Tyr Trp Ile Asn Thr Thr Asp Asn Ser Leu
                195                 200                 205
```

```
ata gac acg gct ctg cag aat aac act gtc tac ttg aac aag ttg ggc      732
Ile Asp Thr Ala Leu Gln Asn Asn Thr Val Tyr Leu Asn Lys Leu Gly
            210                 215                 220 ctg tat gat gta atc agc aca tta agg ctc cct tgg aca tct cgt ggg      780
Leu Tyr Asp Val Ile Ser Thr Leu Arg Leu Pro Trp Thr Ser Arg Gly
        225                 230                 235 gat gtt ctg tgc tgc gta gag aat gtg gct ctc cac cag aac atc act      828
Asp Val Leu Cys Cys Val Glu Asn Val Ala Leu His Gln Asn Ile Thr
    240                 245                 250 agc att agc cag gca gaa agt ttc act gga aat aac aca aag aac cca      876
Ser Ile Ser Gln Ala Glu Ser Phe Thr Gly Asn Asn Thr Lys Asn Pro
255                 260                 265                 270 cag gaa acc cac aat aat gag tta aaa gtc ctt gtc ccc gtc ctt gct      924
Gln Glu Thr His Asn Asn Glu Leu Lys Val Leu Val Pro Val Leu Ala
                275                 280                 285 gta ctg gcg gca gcg gca ttc gtt tcc ttc atc ata tac aga cgc acg      972
Val Leu Ala Ala Ala Ala Phe Val Ser Phe Ile Ile Tyr Arg Arg Thr
            290                 295                 300 cgt ccc cac cga agc tat aca gga ccc aag act gta cag ctt gaa ctt     1020
Arg Pro His Arg Ser Tyr Thr Gly Pro Lys Thr Val Gln Leu Glu Leu
        305                 310                 315 aca gac cac gcc tgacaggact ctgcccagga tatggacagg gtttctgtga         1072
Thr Asp His Ala
    320 gttgccacca ggtggatgtc agacacaact tcagagtgga cccccacagg cctggtgaca   1132 gaggacaacg agctgtctgc ttatgggctg tgatggaggc caggaatccc tggctttacg   1192 aggcacagag acttcatccc agaaaccccg agggagatct ctccagtggg cagcagcaac   1252 atcatcggaa tatggagcct ccggtgagct gtcggcacag agagcagcag cttgtgagaa   1312 gatccttcct tggcacgtta ctactcaggc ctaggagctt tataaagag cgtttgagcc    1372 actctgaaag ccctacagag tctactggag actttccctg caggacct tc agttggggag  1432 gaagcctgac tttatttagg tctcaggcta cttgggcctc ttcgaggata tgtgggattt   1492 tgtctactgc aaacctgttt ctggctgaca atggttgggc tcagaggcac tcagcttcac   1552 aacatcaatg ggacacgcct catccttgac ttcctgtggc tacagaagct ttccgaaagc   1612 cttgagctct ttcagactga acagctctgc ccagtctcag cagcccatga agatctcaac   1672 tccagcttcc tgggtctccg tgttgctggc cagaatagag ctagctcttt tgtttcaaga   1732 tggttctgca aagttggctg cttggaaacc tagggatgta tgtacaagct ccaggctgat   1792 gcagtagggg gcacggactc cccgatggaa cacagtatct gaccctaggt gagggcaagc   1852 tccttcccac gcagaggact ggaaattctg accgtcaag gcctgtctgc tatgtggctg    1912 gggctcagtg ctgatggatg tgtgagatct caggaatgag gagtgagaac cctgggctca   1972 ggactaggaa gacctgtcca tttttttttt tttttaatgc ccacatggac ttttttattct  2032 tcacaccgat gtattcaatg agtgtagaga gaactactta agtccttccc gagtacaaag   2092 cattacctac ctgcagaata gcaactgttg ttatgggtct tgagttggca gctacagcaa   2152 acaagcacaa ggagcagttg gggtgcaaga agatggggtg cagcgcccc aaggacagac    2212 atttgggaat tagtggtctc cctgatgccc atagttcccc aggaactcag gtgggtctgc   2272 ggcagcacag taggagtatt cctcctactt taactttttct tgtcagacgt agtttaggtt  2332 cagaaagagg tcaactcagc aagccagcta gccgccttgg ggcaccagac acactgcccc   2392 ccaccccctg cttatgtagg cattgggaac ccttcacaga ccactggctg tacagtcacc   2452 atcacctgct gattccagca ggcccccacc ttcttgtgga atcctgggag cactcccctc   2512
```

```
ttacccctca ctgccccca ccccctgcac atcagcattc attagatttg ccctgtaacg    2572
tctgattcct cctttatctg ggttgtagat ggggcatagt gacttctaga aacctaacaa    2632
gggaataaat gtaagatgtg ctttcaaaaa aaaaaaaaaa aaaaaaaaaa aaaaaaaaaa    2692
aaaaaaaaaa aaaaaaaaaa aaaaa                                         2718
```

<210> SEQ ID NO 2
<211> LENGTH: 322
<212> TYPE: PRT
<213> ORGANISM: Mus musculus

<400> SEQUENCE: 2

```
Met Gln Leu Lys Cys Pro Cys Phe Val Ser Leu Gly Thr Arg Gln Pro
 1               5                  10                  15

Val Trp Lys Lys Leu His Val Ser Ser Gly Phe Ser Gly Leu Gly
            20                  25                  30

Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp
 50                  55                  60

Pro His Arg His Phe Asn Leu Ser Gly Leu Tyr Val Tyr Trp Gln
 65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
290                 295                 300

His Arg Ser Tyr Thr Gly Pro Lys Thr Val Gln Leu Glu Leu Thr Asp
305                 310                 315                 320

His Ala
```

-continued

```
<210> SEQ ID NO 3
<211> LENGTH: 1759
<212> TYPE: DNA
<213> ORGANISM: Mus musculus
<220> FEATURE:
<221> NAME/KEY: CDS
<222> LOCATION: (1)..(1041)

<400> SEQUENCE: 3 atg cag cta aag tgt ccc tgt ttt gtg tcc ttg gga acc agg cag cct      48
Met Gln Leu Lys Cys Pro Cys Phe Val Ser Leu Gly Thr Arg Gln Pro
 1               5                  10                  15 gtt tgg aag aag ctc cat gtt tct agc ggg ttc ttt tct ggt ctt ggt      96
Val Trp Lys Lys Leu His Val Ser Ser Gly Phe Phe Ser Gly Leu Gly
             20                  25                  30 ctg ttc ttg ctg ctg ttg agc agc ctc tgt gct gcc tct gca gag act     144
Leu Phe Leu Leu Leu Leu Ser Ser Leu Cys Ala Ala Ser Ala Glu Thr
         35                  40                  45 gaa gtc ggt gca atg gtg ggc agc aat gtg gtg ctc agc tgc att gac     192
Glu Val Gly Ala Met Val Gly Ser Asn Val Val Leu Ser Cys Ile Asp
     50                  55                  60 ccc cac aga cgc cat ttc aac ttg agt ggt ctg tat gtc tat tgg caa     240
Pro His Arg Arg His Phe Asn Leu Ser Gly Leu Tyr Val Tyr Trp Gln
 65                  70                  75                  80 atc gaa aac cca gaa gtt tcg gtg act tac tac ctg cct tac aag tct     288
Ile Glu Asn Pro Glu Val Ser Val Thr Tyr Tyr Leu Pro Tyr Lys Ser
                 85                  90                  95 cca ggg atc aat gtg gac agt tcc tac aag aac agg ggc cat ctg tcc     336
Pro Gly Ile Asn Val Asp Ser Ser Tyr Lys Asn Arg Gly His Leu Ser
            100                 105                 110 ctg gac tcc atg aag cag ggt aac ttc tct ctg tac ctg aag aat gtc     384
Leu Asp Ser Met Lys Gln Gly Asn Phe Ser Leu Tyr Leu Lys Asn Val
        115                 120                 125 acc cct cag gat acc cag gag ttc aca tgc cgg gta ttt atg aat aca     432
Thr Pro Gln Asp Thr Gln Glu Phe Thr Cys Arg Val Phe Met Asn Thr
    130                 135                 140 gcc aca gag tta gtc aag atc ttg gaa gag gtg gtc agg ctg cgt gtg     480
Ala Thr Glu Leu Val Lys Ile Leu Glu Glu Val Val Arg Leu Arg Val
145                 150                 155                 160 gca gca aac ttc agt aca cct gtc atc agc acc tct gat agc tcc aac     528
Ala Ala Asn Phe Ser Thr Pro Val Ile Ser Thr Ser Asp Ser Ser Asn
                165                 170                 175 cca ggc cag gaa cgt acc tac acc tgc atg tcc aag aat ggc tac cca     576
Pro Gly Gln Glu Arg Thr Tyr Thr Cys Met Ser Lys Asn Gly Tyr Pro
            180                 185                 190 gag ccc aac ctg tat tgg atc aac aca acg gac aat agc cta ata gac     624
Glu Pro Asn Leu Tyr Trp Ile Asn Thr Thr Asp Asn Ser Leu Ile Asp
        195                 200                 205 acg gct ctg cag aat aac act gtc tac ttg aac aag ttg ggc ctg tat     672
Thr Ala Leu Gln Asn Asn Thr Val Tyr Leu Asn Lys Leu Gly Leu Tyr
    210                 215                 220 gat gta atc agc aca tta agg ctc cct tgg aca tct cat ggg gat gtt     720
Asp Val Ile Ser Thr Leu Arg Leu Pro Trp Thr Ser His Gly Asp Val
225                 230                 235                 240 ctg tgc tgc gta gag aat gtg gct ctc cac cag aac atc act agc att     768
Leu Cys Cys Val Glu Asn Val Ala Leu His Gln Asn Ile Thr Ser Ile
                245                 250                 255 agc cag gca gaa agt ttc act gga aat aac aca aag aac cca cag gaa     816
Ser Gln Ala Glu Ser Phe Thr Gly Asn Asn Thr Lys Asn Pro Gln Glu
            260                 265                 270 acc cac aat aat gag tta aaa gtc ctt gtc ccc gtc ctt gct gta ctg     864
Thr His Asn Asn Glu Leu Lys Val Leu Val Pro Val Leu Ala Val Leu
```

```
                275                 280                 285
gcg gca gcg gca ttc gtt tcc ttc atc ata tac aga cgc acg cgt ccc    912
Ala Ala Ala Ala Phe Val Ser Phe Ile Ile Tyr Arg Arg Thr Arg Pro
290                 295                 300 cac cga agc tat aca gga ccc aag act gta cag ctt gaa ctt aca gac    960
His Arg Ser Tyr Thr Gly Pro Lys Thr Val Gln Leu Glu Leu Thr Asp
305                 310                 315                 320 act tgg gct ccg gtc ccc tac cag gac tat ttg att cca aga tat ttg   1008
Thr Trp Ala Pro Val Pro Tyr Gln Asp Tyr Leu Ile Pro Arg Tyr Leu
                325                 330                 335 atg tct cca tgc ctc aaa aca cgt ggt tta cca taaaagccac tgtctcatct  1061
Met Ser Pro Cys Leu Lys Thr Arg Gly Leu Pro
                340                 345 gttcagacca ctcaggctcc agccaggtgc cagaagtccc acttaccgag tctactgagc  1121
acaagctatg taatgggtct gctctgctcc agcagcatag aacccccaag ccccaggtta  1181
agacattttc aatgagcagg aacccaacca tactcacaga gctggagacc gagccagatg  1241
cagaaaagaa ggcatgttcc agcccattac atagacatct gaggtgccac tggggagatc  1301
ccagagccca aattcaccgt gaatagtgtt tggtttcaga cccaggacaa gggactgagg  1361
tgcatatttt acacatcaaa acggacctgg cttccaggtt ctcccagcat ccctcagtcc  1421
ctacctggca taccctgccc ccaaccctga actctccagc caggacctg gctgcccttt  1481 ccccagagg ctcctcccta tataatccag acattttgtc tcctcctttc ctccctccca   1541
ctctcttctt ttctctcgat gcgatgctca tgcgatgctc gatgctcatg atcaaatgct  1601
cccttctctc tttttctctc cctcccccc ttccacctct ttcctcacgg caactttcct   1661
ggctttggtc ctagtgaact cactcacctg agagtgattc ccaataaacc cacctttata  1721
taaaaaaaaa aaaaaaaaa aaaaaaaaaa aaaaaaa                            1759

<210> SEQ ID NO 4
<211> LENGTH: 347
<212> TYPE: PRT
<213> ORGANISM: Mus musculus

<400> SEQUENCE: 4

Met Gln Leu Lys Cys Pro Cys Phe Val Ser Leu Gly Thr Arg Gln Pro
1               5                   10                  15

Val Trp Lys Lys Leu His Val Ser Ser Gly Phe Ser Gly Leu Gly
            20                  25                  30

Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp
    50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
    130                 135                 140

Ala Thr Glu Leu Val Lys Ile Leu Glu Glu Val Val Arg Leu Arg Val
145                 150                 155                 160
```

```
Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser His Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

Thr Trp Ala Pro Val Pro Tyr Gln Asp Tyr Leu Ile Pro Arg Tyr Leu
                325                 330                 335

Met Ser Pro Cys Leu Lys Thr Arg Gly Leu Pro
            340                 345

<210> SEQ ID NO 5
<211> LENGTH: 953
<212> TYPE: DNA
<213> ORGANISM: Homo sapiens
<220> FEATURE:
<221> NAME/KEY: CDS
<222> LOCATION: (24)..(950)

<400> SEQUENCE: 5
ggcccgaggt ctccgcccgc acc atg cgg ctg ggc agt cct gga ctg ctc ttc    53
                        Met Arg Leu Gly Ser Pro Gly Leu Leu Phe
                         1               5                  10 ctg ctc ttc agc agc ctt cga gct gat act cag gag aag gaa gtc aga    101
Leu Leu Phe Ser Ser Leu Arg Ala Asp Thr Gln Glu Lys Glu Val Arg
            15                  20                  25 gcg atg gta ggc agc gac gtg gag ctc agc tgc gct tgc cct gaa gga    149
Ala Met Val Gly Ser Asp Val Glu Leu Ser Cys Ala Cys Pro Glu Gly
        30                  35                  40 agc cgt ttt gat tta aat gat gtt tac gta tat tgg caa acc agt gag    197
Ser Arg Phe Asp Leu Asn Asp Val Tyr Val Tyr Trp Gln Thr Ser Glu
    45                  50                  55 tcg aaa acc gtg gtg acc tac cac atc cca cag aac agc tcc ttg gaa    245
Ser Lys Thr Val Val Thr Tyr His Ile Pro Gln Asn Ser Ser Leu Glu
60                  65                  70 aac gtg gac agc cgc tac cgg aac cga gcc ctg atg tca ccg gcc ggc    293
Asn Val Asp Ser Arg Tyr Arg Asn Arg Ala Leu Met Ser Pro Ala Gly
75                  80                  85                  90 atg ctg cgg ggc gac ttc tcc ctg cgc ttg ttc aac gtc acc ccc cag    341
Met Leu Arg Gly Asp Phe Ser Leu Arg Leu Phe Asn Val Thr Pro Gln
            95                  100                 105 gac gag cag aag ttt cac tgc ctg gtg ttg agc caa tcc ctg gga ttc    389
Asp Glu Gln Lys Phe His Cys Leu Val Leu Ser Gln Ser Leu Gly Phe
        110                 115                 120 cag gag gtt ttg agc gtt gag gtt aca ctg cat gtg gca gca aac ttc    437
```

```
Gln Glu Val Leu Ser Val Glu Val Thr Leu His Val Ala Ala Asn Phe
        125                 130                 135 agc gtg ccc gtc gtc agc gcc ccc cac agc ccc tcc cag gat gag ctc      485
Ser Val Pro Val Val Ser Ala Pro His Ser Pro Ser Gln Asp Glu Leu
    140                 145                 150 acc ttc acg tgt aca tcc ata aac ggc tac ccc agg ccc aac gtg tac      533
Thr Phe Thr Cys Thr Ser Ile Asn Gly Tyr Pro Arg Pro Asn Val Tyr
155                 160                 165                 170 tgg atc aat aag acg gac aac agc ctg ctg gac cag gct ctg cag aat      581
Trp Ile Asn Lys Thr Asp Asn Ser Leu Leu Asp Gln Ala Leu Gln Asn
                175                 180                 185 gac acc gtc ttc ttg aac atg cgg ggc ttg tat gac gtg gtc agc gtg      629
Asp Thr Val Phe Leu Asn Met Arg Gly Leu Tyr Asp Val Val Ser Val
            190                 195                 200 ctg agg atc gca cgg acc ccc agc gtg aac att ggc tgc tgc ata gag      677
Leu Arg Ile Ala Arg Thr Pro Ser Val Asn Ile Gly Cys Cys Ile Glu
        205                 210                 215 aac gtg ctt ctg cag cag aac ctg act gtc ggc agc cag aca gga aat      725
Asn Val Leu Leu Gln Gln Asn Leu Thr Val Gly Ser Gln Thr Gly Asn
    220                 225                 230 gac atc gga gag aga gac aag atc aca gag aat cca gtc agt acc ggc      773
Asp Ile Gly Glu Arg Asp Lys Ile Thr Glu Asn Pro Val Ser Thr Gly
235                 240                 245                 250 gag aaa aac gcg gcc acg tgg agc atc ctg gct gtc ctg tgc ctg ctt      821
Glu Lys Asn Ala Ala Thr Trp Ser Ile Leu Ala Val Leu Cys Leu Leu
                255                 260                 265 gtg gtc gtg gcg gtg gcc ata ggc tgg gtg tgc agg gac cga tgc ctc      869
Val Val Val Ala Val Ala Ile Gly Trp Val Cys Arg Asp Arg Cys Leu
            270                 275                 280 caa cac agc tat gca ggt gcc tgg gct gtg agt ccg gag aca gag ctc      917
Gln His Ser Tyr Ala Gly Ala Trp Ala Val Ser Pro Glu Thr Glu Leu
        285                 290                 295 act gaa tcc tgg aac ctg ctc ctt ctg ctc tcg tga                      953
Thr Glu Ser Trp Asn Leu Leu Leu Leu Ser
300                 305

<210> SEQ ID NO 6
<211> LENGTH: 309
<212> TYPE: PRT
<213> ORGANISM: Homo sapiens

<400> SEQUENCE: 6

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
```

```
                130                 135                 140
Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
                180                 185                 190

Met Arg Gly Leu Tyr Asp Val Val Ser Val Leu Arg Ile Ala Arg Thr
            195                 200                 205

Pro Ser Val Asn Ile Gly Cys Cys Ile Glu Asn Val Leu Leu Gln Gln
210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Ala Val Ala
            260                 265                 270

Ile Gly Trp Val Cys Arg Asp Arg Cys Leu Gln His Ser Tyr Ala Gly
            275                 280                 285

Ala Trp Ala Val Ser Pro Glu Thr Glu Leu Thr Glu Ser Trp Asn Leu
290                 295                 300

Leu Leu Leu Leu Ser
305

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
cccgcagtct gcgctcgcac c                                          21

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8
gtcgacccac catgcagcta aagtgtccct g                               31

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
cgtgtactgg atcaataaga cgg                                        23

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
```

```
acaacagcct gctggaccag gc                                              22

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ccagtgagca gagtgacg                                                   18

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
gaggactcga gctcaagc                                                   18

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
catcactagc attagccagg c                                               21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
tgatgttgtg aagctgagtg c                                               21

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
tcatgagcat cgagcatcg                                                  19

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
tcacgagagc agaaggagca ggttcc                                          26

<210> SEQ ID NO 17
<211> LENGTH: 25
<212> TYPE: DNA
<213> ORGANISM: Artificial Sequence
```

<220> FEATURE:
<223> OTHER INFORMATION: primer

<400> SEQUENCE: 17
gggcccccca gaacctgctg cttcc                                         25

<210> SEQ ID NO 18
<211> LENGTH: 47
<212> TYPE: DNA
<213> ORGANISM: Artificial Sequence
<220> FEATURE:
<223> OTHER INFORMATION: primer

<400> SEQUENCE: 18
ccagtgagca gagtgacgag gactcgagct caagcttttt tttttt                  47

<210> SEQ ID NO 19
<211> LENGTH: 26
<212> TYPE: DNA
<213> ORGANISM: Artificial Sequence
<220> FEATURE:
<223> OTHER INFORMATION: primer

<400> SEQUENCE: 19
tgaaggtcgg tgtgaacgga tttggc                                        26

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
catgtaggcc atgaggtcca ccac                                          24

<210> SEQ ID NO 21
<211> LENGTH: 13
<212> TYPE: PRT
<213> ORGANISM: Artificial Sequence
<220> FEATURE:
<223> OTHER INFORMATION: consensus motif
<221> NAME/KEY: VARIANT
<222> LOCATION: (1)...(13)
<223> OTHER INFORMATION: Xaa = Any Amino Acid

<400> SEQUENCE: 21

Arg Arg Arg Xaa Xaa Gln His Xaa Ser Tyr Thr Gly Pro
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Caenorhabditis elegans

<400> SEQUENCE: 22

Arg Arg Arg Gln Gln His His Ser Tyr Thr
1               5                   10

<210> SEQ ID NO 23
<211> LENGTH: 1498
<212> TYPE: DNA
<213> ORGANISM: Artificial Sequence
<220> FEATURE:
<223> OTHER INFORMATION: hICOS-mIgG2am nucleotide sequence
<221> NAME/KEY: exon
<222> LOCATION: (24)...(98)
<221> NAME/KEY: exon
<222> LOCATION: (99)...(462)
<221> NAME/KEY: exon
<222> LOCATION: (463)...(510)
<221> NAME/KEY: exon
<222> LOCATION: (620)...(949)
<221> NAME/KEY: exon
<222> LOCATION: (1062)...(1384)

<400> SEQUENCE: 23

```
gaattcgccc ttgtcgaccc accatggggg tactgctcac acagaggacg ctgctcagtc      60
tggtccttgc actcctgttt ccaagcatgg ccagcatgga aatcaatggt tctgccaatt     120
atgagatgtt tatatttcac aacggaggtg tacaaatttt atgcaaatat cctgacattg     180
tccagcaatt taaaatgcag ttgctgaaag gggggcaaat actctgcgat ctcactaaga     240
caaaaggaag tggaaacaca gtgtccatta gagtctgaa attctgccat tctcagttat      300
ccaacaacag cgtctctttt tttctataca acttggacca ttctcatgcc aactattact     360
tctgcaaccct atcaattttt gatcctcctc cttttaaagt aactcttaca ggaggatatt    420
tgcatattta tgaatcacaa ctttgttgcc agctgaagtt cgagcccgc ggaccgacaa      480
tcaagccctg tcctccatgc aaatgcccag gtaagtcact agaccagagc tccactcccg     540
ggagaatggt aagtgctata acatccctg cactagagga taagccatgt acagatccat      600
ttccatctct cctcatcagc acctaacctc gagggtggac catccgtctt catcttccct     660
ccaaagatca aggatgtact catgatctcc ctgagcccca tagtcacatg tgtggtggtg     720
gatgtgagcg aggatgaccc agatgtccag atcagctggt ttgtgaacaa cgtggaagta     780
cacacagctc agacacaaac ccatagagag gattacaaca gtactctccg ggtggtcagt     840
gccctcccca tccagcacca ggactggatg agtggcaagg ctttcgcatg cgccgtcaac     900
aacaaagacc tcccagcgcc catcgagaga accatctcaa acccaaagg tgagagctgc      960
agcctgactg catgggggct gggatgggca taaggataaa ggtctgtgtg acagccttc     1020
tgcttcagcc atgaccttg tgtatgtttc taccctcaca gggtcagtaa gagctccaca     1080
ggtatatgtc ttgcctccac cagaagaaga gatgactaag aaacaggtca ctctgacctg    1140
catggtcaca gacttcatgc ctgaagacat ttacgtggag tggaccaaca cgggaaaac     1200
agagctaaac tacaagaaca ctgaaccagt cctggactct gatggttctt acttcatgta    1260
cagcaagctg agagtggaaa agaagaactg ggtggaaaga aatagctact cctgttcagt    1320
ggtccacgag ggtctgcaca atcaccacac gactaagagc ttctcccgga ctccgggtaa    1380
atgagctcag cacccacaaa actctcaggt ccaaagagac acccacactc atctccatgc    1440
ttcccttgta taaataaagc acccagcaat gcctgggacc atgtaaaagg gcgaattc      1498
```

<210> SEQ ID NO 24
<211> LENGTH: 379
<212> TYPE: PRT
<213> ORGANISM: Artificial Sequence
<220> FEATURE:
<223> OTHER INFORMATION: hICOS-mIgG2am amino acid sequence

<400> SEQUENCE: 24

```
Met Gly Val Leu Leu Thr Gln Arg Thr Leu Leu Ser Leu Val Leu Ala
 1               5                  10                  15

Leu Leu Phe Pro Ser Met Ala Ser Met Glu Ile Asn Gly Ser Ala Asn
            20                  25                  30

Tyr Glu Met Phe Ile Phe His Asn Gly Gly Val Gln Ile Leu Cys Lys
        35                  40                  45
```

```
Tyr Pro Asp Ile Val Gln Gln Phe Lys Met Gln Leu Leu Lys Gly Gly
    50                  55                  60

Gln Ile Leu Cys Asp Leu Thr Lys Thr Lys Gly Ser Gly Asn Thr Val
 65                  70                  75                  80

Ser Ile Lys Ser Leu Lys Phe Cys His Ser Gln Leu Ser Asn Asn Ser
                85                  90                  95

Val Ser Phe Phe Leu Tyr Asn Leu Asp His Ser His Ala Asn Tyr Tyr
            100                 105                 110

Phe Cys Asn Leu Ser Ile Phe Asp Pro Pro Phe Lys Val Thr Leu
            115                 120                 125

Thr Gly Gly Tyr Leu His Ile Tyr Glu Ser Gln Leu Cys Cys Gln Leu
    130                 135                 140

Lys Phe Glu Pro Arg Gly Pro Thr Ile Lys Pro Cys Pro Pro Cys Lys
145                 150                 155                 160

Cys Pro Ala Pro Asn Leu Glu Gly Gly Pro Ser Val Phe Ile Phe Pro
                165                 170                 175

Pro Lys Ile Lys Asp Val Leu Met Ile Ser Leu Ser Pro Ile Val Thr
            180                 185                 190

Cys Val Val Asp Val Ser Glu Asp Asp Pro Asp Val Gln Ile Ser
            195                 200                 205

Trp Phe Val Asn Asn Val Glu Val His Thr Ala Gln Thr Gln Thr His
    210                 215                 220

Arg Glu Asp Tyr Asn Ser Thr Leu Arg Val Val Ser Ala Leu Pro Ile
225                 230                 235                 240

Gln His Gln Asp Trp Met Ser Gly Lys Ala Phe Ala Cys Ala Val Asn
                245                 250                 255

Asn Lys Asp Leu Pro Ala Pro Ile Glu Arg Thr Ile Ser Lys Pro Lys
            260                 265                 270

Gly Ser Val Arg Ala Pro Gln Val Tyr Val Leu Pro Pro Pro Glu Glu
            275                 280                 285

Glu Met Thr Lys Lys Gln Val Thr Leu Thr Cys Met Val Thr Asp Phe
    290                 295                 300

Met Pro Glu Asp Ile Tyr Val Glu Trp Thr Asn Asn Gly Lys Thr Glu
305                 310                 315                 320

Leu Asn Tyr Lys Asn Thr Glu Pro Val Leu Asp Ser Asp Gly Ser Tyr
                325                 330                 335

Phe Met Tyr Ser Lys Leu Arg Val Glu Lys Lys Asn Trp Val Glu Arg
            340                 345                 350

Asn Ser Tyr Ser Cys Ser Val Val His Glu Gly Leu His Asn His His
            355                 360                 365

Thr Thr Lys Ser Phe Ser Arg Thr Pro Gly Lys
    370                 375

<210> SEQ ID NO 25
<211> LENGTH: 1501
<212> TYPE: DNA
<213> ORGANISM: Artificial Sequence
<220> FEATURE:
<223> OTHER INFORMATION: mICOS-mIgG2am nucleotide sequence

<400> SEQUENCE: 25
gaattcgccc ttgtcgaccc accatggggg tactgctcac acagaggacg ctgctcagtc    60
tggtccttgc actcctgttt ccaagcatgg ccagcatgga aatcaatggc tcggccgatc   120
ataggatgtt tcatttcac aatggaggtg tacagatttc ttgtaaatac cctgagactg    180
```

```
tccagcagtt aaaaatgcga ttgttcagag agagagaagt cctctgcgaa ctcaccaaga    240
ccaagggaag cggaaatgcg gtgtccatca agaatccaat gctctgtcta tatcatctgt    300
caaacaacag cgtctctttt ttcctaaaca acccagacag ctcccaggga agctattact    360
tctgcagcct gtccattttt gacccacctc cttttcaaga aggaaccttt agtggaggat    420
atttgcatat ttatgaatcc cagctctgct gccagctgaa gctcgagccc gcggaccga    480 caatcaagcc ctgtcctcca tgcaaatgcc caggtaagtc actagaccag agctccactc    540
ccgggagaat ggtaagtgct ataaacatcc ctgcactaga ggataagcca tgtacagatc    600
catttccatc tctcctcatc agcacctaac ctcgagggtg gaccatccgt cttcatcttc    660
cctccaaaga tcaaggatgt actcatgatc tccctgagcc ccatagtcac atgtgtggtg    720
gtggatgtga gcgaggatga cccagatgtc cagatcagct ggtttgtgaa caacgtggaa    780
gtacacacag ctcagacaca aacccataga gaggattaca acagtactct ccgggtggtc    840
agtgccctcc ccatccagca ccaggactgg atgagtggca aggctttcgc atgcgccgtc    900
aacaacaaag acctcccagc gcccatcgag agaaccatct caaaacccaa aggtgagagc    960
tgcagcctga ctgcatgggg gctgggatgg gcataaggat aaaggtctgt gtggacagcc   1020
ttctgcttca gccatgacct ttgtgtatgt ttctaccctc acagggtcag taagagctcc   1080
acaggtatat gtcttgcctc caccagaaga agagatgact aagaaacagg tcactctgac   1140
ctgcatggtc acagacttca tgcctgaaga catttacgtg gagtggacca caacgggaa    1200 aacagagcta aactcaaga acactgaacc agtcctggac tctgatggtt cttacttcat    1260
gtacagcaag ctgagagtgg aaaagaagaa ctgggtggaa agaaatagct actcctgttc    1320
agtggtccac gagggtctgc acaatcacca cacgactaag agcttctccc ggactccggg    1380
taaatgagct cagcacccac aaaactctca ggtccaaaga gacacccaca ctcatctcca    1440
tgcttccctt gtataaataa agcacccagc aatgcctggg accatgtaaa agggcgaatt    1500
c                                                                   1501
```

<210> SEQ ID NO 26
<211> LENGTH: 380
<212> TYPE: PRT
<213> ORGANISM: Artificial Sequence
<220> FEATURE:
<223> OTHER INFORMATION: mICOS-mIgG2am nucleotide sequence

<400> SEQUENCE: 26

```
Met Gly Val Leu Leu Thr Gln Arg Thr Leu Leu Ser Leu Val Leu Ala
1               5                   10                  15

Leu Leu Phe Pro Ser Met Ala Ser Met Glu Ile Asn Gly Ser Ala Asp
            20                  25                  30

His Arg Met Phe Ser Phe His Asn Gly Gly Val Gln Ile Ser Cys Lys
        35                  40                  45

Tyr Pro Glu Thr Val Gln Gln Leu Lys Met Arg Leu Phe Arg Glu Arg
    50                  55                  60

Glu Val Leu Cys Glu Leu Thr Lys Thr Lys Gly Ser Gly Asn Ala Val
65                  70                  75                  80

Ser Ile Lys Asn Pro Met Leu Cys Leu Tyr His Leu Ser Asn Asn Ser
                85                  90                  95

Val Ser Phe Phe Leu Asn Asn Pro Asp Ser Ser Gln Gly Ser Tyr Tyr
            100                 105                 110

Phe Cys Ser Leu Ser Ile Phe Asp Pro Pro Pro Phe Gln Glu Arg Asn
        115                 120                 125
```

```
Leu Ser Gly Gly Tyr Leu His Ile Tyr Glu Ser Gln Leu Cys Cys Gln
        130                 135                 140

Leu Lys Leu Glu Pro Arg Gly Pro Thr Ile Lys Pro Cys Pro Pro Cys
145                 150                 155                 160

Lys Cys Pro Ala Pro Asn Leu Glu Gly Gly Pro Ser Val Phe Ile Phe
                165                 170                 175

Pro Pro Lys Ile Lys Asp Val Leu Met Ile Ser Leu Ser Pro Ile Val
                180                 185                 190

Thr Cys Val Val Val Asp Val Ser Glu Asp Asp Pro Asp Val Gln Ile
            195                 200                 205

Ser Trp Phe Val Asn Asn Val Glu Val His Thr Ala Gln Thr Gln Thr
        210                 215                 220

His Arg Glu Asp Tyr Asn Ser Thr Leu Arg Val Val Ser Ala Leu Pro
225                 230                 235                 240

Ile Gln His Gln Asp Trp Met Ser Gly Lys Ala Phe Ala Cys Ala Val
                245                 250                 255

Asn Asn Lys Asp Leu Pro Ala Pro Ile Glu Arg Thr Ile Ser Lys Pro
                260                 265                 270

Lys Gly Ser Val Arg Ala Pro Gln Val Tyr Val Leu Pro Pro Pro Glu
            275                 280                 285

Glu Glu Met Thr Lys Lys Gln Val Thr Leu Thr Cys Met Val Thr Asp
        290                 295                 300

Phe Met Pro Glu Asp Ile Tyr Val Glu Trp Thr Asn Asn Gly Lys Thr
305                 310                 315                 320

Glu Leu Asn Tyr Lys Asn Thr Glu Pro Val Leu Asp Ser Asp Gly Ser
                325                 330                 335

Tyr Phe Met Tyr Ser Lys Leu Arg Val Glu Lys Lys Asn Trp Val Glu
                340                 345                 350

Arg Asn Ser Tyr Ser Cys Ser Val Val His Glu Gly Leu His Asn His
            355                 360                 365

His Thr Thr Lys Ser Phe Ser Arg Thr Pro Gly Lys
        370                 375                 380

<210> SEQ ID NO 27
<211> LENGTH: 1831
<212> TYPE: DNA
<213> ORGANISM: Artificial Sequence
<220> FEATURE:
<223> OTHER INFORMATION: hGL50-mIgG2am nucleotide sequence

<400> SEQUENCE: 27
gaattcgccc ttgtcgaccc accatggggg tactgctcac acagaggacg ctgctcagtc     60
tggtccttgc actcctgttt ccaagcatgg ccagcatgga gaaggaagtc agagcgatgg    120
taggcagcga cgtggagctc agctgcgctt gccctgaagg aagccgtttt gatttaaatg    180
atgtttacgt atattggcaa accagtgagt cgaaaaccgt ggtgacctac acatccccac    240
agaacagctc cttggaaaac gtggacagcc gctaccggaa ccgagccctg atgtcaccgg    300
ccggcatgct gcgggcgac ttctccctgc gcttgttcaa cgtcaccccc aggacgagc     360 agaagtttca ctgcctggtg ttgagccaat ccctgggatt ccaggaggtt ttgagcgttg    420
aggttacact gcatgtggca gcaaacttca gcgtgcccgt cgtcagcgcc cccacagcc     480 cctcccagga tgagctcacc ttcacgtgta catccataaa cggctacccc aggcccaacg    540
tgtactggat caataagacg gacaacagcc tgctggacca ggctctgcag aatgacaccg    600
tcttcttgaa catgcggggc ttgtatgacg tggtcagcgt gctgaggatc gcacggaccc    660
```

-continued

| | |
|---|---|
| ccagcgtgaa cattggctgc tgcatagaga acgtgcttct gcagcagaac ctgactgtcg | 720 |
| gcagccagac aggaaatgac atcggagaga gagacaagat cacagagaat ccagtcagta | 780 |
| ccggcgagaa aaacgagccc cgcggaccga caatcaagcc ctgtcctcca tgcaaatgcc | 840 |
| caggtaagtc actagaccag agctccactc ccgggagaat ggtaagtgct ataaacatcc | 900 |
| ctgcactaga ggataagcca tgtacagatc catttccatc tctcctcatc agcacctaac | 960 |
| ctcgagggtg gaccatccgt cttcatcttc cctccaaaga tcaaggatgt actcatgatc | 1020 |
| tccctgagcc ccatagtcac atgtgtggtg gtggatgtga gcgaggatga cccagatgtc | 1080 |
| cagatcagct ggtttgtgaa caacgtggaa gtacacacag ctcagacaca aacccataga | 1140 |
| gaggattaca acagtactct ccgggtggtc agtgccctcc ccatccagca ccaggactgg | 1200 |
| atgagtggca aggctttcgc atgcgccgtc aacaacaaag acctcccagc gcccatcgag | 1260 |
| agaaccatct caaaacccaa aggtgagagc tgcagcctga ctgcatgggg gctgggatgg | 1320 |
| gcataaggat aaaggtctgt gtggacagcc ttctgcttca gccatgacct ttgtgtatgt | 1380 |
| ttctaccctc acagggtcag taagagctcc acaggtatat gtcttgcctc caccagaaga | 1440 |
| agagatgact aagaaacagg tcactctgac ctgcatggtc acagacttca tgcctgaaga | 1500 |
| catttacgtg gagtggacca caacgggaaa acagagcta aactacaaga acactgaacc | 1560 |
| agtcctggac tctgatggtt cttacttcat gtacagcaag ctgagagtgg aaaagaagaa | 1620 |
| ctgggtggaa agaaatagtt actcctgttc agtggtccac gagggtctgc acaatcacca | 1680 |
| cacgactaag agcttctccc ggactccggg taaatgagct cagcacccac aaaactctca | 1740 |
| ggtccaaaga gacacccaca ctcgtctcca tgcttccctt gtataaataa agcacccagc | 1800 |
| aatgcctggg accatgtaaa agggcgaatt c | 1831 |

<210> SEQ ID NO 28
<211> LENGTH: 490
<212> TYPE: PRT
<213> ORGANISM: Artificial Sequence
<220> FEATURE:
<223> OTHER INFORMATION: hGL50-mIgG2am nucleotide sequence

<400> SEQUENCE: 28

```
Met Gly Val Leu Leu Thr Gln Arg Thr Leu Leu Ser Leu Val Leu Ala
 1               5                  10                  15

Leu Leu Phe Pro Ser Met Ala Ser Met Glu Lys Glu Val Arg Ala Met
                20                  25                  30

Val Gly Ser Asp Val Glu Leu Ser Cys Ala Cys Pro Glu Gly Ser Arg
            35                  40                  45

Phe Asp Leu Asn Asp Val Tyr Val Tyr Trp Gln Thr Ser Glu Ser Lys
        50                  55                  60

Thr Val Val Thr Tyr His Ile Pro Gln Asn Ser Ser Leu Glu Asn Val
 65                  70                  75                  80

Asp Ser Arg Tyr Arg Asn Arg Ala Leu Met Ser Pro Ala Gly Met Leu
                85                  90                  95

Arg Gly Asp Phe Ser Leu Arg Leu Phe Asn Val Thr Pro Gln Asp Glu
            100                 105                 110

Gln Lys Phe His Cys Leu Val Leu Ser Gln Ser Leu Gly Phe Gln Glu
        115                 120                 125

Val Leu Ser Val Glu Val Thr Leu His Val Ala Ala Asn Phe Ser Val
    130                 135                 140

Pro Val Val Ser Ala Pro His Ser Pro Ser Gln Asp Glu Leu Thr Phe
145                 150                 155                 160
```

```
Thr Cys Thr Ser Ile Asn Gly Tyr Pro Arg Pro Asn Val Tyr Trp Ile
            165                 170                 175

Asn Lys Thr Asp Asn Ser Leu Leu Asp Gln Ala Leu Gln Asn Asp Thr
        180                 185                 190

Val Phe Leu Asn Met Arg Gly Leu Tyr Asp Val Val Ser Val Leu Arg
            195                 200                 205

Ile Ala Arg Thr Pro Ser Val Asn Ile Gly Cys Cys Ile Glu Asn Val
        210                 215                 220

Leu Leu Gln Gln Asn Leu Thr Val Gly Ser Gln Thr Gly Asn Asp Ile
225                 230                 235                 240

Gly Glu Arg Asp Lys Ile Thr Glu Asn Pro Val Ser Thr Gly Glu Lys
            245                 250                 255

Asn Glu Pro Arg Gly Pro Thr Ile Lys Pro Cys Pro Pro Cys Lys Cys
        260                 265                 270

Pro Ala Pro Asn Leu Glu Gly Gly Pro Ser Val Phe Ile Phe Pro Pro
            275                 280                 285

Lys Ile Lys Asp Val Leu Met Ile Ser Leu Ser Pro Ile Val Thr Cys
        290                 295                 300

Val Val Val Asp Val Ser Glu Asp Asp Pro Asp Val Gln Ile Ser Trp
305                 310                 315                 320

Phe Val Asn Asn Val Glu Val His Thr Ala Gln Thr Gln Thr His Arg
            325                 330                 335

Glu Asp Tyr Asn Ser Thr Leu Arg Val Val Ser Ala Leu Pro Ile Gln
        340                 345                 350

His Gln Asp Trp Met Ser Gly Lys Ala Phe Ala Cys Ala Val Asn Asn
            355                 360                 365

Lys Asp Leu Pro Ala Pro Ile Glu Arg Thr Ile Ser Lys Pro Lys Gly
        370                 375                 380

Ser Val Arg Ala Pro Gln Val Tyr Val Leu Pro Pro Pro Glu Glu Glu
385                 390                 395                 400

Met Thr Lys Lys Gln Val Thr Leu Thr Cys Met Val Thr Asp Phe Met
            405                 410                 415

Pro Glu Asp Ile Tyr Val Glu Trp Thr Asn Asn Gly Lys Thr Glu Leu
        420                 425                 430

Asn Tyr Lys Asn Thr Glu Pro Val Leu Asp Ser Asp Gly Ser Tyr Phe
            435                 440                 445

Met Tyr Ser Lys Leu Arg Val Glu Lys Lys Asn Trp Val Glu Arg Asn
450                 455                 460

Ser Tyr Ser Cys Ser Val Val His Glu Gly Leu His Asn His His Thr
465                 470                 475                 480

Thr Lys Ser Phe Ser Arg Thr Pro Gly Lys
            485                 490

<210> SEQ ID NO 29
<211> LENGTH: 1830
<212> TYPE: DNA
<213> ORGANISM: Artificial Sequence
<220> FEATURE:
<223> OTHER INFORMATION: mGL50-mIgG2am nucleotide sequence

<400> SEQUENCE: 29
cagaattcgc ccttgtcgac ccaccatggg ggtactgctc acacagagga cgctgctcag      60
tctggtcctt gcactcctgt ttccaagcat ggccagcatg gagactgaag tcggtgcaat     120
ggtgggcagc aatgtggtgc tcagctgcat tgacccccac agacgccatt tcaacttgag     180
tggtctgtat gtctattggc aaatcgaaaa cccggaagtt tcggtgactt actacctgcc     240
```

```
ttacaagtct ccagggatca atgtggacag ttcctacaag aacagggcc atctgtccct      300
ggactccatg aagcagggta acttctctct gtacctgaag aatgtcaccc ctcaggatac    360
ccaggagttc acatgccggg tatttatgaa tacagccaca gagttagtca agatcttgga    420
agaggtggtc aggctgcgtg tggcagcaaa cttcagtaca cctgtcatca gcacctctga    480
tagctccaac ccgggccagg aacgtaccta cacctgcatg tccaagaatg gctacccaga    540
gcccaacctg tattggatca acacaacgga caatagccta atagacacgg ctctgcagaa    600
taacactgtc tacttgaaca agttgggcct gtatgatgta atcagcacat taaggctccc    660
ttggacatct cgtggggatg ttctgtgctg cgtagagaat gtggctctcc accagaacat    720
cactagcatt agccaggcag aaagtttcac tggaaataac acaaagaacc acaggaaac     780
ccacaataat gaggagcccc gcggaccgac aatcaagccc tgtcctccat gcaaatgccc    840
aggtaagtca ctagaccaga gctccactcc cgggagaatg gtaagtgcta taaacatccc    900
tgcactagag gataagccat gtacagatcc atttccatct ctcctcatca gcacctaacc    960
tcgagggtgg accatccgtc ttcatcttcc ctccaaagat caaggatgta ctcatgatct    1020
ccctgagccc catagtcaca tgtgtggtgg tggatgtgag cgaggatgac ccagatgtcc    1080
agatcagctg gtttgtgaac aacgtggaag tacacacagc tcagacacaa acccatagag    1140
aggattacaa cagtactctc cgggtggtca gtgccctccc catccagcac caggactgga    1200
tgagtggcaa ggctttcgca tgcgccgtca acaacaaaga cctcccagcg cccatcgaga    1260
gaaccatctc aaaacccaaa ggtgagagct gcagcctgac tgcatggggg ctgggatggg    1320
cataaggata aaggtctgtg tggacagcct tctgcttcag ccatgacctt tgtgtatgtt    1380
tctaccctca cagggtcagt aagagctcca caggtatatg tcttgcctcc accagaagaa    1440
gagatgacta agaaacaggt cactctgacc tgcatggtca cagacttcat gcctgaagac    1500
atttacgtgg agtggaccaa caacgggaaa acagagctaa actacaagaa cactgaacca    1560
gtcctggact ctgatggttc ttacttcatg tacagcaagc tgagagtgga aaagaagaac    1620
tgggtggaaa gaaatagcta ctcctgttca gtggtccacg agggtctgca caatcaccac    1680
acgactaaga gcttctcccg gactccgggt aaatgagctc agcacccgca aaactctcag    1740
gtccaaagag acacccacac tcatctccat gcttcccttg tataaataaa gcacccagca    1800
atgcctggga ccatataaaa gggcgaattc                                    1830
```

<210> SEQ ID NO 30
<211> LENGTH: 489
<212> TYPE: PRT
<213> ORGANISM: Artificial Sequence
<220> FEATURE:
<223> OTHER INFORMATION: mGL50-mIgG2am nucleotide sequence

<400> SEQUENCE: 30

```
Met Gly Val Leu Leu Thr Gln Arg Thr Leu Leu Ser Leu Val Leu Ala
 1               5                  10                  15

Leu Leu Phe Pro Ser Met Ala Ser Met Glu Thr Glu Val Gly Ala Met
            20                  25                  30

Val Gly Ser Asn Val Val Leu Ser Cys Ile Asp Pro His Arg Arg His
        35                  40                  45

Phe Asn Leu Ser Gly Leu Tyr Val Tyr Trp Gln Ile Glu Asn Pro Glu
    50                  55                  60

Val Ser Val Thr Tyr Tyr Leu Pro Tyr Lys Ser Pro Gly Ile Asn Val
65                  70                  75                  80
```

-continued

Asp Ser Ser Tyr Lys Asn Arg Gly His Leu Ser Leu Asp Ser Met Lys
                85                  90                  95

Gln Gly Asn Phe Ser Leu Tyr Leu Lys Asn Val Thr Pro Gln Asp Thr
            100                 105                 110

Gln Glu Phe Thr Cys Arg Val Phe Met Asn Thr Ala Thr Glu Leu Val
        115                 120                 125

Lys Ile Leu Glu Glu Val Val Arg Leu Arg Val Ala Ala Asn Phe Ser
130                 135                 140

Thr Pro Val Ile Ser Thr Ser Asp Ser Ser Asn Pro Gly Gln Glu Arg
145                 150                 155                 160

Thr Tyr Thr Cys Met Ser Lys Asn Gly Tyr Pro Glu Pro Asn Leu Tyr
                165                 170                 175

Trp Ile Asn Thr Thr Asp Asn Ser Leu Ile Asp Thr Ala Leu Gln Asn
            180                 185                 190

Asn Thr Val Tyr Leu Asn Lys Leu Gly Leu Tyr Asp Val Ile Ser Thr
        195                 200                 205

Leu Arg Leu Pro Trp Thr Ser Arg Gly Asp Val Leu Cys Cys Val Glu
210                 215                 220

Asn Val Ala Leu His Gln Asn Ile Thr Ser Ile Ser Gln Ala Glu Ser
225                 230                 235                 240

Phe Thr Gly Asn Asn Thr Lys Asn Pro Gln Glu Thr His Asn Asn Glu
                245                 250                 255

Glu Pro Arg Gly Pro Thr Ile Lys Pro Cys Pro Pro Cys Lys Cys Pro
            260                 265                 270

Ala Pro Asn Leu Glu Gly Gly Pro Ser Val Phe Ile Phe Pro Pro Lys
        275                 280                 285

Ile Lys Asp Val Leu Met Ile Ser Leu Ser Pro Ile Val Thr Cys Val
290                 295                 300

Val Val Asp Val Ser Glu Asp Pro Asp Val Gln Ile Ser Trp Phe
305                 310                 315                 320

Val Asn Asn Val Glu Val His Thr Ala Gln Thr Gln Thr His Arg Glu
                325                 330                 335

Asp Tyr Asn Ser Thr Leu Arg Val Val Ser Ala Leu Pro Ile Gln His
            340                 345                 350

Gln Asp Trp Met Ser Gly Lys Ala Phe Ala Cys Ala Val Asn Asn Lys
        355                 360                 365

Asp Leu Pro Ala Pro Ile Glu Arg Thr Ile Ser Lys Pro Lys Gly Ser
370                 375                 380

Val Arg Ala Pro Gln Val Tyr Val Leu Pro Pro Glu Glu Glu Met
385                 390                 395                 400

Thr Lys Lys Gln Val Thr Leu Thr Cys Met Val Thr Asp Phe Met Pro
                405                 410                 415

Glu Asp Ile Tyr Val Glu Trp Thr Asn Asn Gly Lys Thr Glu Leu Asn
            420                 425                 430

Tyr Lys Asn Thr Glu Pro Val Leu Asp Ser Asp Gly Ser Tyr Phe Met
        435                 440                 445

Tyr Ser Lys Leu Arg Val Glu Lys Asn Trp Val Glu Arg Asn Ser
450                 455                 460

Tyr Ser Cys Ser Val Val His Glu Gly Leu His Asn His His Thr Thr
465                 470                 475                 480

Lys Ser Phe Ser Arg Thr Pro Gly Lys
                485

<210> SEQ ID NO 31

```
<211> LENGTH: 558
<212> TYPE: PRT
<213> ORGANISM: Homo sapiens
<220> FEATURE:
<221> NAME/KEY:
<222> LOCATION:

<400> SEQUENCE: 31
```

| | | | | | | | | | | | | | | | |
|---|---|---|---|---|---|---|---|---|---|---|---|---|---|---|---|
| Ala | Val | Arg | Ala | Asp | Leu | Pro | Arg | Pro | Glu | Val | Ala | Pro | Leu | Arg | Gly |
| 1 | | | | 5 | | | | | 10 | | | | | 15 | |
| Leu | Pro | Arg | Pro | Lys | Phe | Ser | Ala | Pro | Arg | Gly | Leu | Arg | Ala | Pro | Arg |
| | | | 20 | | | | | 25 | | | | | 30 | | |
| Ser | Pro | Arg | Pro | Glu | Val | Ser | Ala | Arg | Thr | Met | Arg | Leu | Gly | Ser | Pro |
| | | 35 | | | | | 40 | | | | | 45 | | | |
| Gly | Leu | Leu | Phe | Leu | Leu | Phe | Ser | Ser | Leu | Arg | Ala | Asp | Thr | Gln | Glu |
| | 50 | | | | | 55 | | | | | 60 | | | | |
| Lys | Glu | Val | Arg | Ala | Met | Val | Gly | Ser | Asp | Val | Glu | Leu | Ser | Cys | Ala |
| 65 | | | | | 70 | | | | | 75 | | | | | 80 |
| Cys | Pro | Glu | Gly | Ser | Arg | Phe | Asp | Leu | Asn | Asp | Val | Tyr | Val | Tyr | Trp |
| | | | | 85 | | | | | 90 | | | | | 95 | |
| Gln | Thr | Ser | Glu | Ser | Lys | Thr | Val | Val | Thr | Tyr | His | Ile | Pro | Gln | Asn |
| | | | 100 | | | | | 105 | | | | | 110 | | |
| Ser | Ser | Leu | Glu | Asn | Val | Asp | Ser | Arg | Tyr | Arg | Asn | Arg | Ala | Leu | Met |
| | | 115 | | | | | 120 | | | | | 125 | | | |
| Ser | Pro | Ala | Gly | Met | Leu | Arg | Gly | Asp | Phe | Ser | Leu | Arg | Leu | Phe | Asn |
| | 130 | | | | | 135 | | | | | 140 | | | | |
| Val | Thr | Pro | Gln | Asp | Glu | Gln | Lys | Phe | His | Cys | Leu | Val | Leu | Ser | Gln |
| 145 | | | | | 150 | | | | | 155 | | | | | 160 |
| Ser | Leu | Gly | Phe | Gln | Glu | Val | Leu | Ser | Val | Glu | Val | Thr | Leu | His | Val |
| | | | | 165 | | | | | 170 | | | | | 175 | |
| Ala | Ala | Asn | Phe | Ser | Val | Pro | Val | Val | Ser | Ala | Pro | His | Ser | Pro | Ser |
| | | | 180 | | | | | 185 | | | | | 190 | | |
| Gln | Asp | Glu | Leu | Thr | Phe | Thr | Cys | Thr | Ser | Ile | Asn | Gly | Tyr | Pro | Arg |
| | | 195 | | | | | 200 | | | | | 205 | | | |
| Pro | Asn | Val | Tyr | Trp | Ile | Asn | Lys | Thr | Asp | Asn | Ser | Leu | Leu | Asp | Gln |
| | 210 | | | | | 215 | | | | | 220 | | | | |
| Ala | Leu | Gln | Asn | Asp | Thr | Val | Phe | Leu | Asn | Met | Arg | Gly | Leu | Tyr | Asp |
| 225 | | | | | 230 | | | | | 235 | | | | | 240 |
| Val | Val | Ser | Val | Leu | Arg | Ile | Ala | Arg | Thr | Pro | Ser | Val | Asn | Ile | Gly |
| | | | | 245 | | | | | 250 | | | | | 255 | |
| Cys | Cys | Ile | Glu | Asn | Val | Leu | Leu | Gln | Gln | Asn | Leu | Thr | Val | Gly | Ser |
| | | | 260 | | | | | 265 | | | | | 270 | | |
| Gln | Thr | Gly | Asn | Asp | Ile | Gly | Glu | Arg | Asp | Lys | Ile | Thr | Glu | Asn | Pro |
| | | 275 | | | | | 280 | | | | | 285 | | | |
| Val | Ser | Thr | Gly | Glu | Lys | Asn | Ala | Ala | Thr | Trp | Ser | Ile | Leu | Ala | Val |
| | 290 | | | | | 295 | | | | | 300 | | | | |
| Leu | Cys | Leu | Leu | Val | Val | Val | Ala | Val | Ala | Ile | Gly | Trp | Val | Cys | Arg |
| 305 | | | | | 310 | | | | | 315 | | | | | 320 |
| Asp | Arg | Cys | Leu | Gln | His | Ser | Tyr | Ala | Gly | Ala | Trp | Ala | Val | Ser | Pro |
| | | | | 325 | | | | | 330 | | | | | 335 | |
| Glu | Thr | Glu | Leu | Thr | Gly | Glu | Phe | Ala | Val | Gly | Ser | Ser | Arg | Phe | Trp |
| | | | 340 | | | | | 345 | | | | | 350 | | |
| Gly | Ala | Gln | Gly | Arg | Leu | Gly | Cys | Gln | Leu | Ser | Phe | Arg | Val | Ser | Lys |
| | | 355 | | | | | 360 | | | | | 365 | | | |
| Asn | Phe | Gln | Lys | Ala | Lys | Val | Pro | Cys | Leu | Glu | Gln | Leu | Leu | Phe | Leu |
| | 370 | | | | | 375 | | | | | 380 | | | | |

```
Glu Thr Gln Arg Ser Pro Arg Trp Cys Ala Arg His Phe Leu Gln Pro
385                 390                 395                 400

Pro Leu Gly Met Gly Trp His Pro Gly Val His Phe Val Thr Leu Arg
                405                 410                 415

Trp Asp Phe Pro Asn Met His Arg Ser Arg Glu Thr Ser Ala Arg Pro
            420                 425                 430

Pro Arg Ser Pro Val Pro Ser Pro Asp Gln Gly Val Gln Gly Gly Ser
            435                 440                 445

Arg His Arg Arg Pro Ala Pro Met Gly Cys Pro Glu Trp Val Gln Ala
        450                 455                 460

Pro Ala Pro Ser Pro Arg Gly Val Ser Arg Ala Gly Pro Gly Thr Gly
465                 470                 475                 480

Ala Gln Pro Pro Trp Gly Val Gln Gly Ser Arg His Arg Arg Pro
                485                 490                 495

Ala Pro Met Gly Cys Pro Glu Trp Val Gln Ala Pro Ala Pro Ser Pro
            500                 505                 510

Arg Gly Val Ser Arg Ala Gly Pro Gly Thr Gly Ala Gln Pro Leu Trp
            515                 520                 525

Gly Val Trp Ser Gly Ser Gly His Arg Gln Leu Leu Ser Val Ala Ala
            530                 535                 540

Thr Pro Ala Ala Leu Val Cys Pro Ser Val Pro Gly Ala Thr
545                 550                 555

<210> SEQ ID NO 32
<211> LENGTH: 329
<212> TYPE: PRT
<213> ORGANISM: Homo sapiens
<220> FEATURE:
<221> NAME/KEY:
<222> LOCATION:

<400> SEQUENCE: 32

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
                20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190
```

```
Val Thr Glu Leu Tyr Asp Val Ser Ile Ser Leu Ser Val Ser Phe Pro
            195                 200                 205

Asp Val Thr Ser Asn Met Thr Ile Phe Cys Ile Leu Glu Thr Asp Lys
210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
                260                 265                 270

Lys Lys Arg Pro Arg Asn Ser Tyr Lys Cys Gly Thr Asn Thr Met Glu
            275                 280                 285

Arg Glu Glu Ser Glu Gln Thr Lys Lys Arg Glu Lys Ile His Ile Pro
        290                 295                 300

Glu Arg Ser Asp Glu Thr Gln Arg Val Phe Lys Ser Ser Lys Thr Ser
305                 310                 315                 320

Ser Cys Asp Lys Ser Asp Thr Cys Phe
                325

<210> SEQ ID NO 33
<211> LENGTH: 309
<212> TYPE: PRT
<213> ORGANISM: Mus musculus
<220> FEATURE:
<223> OTHER INFORMATION:

<400> SEQUENCE: 33

Met Asp Pro Arg Cys Thr Met Gly Leu Ala Ile Leu Ile Phe Val Thr
1               5                   10                  15

Val Leu Leu Ile Ser Asp Ala Val Ser Val Glu Thr Gln Ala Tyr Phe
                20                  25                  30

Asn Gly Thr Ala Tyr Leu Pro Cys Pro Phe Thr Lys Ala Gln Asn Ile
            35                  40                  45

Ser Leu Ser Glu Leu Val Val Phe Trp Gln Asp Gln Gln Lys Leu Val
    50                  55                  60

Leu Tyr Glu His Tyr Leu Gly Thr Glu Lys Leu Asp Ser Val Asn Ala
65                  70                  75                  80

Lys Tyr Leu Gly Arg Thr Ser Phe Asp Arg Asn Asn Trp Thr Leu Arg
                85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
        115                 120                 125

Glu Leu Ser Val Ile Ala Asn Phe Ser Glu Pro Glu Ile Lys Leu Ala
130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
        195                 200                 205

Val Trp His Met Thr Val Val Cys Val Leu Glu Thr Glu Ser Met Lys
210                 215                 220
```

```
Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Ala Leu Leu Leu
            245                 250                 255

Val Met Leu Leu Ile Ile Val Cys His Lys Lys Pro Asn Gln Pro Ser
        260                 265                 270

Arg Pro Ser Asn Thr Ala Ser Lys Leu Glu Arg Asp Ser Asn Ala Asp
            275                 280                 285

Arg Glu Thr Ile Asn Leu Lys Glu Leu Glu Pro Gln Ile Ala Ser Ala
            290                 295                 300

Lys Pro Asn Ala Glu
305
```

<210> SEQ ID NO 34
<211> LENGTH: 288
<212> TYPE: PRT
<213> ORGANISM: Mus musculus
<220> FEATURE:
<223> OTHER INFORMATION:

<400> SEQUENCE: 34

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
```

<210> SEQ ID NO 35
<211> LENGTH: 306
<212> TYPE: PRT
<213> ORGANISM: Mus musculus
<220> FEATURE:
<223> OTHER INFORMATION:

<400> SEQUENCE: 35

```
Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
 65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305
```

<210> SEQ ID NO 36
<211> LENGTH: 296
<212> TYPE: PRT
<213> ORGANISM: Gallus gallus
<220> FEATURE:
<223> OTHER INFORMATION:

<400> SEQUENCE: 36

```
Met Lys Arg Leu Gly Tyr Gly Phe Leu Leu Phe Leu His Ile Leu
 1               5                  10                  15

Arg Ala Val Thr Ala Leu Glu Lys Ile Ile Ser Lys Pro Gly Asp Asn
            20                  25                  30

Ala Thr Leu Ser Cys Ile Tyr Ala Asn Arg Gly Phe Asp Leu Asp Ser
        35                  40                  45

Leu Arg Val Tyr Trp Gln Ile Asp Gly Val Glu Gly Ser Lys Ser Cys
    50                  55                  60

Ser Val Val His Ala Leu Ile Ser Gly Gln Asp Asn Glu Ser Gln Gln
65                  70                  75                  80

Cys Ser Gln Phe Lys Asn Arg Thr Gln Leu Leu Trp Asp Lys Leu Gly
                85                  90                  95

Asp Gly Asp Phe Ser Leu Leu Leu Tyr Asn Val Arg Gln Ser Asp Glu
            100                 105                 110

His Thr Tyr Lys Cys Val Val Met Gln Thr Ile Glu Tyr Thr Arg Val
        115                 120                 125

Ile His Gln Glu Gln Val Val Leu Ser Leu Ala Ala Ser Tyr Ser Gln
    130                 135                 140

Pro Ile Leu Ser Gly Pro Ile Arg Asn Ser Tyr Ser Thr Gly Glu Glu
145                 150                 155                 160

Val Thr Phe Ser Cys Arg Ser Asp Asn Gly Tyr Pro Glu Pro Asn Val
                165                 170                 175

Tyr Trp Ile Asn Arg Thr Asp Asn Thr Arg Leu Ser Gln Ser Asp Phe
            180                 185                 190

Asn Ile Thr Gln His Pro Asp Gly Thr Tyr Ser Val Leu Ser Thr Leu
        195                 200                 205

Lys Val Asn Ala Thr Ser Asp Met Gln Leu Glu Cys Phe Ile Glu Asn
    210                 215                 220

Lys Val Leu Gln Glu Asn Thr Ser Ala Asn Tyr Thr Glu Glu Met Gln
225                 230                 235                 240

Asn Asn Gly Ser Ser Thr Gly Ser His Lys Asp Ala Ala Lys Gly Gly
                245                 250                 255

Gln Gly Ala Gln Ala Ala Ala Val Val Ser Val Val Ile Leu Met Ala
            260                 265                 270

Phe Leu Thr Val Leu Ile Cys Trp Leu Trp Arg Arg Ser Phe Gln
    275                 280                 285

Leu Val Ser Tyr Thr Ala Pro Val
    290                 295
```

<210> SEQ ID NO 37
<211> LENGTH: 460
<212> TYPE: DNA
<213> ORGANISM: Homo sapiens

<400> SEQUENCE: 37

```
acaacagcct gctggaccag gctctgcaga atgacaccgt cttcttgaac atgcggggct      60
tgtatgacgt ggtcagcgtg ctgaggatcg cacggacccc cagcgtgaac attggctgct     120
gcatagagaa cgtgcttctg cagcagaacc tgactgtcgg cagccagaca ggaaatgaca     180
tcggagagag agacaagatc acagagaatc cagtcagtac cggcgagaaa acgcggcca      240 cgtggagcat cctggctgtc ctgtgcctgc ttgtggtcgt ggcggtggcc ataggctggg     300
tgtgcaggga ccgatgcctc caacacagct atgcaggtgc ctgggctgtg agtccggaga     360
cagagctcac tgaatcctgg aacctgctcc ttctgctctc gtgactgact gtgttctcta     420
```

```
tgcaacttcc aataaaacct cttcatttga aaaaaaaaa                    460
```

<210> SEQ ID NO 38
<211> LENGTH: 24
<212> TYPE: PRT
<213> ORGANISM: Mus musculus

<400> SEQUENCE: 38

```
Lys Pro Leu Ser His Leu Phe Arg Pro Leu Arg Leu Gln Pro Gly Ala
1               5                   10                  15

Arg Ser Pro Thr Tyr Arg Val Tyr
            20
```